United States Patent
McGowan et al.

(10) Patent No.: US 9,499,549 B2
(45) Date of Patent: Nov. 22, 2016

(54) PYRROLO[3,2-]PYRIMIDINE DERIVATIVES FOR THE TREATMENT OF VIRAL INFECTIONS AND OTHER DISEASES

(71) Applicant: JANSSEN SCIENCES IRELAND UC, Little Island, Co Cork (IE)

(72) Inventors: David Craig McGowan, Brussels (BE); Stefaan Julien Last, Lint (BE); Serge Maria Aloysius Pieters, Hulst (NL); Werner Embrechts, Beerse (BE); Tim Hugo Maria Jonckers, Heist-op-den-Berg (BE); Pierre Jean-Marie Bernard Raboisson, Rosieres (BE)

(73) Assignee: JANSSEN SCIENCES IRELAND UC, Co Cork (IE)

( * ) Notice: Subject to any disclaimer, the term of this patent is extended or adjusted under 35 U.S.C. 154(b) by 0 days.

(21) Appl. No.: 14/434,021

(22) PCT Filed: Oct. 9, 2013

(86) PCT No.: PCT/EP2013/070990
§ 371 (c)(1),
(2) Date: Apr. 7, 2015

(87) PCT Pub. No.: WO2014/056953
PCT Pub. Date: Apr. 17, 2014

(65) Prior Publication Data
US 2015/0239892 A1    Aug. 27, 2015

(30) Foreign Application Priority Data
Oct. 10, 2012 (EP) .................... 12187994

(51) Int. Cl.
*C07D 487/04* (2006.01)
*A61K 31/519* (2006.01)
*C07D 519/00* (2006.01)

(52) U.S. Cl.
CPC .......... *C07D 487/04* (2013.01); *A61K 31/519* (2013.01); *C07D 519/00* (2013.01)

(58) Field of Classification Search
CPC . C07D 487/04; A61K 31/407; A61K 31/519
USPC ...................... 544/280; 514/259.1
See application file for complete search history.

(56) References Cited

U.S. PATENT DOCUMENTS 6,028,076 A    2/2000 Hirota et al.
6,329,381 B1   12/2001 Kurimoto et al.

FOREIGN PATENT DOCUMENTS

| EP | 1970373 B1 | 9/2008 |
|---|---|---|
| EP | 2133353 B1 | 12/2009 |
| WO | WO00/06577 | 2/2000 |
| WO | WO 2008/147697 A1 | 12/2008 |
| WO | WO 2009/067081 A1 | 5/2009 |
| WO | WO 2010/006025 A1 | 1/2010 |

OTHER PUBLICATIONS

Vippagunta et al., Advanced Drug Delivery Reviews 48: 3-26, 2001.*
Joachim Ulrich J. Kirk-Othmer Encyclopedia of Chemical Technology, pp. 1-7, 2002.*
Ohto et al., Microbes and Infection 16 (2014) 273-282.*
Yu et al., Biochimica et Biophysica Acta 1835(2013) 144-154.*
Cecil Textbook of Medicine, edited by Bennet, J.C., and Plum F., 20th edition,vol. 1, 1004-101 O, 1996.*
Freshney et al.,Culture of Animal Cells, A Manual of Basic Technique, Alan R. Liss, Inc., 1983, New York, p. 4.*
Dermer et al., Bio/Technology, 1994, 12:320.*
Zhao et al., Frontiers in Immunology. 5, 1-6,2014.*
Vedantham, S., et al., Mechanism of Interferon Action in Hairy Cell Leukemia: A Model of Effective Cancer Biotherapy, Cancer Res. 1992, 52, 1056.
Warshakoon, H, et al., Potential adjuvantic properties of innate immune stimuli, Hum. Vaccines 2009, 5, 381-394.
Grimm, M. et al., Toll-like receptor (TLR) 7 and TLR8 expression on CD133+ cells in colorectal cancer points to a specific role for inflammation induced TLRs in tumourigenesis and tumour progression, Eur. J. Cancer 46, (2010), 2849-57.
De Clercq, E.; et al., (S)-9-(2,3-Dihydroproply)adenine: An Aliphatic Nucleoside Analog with Broad-Spectrum Antiviral Activity, *Science* 1978, 200, 563-565.
Fried et. al. Peginterferon-alfa-2a plus ribavirin for chronic hepatitis C virus infection, *N. Engl J Med* 2002; 347: 975-82.
Jules A. Hoffmann, "The Immune Response of *Drosophila*", Nature, 2003, vol. 426, Issue 6, pp. 33-38.
Kiyoshi Takeda, et al., "Toll-Like Receptors", Annu. Rev. Immunol., 2003, vol. 21, pp. 335-376.
Richard J. Ulevitch, "Therapeutics Targeting the Innate Immune System", Nature Reviews: Immunology, 2004, vol. 4, pp. 512-520.
International Search Report for Corresponding International Application PCT/EP2013/070990, mailed Jan. 17, 2014.

* cited by examiner

*Primary Examiner* — Venkataraman Balasubramanian
(74) *Attorney, Agent, or Firm* — Bradley E. Davis

(57) ABSTRACT

This invention concerns pyrrolo[3,2-d]pyrimidine derivatives, processes for their preparation, pharmaceutical compositions, and their use in treatment and/or therapy of diseases.

6 Claims, No Drawings

PYRROLO[3,2-]PYRIMIDINE DERIVATIVES FOR THE TREATMENT OF VIRAL INFECTIONS AND OTHER DISEASES

This application is a 35 U.S.C. 371 nationalization of PCT application PCT/EP2013/070990 filed Oct. 9, 2013, which claims priority to European patent application EP12187994.4 filed Oct. 10, 2012, both of which are incorporated herein by reference.

This invention relates to pyrrolo[3,2-d]pyrimidine derivatives, processes for their preparation, pharmaceutical compositions, and their use in treatment and/or therapy of diseases.

The present invention relates to the use of pyrrolopyrimidine derivatives, more specifically to the use of pyrrolo[3,2-d]pyrimidine derivatives in the treatment of viral infections, immune or inflammatory disorders, whereby the modulation, or agonism, of toll-like-receptors (TLRs) is involved. Toll-Like Receptors are primary transmembrane proteins characterized by an extracellular leucine rich domain and a cytoplasmic extension that contains a conserved region. The innate immune system can recognize pathogen-associated molecular patterns via these TLRs expressed on the cell surface of certain types of immune cells. Recognition of foreign pathogens activates the production of cytokines and upregulation of co-stimulatory molecules on phagocytes. This leads to the modulation of T cell behaviour.

A majority of mammalian species have between ten and fifteen types of Toll-like receptors. Thirteen TLRs (named simply TLR1 to TLR13) have been identified in humans and mice together, and equivalent forms of many of these have been found in other mammalian species. However, equivalents of certain TLR found in humans are not present in all mammals. For example, a gene coding for a protein analogous to TLR10 in humans is present in mice, but appears to have been damaged at some point in the past by a retrovirus. On the other hand, mice express TLRs 11, 12, and 13, none of which are represented in humans. Other mammals may express TLRs which are not found in humans. Other non-mammalian species may have TLRs distinct from mammals, as demonstrated by TLR14, which is found in the Takifugu pufferfish. This may complicate the process of using experimental animals as models of human innate immunity.

For reviews on toll-like receptors see the following journal articles. Hoffmann, J. A., Nature, 426, p 33-38, 2003; Akira, S., Takeda, K., and Kaisho, T., Annual Rev. Immunology, 21, p 335-376, 2003; Ulevitch, R. J., Nature Reviews: Immunology, 4, p 512-520, 2004.

Compounds indicating activity on Toll-Like receptors have been previously described such as heterocyclic derivatives in WO2000006577, adenine derivatives in WO 98/01448 and WO 99/28321, and pyrimidines in WO 2009/067081.

In the treatment of certain viral infections, regular injections of interferon (IFN-alfa) can be administered, as is the case for hepatitis C virus (HCV) (Fried et. al. Peginterferon-alfa plus ribavirin for chronic hepatitis C virus infection, *N Engl J Med* 2002; 347: 975-82). Orally available small molecule IFN inducers offer the potential advantages of reduced immunogenicity and convenience of administration. Thus, novel IFN inducers are potentially effective new class of drugs for treating virus infections. For an example in the literature of a small molecule IFN inducer having antiviral effect see De Clercq, E.; Descamps, J.; De Somer, P. *Science* 1978, 200, 563-565.

Interferon alpha is also given to patients in combination with other drugs in the treatment of certain types of cancer (Eur. J. Cancer (46) p 2849-57, and Cancer Res. 1992 (52) p. 1056). TLR 7/8 agonists are also of interest as vaccine adjuvants because of their ability to induce pronounced Th1 response (Hum. Vaccines, 2009 (5), 381-394).

However, there exists a strong need for novel Toll-Like receptor modulators having preferred selectivity, and an improved safety profile compared to the compounds of the prior art.

In accordance with the present invention a compound of formula (I) is provided

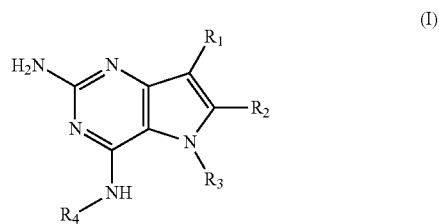

and their pharmaceutically acceptable salt, solvate prodrug, stereoisomers or polymorph thereof wherein $R_1$ is H, fluorine or methyl;

$R_2$ is H, halogen or $C_{1-3}$ alkyl;

$R_3$ is $C_{1-6}$ alkyl optionally substituted by aryl optionally further substituted by one or more substituents independently selected from aryloxy, halogen, aryl, alkylamino, dialkylamino, heterocycloalkyl, $C_{1-6}$ cycloalkyl, $C_{1-6}$ alkyl, carboxylic acid, carboxylic ester, carboxylic amide, nitrile, or $C_{1-6}$ alkoxy; or $R_3$ is $C_{1-6}$ alkyl optionally substituted by $C_{1-6}$ alkene, $C_{3-7}$ cycloalkyl or $C_{3-7}$ heterocycloalkyl; or $R_3$ is $C_{1-6}$ alkyl optionally substituted by $C_{1-6}$ alkoxy optionally further substituted by aryl;

$R_4$ is $C_{1-8}$ alkyl optionally substituted by one or more substituents independently selected from hydroxyl, $C_{1-6}$ alkoxy, $C_{1-6}$ alkyl, $C_{3-7}$ cycloalkyl, $C_{2-6}$ alkenyl, aryl, heteroaryl optionally further substituted by $C_{1-6}$ alkyl, and $C_{3-7}$ cycloalkyl optionally further substituted by $C_{1-6}$ alkyl;

with the proviso that 2-amino-4-(N-butylamino)-5-(alphamethylbenzyl)pyrrolo[3,2-d]pyrimidine is excluded.

Preferred compounds are those of formula (I) wherein $R_3$ is a $C_{1-3}$ alkyl group substituted with an aryl (substituted or unsubstituted), and $R_1$, $R_2$, and $R_4$ are described as above.

In a second embodiment are the compounds of formula (I) wherein $R_3$ and $R_4$ are a $C_{1-3}$ alkyl substituted by an aryl, optionally further substituted as described above.

In a further embodiments are those of formula (I) wherein $R_1$ is hydrogen, $R_2$ is fluorine, and $R_3$ and $R_4$ are described as above.

Other preferred embodiments are those of formula (I) wherein $R_1$ is fluorine, $R_2$ is hydrogen, and $R_3$ and $R_4$ are described as above.

The compounds, as listed in Tables I and II, having the following numbers #89, 94, 101, 144, 154, 156, 175, 192, 209, 213 and 215 are of special interest because of their properties according to the invention disclosed herein.

The compounds of formula (I) and their pharmaceutically acceptable salt, solvate or polymorph thereof have activity as pharmaceuticals, in particular as modulators of Toll-Like Receptor (especially TLR7 and/or TLR8) activity.

In a further aspect the present invention provides a pharmaceutical composition comprising a compound of formula (I) or a pharmaceutically acceptable salt, solvate or polymorph thereof together with one or more pharmaceutically acceptable excipients, diluents or carriers.

Furthermore a compound of formula (I) or a pharmaceutically acceptable salt, solvate or polymorph thereof according to the current invention, or a pharmaceutical composition comprising said compound of formula (I) or a pharmaceutically acceptable salt, solvate or polymorph thereof can be used as a medicament.

Another aspect of the invention is that a compound of formula (I) or a pharmaceutically acceptable salt, solvate or polymorph thereof, or said pharmaceutical composition comprising said compound of formula (I) or a pharmaceutically acceptable salt, solvate or polymorph thereof can be used accordingly in the treatment of any disorder in which the modulation of TLR7 and/or TLR8 is involved.

The term "alkyl" refers to a straight-chain or branched-chain saturated aliphatic hydrocarbon containing the specified number of carbon atoms.

The term "halogen" refers to fluorine, chlorine, bromine or iodine.

The term "alkenyl" refers to an alkyl as defined above consisting of at least two carbon atoms and at least one carbon-carbon double bond.

The term "cycloalkyl" refers to a carbocyclic ring containing the specified number of carbon atoms.

The term "alkoxy" refers to an alkyl (carbon and hydrogen chain) group singular bonded to oxygen like for instance a methoxy group or ethoxy group.

The term "aryl" means an aromatic ring structure optionally comprising one or two heteroatoms selected from N, O and S, in particular from N and O. Said aromatic ring structure may have 5, 6 or 7 ring atoms. In particular, said aromatic ring structure may have 5 or 6 ring atoms. Said aromatic ring structure may also be fused to another aryl ring affording a bicyclic structure (examples include but are not limited to: quinoline, isoquinoline, quinazoline, benzoxazole).

The term "aryloxy" refers to an aromatic ring structure. Said aromatic group is singularly bonded to oxygen (e.g. phenoxy).

The term "alkene" refers to an unsaturated hydrocarbon chain containing the specified number of carbon atoms containing at least one carbon-to carbon double bond.

The term "heterocycle" refers to molecules that are saturated or partially saturated and include tetrahydrofuran, dioxane or other cyclic ethers. Heterocycles containing nitrogen include, for example azetidine, morpholine, piperidine, piperazine, pyrrolidine, and the like. Other heterocycles include, for example, thiomorpholine, dioxolinyl, and cyclic sulfones.

Pharmaceutically acceptable salts of the compounds of formula (I) include the acid addition and base salts thereof. Suitable acid addition salts are formed from acids which form non-toxic salts. Suitable base salts are formed from bases which form non-toxic salts.

The compounds of the invention may also exist in unsolvated and solvated forms. The term "solvate" is used herein to describe a molecular complex comprising the compound of the invention and one or more pharmaceutically acceptable solvent molecules, for example, ethanol.

The term "polymorph" refers to the ability of the compound of the invention to exist in more than one form or crystal structure.

The compounds of the present invention may be administered as crystalline or amorphous products. They may be obtained for example as solid plugs, powders, or films by methods such as precipitation, crystallization, freeze drying, spray drying, or evaporative drying. They may be administered alone or in combination with one or more other compounds of the invention or in combination with one or more other drugs. Generally, they will be administered as a formulation in association with one or more pharmaceutically acceptable excipients. The term "excipient" is used herein to describe any ingredient other than the compound(s) of the invention. The choice of excipient depends largely on factors such as the particular mode of administration, the effect of the excipient on solubility and stability, and the nature of the dosage form.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, for example, for oral, rectal, or percutaneous administration. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions, and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. Also included are solid form preparations that can be converted, shortly before use, to liquid forms. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. The compounds of the present invention may also be administered via inhalation or insufflation by means of methods and formulations employed in the art for administration via this way. Thus, in general the compounds of the present invention may be administered to the lungs in the form of a solution, a suspension or a dry powder.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Those of skill in the treatment of infectious diseases will be able to determine the effective amount from the test results presented hereinafter. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight and general physical condition of the particular patient as well as other medication the individual may be taking, as is well known to those skilled in the art. Furthermore, it is evident that the effective amount may be lowered or increased depending on the response of the treated subject and/or depending on the evaluation of the physician prescribing the compounds of the instant invention. The effective amount ranges mentioned above are therefore only guidelines and are not intended to limit the scope or use of the invention to any extent.

EXPERIMENTAL SECTION

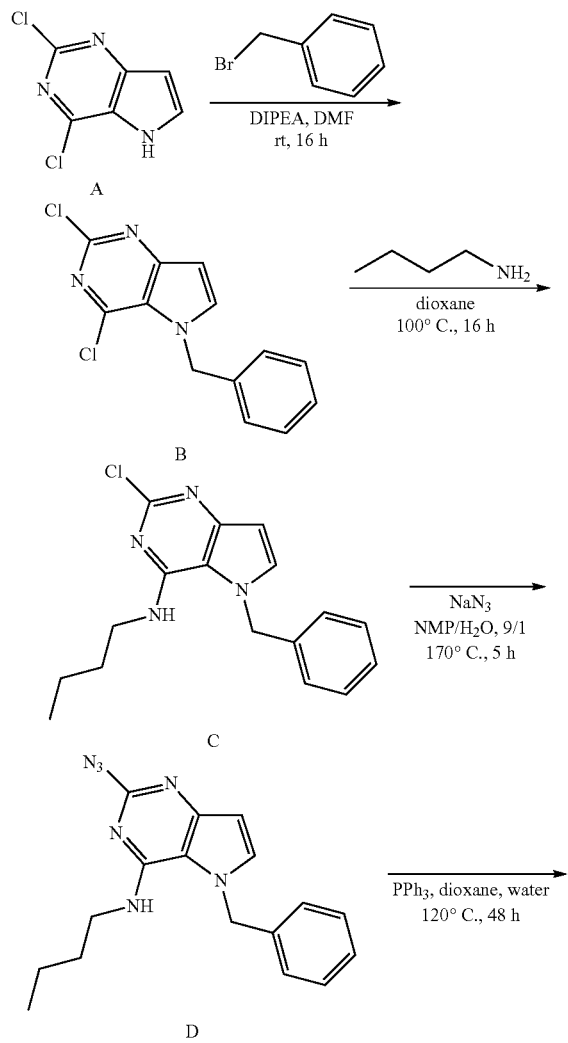

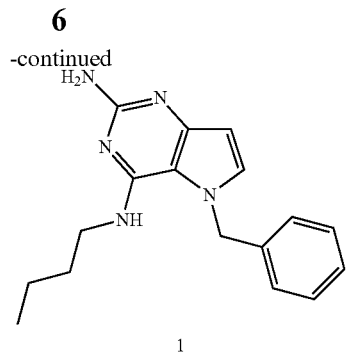

Compounds of type A in scheme 1 can be alkylated with benzyl bromides using a polar aprotic solvent, for example DMF. The reaction of alkyl halides with intermediate A requires a stronger base (e.g. cesium carbonate) and possibly a longer reaction time and/or increased temperature. The displacement of the chlorine in intermediate B with an amine to form compounds of the type C may require additional heating or prolonged reaction time as observed with aminoalcohols (for the preparation of aminoalcohols refer to WO2009067081 and WO2008147697). The displacement of the chlorine in intermediate B with an amine may also proceed at room temperature in a polar solvent (e.g. DMF or acetonitrile). A variety of bases may be used to aid in the reaction from B to C including but not limited to the following: triethylamine, diisopropylamine, cesium carbonate, potassium carbonate, or sodium hydride. The reduction of the azido group in compounds represented by the intermediate D above may also proceed over Pd/C in a hydrogen atmosphere. Intermediates B, C, and D containing fluorine can be substituted under the same protocols as the unsubstituted analogs, thus, reaction schemes described apply to both types of compounds.

Preparation of Intermediate B

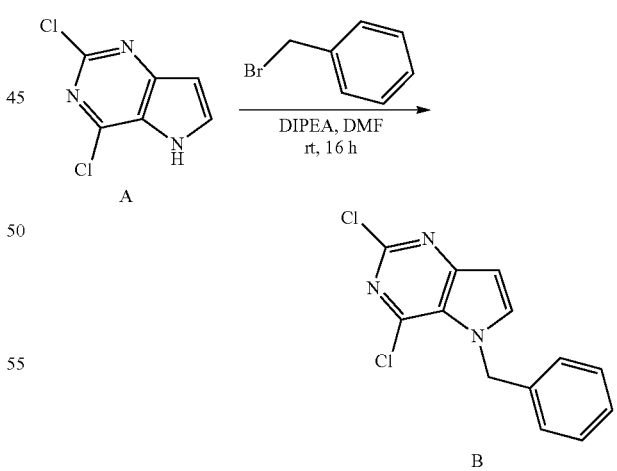

Into a 50 mL vial was placed 2,4-dichloro-5H-pyrrolo[3,2-d]pyrimidine [CAS 63200-54-4] (1 g, 5.319 mmol), DMF (10 mL), DIPEA (2.75 mL, 16 mmol) and benzyl bromide (0.7 mL, 5.85 mmol). The vial was sealed and shaken for 16 hours at room temperature. The solvents were removed under reduced pressure. The crude was purified via silica gel column chromatography using a heptane to ethyl acetate gradient. The best fractions were pooled and the solvents were removed under reduced pressure to afford B.
LC-MS (M+H) m/z=278

Preparation of Intermediate B2

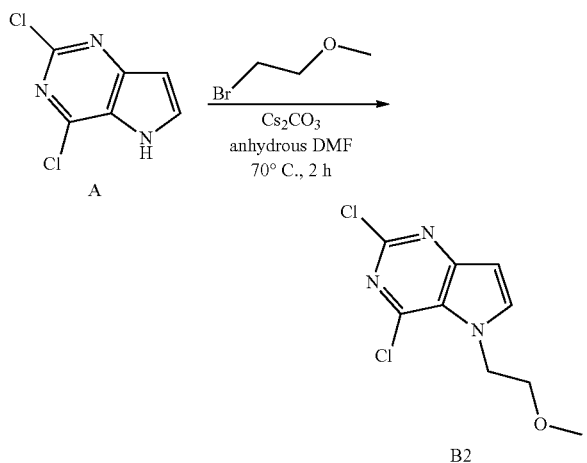

Into a 50 mL vial equipped with a magnetic stir bar was placed A (50 mg, 0.27 mmol), anhydrous DMF (1 mL), cesium carbonate (0.259 g, 0.8 mmol) and then 2-bromo-ethyl methyl ether (0.03 mL, 0.29 mmol). The flask was sealed, and the reaction was allowed to stir at 70° C. for 2 hours. The solvents were removed under reduced pressure. The crude was purified via silica gel column chromatography using a heptane to ethyl acetate gradient. The best fractions were pooled and the solvents were removed under reduced pressure to afford B2.
LC-MS (M+H) m/z=246

Preparation of Intermediate C

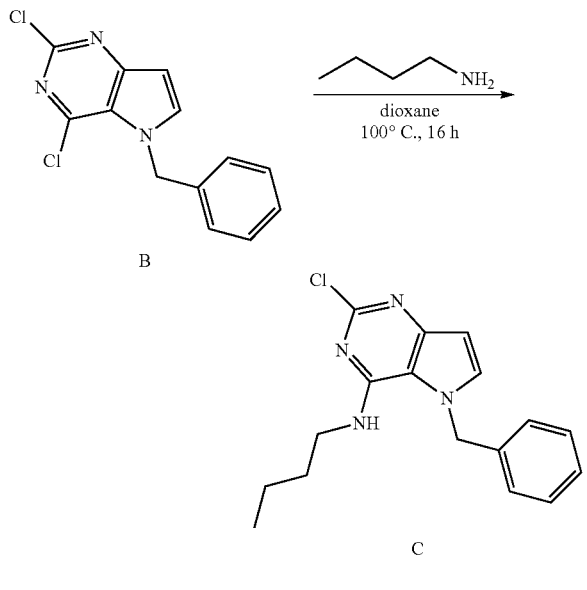

Into a 50 mL round bottom flask equipped with a magnetic stir bar was placed B (1.4 g, 5.03 mmol), n-butylamine (0.59 mL, 6.04 mmol), and 1,4-dioxane (5 mL). The flask was equipped with a reflux condenser and allowed to heat with stirring at 100° C. for 16 hours. After cooling to room temperature, the solvents were removed under reduced pressure. The crude was purified via silica gel column chromatography using a heptane to ethyl acetate gradient. The best fractions were pooled and the solvents were removed under reduced pressure to afford C.
LC-MS (M+H) m/z=315

Preparation of Intermediate D

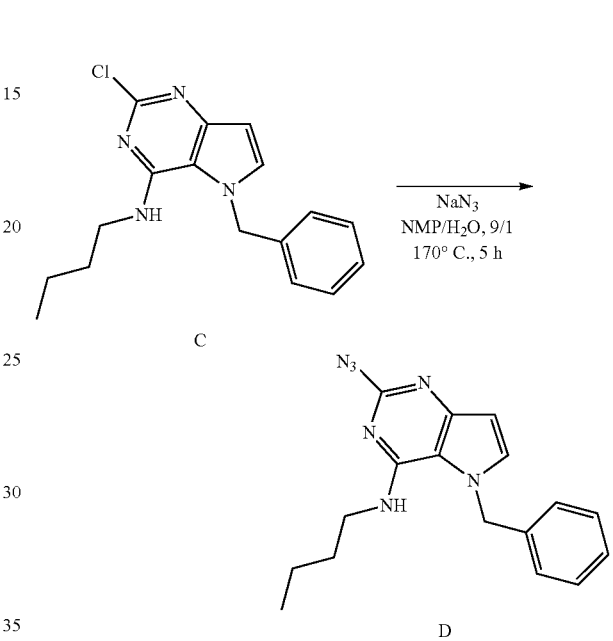

Into a glass vial equipped with a magnetic stir bar was placed C (1 g, 3.18 mmol), sodium azide (0.62 g, 9.53 mmol), and NMP:water (9:1, 4 mL). The glass vial was sealed and the mixture was heated with stirring to 170° C. for 5 hours. After cooling to room temperature, the mixture was diluted with ethyl acetate (20 mL) and washed with water (5×15 mL). The organic layer was dried over magnesium sulfate, the solids were removed via filtration and the solvents of the filtrate were removed under reduced pressure. The crude was purified via silica gel column chromatography using a heptane to ethyl acetate gradient. The best fractions were combined and the solvents were removed under reduced pressure to afford D.
LC-MS (M+H) m/z=322

Preparation of 1

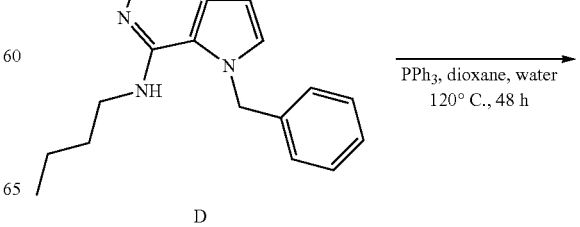

-continued

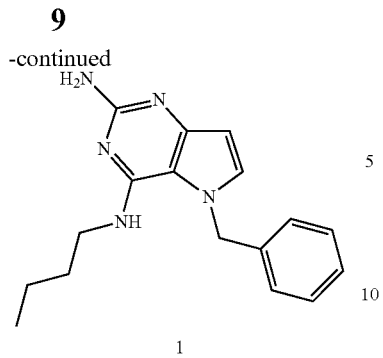

1

Into a glass vial equipped with a magnetic stir bar was placed D (100 mg, 0.311 mmol), 1,4-dioxane (4 mL), water (1 mL), and triphenylphosphine (245 mg, 0.93 mmol). The glass vial was sealed and the mixture heated with stirring to 120° C. for 48 hours. After cooling to room temperature, the solvents were removed under reduced pressure. The crude was purified via silica gel column chromatography using a dichloromethane to 10% methanol in dichloromethane gradient. The best fractions were pooled and the solvents were removed under reduced pressure to afford 1.

LC-MS (M+H) m/z=296

Preparation of 86

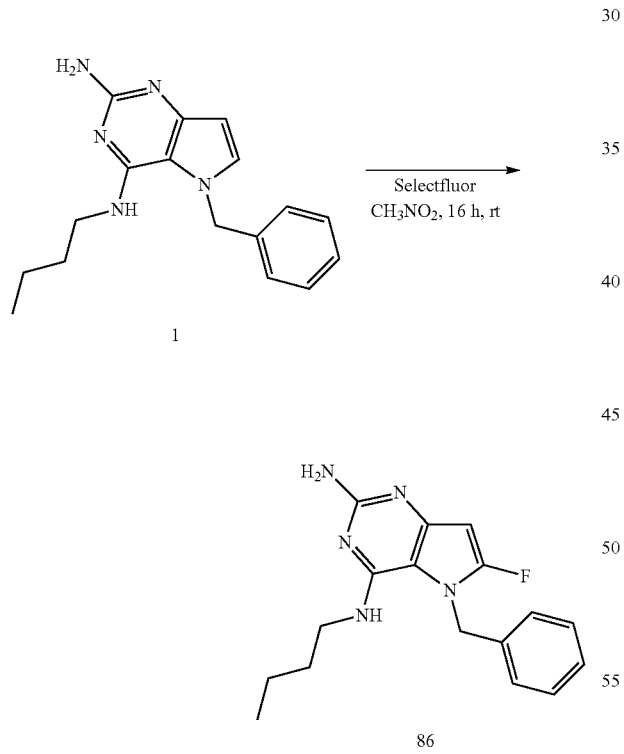

Into a glass vial equipped with a magnetic stir bar was placed 1 (110 mg, 0.372 mmol), nitromethane (1.5 mL), and selectfluor (198 mg, 0.56 mmol). The glass vial was sealed and the mixture stirred at room temperature for 16 hours. The solvents were removed under reduced pressure. The crude was purified via reverse phase chromatography. The best fractions were pooled and the solvents were removed under reduced pressure to afford 86.

Preparation of Intermediate E

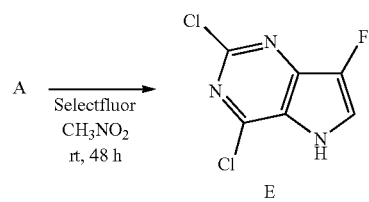

Into a glass vial equipped with a magnetic stir bar was placed A (600 mg, 3.19 mmol), nitromethane (10 mL), and selectfluor (5.67 g, 16 mmol). The glass vial was sealed and the mixture stirred at room temperature for 48 hours. NaHCO$_3$ (sat. aq., 10 mL) was added and extracted with ethyl acetate (3×15 mL). The organic layers were pooled, dried over magnesium sulfate, the solids were removed by filtration, and the solvent of the filtrate was removed under reduced pressure to afford crude E, used as such in the next step.

LC-MS (M+H) m/z=206

Preparation of intermediate G

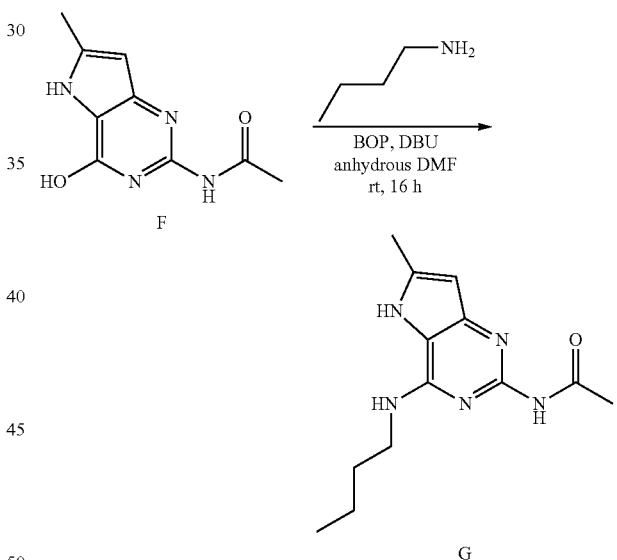

Step 1

Intermediate F was prepared according to the method used to prepare compound 9 in scheme 3 on page 44 of WO2010006025. With the exception that acetyl group was employed in place of the trimethylacetyl group.

Step 2. Preparation of Intermediate G

Into a 50 mL glass vial equipped with a magnetic stir bar was placed F (200 mg, 0.97 mmol), anhydrous DMF (5 mL), DBU (0.435 mL, 2.91 mmol), and BOP (536 mg, 1.2 mmol). The reaction mixture becomes a solution after stirring for several minutes, then n-butylamine (0.48 mL, 4.85 mmol) was added and the stirring continues at room temperature for 16 hours. The solvent was removed under reduced pressure and the crude was purified via reverse phase chromatography.

LC-MS (M+H) m/z=262

Scheme 2. Overall reaction scheme

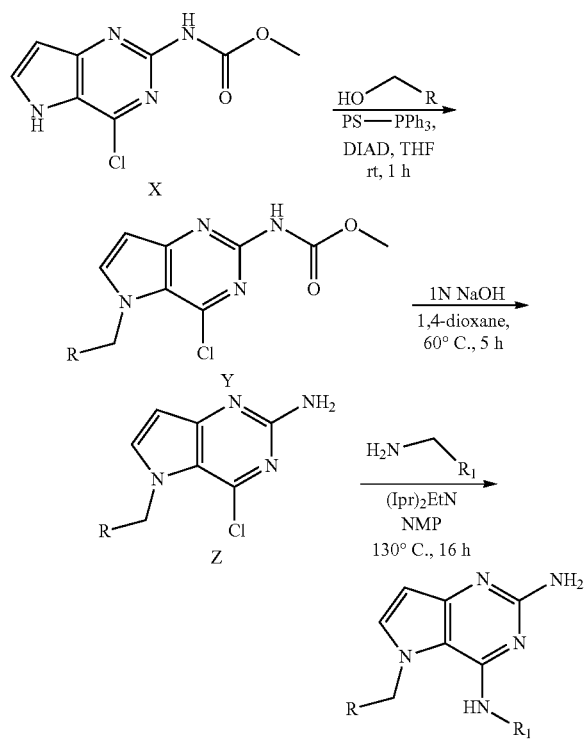

General procedure. Compounds of type X in scheme 2 can be functionalized with alcohols using Mitsunobu conditions in a polar aprotic solvent, for example THF. Cleavage of methyl carbamate was performed under basic conditions in 1,4-dioxane to form intermediate Z. The displacement of the chlorine in intermediate Z was performed with an amine and a base (e.g. NaH) in a polar solvent (e.g. NMP) to form compounds of formula (I).

Preparation of Intermediate X

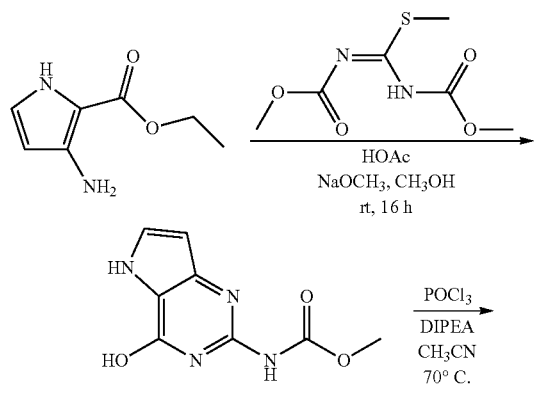

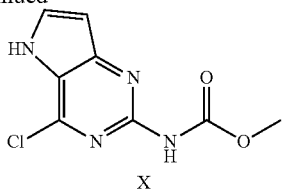

X

3-Amino-2-ethoxycarbonylpyrrole hydrochloride (25.8 g, 135.3 mmol) was partitioned between dichloromethane and sat. NaHCO$_3$, dried over MgSO$_4$, filtered and evaporated to dryness. The residue was dissolved in methanol (500 mL) together with 1,3-bis(methoxycarbonyl)-2-methyl-2-thiopseudourea (32.1 g, 156 mmol) and acetic acid (39 mL, 677 mmol) and stirred 1 hour at room temperature. A precipitate appeared and stirring was continued overnight. Sodium methoxide (73.1 g, 1353 mmol) was added. An exotherm was observed and the reaction mixture was stirred overnight. The reaction mixture was brought to pH 5 via addition of acetic acid and the precipitate was filtered off, triturated with water (2×350 mL), acetonitrile (1×350 mL) and diisopropylether (1×350 mL). The obtained methyl N-(4-hydroxy-5H-pyrrolo[3,2-d]pyrimidin-2-yl)carbamate was dried in the oven.

Methyl N-(4-hydroxy-5H-pyrrolo[3,2-d]pyrimidin-2-yl) carbamate (25 g, 120 mmol) was dispensed into acetonitrile (350 mL) in a 500 mL multi neck flask at room temperature. POCl$_3$ (22.1 mL, 238.2 mmol) was added and the reaction mixture was heated to 70° C. while stirring by an overhead, mechanical stirrer (300 rpm). Hunig's base (41.4 mL, 240.2 mmol) was added dropwise via a syringe pump at a flow rate of 0.2 mL/min. The reaction mixture was cooled to room temperature and poured into a stirred solution of sodium acetate (78.8 g, 961 mmol) in water (500 mL) at 45° C. The organics were evaporated and the remaining liquid was stirred and cooled in an ice bath. The formed solid was isolated by filtration, washed with acetonitrile and triturated with diisopropylether to become intermediate X as a solid which was dried under vacuum.

Preparation of Intermediate Y

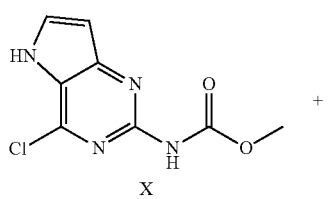

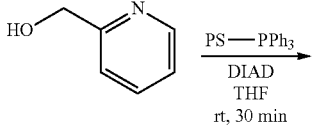

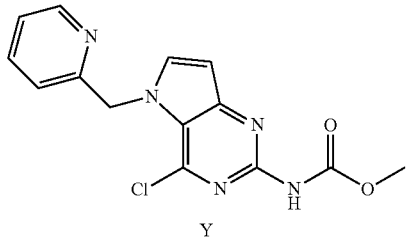

Y

To a suspension of intermediate X (5 g, 22 mmol), 2-pyridinemethanol (2.6 mL, 26.5 mmol) and polystyrene-bound triphenylphosphine (18.4 g, 55.2 mmol) in anhydrous THF (153 mL) was added DIAD (6.9 mL, 33 mmol) at room temperature and the reaction mixture stirred for 30 minutes then was concentrated under reduced pressure. The product was purified via silica gel column chromatography using gradient a dichloromethane:methanol 100:0 to 90:10 gradient. The product fractions were collected and concentrated under reduced pressure. The product was recrystallized in acetonitrile, isolated by filtration and dried under vacuum to afford Y as a white solid.

Preparation of Intermediate Z

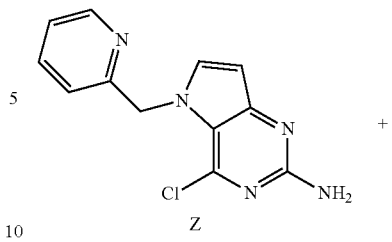

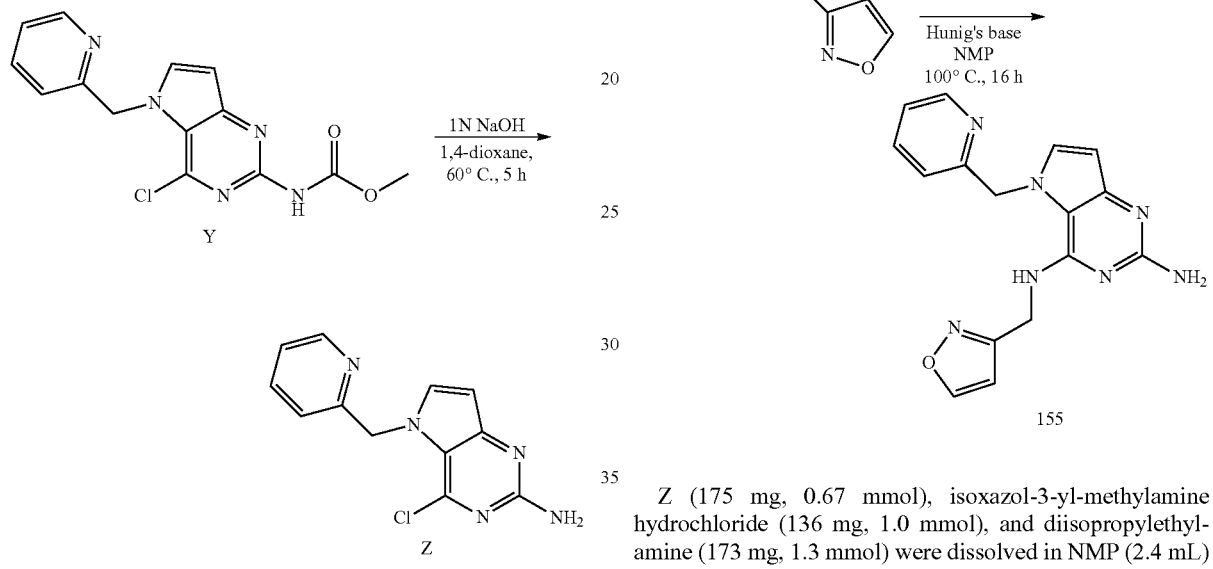

Y (4.5 g, 14.2 mmol) was dissolved in 1,4-dioxane (68 mL) in a 100 mL round bottom flask and 1 N NaOH (34 mL) was added. The mixture was heated to 60° C. for 5 h. The mixture was cooled and concentrated under reduced pressure. The residue was treated with water and the precipitate was isolated by filtration and dried to afford Z. The product was used as such in the next step.

Z (175 mg, 0.67 mmol), isoxazol-3-yl-methylamine hydrochloride (136 mg, 1.0 mmol), and diisopropylethylamine (173 mg, 1.3 mmol) were dissolved in NMP (2.4 mL) in a 7 mL glass vial. The mixture was stirred at 100° C. for 2 h then cooled and concentrated in vacuo. It was purified by Prep HPLC (Stationary phase: RP Vydac Denali C18—10 μm, 200 g, 5 cm), Mobile phase: 0.25% $NH_4OAc$ solution in water, methanol), the desired fractions were collected and concentrated in vacuo. The product was triturated in acetonitrile, isolated by filtration and dried under vacuum to become 155 as a white solid.

TABLE 1

Compounds of formula (I) and corresponding analytical data.

| # | STRUCTURE | $^1$H NMR | LC Method, Rt (min) | LC-MS Mass Found |
|---|---|---|---|---|
| 1 | 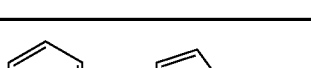 | $^1$H NMR (400 MHz, DMSO-$d_6$) δ ppm 0.77 (t, J = 7.3 Hz, 3 H), 0.98-1.11 (m, 2 H), 1.33 (dt, J = 14.5, 7.2 Hz, 2 H), 3.25-3.30 (m, 2 H), 5.23 (s, 2 H), 5.48 (s, 6 2 H), 5.75 (t, J = 5.5 Hz, 1 H), 5.98 (d, J = 3.0 Hz, 1 H), 6.97 (d, J = 7.0 Hz, 2 H), 7.19-7.35 (m, 4 H) | B, 0.88 | 296 |

TABLE 1-continued

Compounds of formula (I) and corresponding analytical data.

| # | STRUCTURE | $^1$H NMR | LC Method, Rt (min) | LC-MS Mass Found |
|---|---|---|---|---|
| 2 | 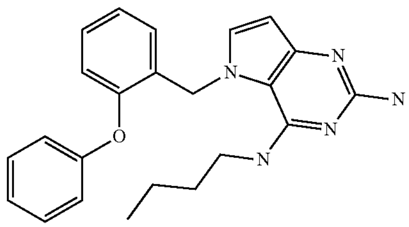 [SMILES: CCCCNc1nc(N)nc2ccn(Cc3ccccc3Oc3ccccc3)c12] | $^1$H NMR (300 MHz, CHLOROFORM-d) δ ppm 0.76 (t, J = 7.2 Hz, 3 H), 1.07 (dq, J = 14.9, 7.3 Hz, 2 H), 1.23-1.35 (m, 2 H), 3.31 (td, J = 6.8, 5.6 Hz, 2 H), 4.90 (t, J = 4.9 Hz, 1 H), 5.12 (br. s., 2 H), 5.31 (s, 2 H), 6.21 (d, J = 3.0 Hz, 1 H), 6.71-6.79 (m, 1 H), 6.86-6.94 (m, 3 H), 6.97-7.05 (m, 2 H), 7.06-7.14 (m, 1 H), 7.20-7.27 (m, 1 H), 7.27-7.36 (m, 2 H) | A, 2.82 | 388 |
| 3 | 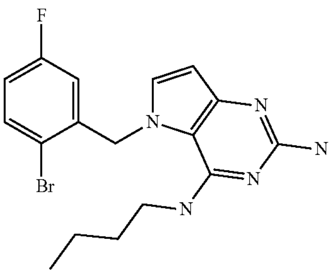 [SMILES: CCCCNc1nc(N)nc2ccn(Cc3cc(F)ccc3Br)c12] | $^1$H NMR (400 MHz, DMSO-d$_6$) δ ppm 0.75 (t, J = 7.3 Hz, 3 H), 0.96-1.09 (m, 2 H), 1.28-1.41 (m, 2 H), 3.25-3.33 (m, 2 H), 5.55 (s, 4 H), 5.85 (dd, J = 9.7, 2.6 Hz, 1 H), 5.98 (t, J = 5.0 Hz, 1 H), 6.08 (d, J = 3.0 Hz, 1 H), 7.11 (td, J = 8.5, 3.1 Hz, 1 H), 7.30 (d, J = 3.0 Hz, 1 H), 7.70 (dd, J = 8.8, 5.3 Hz, 1 H) | A, 2.49 | 393 |
| 4 | 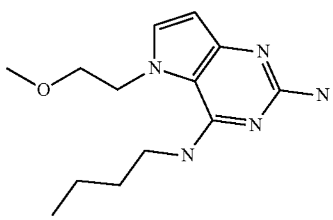 [SMILES: CCCCNc1nc(N)nc2ccn(CCOC)c12] | $^1$H NMR (300 MHz, CHLOROFORM-d) δ ppm 0.91 (t, J = 7.2 Hz, 3 H), 1.30-1.44 (m, 2 H), 1.49-1.61 (m, 2 H), 3.34 (s, 3 H), 3.43 (td, J = 7.1, 5.3 Hz, 2 H), 3.69-3.77 (m, 2 H), 4.20-4.29 (m, 2 H), 5.73 (br. s., 1 H), 6.20 (d, J = 3.0 Hz, 1 H), 6.86 (d, J = 3.2 Hz, 1 H), 7.11 (br. s., 1 H) | A, 1.95 | 264 |
| 5 | 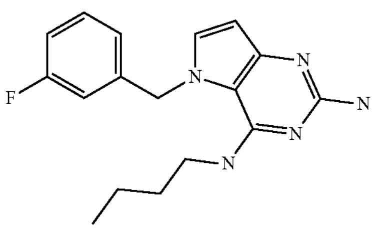 [SMILES: CCCCNc1nc(N)nc2ccn(Cc3cccc(F)c3)c12] | $^1$H NMR (300 MHz, CHLOROFORM-d) δ ppm 0.74 (t, J = 7.2 Hz, 3 H), 0.90-1.07 (m, 2 H), 1.11-1.17 (m, 2 H), 3.18-3.28 (m, 2 H), 4.40 (br. s., 1 H), 4.94 (br. s., 2 H), 5.30 (s, 2 H), 6.23 (d, J = 3.0 Hz, 1 H), 6.70 (d, J = 8.8 Hz, 1 H), 6.79 (d, J = 7.7 Hz, 1 H), 6.94-7.03 (m, 2 H), 7.30 (td, J = 8.0, 5.8 Hz, 1 H) | A, 2.29 | 314 |
| 6 | 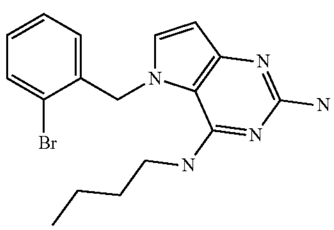 | $^1$H NMR (300 MHz, CHLOROFORM-d) δ ppm 0.72 (t, J = 7.2 Hz, 3 H), 0.88-1.03 (m, 2 H), 1.14-1.27 (m, 2 H), 3.24 (td, J = 6.7, 5.3 Hz, 2 H), 4.29 (br. s., 1 H), 4.89 (br. s., 2 H), 5.33 (s, 2 H), 6.24 (d, J = 3.0 Hz, 1 H), 6.46-6.53 (m, 1 H), 6.99 (d, J = 3.0 Hz, 1 H), 7.10-7.22 (m, 2 H), 7.55-7.60 (m, 1 H) | A, 2.47 | 375 |
| 7 | 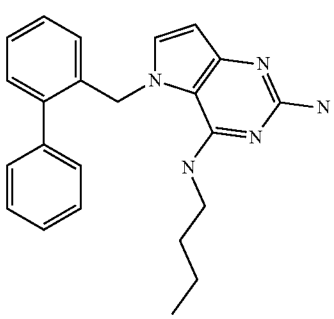 [SMILES: CCCCNc1nc(N)nc2ccn(Cc3ccccc3-c3ccccc3)c12] | $^1$H NMR (300 MHz, CHLOROFORM-d) δ ppm 0.74 (t, J = 7.2 Hz, 3 H), 0.86-1.01 (m, 2 H), 1.06-1.18 (m, 2 H), 3.12-3.22 (m, 2 H), 4.31 (t, J = 5.0 Hz, 1 H), 5.18 (br. s., 2 H), 5.19-5.24 (m, 2 H), 6.20 (d, J = 3.0 Hz, 1 H), 6.71 (d, J = 7.7 Hz, 1 H), 6.96 (d, J = 3.0 Hz, 1 H), 7.21-7.47 (m, 8 H) | A, 2.78 | 372 |

TABLE 1-continued

Compounds of formula (I) and corresponding analytical data.

| # | STRUCTURE | ¹H NMR | LC Method, Rt (min) | LC-MS Mass Found |
|---|---|---|---|---|
| 8 | 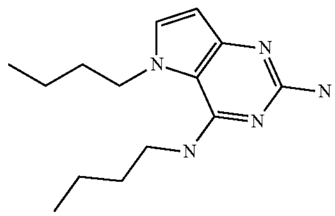 [SMILES: CCCCNc1nc(N)nc2ccn(CCCC)c12] | ¹H NMR (300 MHz, DMSO-d$_6$) δ ppm 0.84 (t, J = 7.4 Hz, 3 H), 0.93 (t, J = 7.3 Hz, 3 H), 1.06-1.27 (m, 2 H), 1.27-1.44 (m, 2 H), 1.50-1.66 (m, 4 H), 3.44-3.54 (m, 2 H), 4.28 (t, J = 6.9 Hz, 2 H), 5.99 (d, J = 2.9 Hz, 1 H), 6.17 (br. s., 2 H), 6.79 (br. s., 1 H), 7.28 (d, J = 2.9 Hz, 1 H) | A, 2.28 | 262 |
| 9 | 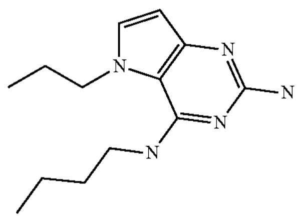 [SMILES: CCCCNc1nc(N)nc2ccn(CCC)c12] | ¹H NMR (300 MHz, CHLOROFORM-d) δ ppm 0.86 (t, J = 7.4 Hz, 3 H), 0.91 (t, J = 7.3 Hz, 3 H), 1.36 (dq, J = 15.0, 7.4 Hz, 2 H), 1.52-1.65 (m, 2 H), 1.76 (sxt, J = 7.3 Hz, 2 H), 3.52 (td, J = 7.1, 5.6 Hz, 2 H), 4.07 (t, J = 7.1 Hz, 2 H), 5.17-5.30 (m, 1 H), 5.52 (br. s., 2 H), 6.09 (d, J = 3.0 Hz, 1 H), 6.88 (d, J = 3.0 Hz, 1 H) | A, 2.06 | 248 |
| 10 | 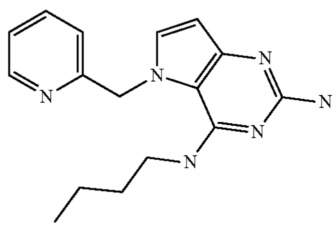 [SMILES: CCCCNc1nc(N)nc2ccn(Cc3ccccn3)c12] | ¹H NMR (300 MHz, CHLOROFORM-d) δ ppm 0.92 (t, J = 7.3 Hz, 3 H), 1.38 (dq, J = 15.0, 7.3 Hz, 2 H), 1.56-1.68 (m, 2 H), 3.49 (td, J = 7.1, 5.1 Hz, 2 H), 5.28 (s, 2 H), 5.78 (br. s., 2 H), 6.18 (d, J = 3.0 Hz, 1 H), 7.06 (d, J = 3.0 Hz, 1 H), 7.25-7.32 (m, 1 H), 7.34 (d, J = 7.7 Hz, 1 H), 7.74 (td, J = 7.7, 1.7 Hz, 1 H), 8.48 (d, J = 4.4 Hz, 1 H), 8.58 (br. s., 1 H) | A, 2.14 | 297 |
| 11 | 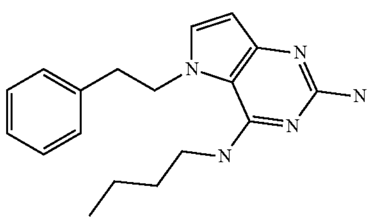 [SMILES: CCCCNc1nc(N)nc2ccn(CCc3ccccc3)c12] | ¹H NMR (300 MHz, DMSO-d$_6$) δ ppm 0.94 (t, J = 7.4 Hz, 3 H), 1.39 (dq, J = 14.9, 7.4 Hz, 2 H), 1.63 (quin, J = 7.3 Hz, 2 H), 2.90 (t, J = 7.1 Hz, 2 H), 3.46-3.55 (m, 2 H), 4.55 (t, J = 7.1 Hz, 2 H), 5.94 (d, J = 3.0 Hz, 1 H), 6.33 (br. s., 2 H), 6.97 (br. s., 1 H), 7.02-7.12 (m, 3 H), 7.16-7.29 (m, 3 H) | A, 2.42 | 310 |
| 12 | 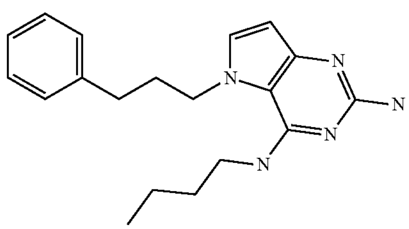 [SMILES: CCCCNc1nc(N)nc2ccn(CCCc3ccccc3)c12] | ¹H NMR (300 MHz, DMSO-d$_6$) δ ppm 0.90 (t, J = 7.3 Hz, 3 H), 1.34 (dq, J = 14.9, 7.3 Hz, 2 H), 1.57 (quin, J = 7.3 Hz, 2 H), 1.91 (quin, J = 7.5 Hz, 2 H), 2.41-2.48 (m, 2 H), 3.41-3.49 (m, 2 H), 4.29 (t, J = 7.0 Hz, 2 H), 5.57 (s, 2 H), 5.94 (d, J = 2.9 Hz, 1 H), 6.32 (t, J = 5.4 Hz, 1 H), 7.10-7.22 (m, 4 H), 7.22-7.31 (m, 2 H) | A, 2.6 | 324 |
| 13 | 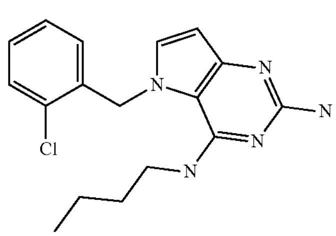 | ¹H NMR (300 MHz, CHLOROFORM-d) δ ppm 0.81 (t, J = 7.2 Hz, 3 H), 1.06 (dq, J = 14.9, 7.3 Hz, 2 H), 1.22-1.35 (m, 2 H), 3.32 (td, J = 6.7, 5.4 Hz, 2 H), 4.20 (br. s., 2 H), 4.51 (br. s., 2 H), 5.44 (s, 2 H), 6.31 (d, J = 3.2 Hz, 1 H), 6.63 (d, J = 7.4 Hz, 1 H), 7.07 (d, J = 3.0 Hz, 1 H), 7.16-7.25 (m, 1 H), 7.29-7.34 (m, 1 H), 7.47 (dd, J = 8.0, 1.2 Hz, 1 H) | A, 2.47 | 330 |

TABLE 1-continued

Compounds of formula (I) and corresponding analytical data.

| # | STRUCTURE | ¹H NMR | LC Method, Rt (min) | LC-MS Mass Found |
|---|---|---|---|---|
| 14 | 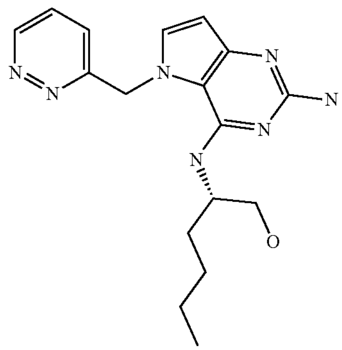 [SMILES: CCCC[C@@H](CO)Nc1nc(N)nc2ccn(Cc3cccnn3)c12] | ¹H NMR (400 MHz, CHLOROFORM-d) ppm 0.89 (t, J = 6.9 Hz, 3 H), 1.20-1.27 (m, 1 H), 1.28-1.41 (m, 4 H), 1.64 (q, J = 7.0 Hz, 2 H), 3.61 (dd, J = 11.2, 6.9 Hz, 1 H), 3.77 (dd, J = 11.0, 2.8 Hz, 1 H), 4.24 (td, J = 6.9, 2.8 Hz, 1 H), 4.57 (br. s., 2 H), 5.48-5.68 (m, 2 H), 6.21 (d, J = 3.0 Hz, 1 H), 6.74 (d, J = 6.8 Hz, 1 H), 7.10 (d, J = 3.0 Hz, 1 H), 7.35 (dd, J = 8.5, 1.3 Hz, 1 H), 7.51 (dd, J = 8.4, 4.9 Hz, 1 H), 9.16 (dd, J = 5.0, 1.3 Hz, 1 H) | B, 0.63 | 342 |
| 15 | 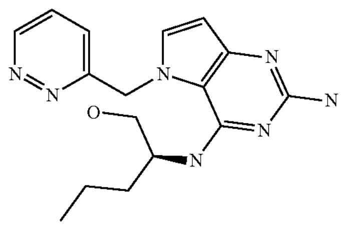 [SMILES: CCC[C@@H](CO)Nc1nc(N)nc2ccn(Cc3cccnn3)c12] | ¹H NMR (400 MHz, METHANOL-d₄) δ ppm 0.88 (t, J = 7.3 Hz, 3 H), 1.13-1.32 (m, 3 H), 1.46-1.69 (m, 3 H), 2.39 (t, J = 6.8 Hz, 1 H), 3.61 (d, J = 5.5 Hz, 2 4 H), 4.31 (dd, J = 8.8, 5.0 Hz, 1 H), 5.62-5.87 (m, 2 H), 6.13 (d, J = 3.0 Hz, 1 H), 7.39 (d, J = 3.0 Hz, 1 H), 7.46 (dd, J = 8.5, 1.8 Hz, 1 H), 7.70 (dd, J = 8.5, 5.0 Hz, 1 H), 9.14 (dd, J = 4.9, 1.6 Hz, 1 H) | B, 0.55 | 328 |
| 16 | 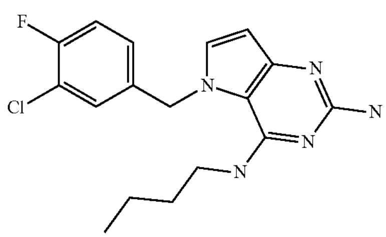 [SMILES: CCCCNc1nc(N)nc2ccn(Cc3ccc(F)c(Cl)c3)c12] | ¹H NMR (300 MHz, CHLOROFORM-d) δ ppm 0.77 (t, J = 7.2 Hz, 3 H), 1.02 (dq, J = 14.9, 7.3 Hz, 2 H), 1.15-1.29 (m, 2 H), 3.25 (td, J = 6.8, 5.4 Hz, 2 H), 4.08-4.22 (m, 1 H), 4.42 (br. s., 2 H), 5.23 (s, 2 H), 6.20 (d, J = 3.0 Hz, 1 H), 6.83 (ddd, J = 8.5, 4.3, 2.2 Hz, 1 H), 6.95 (d, J = 3.0 Hz, 1 H), 7.04-7.12 (m, 2 H) | A, 2.5 | 348 |
| 17 | 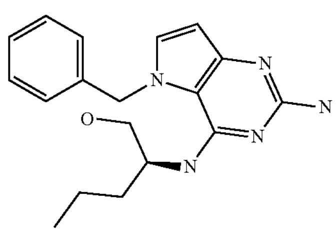 [SMILES: CCC[C@@H](CO)Nc1nc(N)nc2ccn(Cc3ccccc3)c12] | ¹H NMR (400 MHz, DMSO-d₆) δ ppm 0.69 (t, J = 7.3 Hz, 3 H), 0.80-0.93 (m, 2 H), 1.05-1.17 (m, 1 H), 1.34-1.45 (m, 1 H), 3.24 (br. s., 2 H), 4.06-4.16 6 (m, 1 H), 4.63 (br. s., 1 H), 5.03 (d, J = 8.6 Hz, 1 H), 5.24 (s, 2 H), 5.40-5.57 (m, 2 H), 5.99 (d, J = 3.1 Hz, 1 H), 6.98 (d, J = 7.0 Hz, 2 H), 7.22-7.35 (m, 3 H), 7.36 (d, J = 2.9 Hz, 1 H) | B, 0.79 | 326 |
| 18 | 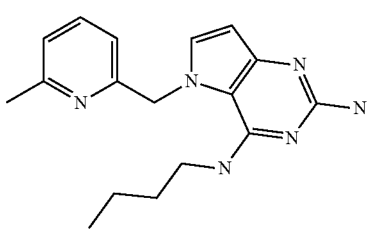 [SMILES: CCCCNc1nc(N)nc2ccn(Cc3cccc(C)n3)c12] | ¹H NMR (300 MHz, DMSO-d₆) δ ppm 0.89 (t, J = 7.4 Hz, 3 H), 1.18-1.39 (m, 2 H), 1.45-1.63 (m, 2 H), 2.50 (s, 3 H), 3.36-3.46 (m, 2 H), 5.33 (s, 2 H), 5.41 (s, 2 H), 5.96 (d, J = 2.9 Hz, 1 H), 7.03 (d, J = 7.6 Hz, 1 H), 7.23 (d, J = 7.7 Hz, 1 H), 7.28 (t, J = 5.2 Hz, 1 H), 7.40 (d, J = 3.0 Hz, 1 H), 7.71 (t, J = 7.7 Hz, 1 H) | A, 1.68 | 311 |
| 19 | 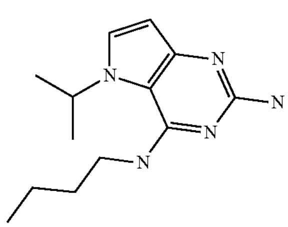 [SMILES: CCCCNc1nc(N)nc2ccn(C(C)C)c12] | ¹H NMR (300 MHz, DMSO-d₆) δ ppm 0.99 (t, J = 7.4 Hz, 3 H), 1.26-1.43 (m, 2 H), 1.45 (d, J = 6.3 Hz, 6 H), 1.67 (quin, J = 7.3 Hz, 2 H), 3.54-3.63 (m, 2 H), 4.95 (dt, J = 12.9, 6.4 Hz, 1 H), 6.18 (d, J = 3.2 Hz, 1 H), 6.73 (br. s., 2 H), 7.29 (br. s., 1 H), 7.57 (d, J = 3.2 Hz, 1 H) | A, 1.51 | 248 |

TABLE 1-continued

Compounds of formula (I) and corresponding analytical data.

| # | STRUCTURE | ¹H NMR | LC Method, Rt (min) | LC-MS Mass Found |
|---|---|---|---|---|
| 20 | 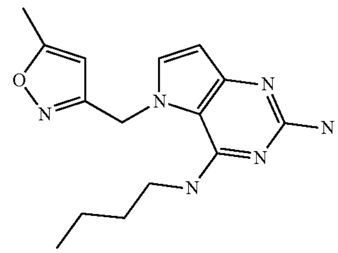 [SMILES: CCCCNc1nc(N)nc2ccn(Cc3cc(C)on3)c12] | ¹H NMR (300 MHz, DMSO-d₆) δ ppm 0.89 (t, J = 7.3 Hz, 3 H), 1.27 (dq, J = 14.9, 7.4 Hz, 2 H), 1.51 (quin, J = 7.2 Hz, 2 H), 2.32 (s, 3 H), 3.26-3.44 (m, 2 H), 5.33 (s, 2 H), 5.51 (s, 2 H), 5.83-5.87 (m, 1 H), 5.97 (d, J = 3.0 Hz, 1 H), 6.11 (t, J = 5.3 Hz, 1 H), 7.29 (d, J = 3.0 Hz, 1 H) | A, 1.45 | 301 |
| 21 | 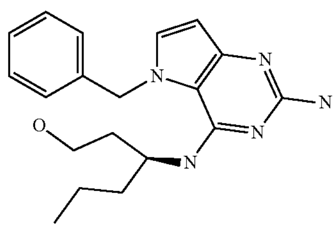 [SMILES: CCC[C@@H](CCO)Nc1nc(N)nc2ccn(Cc3ccccc3)c12] | ¹H NMR (400 MHz, DMSO-d₆) δ ppm 0.70 (t, J = 7.3 Hz, 3 H), 0.82-0.98 (m, 2 H), 1.17-1.36 (m, 2 H), 1.37-1.48 (m, 1 H), 1.51-1.63 (m, 1 H), 3.21-6 3.31 (m, 2 H), 4.17-4.29 (m, 1 H), 4.49 (br. s., 1 H), 5.24 (d, J = 8.5 Hz, 1 H), 5.30 (s, 2 H), 5.41-5.58 (m, 2 H), 6.00 (d, J = 3.0 Hz, 1 H), 6.95 (s, 1 H), 6.96 (s, 1 H), 7.20-7.27 (m, 1 H), 7.27-7.34 (m, 2 H), 7.36 (d, J = 3.0 Hz, 1 H) | B, 0.83 | 340 |
| 22 | 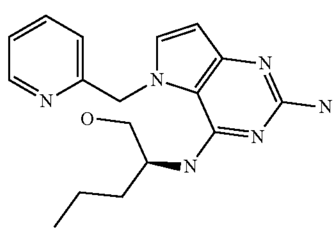 [SMILES: CCC[C@@H](CO)Nc1nc(N)nc2ccn(Cc3ccccn3)c12] | ¹H NMR (400 MHz, DMSO-d₆) δ ppm 0.87 (t, J = 7.3 Hz, 3 H), 1.15-1.32 (m, 2 H), 1.45-1.59 (m, 1 H), 1.64 (td, J = 8.0, 5.0 Hz, 1 H), 3.50-3.54 (m, 2 H), 3.72-3.79 (m, 1 H), 4.35 (td, J = 8.5, 4.8 Hz, 1 H), 5.45-5.64 (m, 2 H), 6.14 (d, J = 3.0 Hz, 1 H), 6.77 (br. s., 2 H), 7.43 (ddd, J = 7.7, 4.9, 1.0 Hz, 1 H), 7.51 (d, J = 7.8 Hz, 1 H), 7.63 (d, J = 3.0 Hz, 1 H), 7.91 (td, J = 7.7, 1.8 Hz, 1 H), 8.42 (d, J = 7.8 Hz, 1 H), 8.50-8.58 (m, 1 H) | B, 0.69 | 327 |
| 23 | 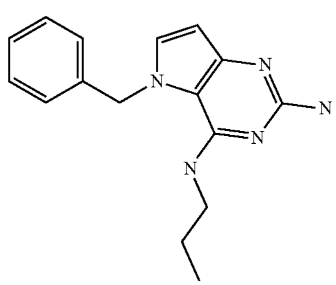 [SMILES: CCCNc1nc(N)nc2ccn(Cc3ccccc3)c12] | ¹H NMR (300 MHz, CHLOROFORM-d) δ ppm 0.67 (t, J = 7.4 Hz, 3 H), 1.25 (sxt, J = 7.3 Hz, 2 H), 3.24 (td, J = 7.0, 5.4 Hz, 2 H), 4.65 (br. s., 1 H), 5.16 (br. s., 2 H), 5.39 (s, 2 H), 6.30 (d, J = 3.0 Hz, 1 H), 7.03-7.13 (m, 3 H), 7.32-7.47 (m, 3 H) | A, 2.15 | 282 |
| 24 | 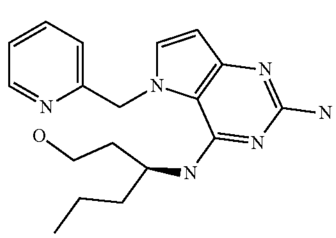 [SMILES: CCC[C@@H](CCO)Nc1nc(N)nc2ccn(Cc3ccccn3)c12] | ¹H NMR (400 MHz, DMSO-d₆) δ ppm 0.82 (t, J = 7.40 Hz, 3 H) 1.13-1.24 (m, 2 H) 1.43-1.54 (m, 2 H) 1.55-1.76 (m, 2 H) 3.38-3.46 (m, 2 H) 4.28-4.37 (m, 1 H) 4.47 (br. s., 1 H) 5.35 (s, 2 H) 5.43-5.51 (m, 2 H) 5.97 (d, J = 3.01 Hz, 1 H) 6.88 (d, J = 8.28 Hz, 1 H) 7.26 (d, J = 7.78 Hz, 1 H) 7.37 (ddd, J = 7.53, 5.02, 1.00 Hz, 1 H) 7.43 (d, J = 3.01 Hz, 1 H) 7.84 (td, J = 7.65, 1.76 Hz, 1 H) 8.53 (dt, J = 4.00, 0.80 Hz, 1 H) | B, 0.71 | 341 |

TABLE 1-continued

Compounds of formula (I) and corresponding analytical data.

| # | STRUCTURE | ¹H NMR | LC Method, Rt (min) | LC-MS Mass Found |
|---|---|---|---|---|
| 25 | 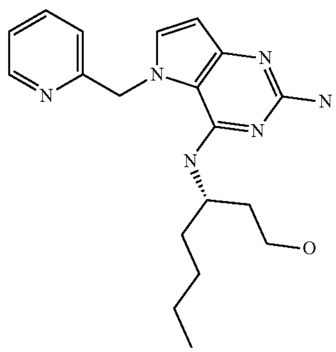 [SMILES: CCCC[C@@H](CCO)Nc1nc(N)nc2ccn(Cc3ccccn3)c12] | ¹H NMR (400 MHz, DMSO-$d_6$) δ ppm 0.74-0.85 (m, 3 H) 1.09-1.18 (m, 2 H) 1.18-1.30 (m, 2 H) 1.40-1.56 (m, 2 H) 1.56-1.65 (m, 1 H) 1.65-1.76 (m, 1 H) 3.34-3.45 (m, 2 H) 4.24-4.34 (m, 1 H) 4.47 (br. s., 1 H) 5.22 (s, 2 H) 5.39-5.53 (m, 2 H) 5.96 (d, J = 2.76 Hz, 1 H) 6.75 (d, J = 8.28 Hz, 1 H) 7.23 (d, J = 7.78 Hz, 1 H) 7.37 (ddd, J = 7.53, 4.89, 1.13 Hz, 1 H) 7.41 (d, J = 3.01 Hz, 1 H) 7.83 (td, J = 7.72, 1.88 Hz, 1 H) 8.50-8.55 (m, 1 H) | B, 0.8 | 355 |
| 26 | 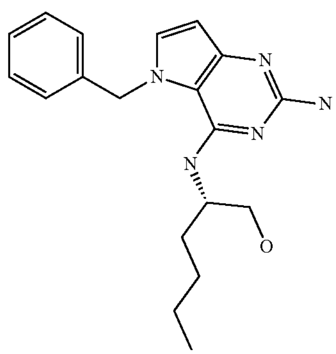 [SMILES: CCCC[C@@H](CO)Nc1nc(N)nc2ccn(Cc3ccccc3)c12] | ¹H NMR (400 MHz, DMSO-$d_6$) δ ppm 0.73 (t, J = 7.4 Hz, 3 H), 0.77-0.93 (m, 2 H), 1.01-1.19 (m, 3 H), 1.38-1.51 (m, 1 H), 3.23-3.30 (m, 2 H), 4.04-6 4.17 (m, 1 H), 4.66 (br. s., 1 H), 5.12 (d, J = 8.5 Hz, 1 H), 5.35 (s, 2 H), 5.40-5.60 (m, 2 H), 6.01 (d, J = 3.0 Hz, 1 H), 6.95-7.03 (m, 2 H), 7.22-7.35 (m, 3 H), 7.38 (d, J = 3.0 Hz, 1 H) | B, 0.86 | 340 |
| 27 | 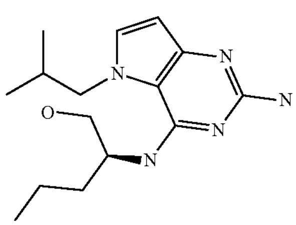 [SMILES: CCC[C@@H](CO)Nc1nc(N)nc2ccn(CC(C)C)c12] | ¹H NMR (400 MHz, DMSO-$d_6$) δ ppm 0.74 (d, J = 6.52 Hz, 3 H) 0.82 (d, J = 6.78 Hz, 3 H) 0.92 (t, J = 7.28 Hz, 3 H) 1.30-1.46 (m, 2 H) 1.50-1.69 (m, 2 H) 1.87-2.01 (m, 1 H) 3.43-3.58 (m, 2 H) 3.88 (dd, J = 14.68, 8.16 Hz, 1 H) 4.12 (dd, J = 14.56, 6.53 Hz, 1 H) 4.28 (m, J = 8.40, 3.90 Hz, 1 H) 4.79 (br. s., 1 H) 5.22 (s, 2 H) 5.41 (d, J = 8.53 Hz, 1 H) 5.89 (d, J = 3.01 Hz, 1 H) 7.15 (d, J = 3.01 Hz, 1 H) | B, 0.76 | 292 |
| 28 | 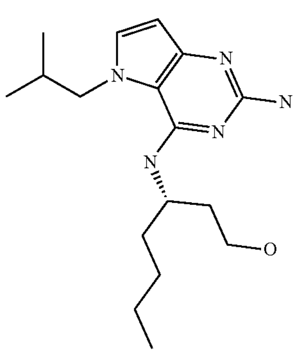 [SMILES: CCCC[C@@H](CCO)Nc1nc(N)nc2ccn(CC(C)C)c12] | ¹H NMR (400 MHz, DMSO-$d_6$) δ ppm 0.69 (d, J = 6.9 Hz, 3 H) 0.79 (d, J = 6.9 Hz, 3 H), 0.82-0.91 (m, 3 H), 1.20-1.39 (m, 4 H), 1.49-1.65 (m, 2 H), 1.66-6 1.79 (m, 2 H), 1.83-1.97 (m, 1 H), 3.43-3.58 (m, 2 H), 3.86 (dd, J = 14.5, 8.5 Hz, 1 H), 4.12 (dd, J = 14.5, 6.5 Hz, 1 H), 4.27-4.44 (m, 1 H), 4.71 (br. s., 1 H), 5.21 (s, 2 H), 5.75 (d, J = 8.5 Hz, 1 H), 5.87 (d, J = 2.8 Hz, 1 H), 7.12 (d, J = 3.2 Hz, 1 H) | B, 0.89 | 320 |

TABLE 1-continued

Compounds of formula (I) and corresponding analytical data.

| # | STRUCTURE | ¹H NMR | LC Method, Rt (min) | LC-MS Mass Found |
|---|---|---|---|---|
| 29 | 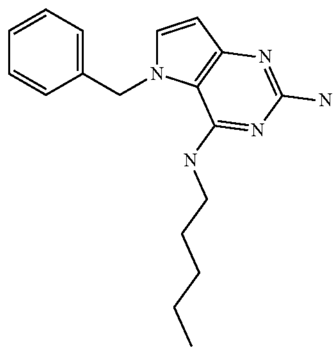 [SMILES: CCCCCNc1nc(N)nc2ccn(Cc3ccccc3)c12] | ¹H NMR (300 MHz, DMSO-$d_6$) δ ppm 0.75-0.85 (m, 3 H), 1.02 (d, J = 7.0 Hz, 2 H), 1.11-1.26 (m, 2 H), 1.34 (d, J = 7.6 Hz, 2 H), 3.28 (s, 2 H), 5.22 (s, 2 H), 5.49 (s, 2 H), 5.76 (s, 1 H), 5.98 (d, J = 3.0 Hz, 1 H), 6.97 (d, J = 6.7 Hz, 2 H), 7.17-7.35 (m, 4 H) | A, 2.47 | 310 |
| 30 | 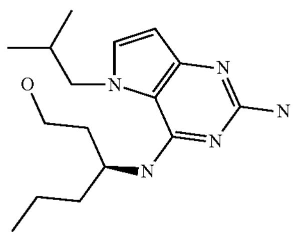 [SMILES: CCC[C@@H](CCO)Nc1nc(N)nc2ccn(CC(C)C)c12] | ¹H NMR (400 MHz, DMSO-$d_6$) δ ppm 0.76 (dd, J = 11.42, 6.65 Hz, 6 H) 0.90 (t, J = 7.28 Hz, 3 H) 1.26-1.37 (m, 2 H) 1.53-1.63 (m, 1 H) 1.63-1.73 (m, 1 H) 1.74-1.90 (m, 3 H) 3.49-3.62 (m, 2 H) 4.11-4.22 (m, 2 H) 4.55 (m, J = 6.50 Hz, 1 H) 4.79 (t, J = 4.52 Hz, 1 H) 6.16 (d, J = 3.01 Hz, 1 H) 7.24 (d, J = 8.28 Hz, 1 H) 7.33 (br. s., 2 H) 7.44 (d, J = 2.76 Hz, 1 H) 12.35 (br. s., 1 H) | B, 0.82 | 306 |
| 31 | 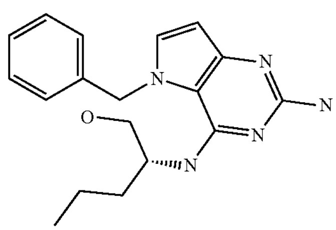 [SMILES: CCC[C@H](CO)Nc1nc(N)nc2ccn(Cc3ccccc3)c12] | ¹H NMR (300 MHz, DMSO-$d_6$) δ ppm 0.64-0.75 (m, 3 H), 0.77-0.97 (m, 2 H), 1.02-1.21 (m, 1 H), 1.30-1.50 (m, 1 H), 3.33 (d, J = 4.3 Hz, 2 H), 4.15 (dd, J = 9.2, 4.5 Hz, 1 H), 4.69 (br. s., 1 H), 5.34 (d, J = 8.5 Hz, 1 H), 5.42-5.64 (m, 2 H), 5.71 (br. s., 2 H), 6.06 (d, J = 3.0 Hz, 1 H), 6.99 (d, J = 6.6 Hz, 2 H), 7.17-7.37 (m, 3 H), 7.44 (d, J = 3.0 Hz, 1 H) | A, 2.07 | 326 |
| 32 | 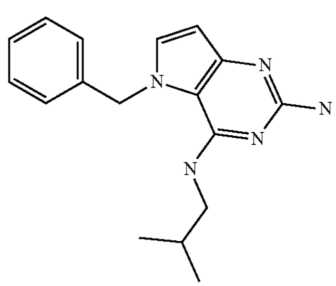 [SMILES: CC(C)CNc1nc(N)nc2ccn(Cc3ccccc3)c12] | ¹H NMR (300 MHz, CHLOROFORM-d) δ ppm 0.57 (d, J = 6.6 Hz, 6 H), 1.19 (s, 2 H), 1.33-1.52 (m, 1 H), 3.05 (dd, J = 6.8, 5.6 Hz, 2 H), 4.61-4.78 (m, 1 H), 5.32 (s, 2 H), 6.25 (d, J = 3.0 Hz, 1 H), 6.97-7.06 (m, 3 H), 7.26-7.39 (m, 3 H) | A, 2.25 | 296 |
| 33 | 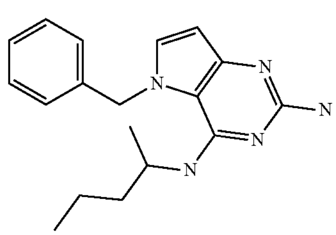 [SMILES: CCCC(C)Nc1nc(N)nc2ccn(Cc3ccccc3)c12] | ¹H NMR (300 MHz, CHLOROFORM-d) δ ppm 0.74-0.82 (m, 3 H), 0.86 (d, J = 6.5 Hz, 3 H), 0.93-1.28 (m, 4 H), 4.01-4.22 (m, 1 H), 4.39 (d, J = 7.8 Hz, 1 H), 5.05 (br. s., 2 H), 5.37 (s, 2 H), 6.29 (d, J = 3.0 Hz, 1 H), 7.02-7.13 (m, 3 H), 7.32-7.47 (m, 3 H) | A, 2.4 | 310 |

TABLE 1-continued

Compounds of formula (I) and corresponding analytical data.

| # | STRUCTURE | ¹H NMR | LC Method, Rt (min) | LC-MS Mass Found |
|---|---|---|---|---|
| 34 | 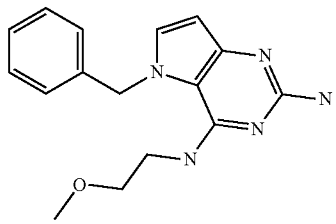 [SMILES: COCCNc1nc(N)nc2ccn(Cc3ccccc3)c12] | ¹H NMR (300 MHz, DMSO-$d_6$) δ ppm 3.24 (s, 3 H), 3.35-3.44 (m, 2 H), 3.57 (q, J = 5.6 Hz, 2 H), 5.55 (s, 2 H), 5.97 (br. s., 2 H), 6.09 (d, J = 2.9 Hz, 1 H), 6.30 (br. s., 1 H), 7.05-7.14 (m, 2 H), 7.25-7.41 (m, 3 H), 7.46 (d, J = 3.0 Hz, 1 H) | A, 1.81 | 298 |
| 35 | 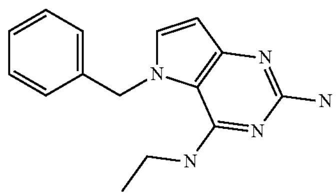 [SMILES: CCNc1nc(N)nc2ccn(Cc3ccccc3)c12] | ¹H NMR (300 MHz, DMSO-$d_6$) δ ppm 0.98 (t, J = 7.1 Hz, 3 H), 3.23-3.44 (m, 2 H), 5.43 (s, 2 H), 5.49 (s, 2 H), 5.96-6.07 (m, 2 H), 7.02 (d, J = 6.7 Hz, 2 H), 7.17-7.38 (m, 4 H) | A, 1.96 | 268 |
| 36 | 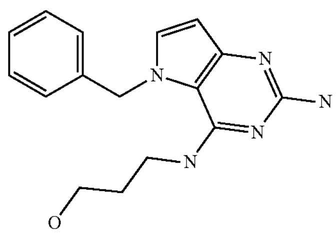 [SMILES: Nc1nc(NCCCO)c2c(ccn2Cc2ccccc2)n1] | ¹H NMR (300 MHz, DMSO-$d_6$) δ ppm 1.56 (quin, J = 6.4 Hz, 2 H), 3.24-3.44 (m, 4 H), 4.45-4.58 (m, 1 H), 5.49 (s, 2 H), 5.61 (br. s., 2 H), 6.03 (d, J = 2.9 Hz, 1 H), 6.19 (t, J = 5.0 Hz, 1 H), 6.96-7.04 (m, 2 H), 7.19-7.34 (m, 3 H), 7.37 (d, J = 3.0 Hz, 1 H) | A, 1.61 | 298 |
| 37 | 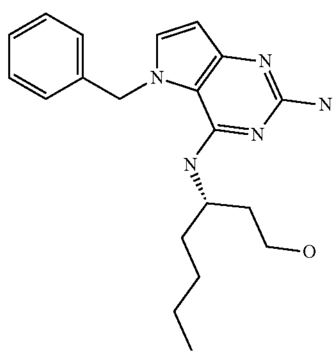 [SMILES: CCCC[C@@H](CCO)Nc1nc(N)nc2ccn(Cc3ccccc3)c12] | ¹H NMR (400 MHz, DMSO-$d_6$) δ ppm 0.74 (t, J = 7.3 Hz, 3 H), 0.80-0.95 (m, 2 H), 1.02-1.17 (m, 2 H), 1.19-1.48 (m, 3 H), 1.51-1.64 (m, 1 H), 3.21-6 3.27 (m, 2 H), 4.20 (tt, J = 8.5, 4.0 Hz, 1 H), 4.49 (br. s., 1 H), 5.18-5.32 (m, 3 H), 5.40-5.59 (m, 2 H), 6.00 (d, J = 3.1 Hz, 1 H), 6.96 (d, J = 7.3 Hz, 2 H), 7.19-7.39 (m, 4 H) | B, 0.92 | 354 |
| 38 | 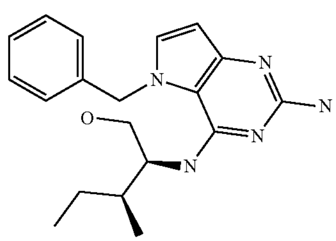 [SMILES: CC[C@H](C)[C@@H](CO)Nc1nc(N)nc2ccn(Cc3ccccc3)c12] | ¹H NMR (400 MHz, DMSO-$d_6$) δ ppm 0.62 (d, J = 4.0 Hz, 3 H), 0.65 (d, J = 6.8 Hz, 3 H), 0.95-1.04 (m, 1 H), 1.35-1.47 (m, 1 H), 1.89 (s, 3 H), 3.35-3.46 6 (m, 2 H), 3.98-4.07 (m, 1 H), 5.06 (d, J = 8.8 Hz, 1 H), 5.42-5.60 (m, 4 H), 6.01 (d, J = 2.9 Hz, 1 H), 6.94-6.98 (m, 2 H), 7.23-7.28 (m, 1 H), 7.29-7.35 (m, 2 H), 7.38 (d, J = 3.1 Hz, 1 H) | B, 0.84 | 340 |
| 39 | 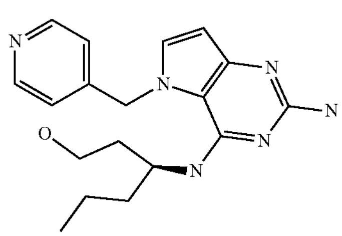 [SMILES: CCC[C@@H](CCO)Nc1nc(N)nc2ccn(Cc3ccncc3)c12] | ¹H NMR (400 MHz, DMSO-$d_6$) δ ppm 0.63-0.73 (m, 3 H), 0.75-0.95 (m, 2 H), 1.18-1.36 (m, 2 H), 1.48 (dd, J = 8.9, 4.7 Hz, 1 H), 1.53-1.64 (m, 1 H), 3.20 6-3.28 (m, 2 H), 4.13-4.29 (m, 1 H), 4.50 (t, J = 5.4 Hz, 1 H), 5.28 (s, 2 H), 5.37 (d, J = 8.6 Hz, 1 H), 5.47-5.69 (m, 2 H), 6.04 (d, J = 3.1 Hz, 1 H), 6.81 (d, J = 5.9 Hz, 2 H), 7.36 (d, J = 2.9 Hz, 1 H), 8.40-8.50 (m, 2 H) | B, 0.57 | 341 |

TABLE 1-continued

Compounds of formula (I) and corresponding analytical data.

| # | STRUCTURE | ¹H NMR | LC Method, Rt (min) | LC-MS Mass Found |
|---|---|---|---|---|
| 40 | 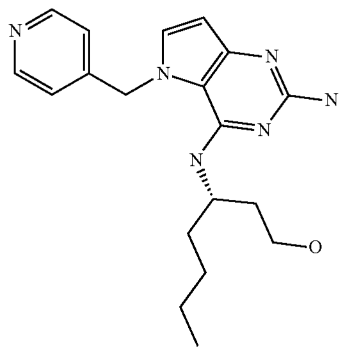 [SMILES: CCCC[C@@H](CCO)Nc1nc(N)nc2ccn(Cc3ccncc3)c12] | ¹H NMR (400 MHz, CHLOROFORM-d) δ ppm 0.76-0.82 (m, 3 H), 0.87-1.00 (m, 2 H), 1.02-1.22 (m, 5 H), 1.28-1.41 (m, 1 H), 1.72-1.85 (m, 1 H), 3.34 (td, J = 11.6, 2.4 Hz, 1 H), 3.44-3.55 (m, 1 H), 4.12-4.27 (m, 2 H), 4.58 (br. s., 2 H), 5.26-5.45 (m, 2 H), 6.27 (d, J = 3.1 Hz, 1 H), 6.89-6.97 (m, 2 H), 7.06 (d, J = 3.1 Hz, 1 H), 8.55-8.62 (m, 2 H) | B, 0.64 | 355 |
| 41 | 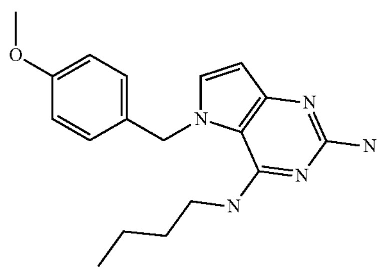 [SMILES: CCCCNc1nc(N)nc2ccn(Cc3ccc(OC)cc3)c12] | ¹H NMR (300 MHz, CHLOROFORM-d) δ ppm 0.65-0.80 (m, 3 H) 0.89-1.07 (m, 2 H) 1.11-1.22 (m, 2 H) 3.14-3.28 (m, 2 H) 3.73 (s, 3 H) 4.76 (br. s., 1 H) 5.08-5.24 (m, 2 H) 5.27 (s, 2 H) 6.18 (d, J = 3.02 Hz, 1 H) 6.84 (d, J = 8.66 Hz, 2 H) 6.94 (d, J = 8.66 Hz, 2 H) 7.00 (d, J = 3.02 Hz, 1 H) | A, 2.26 | 326 |
| 42 | 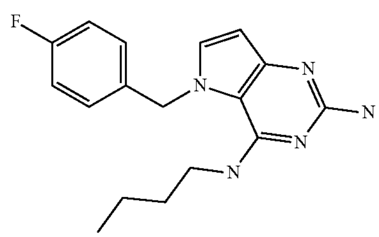 [SMILES: CCCCNc1nc(N)nc2ccn(Cc3ccc(F)cc3)c12] | ¹H NMR (300 MHz, DMSO-d₆) δ ppm 0.70-0.87 (m, 3 H) 0.97-1.14 (m, 2 H) 1.31-1.46 (m, 2 H) 3.36-3.40 (m, 2 H) 5.52 (s, 2 H) 5.62 (s, 2 H) 6.05 (d, J = 3.02 Hz, 1 H) 6.11 (s, 1 H) 6.90-7.09 (m, 2 H) 7.09-7.24 (m, 2 H) 7.39 (d, J = 3.02 Hz, 1 H) | A, 2.23 | 314 |
| 43 | 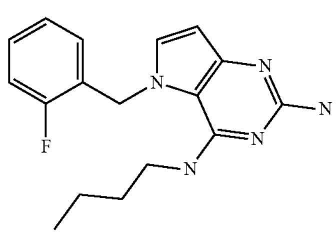 [SMILES: CCCCNc1nc(N)nc2ccn(Cc3ccccc3F)c12] | ¹H NMR (300 MHz, CHLOROFORM-d) δ ppm 0.67-0.85 (m, 3 H) 0.94-1.13 (m, 2 H) 1.16-1.33 (m, 2 H) 3.16-3.43 (m, 2 H) 4.33 (br. s., 1 H) 4.54 (br. s., 2 H) 5.32 (s, 2 H) 6.21 (d, J = 3.02 Hz, 1 H) 6.67 (t, J = 7.35 Hz, 1 H) 6.99 (d, J = 3.02 Hz, 1 H) 7.00-7.13 (m, 2 H) 7.22-7.32 (m, 1 H) | A, 2.27 | 314 |
| 44 | 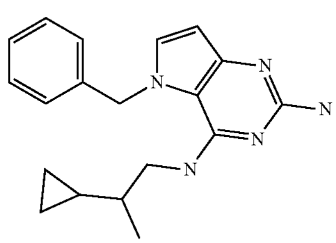 [SMILES: CC(CNc1nc(N)nc2ccn(Cc3ccccc3)c12)C1CC1] | ¹H NMR (300 MHz, CHLOROFORM-d) δ ppm −0.07-0.07 (m, 2 H) 0.21-0.43 (m, 3 H) 0.66-0.75 (m, 3 H) 0.76-0.95 (m, 1 H) 3.22-3.51 (m, 2 H) 4.86 (br. s., 1 H) 5.15 (br. s., 2 H) 5.41 (s, 2 H) 6.33 (d, J = 3.02 Hz, 1 H) 7.07 (br. s., 1 H) 7.10 (s, 2 H) 7.35-7.47 (m, 3 H) | A, 2.46 | 322 |

TABLE 1-continued

Compounds of formula (I) and corresponding analytical data.

| # | STRUCTURE | ¹H NMR | LC Method, Rt (min) | LC-MS Mass Found |
|---|---|---|---|---|
| 45 | 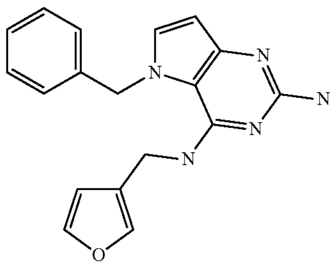 [SMILES: Nc1nc(NCc2ccoc2)c2c(ccn2Cc2ccccc2)n1] | ¹H NMR (300 MHz, CHLOROFORM-d) δ ppm 4.21 (d, J = 4.95 Hz, 2 H) 4.48 (br. s., 1 H) 4.70 (br. s., 2 H) 5.18-5.30 (m, 2 H) 5.97 (s, 1 H) 6.22 (d, J = 3.02 Hz, 1 H) 6.90 (dd, J = 6.53, 2.13 Hz, 2 H) 6.98 (s, 1 H) 7.02 (d, J = 3.02 Hz, 1 H) 7.20-7.29 (m, 4 H) | A, 2.09 | 320 |
| 46 | 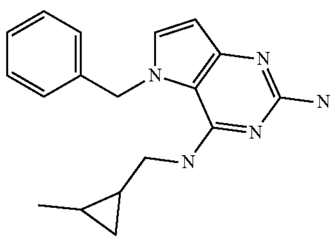 [SMILES: CC1CC1CNc1nc(N)nc2ccn(Cc3ccccc3)c12] | ¹H NMR (300 MHz, CHLOROFORM-d) δ ppm −0.12-0.09 (m, 2 H) 0.24-0.46 (m, 2 H) 0.89 (d, J = 5.64 Hz, 3 H) 2.84-3.06 (m, 1 H) 3.08-3.25 (m, 1 H) 4.51 (br. s., 1 H) 4.63 (br. s., 2 H) 5.34 (s, 2 H) 6.23 (d, J = 3.02 Hz, 1 H) 7.03 (d, J = 2.75 Hz, 2 H) 7.06 (br. s., 1 H) 7.27-7.40 (m, 3 H) | A, 2.26 | 308 |
| 47 | 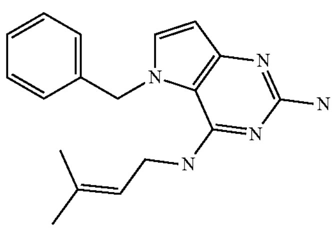 [SMILES: CC(C)=CCNc1nc(N)nc2ccn(Cc3ccccc3)c12] | ¹H NMR (300 MHz, CHLOROFORM-d) δ ppm 1.42 (s, 3 H) 1.58 (s, 3 H) 3.66-3.80 (m, 2 H) 4.42 (br. s., 1 H) 4.71-4.88 (m, 1 H) 5.02 (br. s., 2 H) 5.28 (s, 2 H) 6.21 (d, J = 3.02 Hz, 1 H) 6.96-7.01 (m, 2 H) 7.02 (s, 1 H) 7.24-7.41 (m, 3 H) | A, 2.32 | 308 |
| 48 | 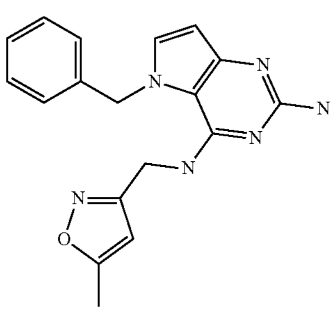 [SMILES: Cc1cc(CNc2nc(N)nc3ccn(Cc4ccccc4)c23)no1] | ¹H NMR (300 MHz, CHLOROFORM-d) δ ppm 2.28 (s, 3 H) 4.46 (d, J = 5.22 Hz, 2 H) 4.65 (br. s., 2 H) 4.92 (br. s., 1 H) 5.30 (s, 2 H) 5.54 (s, 1 H) 6.22 (d, J = 3.02 Hz, 1 H) 6.89-7.01 (m, 2 H) 7.03 (d, J = 3.16 Hz, 1 H) 7.21-7.27 (m, 3 H) | A, 1.97 | 335 |
| 49 | 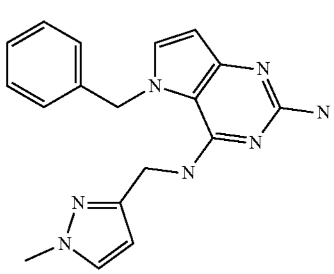 [SMILES: Cn1ccc(CNc2nc(N)nc3ccn(Cc4ccccc4)c23)n1] | ¹H NMR (300 MHz, CHLOROFORM-d) δ ppm 3.79 (s, 3 H) 4.44 (d, J = 4.67 Hz, 2 H) 5.33 (s, 2 H) 5.60 (br. s., 1 H) 5.84 (d, J = 2.06 Hz, 1 H) 6.28 (d, J = 3.02 Hz, 1 H) 6.43 (br. s., 2 H) 6.96 (dd, J = 6.53, 2.82 Hz, 2 H) 7.02 (d, J = 3.02 Hz, 1 H) 7.18 (d, J = 2.20 Hz, 1 H) 7.21-7.28 (m, 3 H) | A, 1.83 | 334 |

TABLE 1-continued

Compounds of formula (I) and corresponding analytical data.

| # | STRUCTURE | ¹H NMR | LC Method, Rt (min) | LC-MS Mass Found |
|---|---|---|---|---|
| 50 | 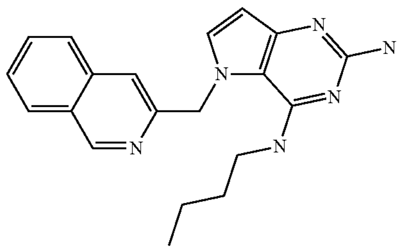 [SMILES: CCCCNc1nc(N)nc2ccn(Cc3cc4ccccc4cn3)c12] | ¹H NMR (300 MHz, CHLOROFORM-d) δ ppm 0.83-0.91 (m, 3 H) 1.30-1.41 (m, 2 H) 1.57-1.67 (m, 2 H) 3.44-3.60 (m, 2 H) 5.41 (s, 2 H) 6.22 (br. s, 2 H) 6.21 (d, J = 3.02 Hz, 1 H) 7.05 (d, J = 3.02 Hz, 1 H) 7.55-7.65 (m, 2 H) 7.70 (t, J = 7.49 Hz, 1 H) 7.76-7.86 (m, 1 H) 7.95 (d, J = 8.11 Hz, 1 H) 8.23 (br. s., 1 H) 9.12 (s, 1 H) | A, 2.52 | 347 |
| 51 | 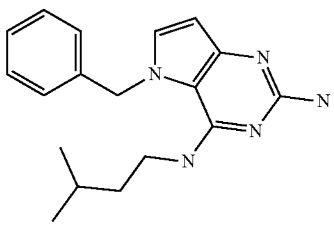 [SMILES: CC(C)CCNc1nc(N)nc2ccn(Cc3ccccc3)c12] | ¹H NMR (300 MHz, CHLOROFORM-d) δ ppm 0.71 (d, J = 6.32 Hz, 6 H) 0.74-0.86 (m, 1 H) 0.93-1.05 (m, 2 H) 3.15-3.28 (m, 2 H) 4.59 (br. s., 1 H) 5.29 (s, 2 H) 6.18 (br. s., 2 H) 6.27 (d, J = 3.02 Hz, 1 H) 6.97-7.01 (m, 2 H) 7.02 (br. s., 1 H) 7.26-7.42 (m, 3 H) | A, 2.45 | 310 |
| 52 | 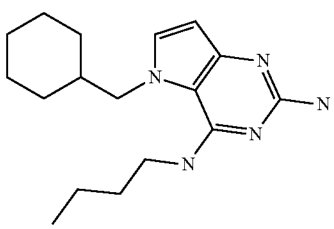 [SMILES: CCCCNc1nc(N)nc2ccn(CC3CCCCC3)c12] | ¹H NMR (300 MHz, CHLOROFORM-d) δ ppm 0.89-0.95 (m, 1 H) 0.92 (t, J = 7.35 Hz, 3 H) 1.00-1.26 (m, 4 H) 1.31-1.44 (m, 2 H) 1.47-1.75 (m, 8 H) 3.43-3.59 (m, 2 H) 3.83 (d, J = 7.29 Hz, 2 H) 4.73 (br. s., 1 H) 4.93 (br. s., 2 H) 6.08 (d, J = 3.02 Hz, 1 H) 6.81 (d, J = 3.02 Hz, 1 H) | A, 2.68 | 302 |
| 53 | 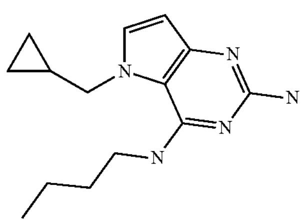 [SMILES: CCCCNc1nc(N)nc2ccn(CC3CC3)c12] | ¹H NMR (300 MHz, CHLOROFORM-d) δ ppm 0.19-0.35 (m, 2 H) 0.50-0.65 (m, 2 H) 0.69-0.86 (m, 1 H) 0.91 (t, J = 7.29 Hz, 3 H) 1.33-1.45 (m, 2 H) 1.49-1.65 (m, 2 H) 3.50 (td, J = 7.11, 5.57 Hz, 2 H) 4.00 (d, J = 6.05 Hz, 2 H) 4.68 (br. s., 2 H) 4.80 (br. s., 1 H) 6.10 (d, J = 3.02 Hz, 1 H) 6.93 (d, J = 3.02 Hz, 1 H) | A, 2.19 | 260 |
| 54 | 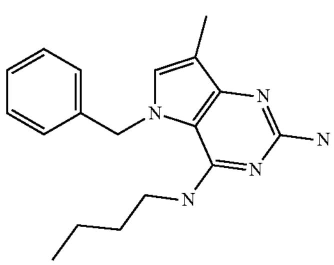 [SMILES: CCCCNc1nc(N)nc2c(C)cn(Cc3ccccc3)c12] | ¹H NMR (300 MHz, CHLOROFORM-d) δ ppm 0.69-0.74 (m, 3 H) 0.89-0.97 (m, 2 H) 1.07-1.13 (m, 2 H) 2.21 (s, 3 H) 3.14-3.27 (m, 2 H) 4.66 (br. s., 1 H) 5.24 (s, 2 H) 6.40 (br. s., 2 H) 6.78-6.86 (m, 1 H) 6.92-7.05 (m, 2 H) 7.26-7.41 (m, 3 H) | A, 2.46 | 310 |
| 55 | 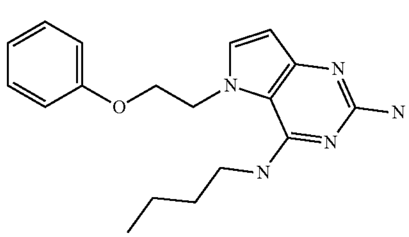 | ¹H NMR (300 MHz, CHLOROFORM-d) δ ppm 0.96 (t, J = 7.29 Hz, 3 H) 1.38-1.57 (m, 2 H) 1.58-1.75 (m, 2 H) 3.54-3.64 (m, 2 H) 4.29-4.42 (m, 2 H) 4.56 (t, J = 4.88 Hz, 2 H) 4.59 (br. s., 2 H) 5.96 (br. s., 1 H) 6.26 (d, J = 3.02 Hz, 1 H) 6.79-6.91 (m, 2 H) 6.99 (d, J = 3.02 Hz, 1 H) 7.00-7.08 (m, 1 H) 7.28-7.34 (m, 2 H) | A, 2.47 | 326 |

TABLE 1-continued

Compounds of formula (I) and corresponding analytical data.

| # | STRUCTURE | ¹H NMR | LC Method, Rt (min) | LC-MS Mass Found |
|---|---|---|---|---|
| 56 | 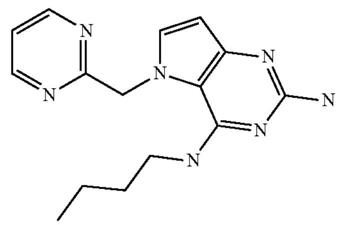 [SMILES: CCCCNc1nc(N)nc2ccn(Cc3ncccn3)c12] | ¹H NMR (300 MHz, CHLOROFORM-d) δ ppm 0.93 (t, J = 7.35 Hz, 3 H) 1.36-1.52 (m, 2 H) 1.52-1.71 (m, 2 H) 3.46-3.65 (m, 2 H) 5.35 (s, 2 H) 6.06 (br. s., 2 H) 6.22 (d, J = 3.02 Hz, 1 H) 7.13 (d, J = 3.02 Hz, 1 H) 7.31 (t, J = 5.02 Hz, 1 H) 8.02 (br. s., 1 H) 8.71 (d, J = 5.09 Hz, 2 H) | C, 4.68 | 298 |
| 57 | 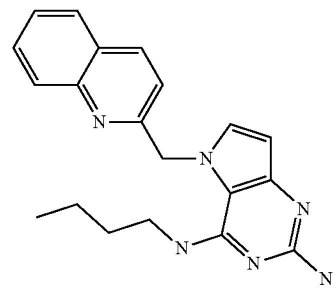 [SMILES: CCCCNc1nc(N)nc2ccn(Cc3ccc4ccccc4n3)c12] | ¹H NMR (300 MHz, CHLOROFORM-d) δ ppm 0.79 (t, J = 7.29 Hz, 3 H) 1.22 (dd, J = 15.19, 7.49 Hz, 2 H) 1.39-1.56 (m, 2 H) 3.29-3.45 (m, 2 H) 4.63 (br. s., 2 H) 5.44 (s, 2 H) 6.17 (d, J = 3.02 Hz, 1 H) 7.00 (br. s., 1 H) 7.09 (d, J = 3.02 Hz, 1 H) 7.18-7.28 (m, 1 H) 7.42-7.57 (m, 1 H) 7.62-7.83 (m, 2 H) 7.97 (d, J = 8.39 Hz, 1 H) 8.10 (d, J = 8.39 Hz, 1 H) | A, 2.49 | 347 |
| 58 | 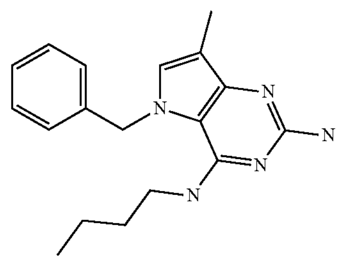 [SMILES: CCCCNc1nc(N)nc2c(C)cn(Cc3ccccc3)c12] | ¹H NMR (300 MHz, CHLOROFORM-d) δ ppm 0.69-0.74 (m, 3 H) 0.89-0.97 (m, 2 H) 1.07-1.13 (m, 2 H) 2.21 (s, 3 H) 3.14-3.27 (m, 2 H) 4.66 (br. s., 1 H) 5.24 (s, 2 H) 6.40 (br. s., 2 H) 6.78-6.86 (m, 1 H) 6.92-7.05 (m, 2 H) 7.26-7.41 (m, 3 H) | A, 2.56 | 310 |
| 59 | 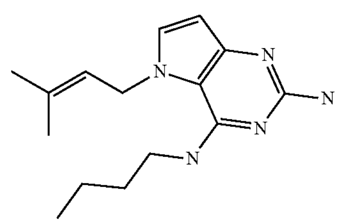 [SMILES: CCCCNc1nc(N)nc2ccn(CC=C(C)C)c12] | ¹H NMR (300 MHz, CHLOROFORM-d) δ ppm 0.89 (t, J = 7.22 Hz, 3 H) 1.26-1.40 (m, 2 H) 1.41-1.57 (m, 2 H) 1.70-1.77 (m, 6 H) 3.32-3.51 (m, 2 H) 4.47 (br. s., 2 H) 4.66 (d, J = 5.64 Hz, 2 H) 4.98 (br. s., 1 H) 5.28-5.41 (m, 1 H) 6.06 (d, J = 3.02 Hz, 1 H) 6.84 (d, J = 3.02 Hz, 1 H) | A, 2.37 | 274 |
| 60 | 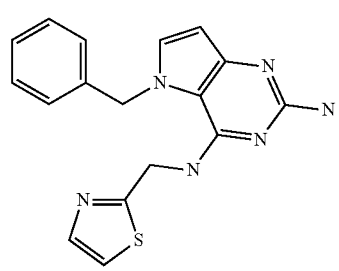 [SMILES: Nc1nc(NCc2nccs2)c2c(ccn2Cc2ccccc2)n1] | ¹H NMR (300 MHz, CHLOROFORM-d) δ ppm 4.47 (br. s., 2 H) 4.74 (d, J = 5.50 Hz, 2 H) 5.15 (t, J = 5.16 Hz, 1 H) 5.32 (s, 2 H) 6.22 (d, J = 3.02 Hz, 1 H) 6.94-7.01 (m, 2 H) 7.03 (d, J = 3.02 Hz, 1 H) 7.14 (d, J = 3.30 Hz, 1 H) 7.17-7.27 (m, 3 H) 7.58 (d, J = 3.30 Hz, 1 H) | A, 1.86 | 337 |
| 61 | 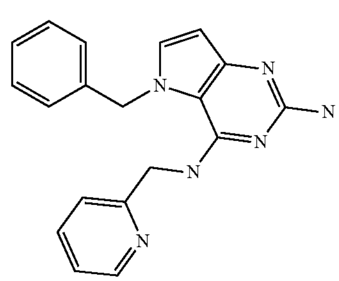 [SMILES: Nc1nc(NCc2ccccn2)c2c(ccn2Cc2ccccc2)n1] | ¹H NMR (300 MHz, chloroform-d) δ ppm 4.38 (d, J = 5.36 Hz, 2 H) 4.49 (br. s., 2 H) 4.54-4.66 (m, 1 H) 5.26 (s, 2 H) 6.21 (d, J = 3.02 Hz, 1 H) 6.84-6.92 (m, 2 H) 7.00-7.08 (m, 2 H) 7.08-7.14 (m, 1 H) 7.14-7.23 (m, 3 H) 8.15-8.23 (m, 1 H) 8.36-8.44 (m, 1 H) | A, 1.28 | 331 |

TABLE 1-continued

Compounds of formula (I) and corresponding analytical data.

| # | STRUCTURE | ¹H NMR | LC Method, Rt (min) | LC-MS Mass Found |
|---|---|---|---|---|
| 62 | 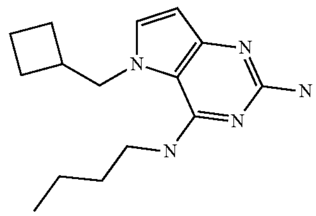 [SMILES: CCCCNc1nc(N)nc2ccn(CC3CCC3)c12] | ¹H NMR (300 MHz, CHLOROFORM-d) δ ppm 0.92 (t, J = 7.35 Hz, 3 H) 1.37 (dq, J = 14.90, 7.31 Hz, 2 H) 1.52-1.63 (m, 2 H) 1.65-1.78 (m, 2 H) 1.78-1.90 (m, 2 H) 1.91-2.05 (m, 2 H) 2.47-2.83 (m, 2 H) 3.41-3.54 (m, 1 H) 4.05 (d, J = 7.01 Hz, 2 H) 4.73 (br. s., 1 H) 4.89 (br. s., 2 H) 6.09 (d, J = 3.02 Hz, 1 H) 6.85 (d, J = 3.02 Hz, 1 H) | A, 2.33 | 274 |
| 63 | 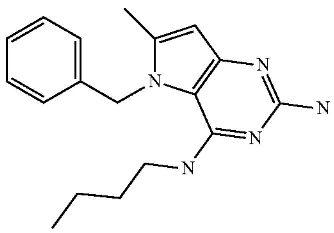 [SMILES: CCCCNc1nc(N)nc2cc(C)n(Cc3ccccc3)c12] | ¹H NMR (400 MHz, DMSO-d₆) δ ppm 0.75 (t, J = 7.3 Hz, 3 H), 0.98-1.06 (m, 2 H), 1.32 (quin, J = 7.2 Hz, 2 H), 2.27 (s, 3 H), 3.24-3.28 (m, 2 H), 5.25 (br. s., 6 2 H), 5.44 (s, 2 H), 5.75 (t, J = 5.4 Hz, 1 H), 5.87 (s, 1 H), 6.87 (d, J = 7.0 Hz, 2 H), 7.19-7.25 (m, 1 H), 7.25-7.32 (m, 2 H) | B, 0.97 | 310 |
| 64 | 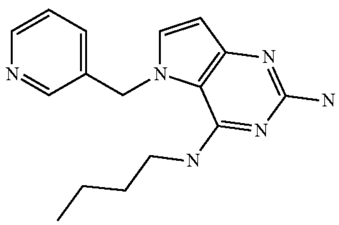 [SMILES: CCCCNc1nc(N)nc2ccn(Cc3cccnc3)c12] | ¹H NMR (300 MHz, CHLOROFORM-d) δ ppm 0.75 (t, J = 7.30 Hz, 3 H) 0.89-1.06 (m, 2 H) 1.11-1.29 (m, 2 H) 3.24-3.34 (m, 2 H) 5.16 (br. s., 1 H) 5.47 (s, 2 H) 5.96 (br. s., 2 H) 6.21 (d, J = 3.02 Hz, 1 H) 7.00 (d, J = 3.02 Hz, 1 H) 7.18-7.26 (m, 2 H) 8.33-8.42 (m, 1 H) 8.49-8.59 (m, 1 H) | C, 4.21 | 297 |
| 65 | 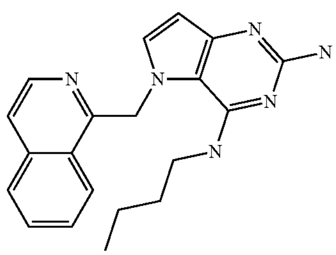 [SMILES: CCCCNc1nc(N)nc2ccn(Cc3nccc4ccccc34)c12] | ¹H NMR (300 MHz, CHLOROFORM-d) δ ppm 0.95 (t, J = 7.29 Hz, 3 H) 1.30-1.54 (m, 2 H) 1.70 (quin, J = 7.32 Hz, 2 H) 3.50 (td, J = 7.11, 5.02 Hz, 2 H) 4.76 (br. s., 2 H) 5.77 (s, 2 H) 6.14 (d, J = 3.02 Hz, 1 H) 7.17-7.21 (m, 1 H) 7.62-7.73 (m, 3 H) 7.80-7.87 (m, 1 H) 8.25-8.34 (m, 1 H) 8.37 (d, J = 5.77 Hz, 1 H) 8.59 (br. s., 1 H) | A, 2.61 | 347 |
| 66 | 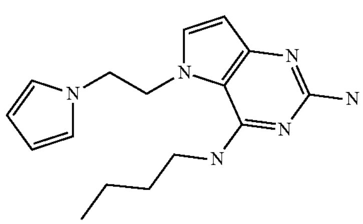 [SMILES: CCCCNc1nc(N)nc2ccn(CCn3cccc3)c12] | ¹H NMR (300 MHz, CHLOROFORM-d) δ ppm 0.90 (t, J = 7.22 Hz, 3 H) 1.25-1.40 (m, 2 H) 1.43-1.54 (m, 2 H) 3.29 (td, J = 7.11, 5.57 Hz, 2 H) 3.87 (br. s., 1 H) 4.07-4.22 (m, 2 H) 4.23-4.31 (m, 2 H) 4.61 (br. s., 2 H) 6.06 (t, J = 2.06 Hz, 2 H) 6.14 (d, J = 3.02 Hz, 1 H) 6.29 (t, J = 2.06 Hz, 2 H) 6.70 (d, J = 3.02 Hz, 1 H) | A, 2.15 | 299 |
| 67 | 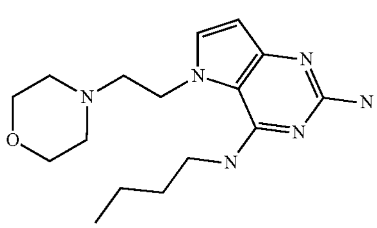 [SMILES: CCCCNc1nc(N)nc2ccn(CCN3CCOCC3)c12] | ¹H NMR (300 MHz, CHLOROFORM-d) δ ppm 0.92 (t, J = 7.29 Hz, 3 H) 1.26-1.47 (m, 2 H) 1.49-1.67 (m, 2 H) 2.34-2.46 (m, 4 H) 2.72-2.81 (m, 2 H) 3.52 (td, J = 7.22, 5.77 Hz, 2 H) 3.57-3.64 (m, 4 H) 4.17-4.24 (m, 2 H) 5.75-6.08 (m, 2 H) 6.19 (d, J = 3.02 Hz, 1 H) 6.87 (d, J = 3.02 Hz, 1 H) 8.19 (br. s., 1 H) | A, 1.16 | 319 |

TABLE 1-continued

Compounds of formula (I) and corresponding analytical data.

| # | STRUCTURE | ¹H NMR | LC Method, Rt (min) | LC-MS Mass Found |
|---|---|---|---|---|
| 68 | 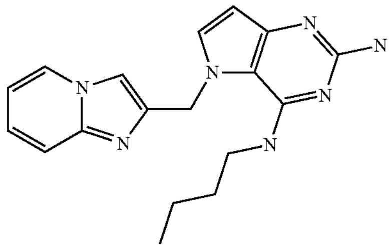 [SMILES: CCCCNc1nc(N)nc2ccn(Cc3cn4ccccc4n3)c12] | ¹H NMR (300 MHz, CHLOROFORM-d) δ ppm 0.90 (t, J = 7.29 Hz, 3 H) 1.30-1.46 (m, 2 H) 1.58-1.73 (m, 2 H) 3.53 (td, J = 7.01, 5.22 Hz, 2 H) 5.32 (s, 2 H) 5.78-6.11 (m, 2 H) 6.18 (d, J = 3.02 Hz, 1 H) 6.78-6.84 (m, 1 H) 7.01 (d, J = 3.02 Hz, 1 H) 7.18-7.24 (m, 2 H) 7.46 (d, J = 9.07 Hz, 1 H) 7.54 (s, 1 H) 8.06 (d, J = 6.74 Hz, 1 H) 8.92-9.11 (m, 0 H) | A, 1.76 | 336 |
| 69 | 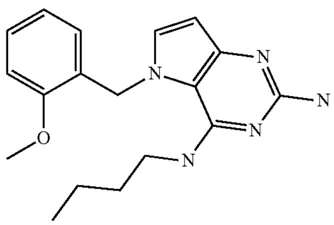 [SMILES: CCCCNc1nc(N)nc2ccn(Cc3ccccc3OC)c12] | ¹H NMR (300 MHz, CHLOROFORM-d) δ ppm 0.74 (t, J = 7.30 Hz, 3 H) 0.90-1.12 (m, 2 H) 1.14-1.27 (m, 2 H) 3.20-3.28 (m, 2 H) 3.85 (s, 3 H) 4.55 (br. s., 3 H) 5.22-5.27 (m, 2 H) 6.18 (d, J = 3.02 Hz, 1 H) 6.62 (d, J = 7.01 Hz, 1 H) 6.82 (t, J = 7.56 Hz, 1 H) 6.87 (d, J = 8.25 Hz, 1 H) 6.98 (d, J = 3.02 Hz, 1 H) 7.20-7.27 (m, 1 H) | A, 2.44 | 326 |
| 70 | 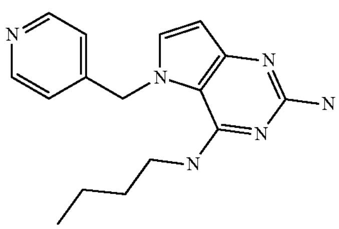 [SMILES: CCCCNc1nc(N)nc2ccn(Cc3ccncc3)c12] | ¹H NMR (300 MHz, CHLOROFORM-d) δ ppm 0.74 (t, J = 7.40 Hz, 3 H) 0.88-1.09 (m, 2 H) 1.10-1.25 (m, 2 H) 3.18-3.28 (m, 2 H) 4.21 (br. s., 1 H) 4.66 (br. s., 2 H) 5.23 (s, 2 H) 6.22 (d, J = 3.16 Hz, 2 H) 6.89 (d, J = 5.77 Hz, 1 H) 6.96 (d, J = 3.02 Hz, 1 H) 8.51-8.59 (m, 2 H) | A, 1.14 | 297 |
| 71 | 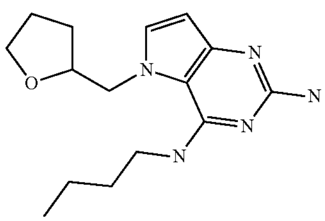 [SMILES: CCCCNc1nc(N)nc2ccn(CC3CCCO3)c12] | ¹H NMR (300 MHz, CHLOROFORM-d) δ ppm 0.91 (t, J = 7.29 Hz, 3 H) 1.27-1.45 (m, 2 H) 1.49-1.67 (m, 3 H) 1.85 (d, J = 7.01 Hz, 1 H) 1.91-2.12 (m, 2 H) 3.39-3.49 (m, 2 H) 3.72 (t, J = 6.67 Hz, 2 H) 4.02 (dd, J = 15.81, 4.54 Hz, 1 H) 4.12-4.23 (m, 1 H) 4.42 (dd, J = 15.74, 1.72 Hz, 1 H) 5.76-6.13 (m, 2 H) 6.23 (d, J = 3.02 Hz, 1 H) 6.82 (d, J = 3.02 Hz, 1 H) 7.61-7.79 (m, 1 H) | A, 2.17 | 290 |
| 72 | 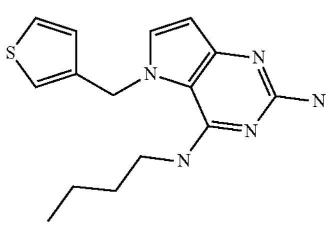 [SMILES: CCCCNc1nc(N)nc2ccn(Cc3ccsc3)c12] | ¹H NMR (300 MHz, CHLOROFORM-d) δ ppm 0.78 (t, J = 7.30 Hz, 3 H) 1.00-1.15 (m, 2 H) 1.16-1.29 (m, 2 H) 3.19-3.31 (m, 2 H) 4.46 (br. s., 1 H) 4.59 (br. s., 2 H) 5.27 (s, 2 H) 6.17 (d, J = 3.02 Hz, 1 H) 6.82 (dd, J = 4.95, 1.10 Hz, 1 H) 6.91-6.95 (m, 1 H) 6.97 (d, J = 3.02 Hz, 1 H) 7.34 (dd, J = 4.95, 2.89 Hz, 1 H) | A, 2.27 | 302 |
| 73 | 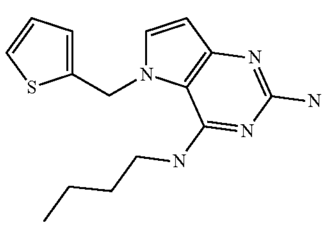 [SMILES: CCCCNc1nc(N)nc2ccn(Cc3cccs3)c12] | ¹H NMR (300 MHz, CHLOROFORM-d) δ ppm 0.79 (t, J = 7.20 Hz, 3 H) 1.02-1.33 (m, 4 H) 1.90-2.08 (m, 2 H) 3.27 (td, J = 6.80, 5.36 Hz, 2 H) 4.58 (br. s., 2 H) 5.41 (s, 2 H) 6.19 (d, J = 3.02 Hz, 1 H) 6.67-6.84 (m, 1 H) 6.93 (dd, J = 5.02, 3.51 Hz, 1 H) 6.98 (d, J = 3.16 Hz, 1 H) 7.26 (dd, J = 5.09, 0.96 Hz, 1 H) | A, 2.28 | 302 |

TABLE 1-continued

Compounds of formula (I) and corresponding analytical data.

| # | STRUCTURE | ¹H NMR | LC Method, Rt (min) | LC-MS Mass Found |
|---|---|---|---|---|
| 74 | 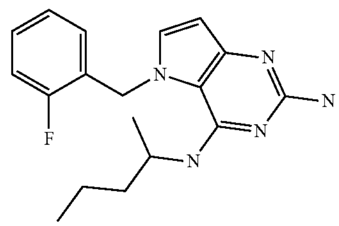 | ¹H NMR (300 MHz, CHLOROFORM-d) δ ppm 0.73 (t, J = 7.20 Hz, 3 H) 0.89 (d, J = 6.46 Hz, 3 H) 0.93-1.07 (m, 2 H) 1.07-1.29 (m, 2 H) 4.05-4.20 (m, 1 H) 4.43 (d, J = 7.84 Hz, 1 H) 5.16-5.29 (m, 2 H) 5.33 (s, 2 H) 6.25 (d, J = 3.02 Hz, 1 H) 6.68 (t, J = 7.49 Hz, 1 H) 7.02-7.13 (m, 3 H) 7.23-7.34 (m, 1 H) | A, 2.53 | 328 |
| 75 | 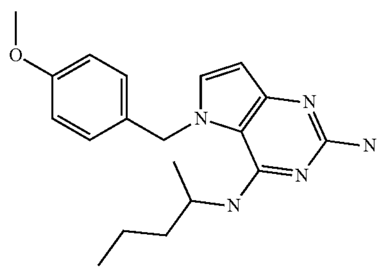 [SMILES: CCCC(C)Nc1nc(N)nc2ccn(Cc3ccc(OC)cc3)c12] | ¹H NMR (300 MHz, CHLOROFORM-d) δ ppm 0.72 (t, J = 7.00 Hz, 3 H) 0.83 (d, J = 6.46 Hz, 3 H) 0.86-1.07 (m, 2 H) 1.08-1.22 (m, 2 H) 3.74 (s, 3 H) 4.07 (s, 1 H) 4.57-4.62 (m, 1 H) 5.23 (s, 2 H) 5.30-5.55 (m, 2 H) 6.24 (d, J = 3.02 Hz, 1 H) 6.82-6.89 (m, 2 H) 6.90-6.97 (m, 2 H) 7.02 (d, J = 3.02 Hz, 1 H) | A, 2.58 | 340 |
| 76 | 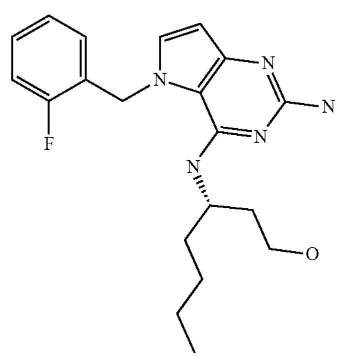 [SMILES: CCCC[C@@H](CCO)Nc1nc(N)nc2ccn(Cc3ccccc3F)c12] | ¹H NMR (300 MHz, DMSO-d₆) δ ppm 0.68 (t, J = 7.20 Hz, 1 H) 0.81-0.95 (m, 2 H) 0.96-1.14 (m, 2 H) 1.16-1.36 (m, 2 H) 1.36-1.62 (m, 2 H) 3.21-3.28 (m, 2 H) 4.09-4.25 (m, 1 H) 4.39-4.48 (m, 1 H) 5.15-5.26 (m, 2 H) 5.32-5.39 (m, 1 H) 5.40-5.50 (m, 1 H) 5.55-5.65 (m, 1 H) 5.96 (d, J = 2.90 Hz, 1 H) 6.34-6.44 (m, 1 H) 6.97-7.05 (m, 1 H) 7.10-7.30 (m, 3 H) | A, 2.34 | 372 |
| 77 | 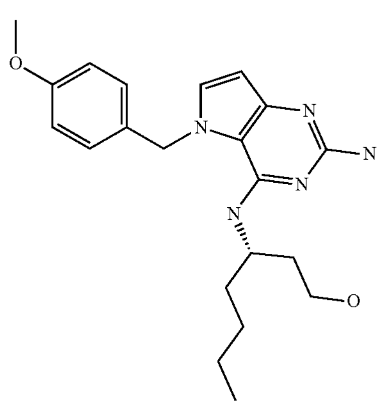 [SMILES: CCCC[C@@H](CCO)Nc1nc(N)nc2ccn(Cc3ccc(OC)cc3)c12] | ¹H NMR (300 MHz, CHLOROFORM-d) δ ppm 0.73 (t, J = 7.20 Hz, 3 H) 0.80-1.00 (m, 4 H) 1.00-1.33 (m, 2 H) 1.47-1.83 (m, 3 H) 3.15-3.26 (m, 1 H) 3.32-3.43 (m, 1 H) 3.72 (s, 3 H) 4.01-4.14 (m, 1 H) 4.22 (d, J = 8.25 Hz, 1 H) 4.40 (br. s., 2 H) 5.16-5.29 (m, 2 H) 6.18 (d, J = 3.02 Hz, 1 H) 6.80-6.95 (m, 4 H) 7.03 (d, J = 3.02 Hz, 1 H) | A, 2.34 | 384 |

TABLE 1-continued

Compounds of formula (I) and corresponding analytical data.

| # | STRUCTURE | ¹H NMR | LC Method, Rt (min) | LC-MS Mass Found |
|---|---|---|---|---|
| 78 | 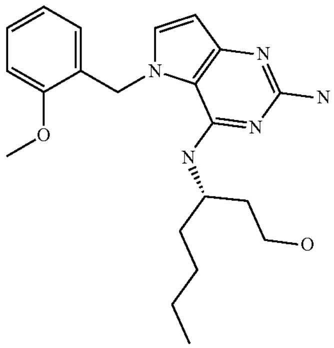 [SMILES: CCCC[C@@H](CCO)Nc1nc(N)nc2ccn(Cc3ccccc3OC)c12] | ¹H NMR (300 MHz, CDCl₃) δ 7.31 (t, J = 7.9 Hz, 1 H), 7.12 (d, J = 3.0 Hz, 1 H), 6.95 (d, J = 8.5 Hz, 1 H), 6.89 (d, J = 7.6 Hz, 1 H), 6.63 (d, J = 6.9 Hz, 1 H), 6.29 (d, J = 3.0 Hz, 1 H), 5.33 (d, J = 6.0 Hz, 2 H), 5.02 (s, 2 H), 4.60 (s, 1 H), 4.20 (s, 1 H), 3.92 (s, 3 H), 3.50-3.35 (m, 1 H), 3.24 (td, J = 11.6, 2.7 Hz, 1 H), 1.86-1.69 (m, 2 H), 1.44-1.29 (m, 1 H), 1.29-0.92 (m, 6 H), 0.81 (t, J = 7.2 Hz, 3 H). | A, 2.42 | 384 |
| 79 | 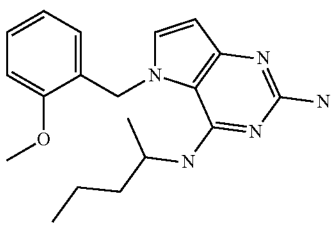 [SMILES: CCCC(C)Nc1nc(N)nc2ccn(Cc3ccccc3OC)c12] | ¹H NMR (300 MHz, CDCl₃) δ 7.34 (t, J = 7.8 Hz, 1 H), 7.10 (d, J = 3.0 Hz, 1 H), 6.97 (d, J = 8.5 Hz, 1 H), 6.91 (d, J = 7.4 Hz, 1 H), 6.65 (d, J = 7.4 Hz, 1 H), 6.31 (d, J = 3.0 Hz, 1 H), 5.33 (s, 2 H), 4.76 (d, J = 7.2 Hz, 1 H), 4.18 (dt, J = 14.2, 6.9 Hz, 1 H), 3.93 (s, 3 H), 1.24-0.95 (m, 6 H), 0.91 (d, J = 6.5 Hz, 3 H), 0.79 (t, J = 7.0 Hz, 3 H). | A, 2.60 | 340 |
| 80 | 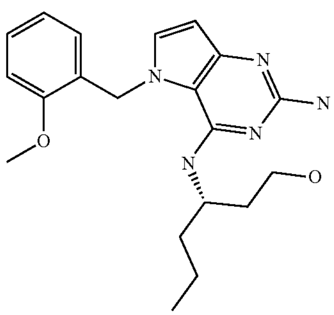 [SMILES: CCC[C@@H](CCO)Nc1nc(N)nc2ccn(Cc3ccccc3OC)c12] | ¹H NMR (300 MHz, CDCl₃) δ 7.24 (t, J = 7.8 Hz, 1 H), 7.05 (d, J = 3.0 Hz, 1 H), 6.88 (d, J = 8.3 Hz, 1 H), 6.83 (t, J = 7.8 Hz, 1 H), 6.56 (d, J = 7.3 Hz, 1 H), 6.21 (d, J = 3.0 Hz, 1 H), 5.26 (2d, J = 6.0 Hz, 2 H), 4.90 (s, 2 H), 4.52 (d, J = 8.3 Hz, 1 H), 4.17 (dd, J = 9.1, 6.4 Hz, 1 H), 3.86 (s, 3 H), 3.36 (ddd, J = 11.8, 5.0, 2.7 Hz, 1 H), 3.17 (td, J = 11.5, 2.7 Hz, 1 H), 1.77-1.60 (m, 1 H), 1.37-1.13 (m, 2 H), 1.09-0.75 (m, 4 H), 0.71 (t, J = 7.0 Hz, 3 H). | A, 2.25 | 370 |
| 81 | 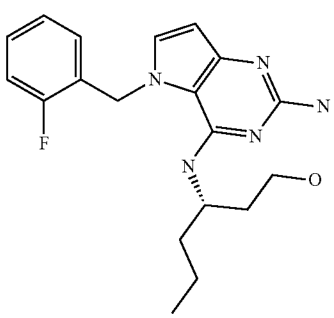 [SMILES: CCC[C@@H](CCO)Nc1nc(N)nc2ccn(Cc3ccccc3F)c12] | ¹H NMR (300 MHz, CDCl₃) δ 7.27 (dd, J = 13.6, 6.2 Hz, 1 H), 7.09 (d, J = 10.1 Hz, 1 H), 7.05 (d, J = 3.1 Hz, 1 H), 7.02 (d, J = 7.7 Hz, 1 H), 6.63 (t, J = 7.2 Hz, 1 H), 6.24 (d, J = 3.0 Hz, 1 H), 5.42-5.25 (m, 2 H), 4.78 (s, 2 H), 4.43 (s, 1 H), 4.20 (s, 1 H), 3.48-3.36 (m, 1 H), 3.25 (td, J = 11.6, 2.5 Hz, 1 H), 1.82-1.65 (m, 2 H), 1.39-0.86 (m, 5 H), 0.71 (t, J = 7.1 Hz, 3 H). | A, 2.19 | 358 |
| 82 | 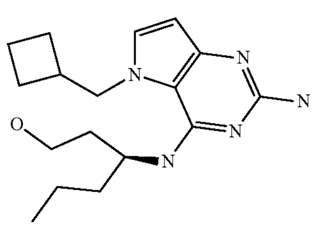 [SMILES: CCC[C@@H](CCO)Nc1nc(N)nc2ccn(CC3CCC3)c12] | ¹H NMR (300 MHz, CDCl₃) δ 6.92 (d, J = 3.0 Hz, 1 H), 6.16 (J = 3.0 Hz, 1 H), 5.85 (s, 1 H), 5.51 (s, 2 H), 4.60-4.39 (m, 1 H), 4.24-4.04 (m, 2 H), 3.81 (d, J = 6.6 Hz, 2 H), 2.71 (dt, J = 14.9, 7.5 Hz, 1 H), 2.15-1.32 (m, 13 H), 0.97 (t, J = 7.3 Hz, 3 H). | A, 2.22 | 318 |

TABLE 1-continued

Compounds of formula (I) and corresponding analytical data.

| # | STRUCTURE | ¹H NMR | LC Method, Rt (min) | LC-MS Mass Found |
|---|---|---|---|---|
| 83 | 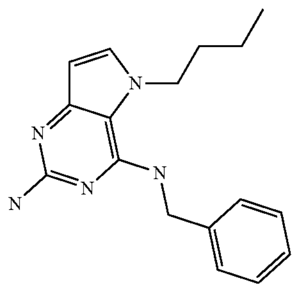 [SMILES: CCCCn1ccc2nc(N)nc(NCc3ccccc3)c21] | ¹H NMR (300 MHz, CDCl₃) δ 7.44-7.28 (m, 5 H), 6.93 (d, J = 3.0 Hz, 1 H), 6.17 (d, J = 3.0 Hz, 4.95 (s, 1 H), 4.83 (s, 2 H), 4.78 (d, J = 5.2 Hz, 2 H), 4.03 (t, J = 7.2 Hz, 2 H), 1.85-1.59 (m, 2 H), 1.35-1.10 (m, 2 H), 0.84 (t, J = 7.3 Hz, 3 H). | A, 2.55 | 296 |
| 84 | 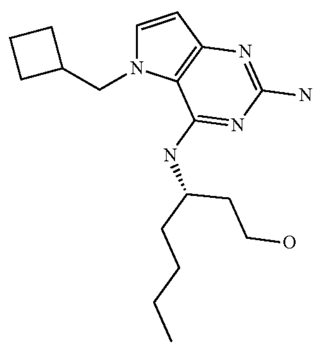 [SMILES: CCCC[C@@H](CCO)Nc1nc(N)nc2ccn(CC3CCC3)c12] | ¹H NMR (300 MHz, CDCl₃) δ 6.94 (d, J = 3.0 Hz, 1 H), 6.17 (d, J = 3.0 Hz, 1 H), 5.08 (s, 2 H), 4.46 (s, 1 H), 4.27-3.99 (m, 2 H), 3.72 (d, J = 6.9 Hz, 2 H), 8.12--0.50 (m, 60 H), 2.71 (dd, J = 14.9, 7.4 Hz, 1 H), 2.13-1.31 (m, 16 H), 0.92 (t, J = 6.8 Hz, 3 H). | A, 2.65 | 332 |
| 85 | 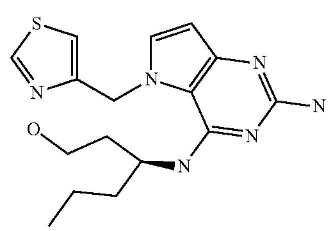 [SMILES: CCC[C@@H](CCO)Nc1nc(N)nc2ccn(Cc3cscn3)c12] | ¹H NMR (300 MHz, CDCl₃) δ 8.75 (d, J = 1.9 Hz, 1 H), 7.19 (s, J = 1.9 Hz, 1 H), 7.02 (d, J = 3.0 Hz, 2 H), 6.19 (d, J = 3.0 Hz, 1 H), 5.36 (s, 2 H), 5.22-4.88 (m, 2 H), 4.37 (s, 2 H), 3.48 (dd, J = 23.1, 14.8 Hz, 3 H), 2.03-1.83 (m, 2 H), 1.81-1.05 (m, 5 H), 0.82 (dt, J = 19.4, 7.1 Hz, 3 H). | A, 1.35 | 347 |
| 86 | 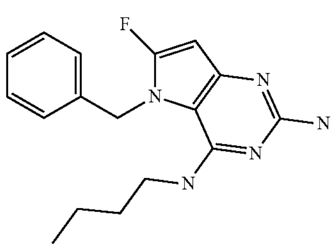 [SMILES: CCCCNc1nc(N)nc2cc(F)n(Cc3ccccc3)c12] | ¹H NMR (300 MHz, CDCl₃) δ 7.48-7.28 (m, 3 H), 7.15 (d, J = 6.8 Hz, 2 H), 5.72 (d, J = 3.3 Hz, 1 H), 5.25 (s, 2 H), 4.44 (s, 2 H), 4.16 (s, 1 H), 3.23 (dd, J = 12.0, 6.8 Hz, 2 H), 1.18 (dd, J = 14.4, 7.1 Hz, 2 H), 1.03 (dd, J = 15.0, 7.1 Hz, 2 H), 0.79 (t, J = 7.1 Hz, 3 H). | A, 2.58 | 314 |
| 87 | 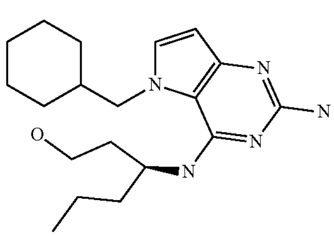 [SMILES: CCC[C@@H](CCO)Nc1nc(N)nc2ccn(CC3CCCCC3)c12] | ¹H NMR (300 MHz, CDCl₃) δ 6.88 (d, J = 3.0 Hz, 1 H), 6.13 (d, J = 2.9 Hz, 1 H), 5.60 (s, 1 H), 5.46 (s, 2 H), 4.57-4.45 (m, 1 H), 4.00 (dd, J = 15.0, 6.2 Hz, 1 H), 3.89-3.69 (m, 3 H), 2.10-1.91 (m, 2 H), 1.85-1.06 (m, 16 H), 0.95 (dd, J = 15.9, 8.6 Hz, 3 H). | A, 1.89 | 346 |

TABLE 1-continued

Compounds of formula (I) and corresponding analytical data.

| # | STRUCTURE | ¹H NMR | LC Method, Rt (min) | LC-MS Mass Found |
|---|---|---|---|---|
| 88 | 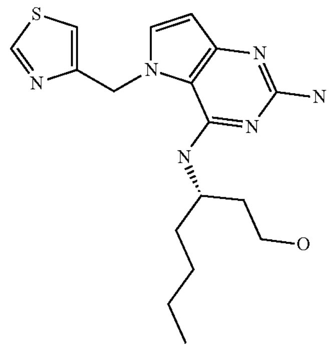 [SMILES: CCCC[C@@H](CCO)Nc1nc(N)nc2ccn(Cc3cscn3)c12] | ¹H NMR (300 MHz, CDCl₃) δ 8.79 (d, J = 1.9 Hz, 1 H), 7.19 (d, J = 1.6 Hz, 1 H), 7.07 (s, 1 H), 6.25 (d, J = 8.1 Hz, 1 H), 6.22 (d, J = 3.0 Hz, 1 H), 5.43 (d, J = 1.3 Hz, 2 H), 4.42 (s, 2 H), 4.34 (ddd, J = 11.0, 5.5, 2.9 Hz, 1 H), 3.57 (dd, J = 11.8, 2.6 Hz, 1 H), 3.44 (td, J = 11.7, 2.4 Hz, 2 H), 2.03-1.87 (m, 2 H), 1.70-1.45 (m, 2 H), 1.41-1.18 (m, 4 H), 0.87 (t, J = 6.5 Hz, 3 H). | A, 1.51 | 361 |
| 89 | 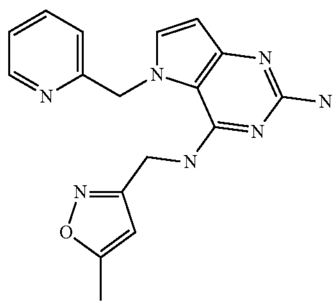 [SMILES: Cc1cc(CNc2nc(N)nc3ccn(Cc4ccccn4)c23)no1] | ¹H NMR (300 MHz, CDCl₃) δ 9.55 (s, 1H), 8.34 (d, J = 4.5 Hz, 1 H), 7.70 (td, J = 7.7, 1.7 Hz, 1 H), 7.30 (d, J = 7.8 Hz, 1 H), 7.23 (dd, J = 7.0, 5.1 Hz, 1 H), 7.04 (d, J = 3.0 Hz, 1 H), 6.21 (d, J = 3.0 Hz, 1 H), 5.92 (s, 3 H), 5.25 (s, 2 H), 4.75 (d, J = 5.5 Hz, 2 H), 2.32 (s, 3 H). | A, 1.25 | 336 |
| 90 | 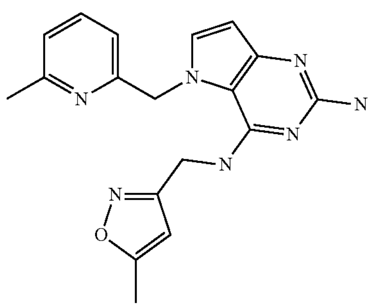 [SMILES: Cc1cccc(Cn2ccc3nc(N)nc(NCc4cc(C)on4)c32)n1] | ¹H NMR (300 MHz, CDCl₃) δ 9.39 (s, 1 H), 7.63 (t, J = 7.7 Hz, 1 H), 7.17 (s, 1 H), 7.14 (d, J = 5.5 Hz, 1 H), 7.10 (d, J = 3.2 Hz, 1 H), 6.24 (d, J = 3.0 Hz, 1 H), 6.01 (s, 1 H), 5.33 (s, 2 H), 5.27 (s, 2 H), 4.83 (d, J = 5.6 Hz, 2 H), 2.39 (s, 3 H), 2.38 (s, 3 H). | A, 1.37 | 350 |
| 91 | 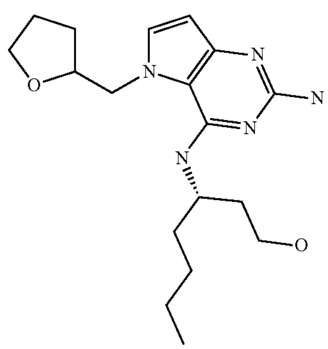 [SMILES: CCCC[C@@H](CCO)Nc1nc(N)nc2ccn(CC3CCCO3)c12] | ¹H NMR (300 MHz, CDCl₃) δ 6.90 (d, J = 3.0 Hz, 1 H), 6.26 (d, J = 3.0 Hz, 1 H), 5.49 (s, 1 H), 5.34 (d, J = 23.9 Hz, 2 H), 4.55-4.31 (m, 2 H), 4.23 (s, 1 H), 4.09 (dd, J = 15.8, 4.2 Hz, 1 H), 3.85-3.49 (m, 4 H), 2.15-1.81 (m, 6 H), 1.75-1.54 (m, 4 H), 1.54-1.30 (m, 3 H), 0.89 (dd, J = 14.3, 7.3 Hz, 3 H). | A, 2.22 | 348 |
| 92 | 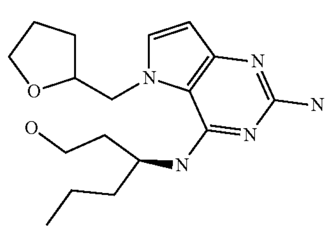 [SMILES: CCC[C@@H](CCO)Nc1nc(N)nc2ccn(CC3CCCO3)c12] | ¹H NMR (300 MHz, CDCl₃) δ 6.70 (d, J = 2.9 Hz, 1 H), 6.06 (d, J = 3.0 Hz, 1 H), 5.43 (s, 1 H), 5.31 (s, 2 H), 4.26 (t, J = 12.8 Hz, 2 H), 4.03 (s, 1 H), 3.89 (dd, J = 15.8, 4.3 Hz, 1 H), 3.69-3.24 (m, 4 H), 2.09-1.61 (m, 4 H), 1.60-1.33 (m, 4 H), 1.31-1.09 (m, 3 H), 0.74 (t, J = 7.2 Hz, 3 H). | A, 2.00 | 334 |

TABLE 1-continued

Compounds of formula (I) and corresponding analytical data.

| # | STRUCTURE | ¹H NMR | LC Method, Rt (min) | LC-MS Mass Found |
|---|---|---|---|---|
| 93 | 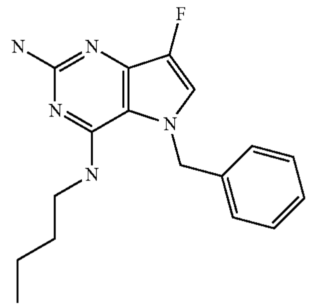 [SMILES: CCCCNc1nc(N)nc2c(F)cn(Cc3ccccc3)c12] | ¹H NMR (300 MHz, CDCl$_3$) δ 7.37 (t, J = 7.4 Hz, 3 H), 7.08 (d, J = 6.6 Hz, 2 H), 6.90 (d, J = 2.7 Hz, 1 H), 5.25 (s, 2 H), 4.53 (s, 2 H), 4.35 (s, 1 H), 3.25 (dd, J = 12.1, 6.8 Hz, 2 H), 1.32-1.13 (m, 2 H), 1.04 (dq, J = 13.9, 7.1 Hz, 2 H), 0.79 (t, J = 7.2 Hz, 3 H). | A, 2.40 | 314 |
| 94 | 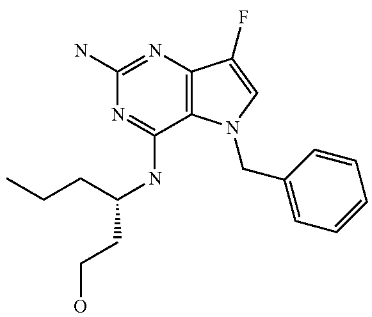 [SMILES: CCC[C@@H](CCO)Nc1nc(N)nc2c(F)cn(Cc3ccccc3)c12] | ¹H NMR (300 MHz, CDCl$_3$) δ 7.38 (q, J = 6.2 Hz, 3 H), 7.07 (d, J = 6.5 Hz, 2 H), 6.97 (d, J = 2.7 Hz, 1 H), 5.26 (d, J = 2.4 Hz, 2 H), 4.52 (s, 2 H), 4.20 (d, J = 11.6 Hz, 1 H), 3.42 (d, J = 11.7 Hz, 1 H), 3.22 (td, J = 11.7, 2.4 Hz, 2 H), 1.85-1.66 (m, 2 H), 1.24 (d, J = 7.1 Hz, 2 H), 0.95 (ddd, J = 24.8, 13.8, 9.0 Hz, 3 H), 0.75 (t, J = 6.8 Hz, 3 H). | A, 2.24 | 358 |
| 95 | 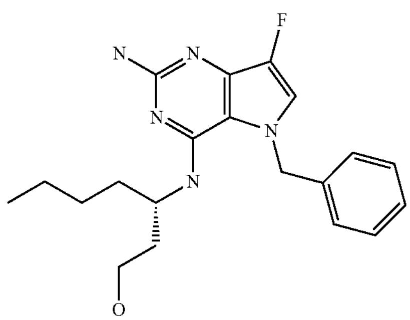 [SMILES: CCCC[C@@H](CCO)Nc1nc(N)nc2c(F)cn(Cc3ccccc3)c12] | ¹H NMR (300 MHz, CDCl$_3$) δ 7.46-7.31 (m, 3 H), 7.07 (d, J = 6.5 Hz, 2 H), 6.97 (d, J = 2.7 Hz, 1 H), 5.26 (d, J = 3.3 Hz, 2 H), 4.55 (s, 2 H), 4.32-4.02 (m, 1 H), 3.53-3.33 (m, 1 H), 3.22 (td, J = 11.7, 2.5 Hz, 2 H), 1.74 (ddd, J = 14.3, 8.6, 4.1 Hz, 2 H), 1.38-1.08 (m, 3 H), 0.93 (ddd, J = 13.8, 11.7, 4.3 Hz, 4 H), 0.80 (t, J = 7.2 Hz, 3 H). | A, 2.44 | 372 |
| 96 | 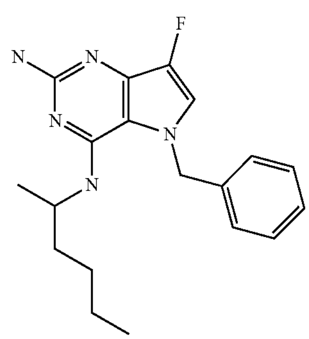 [SMILES: CCCCC(C)Nc1nc(N)nc2c(F)cn(Cc3ccccc3)c12] | ¹H NMR (300 MHz, CDCl$_3$) δ 7.49-7.30 (m, 3 H), 7.08 (d, J = 6.3 Hz, 2 H), 6.91 (d, J = 2.7 Hz, 1 H), 5.24 (s, 2 H), 4.51 (s, 2 H), 4.28-3.96 (m, 1 H), 1.08 (dddd, J = 18.0, 16.8, 13.6, 10.8 Hz, 7 H), 0.85 (d, J = 6.4 Hz, 3 H), 0.77 (dd, J = 9.4, 4.5 Hz, 3 H). | A, 2.55 | 328 |
| 97 | 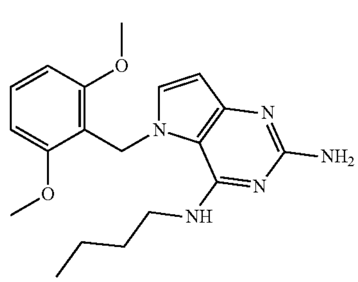 [SMILES: CCCCNc1nc(N)nc2ccn(Cc3c(OC)cccc3OC)c12] | ¹H NMR (300 MHz, DMSO-d$_6$) δ ppm 0.94 (t, J = 7.4 Hz, 3 H), 1.29-1.47 (m, 2 H), 1.61 (t, J = 7.1 Hz, 2 H), 3.46 (q, J = 6.7 Hz, 2 H), 3.80 (s, 6 H), 5.17 (s, 2 H), 5.31 (s, 2 H), 5.80 (d, J = 2.9 Hz, 1 H), 6.33 (t, J = 5.4 Hz, 1 H), 6.66-6.83 (m, 3 H), 7.38 (t, J = 8.5 Hz, 1 H) | A, 2.79 | 356 |

TABLE 1-continued

Compounds of formula (I) and corresponding analytical data.

| # | STRUCTURE | ¹H NMR | LC Method, Rt (min) | LC-MS Mass Found |
|---|---|---|---|---|
| 98 | 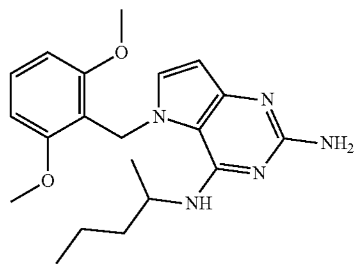 [SMILES: CCCC(C)Nc1nc(N)nc2ccn(Cc3c(OC)cccc3OC)c12] | ¹H NMR (300 MHz, DMSO-d₆) δ ppm 0.91 (t, J = 7.29 Hz, 3 H) 1.14-1.43 (m, 5 H) 1.46-1.72 (m, 2 H) 3.79 (s, 6 H) 4.41-4.60 (m, 1 H) 5.32-5.49 (m, 2 H) 6.02 (d, J = 3.02 Hz, 1 H) 6.72-6.88 (m, 5 H) 6.92 (d, J = 3.02 Hz, 1 H) 7.40 (t, J = 8.39 Hz, 1 H) | A, 2.97 | 370 |
| 99 | 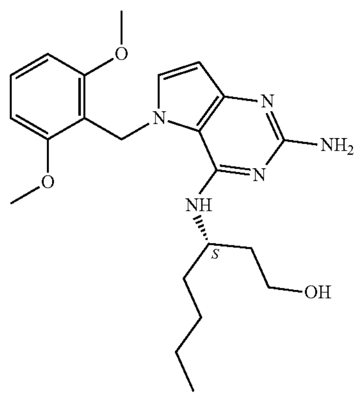 | ¹H NMR (300 MHz, DMSO-d₆) δ ppm 0.79-0.93 (m, 3 H) 1.18-1.39 (m, 4 H) 1.49-1.86 (m, 4 H) 3.41-3.54 (m, 2 H) 3.78 (s, 6 H) 4.30-4.48 (m, 1 H) 4.56-4.70 (m, 1 H) 5.10-5.24 (m, 2 H) 5.32 (s, 2 H) 5.78-5.83 (m, 1 H) 5.85-5.93 (m, 1 H) 6.76 (s, 3 H) 7.30-7.44 (m, 1 H) | A, 2.70 | 414 |
| 100 | 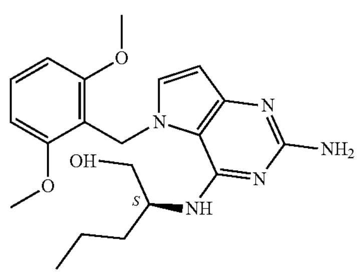 | ¹H NMR (300 MHz, DMSO-d₆) δ ppm 0.74-1.01 (m, 3 H) 1.19-1.44 (m, 2 H) 1.46-1.74 (m, 2 H) 3.45-3.58 (m, 2 H) 3.80 (s, 6 H) 4.24-4.43 (m, 1 H) 4.75-4.88 (m, 1 H) 5.11-5.22 (m, 2 H) 5.23-5.36 (m, 2 H) 5.74-5.81 (m, 1 H) 5.81-5.85 (m, 1 H) 6.78 (s, 3 H) 7.29-7.44 (m, 1 H) | A, 2.49 | 386 |
| 101 | 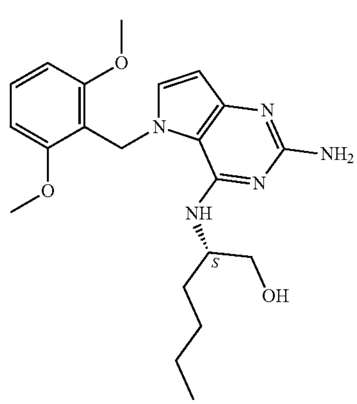 | ¹H NMR (300 MHz, DMSO-d₆) δ ppm 0.75-0.93 (m, 3 H) 1.19-1.40 (m, 4 H) 1.45-1.61 (m, 1 H) 1.61-1.78 (m, 1 H) 3.44-3.63 (m, 2 H) 3.80 (s, 6 H) 4.31 (d, J = 4.95 Hz, 1 H) 4.81 (br. s., 1 H) 5.17 (s, 2 H) 5.30 (s, 2 H) 5.78 (d, J = 8.52 Hz, 1 H) 5.83 (d, J = 3.02 Hz, 1 H) 6.69-6.82 (m, 1 H) 6.69-6.82 (m, 2 H) 7.37 (t, J = 8.39 Hz, 1 H) | A, 2.69 | 400 |

TABLE 1-continued

Compounds of formula (I) and corresponding analytical data.

| # | STRUCTURE | ¹H NMR | LC Method, Rt (min) | LC-MS Mass Found |
|---|---|---|---|---|
| 102 | 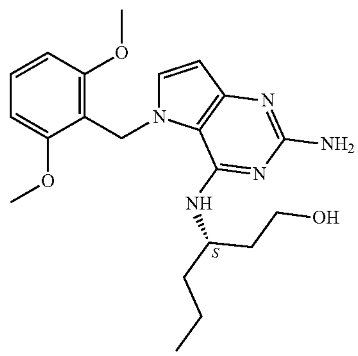 | ¹H NMR (300 MHz, DMSO-d$_6$) δ ppm 0.89 (t, J = 7.40 Hz, 3 H) 1.20-1.42 (m, 2 H) 1.44-1.85 (m, 4 H) 3.42-3.54 (m, 2 H) 3.78 (s, 6 H) 4.32-4.51 (m, 1 H) 4.56-4.69 (m, 1 H) 5.12-5.23 (m, 2 H) 5.32 (s, 2 H) 5.81 (d, J = 2.90 Hz, 1 H) 5.85-5.93 (m, 1 H) 6.71-6.79 (m, 3 H) 7.31-7.44 (m, 1 H) | A, 2.57 | 400 |
| 103 | 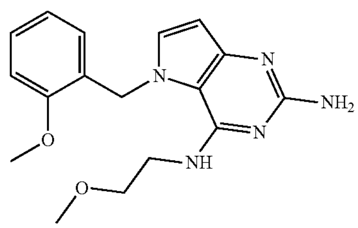 [SMILES: COCCNc1nc(N)nc2ccn(Cc3ccccc3OC)c12] | ¹H NMR (400 MHz, DMSO-d$_6$) δ ppm 3.17 (s, 3 H) 3.31-3.42 (m, 3 H) 3.45-3.56 (m, 3 H) 3.86 (s, 3 H) 5.11 (br. s., 2 H) 5.35 (s, 2 H) 5.62 (t, J = 5.05 Hz, 1 H) 5.97 (d, J = 2.83 Hz, 1 H) 6.60-6.69 (m, 1 H) 6.84 (td, J = 7.47, 0.81 Hz, 1 H) 7.05 (d, J = 8.07 Hz, 1 H) 7.18 (d, J = 3.23 Hz, 1 H) 7.22-7.33 (m, 1 H) | D, 0.74 | 328 |
| 104 | 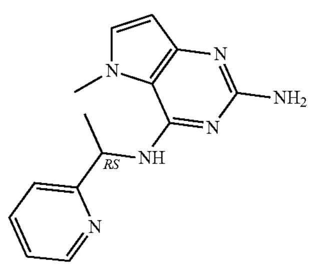 | ¹H NMR (300 MHz, DMSO-d$_6$) δ ppm 1.56 (d, J = 6.87 Hz, 3 H) 4.01 (s, 3 H) 5.26 (s, 2 H) 5.49 (t, J = 7.01 Hz, 1 H) 5.89 (d, J = 2.89 Hz, 1 H) 6.67 (d, J = 7.42 Hz, 1 H) 7.14 (d, J = 2.89 Hz, 1 H) 7.28 (dd, J = 7.01, 5.22 Hz, 1 H) 7.50 (d, J = 7.84 Hz, 1 H) 7.78 (td, J = 7.70, 1.65 Hz, 1 H) 8.56 (d, J = 4.67 Hz, 1 H) | A, 1.23 | 269 |
| 105 | 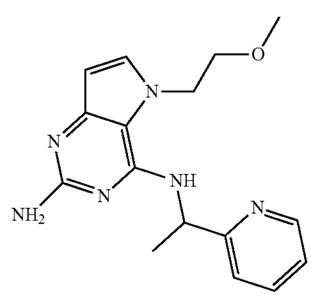 [SMILES: COCCn1ccc2nc(N)nc(NC(C)c3ccccn3)c21] | ¹H NMR (300 MHz, DMSO-d$_6$) δ ppm 1.53 (d, J = 6.87 Hz, 3 H) 3.24 (s, 3 H) 3.68 (t, J = 4.81 Hz, 2 H) 4.42 (t, J = 4.81 Hz, 2 H) 5.24 (s, 2 H) 5.47 (t, J = 7.01 Hz, 1 H) 5.94 (d, J = 2.89 Hz, 1 H) 6.93 (d, J = 7.42 Hz, 1 H) 7.20 (d, J = 3.02 Hz, 1 H) 7.26 (dd, J = 7.22, 5.02 Hz, 1 H) 7.47 (d, J = 7.84 Hz, 1 H) 7.75 (td, J = 7.63, 1.37 Hz, 1 H) 8.55 (d, J = 4.81 Hz, 1 H) | A, 1.45 | 313 |
| 106 | 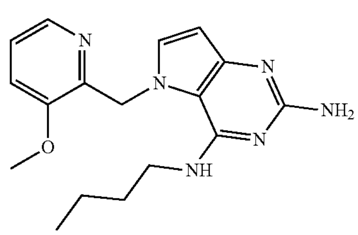 [SMILES: CCCCNc1nc(N)nc2ccn(Cc3ncccc3OC)c12] | ¹H NMR (400 MHz, DMSO-d$_6$) δ ppm 0.95 (t, J = 7.37 Hz, 3 H) 1.37-1.46 (m, 2 H) 1.64 (quin, J = 7.26 Hz, 2 H) 3.42 (td, J = 6.93, 5.28 Hz, 2 H) 3.90 (s, 3 H) 5.18 (s, 2 H) 5.38 (s, 2 H) 5.89 (d, J = 3.08 Hz, 1 H) 7.21 (d, J = 3.08 Hz, 1 H) 7.42 (dd, J = 8.47, 4.73 Hz, 1 H) 7.54-7.60 (m, 2 H) 8.11 (dd, J = 4.73, 1.21 Hz, 1 H) | D, 0.90 | 327 |

TABLE 1-continued

Compounds of formula (I) and corresponding analytical data.

| # | STRUCTURE | ¹H NMR | LC Method, Rt (min) | LC-MS Mass Found |
|---|---|---|---|---|
| 107 | 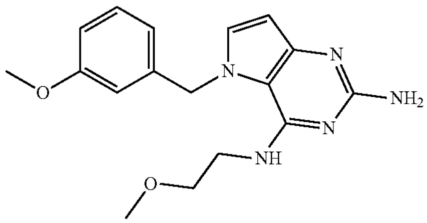 [SMILES: COCCNc1nc(N)nc2ccn(Cc3cccc(OC)c3)c12] | ¹H NMR (400 MHz, DMSO-d$_6$) δ ppm 3.20 (s, 3 H) 3.36 (t, J = 6.05 Hz, 2 H) 3.47-3.54 (m, 2 H) 3.71 (s, 3 H) 5.29 (s, 2 H) 5.42 (s, 2 H) 5.88 (t, J = 5.50 Hz, 1 H) 6.00 (d, J = 2.86 Hz, 1 H) 6.61 (d, J = 7.48 Hz, 1 H) 6.63-6.66 (m, 1 H) 6.83 (dd, J = 8.14, 2.20 Hz, 1 H) 7.23 (t, J = 7.92 Hz, 1 H) 7.35 (d, J = 3.08 Hz, 1 H) | D, 0.71 | 328 |
| 108 | 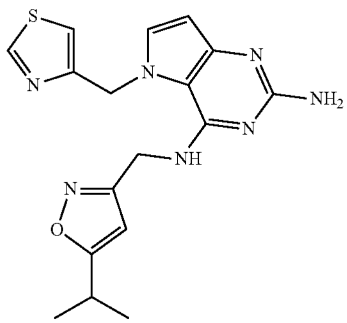 [SMILES: CC(C)c1cc(CNc2nc(N)nc3ccn(Cc4cscn4)c23)no1] | ¹H NMR (400 MHz, DMSO-d$_6$) δ ppm 1.21 (d, J = 7.04 Hz, 6 H) 3.02 (m, J = 6.60, 6.60, 6.60, 6.60, 6.60, 6.60 Hz, 0 H) 4.64 (d, J = 5.72 Hz, 2 H) 5.35 (s, 2 H) 5.56 (s, 2 H) 5.97 (d, J = 3.08 Hz, 1 H) 6.01 (d, J = 0.66 Hz, 1 H) 7.24 (t, J = 5.83 Hz, 1 H) 7.32 (d, J = 3.08 Hz, 1 H) 7.40 (d, J = 1.98 Hz, 1 H) 9.03 (d, J = 1.76 Hz, 1 H) | D, 0.77 | 370 |
| 109 | 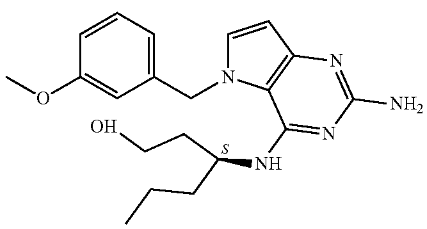 | ¹H NMR (400 MHz, DMSO-d$_6$) δ ppm 0.70 (t, J = 7.04 Hz, 3 H) 0.84-0.95 (m, 2 H) 1.17-1.35 (m, 2 H) 1.38-1.46 (m, 1 H) 1.53-1.62 (m, 1 H) 3.23-3.34 (m, 2 H) 3.68 (s, 3 H) 4.22 (dt, J = 8.53, 4.43 Hz, 1 H) 4.49 (t, J = 5.50 Hz, 1 H) 5.14 (d, J = 8.58 Hz, 1 H) 5.23 (s, 2 H) 5.45 (q, J = 16.95 Hz, 2 H) 5.98 (d, J = 2.86 Hz, 1 H) 6.48 (d, J = 7.70 Hz, 1 H) 6.56-6.58 (m, 1 H) 6.82 (dd, J = 8.14, 2.20 Hz, 1 H) 7.21 (t, J = 7.92 Hz, 1 H) 7.34 (d, J = 3.08 Hz, 1 H) | D, 0.8 | 370 |
| 110 | 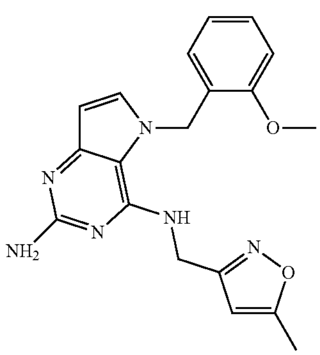 [SMILES: COc1ccccc1Cn1ccc2nc(N)nc(NCc3cc(C)on3)c21] | ¹H NMR (400 MHz, DMSO-d$_6$) δ ppm 2.30 (s, 3 H) 3.80 (s, 3 H) 4.55 (d, J = 5.72 Hz, 2 H) 5.34 (s, 2 H) 5.41 (s, 2 H) 5.71 (d, J = 0.88 Hz, 1 H) 5.99 (d, J = 2.86 Hz, 1 H) 6.44 (dd, J = 7.59, 1.43 Hz, 1 H) 6.50 (t, J = 5.83 Hz, 1 H) 6.80 (td, J = 7.43, 0.99 Hz, 1 H) 7.01 (d, J = 7.48 Hz, 1 H) 7.21-7.27 (m, 2 H) | D, 0.79 | 365 |
| 111 | 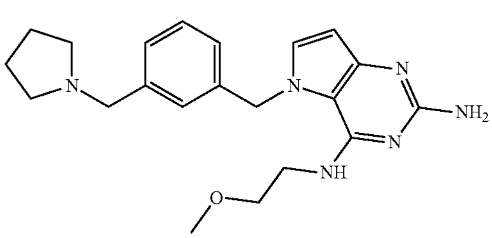 [SMILES: COCCNc1nc(N)nc2ccn(Cc3cccc(CN4CCCC4)c3)c12] | ¹H NMR (400 MHz, DMSO-d$_6$) δ ppm 1.59-1.70 (m, 4 H) 2.28-2.39 (m, 4 H) 3.18 (s, 3 H) 3.32 (t, J = 6.46 Hz, 2 H) 3.44-3.50 (m, 4 H) 5.26 (s, 2 H) 5.43 (s, 2 H) 5.86 (t, J = 4.84 Hz, 1 H) 5.97 (d, J = 2.83 Hz, 1 H) 6.84-6.90 (m, 0 H) 7.03 (s, 1 H) 7.15 (m, J = 7.67 Hz, 1 H) 7.22 (t, J = 7.30 Hz, 1 H) 7.32 (d, J = 3.23 Hz, 1 H) | E, 1.18 | 381 |

TABLE 1-continued

Compounds of formula (I) and corresponding analytical data.

| # | STRUCTURE | ¹H NMR | LC Method, Rt (min) | LC-MS Mass Found |
|---|---|---|---|---|
| 112 | 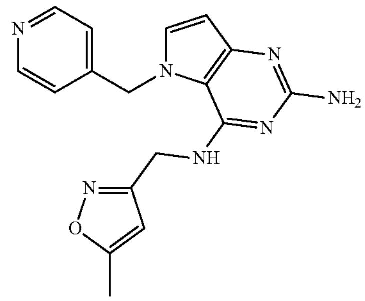 [SMILES: Cc1cc(CNc2nc(N)nc3ccn(Cc4ccncc4)c23)no1] | ¹H NMR (300 MHz, DMSO-d₆) δ ppm 2.29 (s, 3 H) 4.55 (d, J = 5.50 Hz, 2 H) 5.55 (s, 1 H) 5.61 (s, 2 H) 5.68 (br. s., 2 H) 6.11 (d, J = 2.89 Hz, 1 H) 6.83 (d, J = 5.64 Hz, 2 H) 6.92 (t, J = 5.43 Hz, 1 H) 7.43 (d, J = 3.02 Hz, 1 H) 8.44 (d, J = 5.77 Hz, 2 H) | A, 0.994 | 336 |
| 113 | 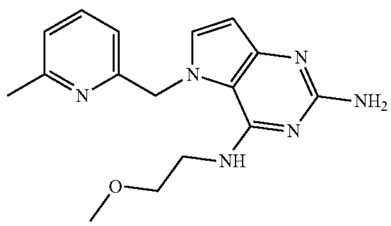 [SMILES: COCCNc1nc(N)nc2ccn(Cc3cccc(C)n3)c12] | ¹H NMR (400 MHz, DMSO-d₆) δ ppm 2.60 (s, 3 H) 3.22 (s, 3 H) 3.52 (t, J = 5.70 Hz, 2 H) 3.72 (q, J = 5.58 Hz, 2 H) 5.71 (br. s., 2 H) 6.26 (d, J = 3.08 Hz, 1 H) 7.21 (d, J = 7.48 Hz, 1 H) 7.34-7.58 (m, 3 H) 7.72 (d, J = 2.86 Hz, 1 H) 7.94 (t, J = 7.70 Hz, 1 H) 8.81-8.97 (m, 1 H) 12.60 (br. s., 1 H) | E, 1.28 | 313 |
| 114 | 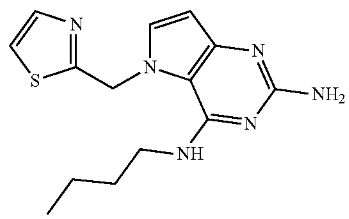 [SMILES: CCCCNc1nc(N)nc2ccn(Cc3nccs3)c12] | ¹H NMR (400 MHz, DMSO-d₆) δ ppm 0.87 (t, J = 7.37 Hz, 3 H) 1.18-1.32 (m, 2 H) 1.50 (quin, J = 7.21 Hz, 2 H) 3.33-3.38 (m, 2 H) 5.27 (s, 2 H) 5.79 (s, 2 H) 5.99 (d, J = 3.08 Hz, 1 H) 6.47 (t, J = 5.28 Hz, 1 H) 7.35 (d, J = 2.86 Hz, 1 H) 7.67 (d, J = 3.08 Hz, 1 H) 7.77 (d, J = 3.30 Hz, 1 H) | E, 1.6 | 303 |
| 115 | 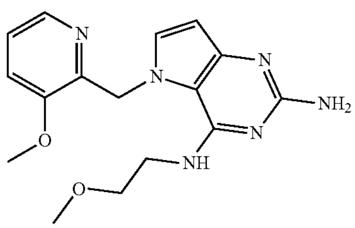 [SMILES: COCCNc1nc(N)nc2ccn(Cc3ncccc3OC)c12] | ¹H NMR (400 MHz, DMSO-d₆) δ ppm 3.30 (s, 3 H) 3.52-3.57 (m, 2 H) 3.57-3.64 (m, 2 H) 3.90 (s, 3 H) 5.23 (s, 2 H) 5.37 (s, 2 H) 5.90 (d, J = 3.08 Hz, 1 H) 7.21 (d, J = 2.86 Hz, 1 H) 7.41 (dd, J = 8.36, 4.62 Hz, 1 H) 7.54 (dd, J = 8.58, 1.10 Hz, 1 H) 7.80 (t, J = 4.95 Hz, 1 H) 8.12 (dd, J = 4.73, 1.21 Hz, 1 H) | D, 0.68 | 329 |
| 116 | 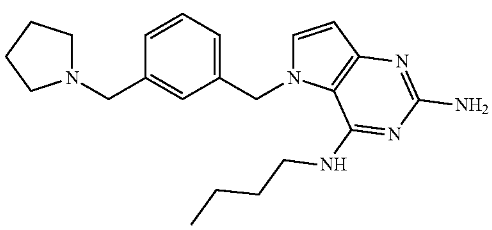 [SMILES: CCCCNc1nc(N)nc2ccn(Cc3cccc(CN4CCCC4)c3)c12] | ¹H NMR (400 MHz, DMSO-d₆) δ ppm 0.78 (t, J = 7.30 Hz, 3 H) 1.01-1.11 (m, 2 H) 1.33 (quin, J = 7.26 Hz, 2 H) 1.62-1.68 (m, 4 H) 2.31-2.37 (m, 4 H) 3.25-3.29 (m, 2 H) 3.48 (s, 2 H) 5.21 (s, 2 H) 5.47 (s, 2 H) 5.69 (t, J = 5.39 Hz, 1 H) 5.97 (d, J = 2.86 Hz, 1 H) 6.79 (d, J = 7.48 Hz, 1 H) 7.01 (s, 1 H) 7.15 (d, J = 7.70 Hz, 1 H) 7.21 (t, J = 7.59 Hz, 1 H) 7.31 (d, J = 2.86 Hz, 1 H) | D, 0.73 | 379 |
| 117 | 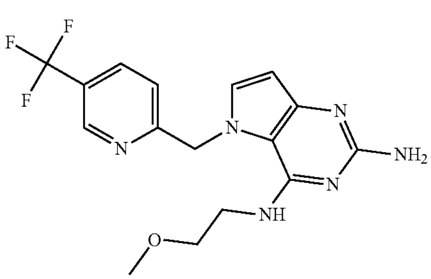 [SMILES: COCCNc1nc(N)nc2ccn(Cc3ccc(C(F)(F)F)cn3)c12] | ¹H NMR (400 MHz, DMSO-d₆) δ ppm 3.15 (s, 3 H) 3.35 (t, J = 5.83 Hz, 2 H) 3.50 (q, J = 5.65 Hz, 2 H) 5.30 (s, 2 H) 5.63 (s, 2 H) 6.01 (d, J = 3.08 Hz, 1 H) 6.56 (t, J = 5.39 Hz, 1 H) 7.17 (d, J = 8.36 Hz, 1 H) 7.39 (d, J = 3.08 Hz, 1 H) 8.21 (dd, J = 8.36, 1.98 Hz, 1 H) 8.91-8.94 (m, 1 H) | D, 0.77 | 367 |

TABLE 1-continued

Compounds of formula (I) and corresponding analytical data.

| # | STRUCTURE | ¹H NMR | LC Method, Rt (min) | LC-MS Mass Found |
|---|---|---|---|---|
| 118 | 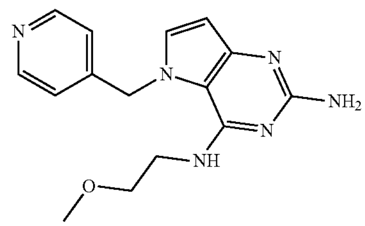 [SMILES: COCCNc1nc(N)nc2ccn(Cc3ccncc3)c12] | ¹H NMR (300 MHz, DMSO-d$_6$) δ ppm 3.15 (s, 3 H) 3.25-3.31 (m, 2 H) 3.47 (d, J = 5.77 Hz, 2 H) 5.32 (s, 2 H) 5.53 (s, 2 H) 5.97 (s, 1 H) 6.03 (d, J = 2.89 Hz, 1 H) 6.91 (d, J = 5.91 Hz, 2 H) 7.36 (d, J = 3.02 Hz, 1 H) 8.47 (d, J = 5.91 Hz, 2 H) | A, 0.83 | 299 |
| 119 | 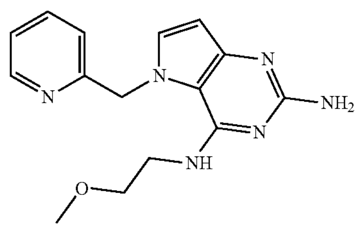 [SMILES: COCCNc1nc(N)nc2ccn(Cc3ccccn3)c12] | ¹H NMR (300 MHz, DMSO-d$_6$) δ ppm 3.26 (s, 3 H) 3.44-3.52 (m, 2 H) 3.52-3.62 (m, 2 H) 5.30 (s, 2 H) 5.44 (s, 2 H) 5.96 (d, J = 3.02 Hz, 1 H) 7.29 (d, J = 7.70 Hz, 1 H) 7.33-7.45 (m, 1 H) 7.33-7.45 (m, 2 H) 7.83 (td, J = 7.70, 1.65 Hz, 1 H) 8.56 (d, J = 4.26 Hz, 1 H) | A, 0.83 | 299 |
| 120 | 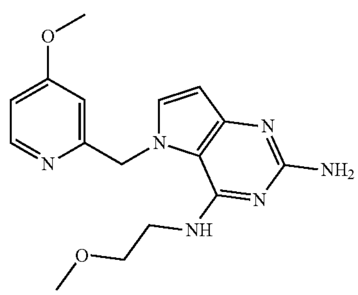 [SMILES: COCCNc1nc(N)nc2ccn(Cc3cc(OC)ccn3)c12] | ¹H NMR (400 MHz, DMSO-d$_6$) δ ppm 3.25-3.29 (m, 3 H) 3.47-3.54 (m, 2 H) 3.54-3.61 (m, 2 H) 3.81 (s, 3 H) 5.25 (s, 2 H) 5.33 (s, 2 H) 5.94 (d, J = 3.08 Hz, 1 H) 6.95 (dd, J = 5.72, 2.64 Hz, 1 H) 6.98 (d, J = 2.42 Hz, 1 H) 7.39 (d, J = 3.08 Hz, 1 H) 7.74 (t, J = 5.06 Hz, 1 H) 8.37 (d, J = 5.72 Hz, 1 H) | D, 0.65 | 329 |
| 121 | 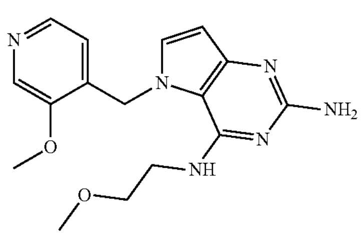 [SMILES: COCCNc1nc(N)nc2ccn(Cc3ccncc3OC)c12] | ¹H NMR (400 MHz, DMSO-d$_6$) δ ppm 3.18 (s, 3 H) 3.38 (t, J = 5.70 Hz, 2 H) 3.51 (q, J = 5.65 Hz, 2 H) 3.91 (s, 3 H) 5.31 (s, 2 H) 5.40 (s, 2 H) 5.95-6.00 (m, 2 H) 7.08 (d, J = 5.72 Hz, 1 H) 7.21 (d, J = 3.08 Hz, 1 H) 7.65 (s, 1 H) 8.38 (d, J = 5.72 Hz, 1 H) | D, 0.52 | 329 |
| 122 | 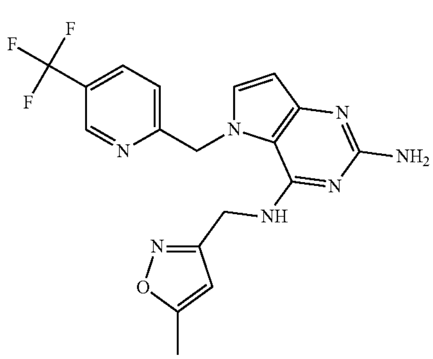 [SMILES: Cc1cc(CNc2nc(N)nc3ccn(Cc4ccc(C(F)(F)F)cn4)c23)no1] | ¹H NMR (400 MHz, DMSO-d$_6$) δ ppm 2.28 (s, 3 H) 4.56 (d, J = 5.94 Hz, 2 H) 5.38 (s, 2 H) 5.68 (s, 2 H) 5.76 (d, J = 0.88 Hz, 1 H) 6.05 (d, J = 3.08 Hz, 1 H) 7.04 (d, J = 8.36 Hz, 1 H) 7.08 (t, J = 5.83 Hz, 1 H) 7.41 (d, J = 3.08 Hz, 1 H) 8.16 (dd, J = 8.36, 1.98 Hz, 1 H) 8.82-8.85 (m, 1 H) | D, 0.80 | 404 |

TABLE 1-continued

Compounds of formula (I) and corresponding analytical data.

| # | STRUCTURE | ¹H NMR | LC Method, Rt (min) | LC-MS Mass Found |
|---|---|---|---|---|
| 123 | 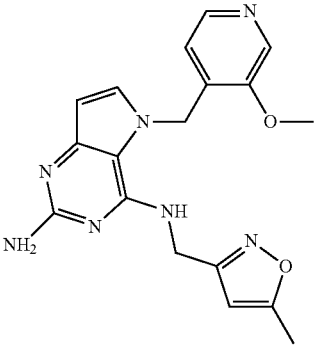 [SMILES: COc1cnccc1Cn1ccc2nc(N)nc(NCc3cc(C)on3)c21] | ¹H NMR (400 MHz, DMSO-d$_6$) δ ppm 2.31 (s, 3 H) 3.85 (s, 3 H) 4.56 (d, J = 5.72 Hz, 2 H) 5.37 (s, 2 H) 5.44 (s, 2 H) 5.82 (s, 1 H) 6.01 (d, J = 3.08 Hz, 1 H) 6.70 (t, J = 5.72 Hz, 1 H) 7.05 (d, J = 5.72 Hz, 1 H) 7.22 (d, J = 2.86 Hz, 1 H) 7.53 (s, 1 H) 8.37 (d, J = 5.50 Hz, 1 H) | D, 0.58 | 366 |
| 124 | 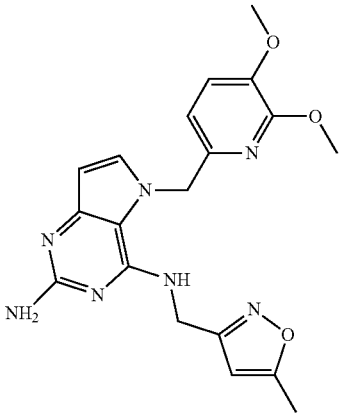 [SMILES: COc1ccc(Cn2ccc3nc(N)nc(NCc4cc(C)on4)c32)nc1OC] | ¹H NMR (400 MHz, DMSO-d$_6$) δ ppm 2.31 (s, 3 H) 3.71 (s, 3 H) 3.72 (s, 3 H) 4.60 (d, J = 5.72 Hz, 2 H) 5.32-5.37 (m, 4 H) 5.86 (s, 1 H) 5.99 (d, J = 2.86 Hz, 1 H) 6.55 (d, J = 7.92 Hz, 1 H) 6.83 (t, J = 5.83 Hz, 1 H) 7.19 (d, J = 7.92 Hz, 1 H) 7.34 (d, J = 2.86 Hz, 1 H) | D, 0.70 | 396 |
| 125 | 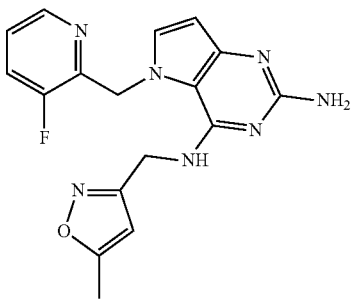 | ¹H NMR (400 MHz, DMSO-d$_6$) δ ppm 2.34 (s, 3 H) 4.63 (d, J = 5.50 Hz, 2 H) 5.36 (s, 2 H) 5.58 (d, J = 1.76 Hz, 2 H) 5.97 (d, J = 3.08 Hz, 1 H) 6.06 (d, J = 0.88 Hz, 1 H) 7.26 (dd, J = 3.08, 0.88 Hz, 1 H) 7.44-7.49 (m, 1 H) 7.62 (t, J = 5.72 Hz, 1 H) 7.78 (ddd, J = 9.90, 8.47, 1.21 Hz, 1 H) 8.21-8.24 (m, 1 H) | D, 0.67 | 354 |
| 126 | 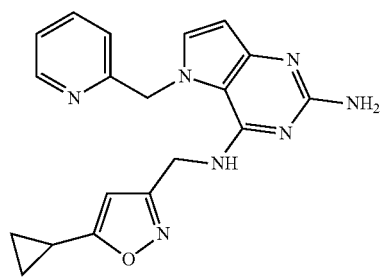 [SMILES: Nc1nc(NCc2cc(C3CC3)on2)c2c(ccn2Cc2ccccn2)n1] | ¹H NMR (400 MHz, DMSO-d$_6$) δ ppm 0.76-0.83 (m, 2 H) 0.99-1.04 (m, 2 H) 2.06 (tt, J = 8.47, 4.95 Hz, 1 H) 4.59 (d, J = 5.50 Hz, 2 H) 5.36 (s, 2 H) 5.48 (s, 2 H) 5.90 (s, 1 H) 5.99 (d, J = 2.86 Hz, 1 H) 7.14-7.17 (m, 1 H) 7.31-7.35 (m, 1 H) 7.40 (d, J = 2.86 Hz, 1 H) 7.74 (t, J = 5.61 Hz, 1 H) 7.76-7.82 (m, 1 H) 8.40-8.43 (m, 1 H) | D, 0.74 | 362 |

TABLE 1-continued

Compounds of formula (I) and corresponding analytical data.

| # | STRUCTURE | ¹H NMR | LC Method, Rt (min) | LC-MS Mass Found |
|---|---|---|---|---|
| 127 | 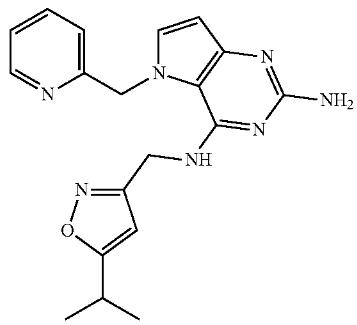 [SMILES: CC(C)c1cc(CNc2nc(N)nc3ccn(Cc4ccccn4)c23)no1] | ¹H NMR (400 MHz, DMSO-d₆) δ ppm 1.19 (d, J = 7.04 Hz, 6 H) 2.94-3.08 (m, 1 H) 4.63 (d, J = 5.72 Hz, 2 H) 5.37 (s, 2 H) 5.49 (s, 2 H) 5.93 (s, 1 H) 5.99 (d, J = 3.08 Hz, 1 H) 7.15 (d, J = 7.92 Hz, 1 H) 7.32 (dd, J = 7.04, 5.06 Hz, 1 H) 7.41 (d, J = 2.86 Hz, 1 H) 7.74 (t, J = 5.61 Hz, 1 H) 7.78 (td, J = 7.70, 1.76 Hz, 1 H) 8.40 (d, J = 4.18 Hz, 1 H) | D, 0.79 | 364 |
| 128 | 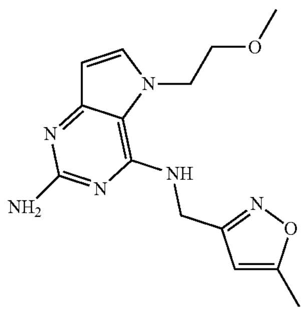 [SMILES: COCCn1ccc2nc(N)nc(NCc3cc(C)on3)c21] | ¹H NMR (400 MHz, DMSO-d₆) δ ppm 2.35 (d, J = 0.66 Hz, 3 H) 3.15 (s, 3 H) 3.55 (t, J = 5.06 Hz, 2 H) 4.36 (t, J = 4.95 Hz, 2 H) 4.62 (d, J = 5.72 Hz, 2 H) 5.31 (s, 2 H) 5.92 (d, J = 3.08 Hz, 1 H) 6.18 (d, J = 0.88 Hz, 1 H) 6.84 (t, J = 5.83 Hz, 1 H) 7.17 (d, J = 3.08 Hz, 1 H) | E, 1.09 | 303 |
| 129 | 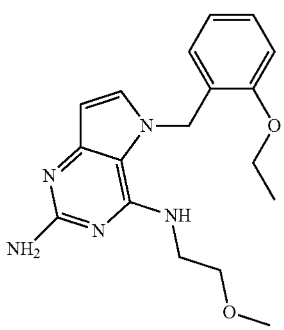 [SMILES: CCOc1ccccc1Cn1ccc2nc(N)nc(NCCOC)c21] | ¹H NMR (400 MHz, DMSO-d₆) δ ppm 1.38 (t, J = 6.9 Hz, 3 H), 3.15 (s, 3 H), 3.27-3.33 (m, 2 H), 3.47 (q, J = 5.6 Hz, 2 H), 4.10 (q, J = 7.0 Hz, 2 H), 5.29 (s, 26 H), 5.37 (s, 2 H), 5.72 (t, J = 5.4 Hz, 1 H), 5.97 (d, J = 2.9 Hz, 1 H), 6.59 (dd, J = 7.5, 1.5 Hz, 1 H), 6.79-6.85 (m, 1 H), 7.02 (d, J = 7.7 Hz, 1 H), 7.20-7.27 (m, 2 H) | E, 1.52 | 342 |
| 130 | 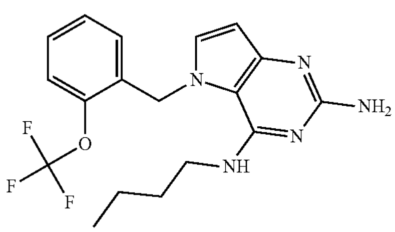 [SMILES: CCCCNc1nc(N)nc2ccn(Cc3ccccc3OC(F)(F)F)c12] | ¹H NMR (400 MHz, DMSO-d₆) δ ppm 0.71-0.78 (m, 3 H), 0.96-1.08 (m, 2 H), 1.28-1.38 (m, 2 H), 3.22-3.29 (m, 2 H), 5.28 (s, 2 H), 5.59 (s, 2 H), 5.77 6 (t, J = 5.4 Hz, 1 H), 6.03 (d, J = 3.1 Hz, 1 H), 6.35 (d, J = 7.7 Hz, 1 H), 7.19-7.25 (m, 1 H), 7.28 (d, J = 3.1 Hz, 1 H), 7.35-7.40 (m, 2 H) SLAST_1343_1.1.esp | E, 1.84 | 380 |
| 131 | 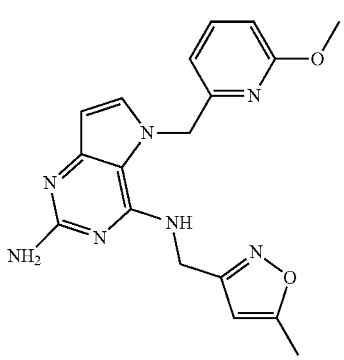 [SMILES: COc1cccc(Cn2ccc3nc(N)nc(NCc4cc(C)on4)c32)n1] | ¹H NMR (400 MHz, DMSO-d₆) δ ppm 2.29-2.33 (m, 3 H) 3.71 (s, 3 H) 4.59 (d, J = 5.72 Hz, 2 H) 5.36 (s, 2 H) 5.44 (s, 2 H) 5.82-5.85 (m, 1 H) 6.01 (d, J = 3.08 Hz, 1 H) 6.50 (d, J = 7.26 Hz, 1 H) 6.70 (d, J = 8.14 Hz, 1 H) 6.90 (t, J = 5.72 Hz, 1 H) 7.36 (d, J = 2.86 Hz, 1 H) 7.62 (dd, J = 8.25, 7.37 Hz, 1 H) | D, 0.74 | 366 |

TABLE 1-continued

Compounds of formula (I) and corresponding analytical data.

| # | STRUCTURE | ¹H NMR | LC Method, Rt (min) | LC-MS Mass Found |
|---|---|---|---|---|
| 132 | 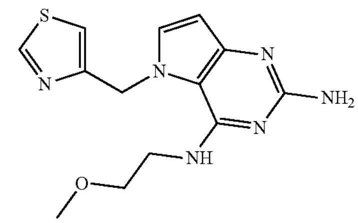 [SMILES: COCCNc1nc(N)nc2ccn(Cc3cscn3)c12] | ¹H NMR (300 MHz, chloroform-d) δ ppm 3.30 (s, 3 H) 3.47-3.60 (m, 2 H) 3.68 (m, J = 5.10, 5.10, 5.10 Hz, 2 H) 5.37 (s, 2 H) 5.77 (br. s., 2 H) 6.20 (d, J = 3.02 Hz, 1 H) 7.02 (d, J = 3.16 Hz, 1 H) 7.23-7.31 (m, 1 H) 7.85 (br. s., 1 H) 8.78 (d, J = 1.79 Hz, 1 H) | A, 1.61 | 305 |
| 133 | 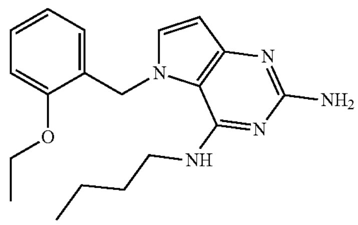 [SMILES: CCCCNc1nc(N)nc2ccn(Cc3ccccc3OCC)c12] | ¹H NMR (400 MHz, DMSO-d₆) δ ppm 0.79 (t, J = 7.3 Hz, 3 H), 1.09 (dq, J = 15.0, 7.4 Hz, 2 H), 1.30-1.35 (m, 2 H), 1.38 (t, J = 6.9 Hz, 3 H), 3.24-3.29 (m, 2 6 H), 4.10 (q, J = 6.9 Hz, 2 H), 5.22 (s, 2 H), 5.39 (s, 2 H), 5.50 (t, J = 5.4 Hz, 1 H), 5.96 (d, J = 2.9 Hz, 1 H), 6.48 (dd, J = 7.5, 1.3 Hz, 1 H), 6.77-6.84 (m, 1 H), 7.03 (d, J = 7.9 Hz, 1 H), 7.20-7.26 (m, 2 H) | D, 1.0 | 340 |
| 134 | 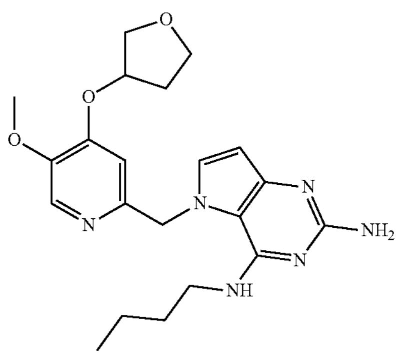 [SMILES: CCCCNc1nc(N)nc2ccn(Cc3cc(OC4CCOC4)c(OC)cn3)c12] | ¹H NMR (400 MHz, DMSO-d₆) δ ppm 0.91 (t, J = 7.4 Hz, 3 H), 1.29-1.39 (m, 2 H), 1.54-1.65 (m, 2 H), 1.84-1.94 (m, 1 H), 2.17-2.30 (m, 1 H), 3.37-6 3.44 (m, 2 H), 3.70-3.79 (m, 2 H), 3.82 (s, 3 H), 3.83-3.90 (m, 2 H), 4.97-5.04 (m, 1 H), 5.22 (s, 2 H), 5.30 (s, 2 H), 5.93 (d, J = 3.1 Hz, 1 H), 7.03 (s, 1 H), 7.40 (d, J = 2.9 Hz, 1 H), 7.47 (t, J = 5.1 Hz, 1 H), 8.10 (s, 1 H) | D, 0.82 | 413 |
| 135 | 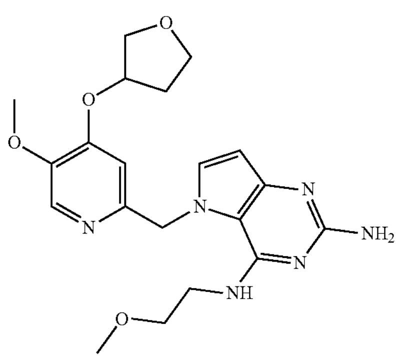 [SMILES: COCCNc1nc(N)nc2ccn(Cc3cc(OC4CCOC4)c(OC)cn3)c12] | ¹H NMR (400 MHz, DMSO-d₆) δ ppm 0.91 (t, J = 7.4 Hz, 3 H), 1.29-1.39 (m, 2 H), 1.54-1.65 (m, 2 H), 1.84-1.94 (m, 1 H), 2.17-2.30 (m, 1 H), 3.37-6 3.44 (m, 2 H), 3.70-3.79 (m, 2 H), 3.82 (s, 3 H), 3.83-3.90 (m, 2 H), 4.97-5.04 (m, 1 H), 5.22 (s, 2 H), 5.30 (s, 2 H), 5.93 (d, J = 3.1 Hz, 1 H), 7.03 (s, 1 H), 7.40 (d, J = 2.9 Hz, 1 H), 7.47 (t, J = 5.1 Hz, 1 H), 8.10 (s, 1 H) | D, 0.64 | 415 |
| 136 | 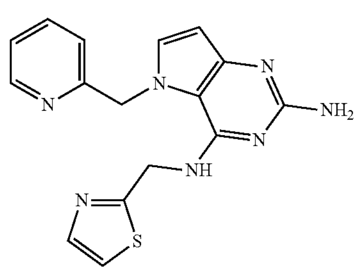 [SMILES: Nc1nc(NCc2nccs2)c2c(ccn2Cc2ccccn2)n1] | ¹H NMR (400 MHz, DMSO-d₆) δ ppm 4.94 (d, J = 5.9 Hz, 2 H), 5.37 (s, 2 H), 5.53 (s, 2 H), 6.01 (d, J = 3.1 Hz, 1 H), 7.15 (d, J = 7.7 Hz, 1 H), 7.31 (ddd, J = 7.7, 6 4.8, 1.1 Hz, 1 H), 7.43 (d, J = 3.1 Hz, 1 H), 7.52 (d, J = 3.3 Hz, 1 H), 7.71 (d, J = 3.3 Hz, 1 H), 7.78 (td, J = 7.7, 2.0 Hz, 1 H), 8.10 (t, J = 5.8 Hz, 1 H), 8.42-8.46 (m, 1 H) | D, 0.60 | 338 |

TABLE 1-continued

Compounds of formula (I) and corresponding analytical data.

| # | STRUCTURE | ¹H NMR | LC Method, Rt (min) | LC-MS Mass Found |
|---|---|---|---|---|
| 137 | 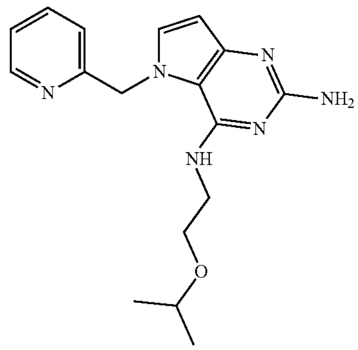 [SMILES: CC(C)OCCNc1nc(N)nc2ccn(Cc3ccccn3)c12] | ¹H NMR (400 MHz, DMSO-d₆) δ ppm 1.05 (d, J = 6.2 Hz, 6 H), 3.46-3.59 (m, 5 H), 5.27 (s, 2 H), 5.44 (s, 2 H), 5.96 (d, J = 3.1 Hz, 1 H), 7.17-7.25 (m, 2 H), 6 7.31-7.39 (m, 2 H), 7.77-7.85 (m, 1 H), 8.51-8.59 (m, 1 H) | D, 0.73 | 327 |
| 138 | 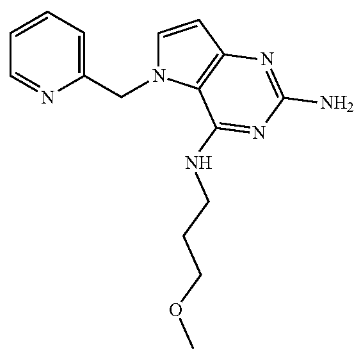 [SMILES: COCCCNc1nc(N)nc2ccn(Cc3ccccn3)c12] | ¹H NMR (400 MHz, DMSO-d₆) δ ppm 1.78 (quin, J = 6.6 Hz, 2 H), 3.20 (s, 3 H), 3.28-3.32 (m, 2 H), 3.37-3.44 (m, 2 H), 5.25 (s, 2 H), 5.47 (s, 2 H), 5.96 (d, 6 J = 2.9 Hz, 1 H), 7.01 (t, J = 5.2 Hz, 1 H), 7.16 (d, J = 7.9 Hz, 1 H), 7.32-7.39 (m, 2 H), 7.81 (td, J = 7.7, 1.8 Hz, 1 H), 8.53-8.56 (m, 1 H) | D, 0.63 | 313 |
| 139 | 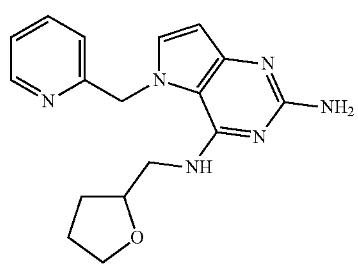 [SMILES: Nc1nc(NCC2CCCO2)c2c(ccn2Cc2ccccn2)n1] | ¹H NMR (400 MHz, DMSO-d₆) δ ppm 1.47-1.58 (m, 1 H), 1.72-1.88 (m, 3 H), 3.39-3.54 (m, 2 H), 3.58-3.66 (m, 1 H), 3.70-3.78 (m, 1 H), 4.00 (quin, 6 J = 6.2 Hz, 1 H), 5.26 (s, 2 H), 5.38-5.50 (m, 2 H), 5.96 (d, J = 2.9 Hz, 1 H), 7.24 (d, J = 7.7 Hz, 1 H), 7.30 (t, J = 5.4 Hz, 1 H), 7.35 (ddd, J = 7.6, 5.0, 1.1 Hz, 1 H), 7.39 (d, J = 3.1 Hz, 1 H), 7.82 (td, J = 7.7, 1.8 Hz, 1 H), 8.55 (ddd, J = 4.8, 1.5, 0.9 Hz, 1 H) | D, 0.65 | 325 |
| 140 | 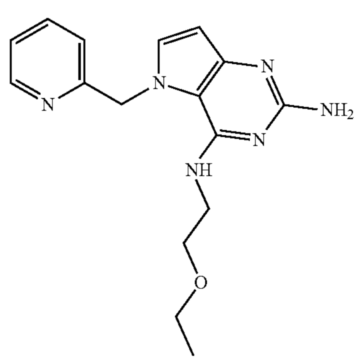 [SMILES: CCOCCNc1nc(N)nc2ccn(Cc3ccccn3)c12] | ¹H NMR (400 MHz, DMSO-d₆) δ ppm 1.08 (t, J = 7.0 Hz, 3 H), 3.43 (q, J = 7.0 Hz, 2 H), 3.48-3.59 (m, 4 H), 5.27 (s, 2 H), 5.44 (s, 2 H), 5.96 (d, J = 3.1 Hz, 1 6 H), 7.23-7.31 (m, 2 H), 7.35 (ddd, J = 7.6, 5.0, 1.1 Hz, 1 H), 7.38 (d, J = 3.1 Hz, 1 H), 7.81 (td, J = 7.7, 1.8 Hz, 1 H), 8.53-8.57 (m, 1 H) | D, 0.66 | 313 |

TABLE 1-continued

Compounds of formula (I) and corresponding analytical data.

| # | STRUCTURE | ¹H NMR | LC Method, Rt (min) | LC-MS Mass Found |
|---|---|---|---|---|
| 141 | 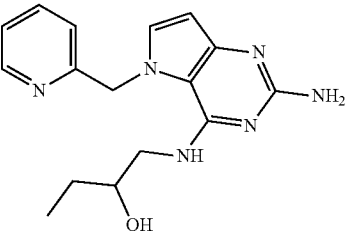 [SMILES: CCC(O)CNc1nc(N)nc2ccn(Cc3ccccn3)c12] | ¹H NMR (400 MHz, DMSO-d₆) δ ppm 0.87 (t, J = 7.4 Hz, 3 H), 1.21-1.33 (m, 1 H), 1.33-1.45 (m, 1 H), 3.26-3.33 (m, 1 H), 3.45 (dt, J = 13.1, 5.4 Hz, 1 H), 6 3.50-3.60 (m, 1 H), 4.81 (br. s., 1 H), 5.27 (s, 2 H), 5.47 (s, 2 H), 5.96 (d, J = 3.1 Hz, 1 H), 7.17-7.26 (m, 2 H), 7.34 (ddd, J = 7.7, 4.8, 1.1 Hz, 1 H), 7.38 (d, J = 3.1 Hz, 1 H), 7.81 (td, J = 7.7, 1.8 Hz, 1 H), 8.52-8.56 (m, 1 H) | D, 0.58 | 313 |
| 142 | 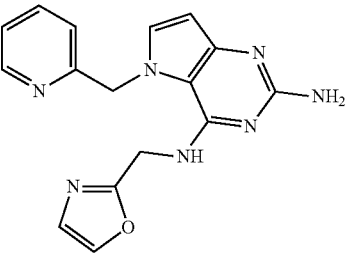 | ¹H NMR (400 MHz, DMSO-d₆) δ ppm 4.79 (d, J = 5.7 Hz, 2 H), 5.31 (s, 2 H), 5.47 (s, 2 H), 5.99 (d, J = 2.9 Hz, 1 H), 7.14 (d, J = 0.7 Hz, 1 H), 7.28-7.36 (m, 2 6 H), 7.42 (d, J = 2.9 Hz, 1 H), 7.81 (td, J = 7.7, 1.8 Hz, 1 H), 7.99 (d, J = 0.9 Hz, 1 H), 8.06 (t, J = 5.6 Hz, 1 H), 8.40-8.45 (m, 1 H) | D, 0.57 | 322 |
| 143 | 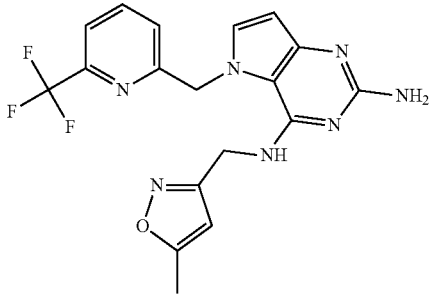 [SMILES: Cc1cc(CNc2nc(N)nc3ccn(Cc4cccc(C(F)(F)F)n4)c23)no1] | ¹H NMR (400 MHz, DMSO-d₆) δ ppm 2.23-2.32 (m, 3 H) 4.53 (d, J = 5.94 Hz, 2 H) 5.40 (s, 2 H) 5.67-5.71 (m, 3 H) 6.07 (d, J = 3.08 Hz, 1 H) 6.90 (d, J = 7.92 Hz, 1 H) 6.96 (t, J = 5.83 Hz, 1 H) 7.41 (d, J = 3.08 Hz, 1 H) 7.81 (d, J = 7.70 Hz, 1 H) 8.01 (t, J = 7.92 Hz, 1 H) | E, 1.43 | 404 |
| 144 | 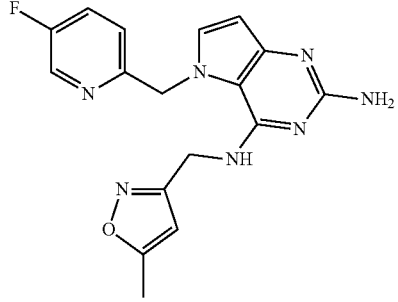 [SMILES: Cc1cc(CNc2nc(N)nc3ccn(Cc4ccc(F)cn4)c23)no1] | ¹H NMR (400 MHz, DMSO-d₆) δ ppm 2.31-2.35 (m, 3 H) 4.59 (d, J = 5.72 Hz, 2 H) 5.36 (s, 2 H) 5.52 (s, 2 H) 5.89 (d, J = 0.88 Hz, 1 H) 6.00 (d, J = 3.08 Hz, 1 H) 7.11 (dd, J = 8.69, 4.51 Hz, 1 H) 7.28 (t, J = 5.83 Hz, 1 H) 7.39 (d, J = 3.08 Hz, 1 H) 7.70 (td, J = 8.80, 2.86 Hz, 1 H) 8.42 (d, J = 2.86 Hz, 1 H) | E, 1.49 | 354 |
| 145 | 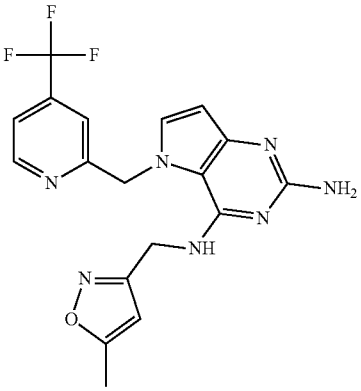 [SMILES: Cc1cc(CNc2nc(N)nc3ccn(Cc4cc(C(F)(F)F)ccn4)c23)no1] | ¹H NMR (400 MHz, DMSO-d₆) δ ppm 2.31 (d, J = 0.66 Hz, 3 H) 4.59 (d, J = 5.72 Hz, 2 H) 5.38 (s, 2 H) 5.64 (s, 2 H) 5.84 (d, J = 0.66 Hz, 1 H) 6.02 (d, J = 3.08 Hz, 1 H) 7.29 (t, J = 5.72 Hz, 1 H) 7.42-7.45 (m, 2 H) 7.69-7.72 (m, 1 H) 8.71 (d, J = 5.06 Hz, 1 H) | D, 0.79 | 404 |

TABLE 1-continued

Compounds of formula (I) and corresponding analytical data.

| # | STRUCTURE | ¹H NMR | LC Method, Rt (min) | LC-MS Mass Found |
|---|---|---|---|---|
| 146 | 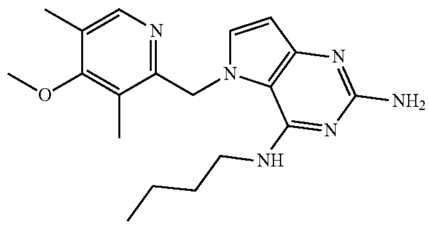 | ¹H NMR (400 MHz, DMSO-d₆) δ ppm 0.93 (t, J = 7.3 Hz, 3 H), 1.37 (dq, J = 15.0, 7.3 Hz, 2 H), 1.56-1.66 (m, 2 H), 2.21 (s, 3 H), 2.33 (s, 3 H), 3.36-3.42 (m, 6 3 H), 3.72 (s, 3 H), 5.21 (s, 2 H), 5.44 (s, 2 H), 5.92 (d, J = 3.1 Hz, 1 H), 7.30 (d, J = 3.1 Hz, 1 H), 7.85 (t, J = 5.1 Hz, 1 H), 8.21 (s, 1 H) SLAST_1354_1.1.esp M07(s) | E, 1.83 | 355 |
| 147 | 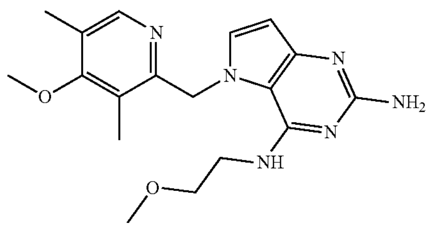 [SMILES: COCCNc1nc(N)nc2ccn(Cc3ncc(C)c(OC)c3C)c12] | ¹H NMR (400 MHz, DMSO-d₆) δ ppm 2.21 (s, 3 H), 2.34 (s, 3 H), 3.28 (s, 3 H), 3.50-3.60 (m, 4 H), 3.72 (s, 3 H), 5.25 (s, 2 H), 5.42 (s, 2 H), 5.92 (d, J = 3.16 Hz, 1 H), 7.31 (d, J = 2.9 Hz, 1 H), 8.14 (t, J = 4.7 Hz, 1 H), 8.22 (s, 1 H) SLAST_1354_2.1.esp M04(m) | E, 1.45 | 357 |
| 148 | 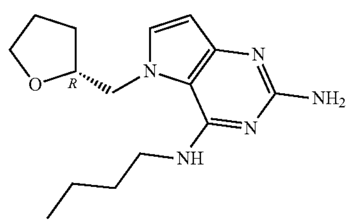 | ¹H NMR (400 MHz, DMSO-d₆) δ ppm 0.93 (t, J = 7.4 Hz, 3 H), 1.38 (dq, J = 14.9, 7.4 Hz, 2 H), 1.47-1.67 (m, 4 H), 1.69-1.84 (m, 1 H), 1.85-1.99 (m, 1 H), 6 3.34-3.42 (m, 2 H), 3.56-3.74 (m, 2 H), 4.01-4.11 (m, 1 H), 4.17 (dd, J = 15.2, 6.2 Hz, 1 H), 4.37 (dd, J = 15.2, 2.9 Hz, 1 H), 5.26 (s, 2 H), 5.91 (d, J = 3.1 Hz, 1 H), 6.51 (t, J = 5.2 Hz, 1 H), 7.14 (d, J = 2.9 Hz, 1 H) | D, 0.81 | 290 |
| 149 | 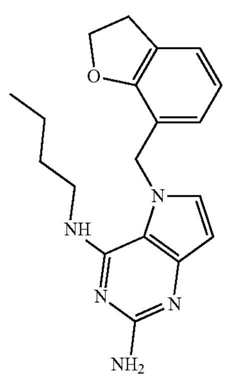 | ¹H NMR (400 MHz, DMSO-d₆) δ ppm 0.83 (t, J = 7.4 Hz, 3 H), 1.17 (dq, J = 14.9, 7.4 Hz, 2 H), 1.42 (quin, J = 7.3 Hz, 2 H), 3.21 (t, J = 8.7 Hz, 2 H), 3.29-3.35 6 (m, 2 H), 4.60 (t, J = 8.7 Hz, 2 H), 5.23 (s, 2 H), 5.34 (s, 2 H), 5.71 (t, J = 5.3 Hz, 1 H), 5.95 (d, J = 2.9 Hz, 1 H), 6.46 (d, J = 7.7 Hz, 1 H), 6.72 (t, J = 7.6 Hz, 1 H), 7.14 (d, J = 6.6 Hz, 1 H), 7.23 (d, J = 3.1 Hz, 1 H) | E, 1.72 | 338 |
| 150 | 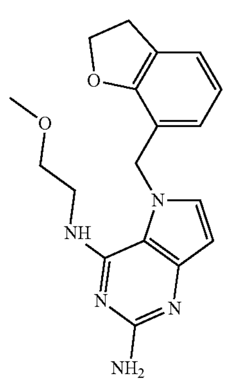 [SMILES: CCCCNc1nc(N)nc2ccn(Cc3cccc4c3OCC4)c12] | ¹H NMR (400 MHz, DMSO-d₆) δ ppm 3.16-3.24 (m, 5 H), 3.40 (t, J = 5.8 Hz, 2 H), 3.52 (q, J = 5.6 Hz, 2 H), 4.60 (t, J = 8.7 Hz, 2 H), 5.28 (s, 2 H), 5.31 (s, 2 6 H), 5.92 (t, J = 5.5 Hz, 1 H), 5.95 (d, J = 2.9 Hz, 1 H), 6.58 (d, J = 7.5 Hz, 1 H), 6.73 (t, J = 7.5 Hz, 1 H), 7.14 (d, J = 6.6 Hz, 1 H), 7.22 (d, J = 2.9 Hz, 1 H) | E, 1.4 | 340 |

TABLE 1-continued

Compounds of formula (I) and corresponding analytical data.

| # | STRUCTURE | ¹H NMR | LC Method, Rt (min) | LC-MS Mass Found |
|---|---|---|---|---|
| 151 | 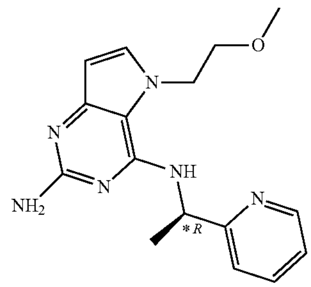 | ¹H NMR (400 MHz, chloroform-d) δ ppm 1.58 (d, J = 6.8 Hz, 3 H), 3.29 (s, 3 H), 3.70-3.79 (m, 2 H), 4.32-4.41 (m, 2 H), 4.50 (br. s., 2 H), 5.49 (t, J = 6.8 Hz, 1 H), 6.17 (d, J = 3.1 Hz, 1 H), 6.91 (d, J = 3.1 Hz, 1 H), 7.14 (ddd, J = 7.5, 4.8, 1.1 Hz, 2 H), 7.33 (d, J = 7.7 Hz, 1 H), 7.61 (td, J = 7.6, 1.8 Hz, 1 H), 8.50-8.60 (m, 1 H) | E, 1.2 | 313 |
| 152 | 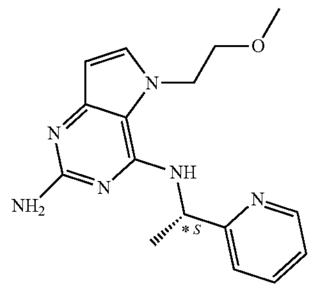 | ¹H NMR (400 MHz, chloroform-d) δ ppm 1.59 (d, J = 6.8 Hz, 3 H), 3.31 (s, 3 H), 3.71-3.82 (m, 2 H), 4.39 (d, J = 5.1 Hz, 2 H), 4.42 (br. s., 2 H), 5.50 (t, J = 6.7 Hz, 1 H), 6.18 (d, J = 2.9 Hz, 1 H), 6.93 (d, J = 3.1 Hz, 1 H), 7.10-7.20 (m, 2 H), 7.35 (d, J = 7.9 Hz, 1 H), 7.63 (td, J = 7.6, 1.8 Hz, 1 H), 8.53-8.60 (m, 1 H) | E, 1.44 | 313 |
| 153 | 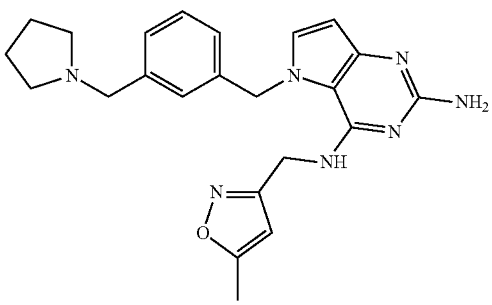 [SMILES: Cc1cc(CNc2nc(N)nc3ccn(Cc4cccc(CN5CCCC5)c4)c23)no1] | ¹H NMR (400 MHz, DMSO-d₆) δ ppm 1.63 (dt, J = 6.66, 3.16 Hz, 4 H) 2.27 (s, 3 H) 2.28-2.34 (m, 4 H) 3.44 (s, 2 H) 4.54 (d, J = 5.72 Hz, 2 H) 5.32 (s, 2 H) 5.48 (s, 2 H) 5.56 (d, J = 0.88 Hz, 1 H) 6.01 (d, J = 2.86 Hz, 1 H) 6.61 (t, J = 5.94 Hz, 1 H) 6.76 (d, J = 7.26 Hz, 1 H) 6.98 (s, 1 H) 7.12-7.20 (m, 2 H) 7.35 (d, J = 2.86 Hz, 1 H) | E, 1.07 | 418 |
| 154 | 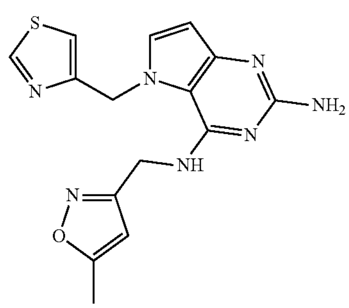 [SMILES: Cc1cc(CNc2nc(N)nc3ccn(Cc4cscn4)c23)no1] | ¹H NMR (400 MHz, DMSO-d₆) δ ppm 2.34 (s, 3 H) 4.62 (d, J = 5.72 Hz, 2 H) 5.34 (s, 2 H) 5.55 (s, 2 H) 5.97 (d, J = 3.08 Hz, 1 H) 6.02 (s, 1 H) 7.28 (t, J = 5.83 Hz, 1 H) 7.32 (d, J = 2.86 Hz, 1 H) 7.40 (d, J = 1.98 Hz, 1 H) 9.04 (d, J = 1.98 Hz, 1 H) | E, 1.14 | 342 |
| 155 | 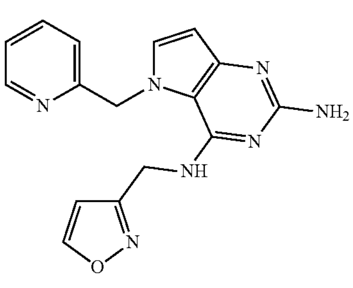 [SMILES: Nc1nc(NCc2ccon2)c2c(ccn2Cc2ccccn2)n1] | ¹H NMR (400 MHz, DMSO-d₆) δ ppm 4.70 (d, J = 5.72 Hz, 2 H) 5.37 (s, 2 H) 5.48 (s, 2 H) 5.98 (d, J = 3.08 Hz, 1 H) 6.38 (d, J = 1.76 Hz, 1 H) 7.20 (d, J = 7.70 Hz, 1 H) 7.32 (ddd, J = 7.54, 5.01, 1.10 Hz, 1 H) 7.41 (d, J = 3.08 Hz, 1 H) 7.79 (td, J = 7.70, 1.76 Hz, 1 H) 7.87 (t, J = 5.61 Hz, 1 H) 8.39-8.42 (m, 1 H) 8.77 (d, J = 1.76 Hz, 1 H) | E, 1.34 | 322 |

TABLE 1-continued

Compounds of formula (I) and corresponding analytical data.

| # | STRUCTURE | ¹H NMR | LC Method, Rt (min) | LC-MS Mass Found |
|---|---|---|---|---|
| 156 | 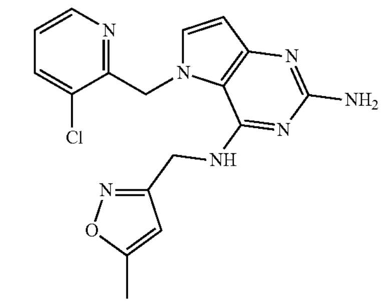 | ¹H NMR (400 MHz, DMSO-d₆) δ ppm 2.34 (d, J = 0.66 Hz, 3 H) 4.62 (d, J = 5.50 Hz, 2 H) 5.36 (s, 2 H) 5.62 (s, 2 H) 5.97 (d, J = 3.08 Hz, 1 H) 6.03 (d, J = 0.66 Hz, 1 H) 7.29 (d, J = 3.08 Hz, 1 H) 7.42 (dd, J = 8.14, 4.84 Hz, 1 H) 7.68 (t, J = 5.72 Hz, 1 H) 8.00 (dd, J = 8.14, 1.54 Hz, 1 H) 8.32 (dd, J = 4.73, 1.43 Hz, 1 H) | D, 0.74 | 370 |
| 157 | 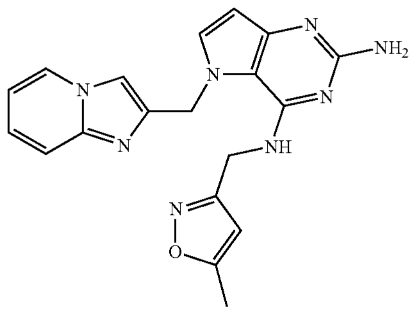 [SMILES: Cc1cc(CNc2nc(N)nc3ccn(Cc4cn5ccccc5n4)c23)no1] | ¹H NMR (400 MHz, DMSO-d₆) δ ppm 2.27 (s, 3 H) 4.68 (d, J = 5.72 Hz, 2 H) 5.33 (s, 2 H) 5.48 (s, 2 H) 5.94 (d, J = 2.86 Hz, 1 H) 6.01 (s, 1 H) 6.89 (td, J = 6.77, 1.21 Hz, 1 H) 7.26 (ddd, J = 9.08, 6.66, 1.21 Hz, 1 H) 7.35-7.38 (m, 2 H) 7.79 (s, 1 H) 8.30 (t, J = 5.72 Hz, 1 H) 8.51 (dt, J = 6.82, 1.10 Hz, 1 H) | D, 0.65 | 375 |
| 158 | 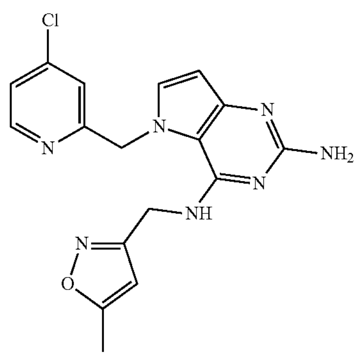 [SMILES: Cc1cc(CNc2nc(N)nc3ccn(Cc4cc(Cl)ccn4)c23)no1] | ¹H NMR (400 MHz, DMSO-d₆) δ ppm 2.33 (s, 3 H) 4.60 (d, J = 5.72 Hz, 2 H) 5.38 (s, 2 H) 5.52 (s, 2 H) 5.89 (s, 1 H) 6.01 (d, J = 3.08 Hz, 1 H) 7.18-7.22 (m, 1 H) 7.39-7.50 (m, 3 H) 8.41 (d, J = 5.50 Hz, 1 H) | E, 1.35 | 370 |
| 159 | 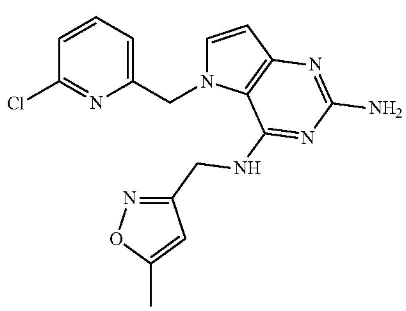 [SMILES: Cc1cc(CNc2nc(N)nc3ccn(Cc4cccc(Cl)n4)c23)no1] | ¹H NMR (400 MHz, DMSO-d₆) δ ppm 2.31 (s, 3 H) 4.56 (d, J = 5.72 Hz, 2 H) 5.39 (s, 2 H) 5.56 (s, 2 H) 5.75 (s, 1 H) 6.05 (d, J = 3.08 Hz, 1 H) 6.68 (d, J = 7.48 Hz, 1 H) 6.99 (t, J = 5.83 Hz, 1 H) 7.38 (d, J = 2.86 Hz, 1 H) 7.41 (d, J = 7.92 Hz, 1 H) 7.78 (t, J = 7.81 Hz, 1 H) | D, 0.73 | 370 |
| 160 | 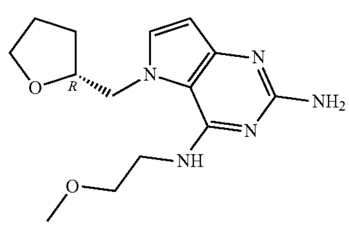 | ¹H NMR (400 MHz, DMSO-d₆) δ ppm 1.46-1.70 (m, 2 H), 1.70-1.83 (m, 1 H), 1.87-1.99 (m, 1 H), 3.29 (s, 3 H), 3.48-3.56 (m, 3 H), 3.56-3.65 (m, 2 H), 6 3.68-3.77 (m, 1 H), 4.05 (qd, J = 6.7, 2.8 Hz, 1 H), 4.14 (dd, J = 15.1, 6.5 Hz, 1 H), 4.35 (dd, J = 15.1, 2.8 Hz, 1 H), 5.23 (s, 2 H), 5.92 (d, J = 2.9 Hz, 1 H), 6.61 (t, J = 4.8 Hz, 1 H), 7.15 (d, J = 3.1 Hz, 1 H) | D, 0.58 | 292 |

TABLE 1-continued

Compounds of formula (I) and corresponding analytical data.

| # | STRUCTURE | ¹H NMR | LC Method, Rt (min) | LC-MS Mass Found |
|---|---|---|---|---|
| 161 | 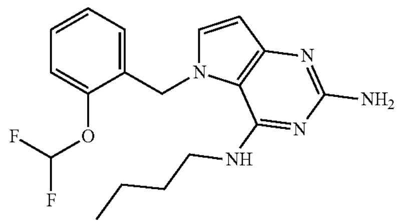 [SMILES: CCCCNc1nc(N)nc2ccn(Cc3ccccc3OC(F)F)c12] | ¹H NMR (400 MHz, DMSO-d₆) δ ppm 0.76 (t, J = 7.3 Hz, 3 H), 1.05 (dq, J = 15.0, 7.3 Hz, 2 H), 1.30-1.40 (m, 2 H), 3.24-3.30 (m, 2 H), 5.26 (s, 2 H), 5.51 (s, 6 2 H), 5.70 (t, J = 5.5 Hz, 1 H), 6.00 (d, J = 2.9 Hz, 1 H), 6.36-6.41 (m, 1 H), 7.06-7.12 (m, 1 H), 7.20-7.25 (m, 2 H), 7.29 (t, J = 73.8 Hz, 1 H), 7.30-7.36 (m, 1 H) | D, 0.94 | 362 |
| 162 | 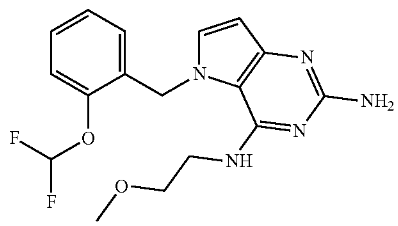 [SMILES: COCCNc1nc(N)nc2ccn(Cc3ccccc3OC(F)F)c12] | ¹H NMR (400 MHz, DMSO-d₆) δ ppm 3.13 (s, 3 H), 3.32-3.35 (m, 2 H), 3.46 (q, J = 5.6 Hz, 2 H), 5.32 (s, 2 H), 5.48 (s, 2 H), 5.80 (t, J = 5.4 Hz, 1 H), 6.01 (d, 6 J = 3.1 Hz, 1 H), 6.51 (dd, J = 7.7, 1.3 Hz, 1 H), 7.08-7.14 (m, 1 H), 7.20-7.25 (m, 2 H), 7.28 (t, J = 73.8 Hz, 1 H), 7.31-7.36 (m, 1 H) | D, 0.78 | 364 |
| 163 | 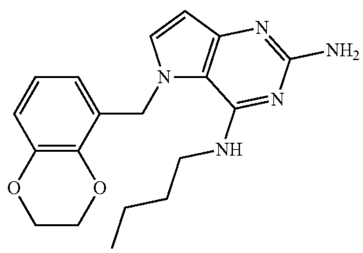 [SMILES: CCCCNc1nc(N)nc2ccn(Cc3cccc4c3OCCO4)c12] | ¹H NMR (400 MHz, DMSO-d₆) δ ppm 0.80 (t, J = 7.3 Hz, 3 H), 1.12 (dq, J = 15.0, 7.4 Hz, 2 H), 1.34-1.44 (m, 2 H), 3.26-3.31 (m, 2 H), 4.23-4.30 (m, 2 H), 6 4.30-4.37 (m, 2 H), 5.24 (s, 2 H), 5.38 (s, 2 H), 5.59 (t, J = 5.4 Hz, 1 H), 5.96 (d, J = 3.1 Hz, 1 H), 6.02 (dd, J = 7.6, 1.4 Hz, 1 H), 6.68 (t, J = 7.8 Hz, 1 H), 6.77 (dd, J = 8.1, 1.5 Hz, 1 H), 7.20 (d, J = 2.9 Hz, 1 H) | D, 0.9 | 354 |
| 164 | 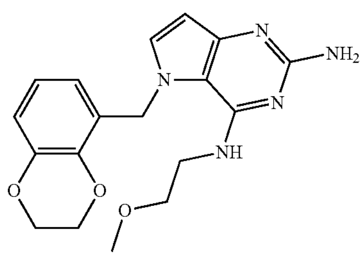 [SMILES: COCCNc1nc(N)nc2ccn(Cc3cccc4c3OCCO4)c12] | ¹H NMR (400 MHz, DMSO-d₆) δ ppm 3.16 (s, 3 H), 3.35-3.40 (m, 2 H), 3.51 (q, J = 5.6 Hz, 2 H), 4.24-4.31 (m, 2 H), 4.31-4.37 (m, 2 H), 5.35 (s, 2 H), 6 5.37 (br. s., 2 H), 5.78 (t, J = 5.4 Hz, 1 H), 5.97 (d, J = 3.1 Hz, 1 H), 6.16 (dd, J = 7.7, 1.5 Hz, 1 H), 6.70 (t, J = 7.8 Hz, 1 H), 6.76-6.81 (m, 1 H), 7.22 (d, J = 2.9 Hz, 1 H) | D, 0.74 | 356 |
| 165 | 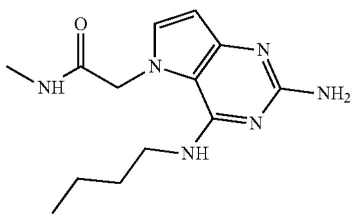 [SMILES: CCCCNc1nc(N)nc2ccn(CC(=O)NC)c12] | ¹H NMR (400 MHz, DMSO-d₆) δ ppm 3.16 (s, 3 H), 3.35-3.40 (m, 2 H), 3.51 (q, J = 5.6 Hz, 2 H), 4.24-4.31 (m, 2 H), 4.31-4.37 (m, 2 H), 5.35 (s, 2 H), 6 5.37 (br. s., 2 H), 5.78 (t, J = 5.4 Hz, 1 H), 5.97 (d, J = 3.1 Hz, 1 H), 6.16 (dd, J = 7.7, 1.5 Hz, 1 H), 6.70 (t, J = 7.8 Hz, 1 H), 6.76-6.81 (m, 1 H), 7.22 (d, J = 2.9 Hz, 1 H) | D, 0.6 | 277 |
| 166 | 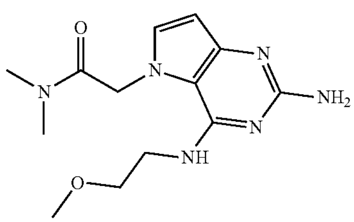 [SMILES: COCCNc1nc(N)nc2ccn(CC(=O)N(C)C)c12] | ¹H NMR (400 MHz, DMSO-d₆) δ ppm 0.92 (t, J = 7.4 Hz, 3 H), 1.37 (dq, J = 15.0, 7.3 Hz, 2 H), 1.51-1.62 (m, 2 H), 2.63 (d, J = 4.6 Hz, 3 H), 3.33-3.41 (m, 2 6 H), 4.74 (s, 2 H), 5.40 (br. s., 2 H), 5.94 (d, J = 2.9 Hz, 1 H), 6.93 (t, J = 5.2 Hz, 1 H), 7.11 (d, J = 3.1 Hz, 1 H), 8.31 (d, J = 4.4 Hz, 1 H) | D, 0.42 | 293 |

TABLE 1-continued

Compounds of formula (I) and corresponding analytical data.

| # | STRUCTURE | $^1$H NMR | LC Method, Rt (min) | LC-MS Mass Found |
|---|---|---|---|---|
| 167 | 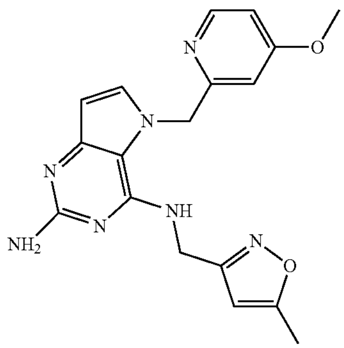 [SMILES: COc1ccnc(Cn2ccc3nc(N)nc(NCc4cc(C)on4)c32)c1] | $^1$H NMR (400 MHz, DMSO-d$_6$) δ ppm 2.34 (s, 3 H) 3.78 (s, 3 H) 4.63 (d, J = 5.50 Hz, 2 H) 5.33-5.39 (m, 4 H) 5.97 (d, J = 3.08 Hz, 1 H) 6.02 (s, 1 H) 6.90 (d, J = 2.42 Hz, 1 H) 6.93 (dd, J = 5.72, 2.42 Hz, 1 H) 7.41 (d, J = 3.08 Hz, 1 H) 8.16 (t, J = 5.61 Hz, 1 H) 8.22 (d, J = 5.94 Hz, 1 H) | D, 0.7 | 366 |
| 168 | 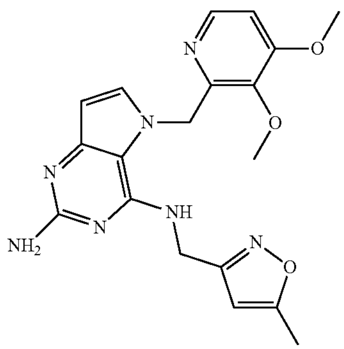 [SMILES: COc1ccnc(Cn2ccc3nc(N)nc(NCc4cc(C)on4)c32)c1OC] | $^1$H NMR (400 MHz, DMSO-d$_6$) δ ppm 2.36 (s, 3 H) 3.79 (s, 3 H) 3.88 (s, 3 H) 4.66 (d, J = 5.50 Hz, 2 H) 5.33 (s, 2 H) 5.36 (s, 2 H) 5.94 (d, J = 2.86 Hz, 1 H) 6.18 (s, 1 H) 7.14 (d, J = 5.72 Hz, 1 H) 7.23 (d, J = 3.08 Hz, 1 H) 8.00 (d, J = 5.50 Hz, 1 H) 8.50 (t, J = 5.50 Hz, 1 H) | E, 1.62 | 396 |
| 169 | 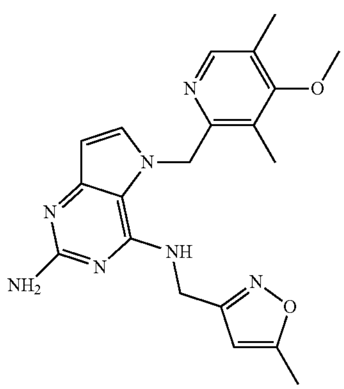 [SMILES: COc1c(C)cnc(Cn2ccc3nc(N)nc(NCc4cc(C)on4)c32)c1C] | $^1$H NMR (400 MHz, DMSO-d$_6$) δ ppm 2.17 (s, 3 H) 2.31 (s, 3 H) 2.35 (s, 3 H) 3.71 (s, 3 H) 4.63 (d, J = 5.50 Hz, 2 H) 5.32 (s, 2 H) 5.44 (s, 2 H) 5.94 (d, J = 3.08 Hz, 1 H) 6.10 (s, 1 H) 7.33 (d, J = 2.86 Hz, 1 H) 8.01 (s, 1 H) 8.49 (t, J = 5.50 Hz, 1 H) | E, 1.76 | 394 |
| 170 | 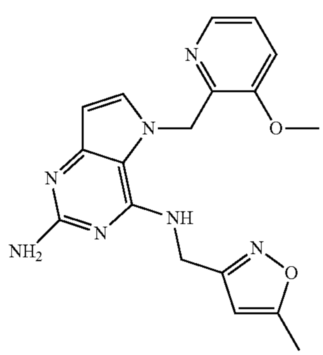 [SMILES: COc1cccnc1Cn1ccc2nc(N)nc(NCc3cc(C)on3)c21] | $^1$H NMR (400 MHz, DMSO-d$_6$) δ ppm 2.35 (s, 3 H) 3.88 (s, 3 H) 4.66 (d, J = 5.50 Hz, 2 H) 5.33 (s, 2 H) 5.40 (s, 2 H) 5.93 (d, J = 2.86 Hz, 1 H) 6.13 (s, 1 H) 7.23 (d, J = 3.08 Hz, 1 H) 7.38 (dd, J = 8.36, 4.62 Hz, 1 H) 7.52 (d, J = 7.92 Hz, 1 H) 7.92 (dd, J = 4.62, 1.10 Hz, 1 H) 8.19 (t, J = 5.50 Hz, 1 H) | E, 1.59 | 366 |

TABLE 1-continued

Compounds of formula (I) and corresponding analytical data.

| # | STRUCTURE | ¹H NMR | LC Method, Rt (min) | LC-MS Mass Found |
|---|---|---|---|---|
| 171 | 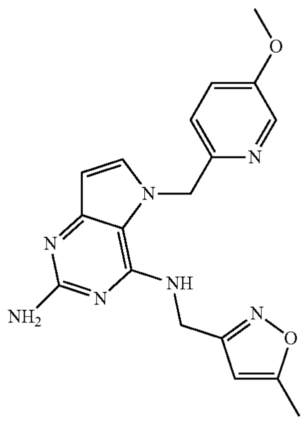 [SMILES: COc1ccc(Cn2ccc3nc(N)nc(NCc4cc(C)on4)c32)nc1] | ¹H NMR (400 MHz, DMSO-d$_6$) δ ppm 2.33 (s, 3 H) 3.79 (s, 3 H) 4.63 (d, J = 5.50 Hz, 2 H) 5.34 (s, 2 H) 5.40 (s, 2 H) 5.96 (d, J = 2.86 Hz, 1 H) 5.98 (d, J = 0.88 Hz, 1 H) 7.20 (d, J = 8.58 Hz, 1 H) 7.37-7.41 (m, 2 H) 7.79 (t, J = 5.72 Hz, 1 H) 8.09 (d, J = 2.64 Hz, 1 H) | E, 1.53 | 366 |
| 172 | 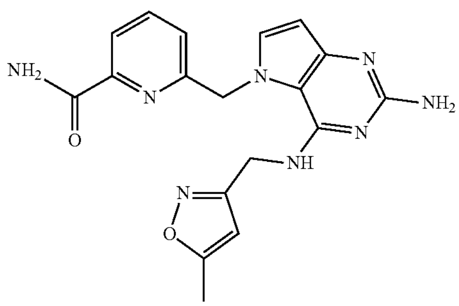 [SMILES: Cc1cc(CNc2nc(N)nc3ccn(Cc4cccc(C(N)=O)n4)c23)no1] | ¹H NMR (400 MHz, DMSO-d$_6$) δ ppm 2.27 (s, 3 H) 4.56 (d, J = 5.72 Hz, 2 H) 5.35 (s, 2 H) 5.59-5.64 (m, 3 H) 6.04 (d, J = 3.08 Hz, 1 H) 6.84 (t, J = 5.83 Hz, 1 H) 7.03 (dd, J = 6.05, 2.75 Hz, 1 H) 7.45 (d, J = 2.86 Hz, 1 H) 7.65 (br. s., 1 H) 7.80 (br. s., 1 H) 7.86-7.92 (m, 2 H) | E, 1.1 | 379 |
| 173 | 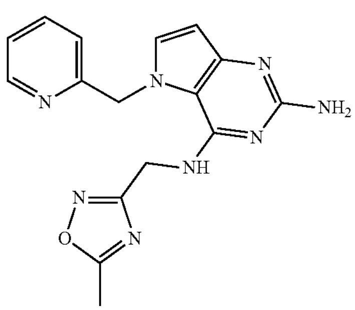 | ¹H NMR (400 MHz, DMSO-d$_6$) δ ppm 2.55 (s, 3 H) 4.76 (d, J = 5.50 Hz, 2 H) 5.30 (s, 2 H) 5.46 (s, 2 H) 5.98 (d, J = 2.86 Hz, 1 H) 7.31-7.36 (m, 2 H) 7.42 (d, J = 3.08 Hz, 1 H) 7.81 (td, J = 7.70, 1.76 Hz, 1 H) 8.06 (t, J = 5.61 Hz, 1 H) 8.44-8.47 (m, 1 H) | E, 1.34 | 337 |
| 174 | 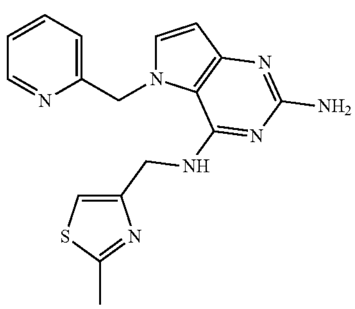 [SMILES: Cc1nc(CNc2nc(N)nc3ccn(Cc4ccccn4)c23)cs1] | ¹H NMR (400 MHz, DMSO-d$_6$) δ ppm 2.63 (s, 3 H) 4.67 (d, J = 5.28 Hz, 2 H) 5.32 (s, 2 H) 5.49 (s, 2 H) 5.98 (d, J = 2.86 Hz, 1 H) 7.02 (s, 1 H) 7.23 (d, J = 7.70 Hz, 1 H) 7.33 (dd, J = 6.93, 5.17 Hz, 1 H) 7.40 (d, J = 3.08 Hz, 1 H) 7.75-7.83 (m, 2 H) 8.43 (d, J = 4.40 Hz, 1 H) | D, 0.66 | 352 |

TABLE 1-continued

Compounds of formula (I) and corresponding analytical data.

| # | STRUCTURE | ¹H NMR | LC Method, Rt (min) | LC-MS Mass Found |
|---|---|---|---|---|
| 175 | 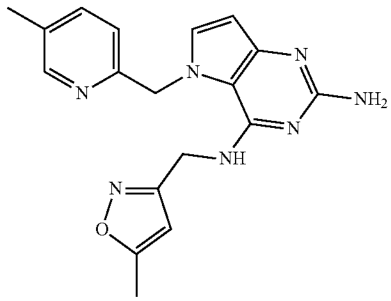 [SMILES: Cc1ccc(Cn2ccc3nc(N)nc(NCc4cc(C)on4)c32)nc1] | ¹H NMR (400 MHz, DMSO-$d_6$) δ ppm 2.25 (s, 3 H) 2.34 (s, 3 H) 4.62 (d, J = 5.50 Hz, 2 H) 5.34 (s, 2 H) 5.42 (s, 2 H) 5.96-5.99 (m, 2 H) 7.12 (d, J = 7.92 Hz, 1 H) 7.39 (d, J = 2.86 Hz, 1 H) 7.60 (dd, J = 8.03, 2.09 Hz, 1 H) 7.84 (t, J = 5.61 Hz, 1 H) 8.22-8.25 (m, 1 H) | D, 0.72 | 350 |
| 176 | 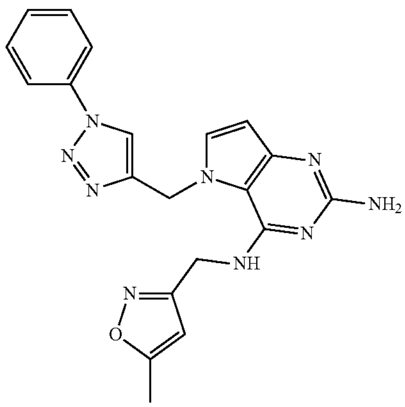 [SMILES: Cc1cc(CNc2nc(N)nc3ccn(Cc4cn(-c5ccccc5)nn4)c23)no1] | ¹H NMR (400 MHz, DMSO-$d_6$) δ ppm 2.22 (s, 3 H) 4.67 (d, J = 5.72 Hz, 2 H) 5.35 (s, 2 H) 5.63 (s, 2 H) 5.98 (d, J = 3.08 Hz, 1 H) 6.07-6.09 (m, 1 H) 7.07 (t, J = 5.83 Hz, 1 H) 7.34 (d, J = 3.08 Hz, 1 H) 7.46-7.51 (m, 1 H) 7.55-7.61 (m, 2 H) 7.79-7.84 (m, 2 H) 8.57 (s, 1 H) | E, 1.35 | 402 |
| 177 | 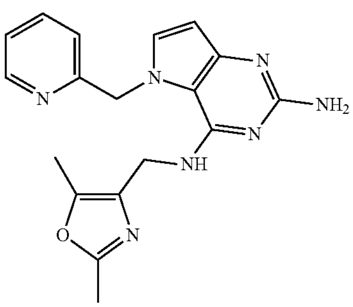 [SMILES: Cc1nc(CNc2nc(N)nc3ccn(Cc4ccccn4)c23)c(C)o1] | ¹H NMR (400 MHz, DMSO-$d_6$) δ ppm 2.25 (s, 3 H) 2.32 (s, 3 H) 4.37 (d, J = 5.06 Hz, 2 H) 5.26 (s, 2 H) 5.40 (s, 2 H) 5.95 (d, J = 3.08 Hz, 1 H) 7.31-7.37 (m, 2 H) 7.39 (d, J = 3.08 Hz, 1 H) 7.77-7.82 (m, 2 H) 8.45-8.48 (m, 1 H) | E, 1.23 | 350 |
| 178 | 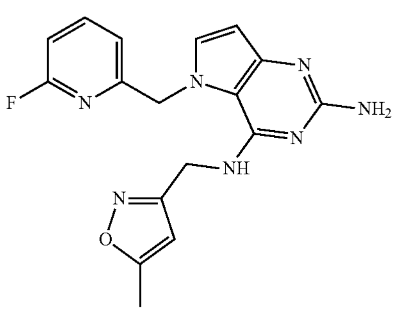 [SMILES: Cc1cc(CNc2nc(N)nc3ccn(Cc4cccc(F)n4)c23)no1] | ¹H NMR (400 MHz, DMSO-$d_6$) δ ppm 2.30 (s, 3 H) 4.56 (d, J = 5.72 Hz, 2 H) 5.38 (s, 2 H) 5.54 (s, 2 H) 5.75-5.80 (m, 1 H) 6.04 (d, J = 2.86 Hz, 1 H) 6.66 (dd, J = 7.37, 2.31 Hz, 1 H) 6.87 (t, J = 5.83 Hz, 1 H) 7.06 (dd, J = 8.14, 2.20 Hz, 1 H) 7.36 (d, J = 2.86 Hz, 1 H) 7.85-7.92 (m, 1 H) | F, 4 | 354 |

TABLE 1-continued

Compounds of formula (I) and corresponding analytical data.

| # | STRUCTURE | ¹H NMR | LC Method, Rt (min) | LC-MS Mass Found |
|---|---|---|---|---|
| 179 | 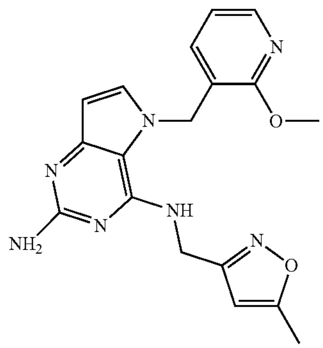 [SMILES: COc1ncccc1Cn1ccc2nc(N)nc(NCc3cc(C)on3)c21] | ¹H NMR (400 MHz, DMSO-d$_6$) δ ppm 2.30 (s, 3 H) 3.90 (s, 3 H) 4.53 (d, J = 5.72 Hz, 2 H) 5.38 (s, 2 H) 5.42 (s, 2 H) 5.72 (s, 1 H) 6.03 (d, J = 3.08 Hz, 1 H) 6.60-6.65 (m, 2 H) 6.84 (dd, J = 7.26, 5.06 Hz, 1 H) 7.27 (d, J = 2.86 Hz, 1 H) 8.05 (dd, J = 4.95, 1.65 Hz, 1 H) | E, 1.27 | 366 |
| 180 | 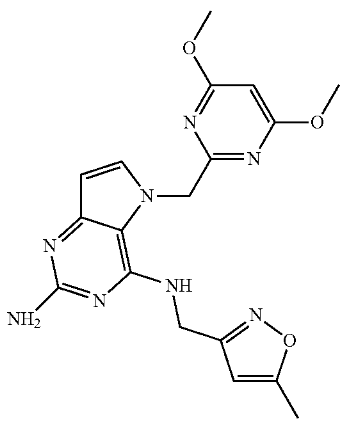 [SMILES: COc1cc(OC)nc(Cn2ccc3nc(N)nc(NCc4cc(C)on4)c32)n1] | ¹H NMR (400 MHz, DMSO-d$_6$) δ ppm 2.31 (s, 3 H) 3.69 (s, 6 H) 4.58 (d, J = 5.50 Hz, 2 H) 5.33 (s, 2 H) 5.43 (s, 2 H) 5.92 (s, 1 H) 5.99 (d, J = 2.64 Hz, 1 H) 6.11 (s, 1 H) 6.80 (t, J = 5.61 Hz, 1 H) 7.27 (d, J = 2.64 Hz, 1 H) | E, 1.34 | 397 |
| 181 | 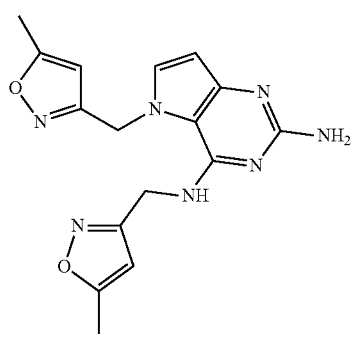 [SMILES: Cc1cc(CNc2nc(N)nc3ccn(Cc4cc(C)on4)c23)no1] | ¹H NMR (400 MHz, DMSO-d$_6$) δ ppm 2.30 (s, 3 H) 2.34 (s, 3 H) 4.61 (d, J = 5.72 Hz, 2 H) 5.38 (s, 2 H) 5.52 (s, 2 H) 5.83 (s, 1 H) 6.00 (d, J = 3.08 Hz, 1 H) 6.04 (s, 1 H) 6.85 (t, J = 5.72 Hz, 1 H) 7.29 (d, J = 3.08 Hz, 1 H) | E, 1.17 | 340 |
| 182 | 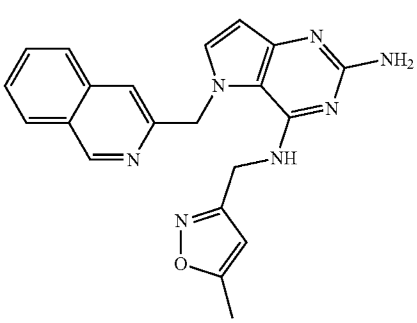 [SMILES: Cc1cc(CNc2nc(N)nc3ccn(Cc4cc5ccccc5cn4)c23)no1] | ¹H NMR (400 MHz, DMSO-d$_6$) δ ppm 2.20 (s, 3 H) 4.63 (d, J = 5.72 Hz, 2 H) 5.34 (s, 2 H) 5.64 (s, 2 H) 5.82 (s, 1 H) 6.01 (d, J = 3.08 Hz, 1 H) 7.45 (d, J = 3.08 Hz, 1 H) 7.58 (s, 1 H) 7.66-7.70 (m, 1 H) 7.75-7.80 (m, 2 H) 7.85-7.89 (m, 1 H) 8.13 (d, J = 8.14 Hz, 1 H) 9.20 (s, 1 H) | E, 1.47 | 386 |

TABLE 1-continued

Compounds of formula (I) and corresponding analytical data.

| # | STRUCTURE | ¹H NMR | LC Method, Rt (min) | LC-MS Mass Found |
|---|---|---|---|---|
| 183 | 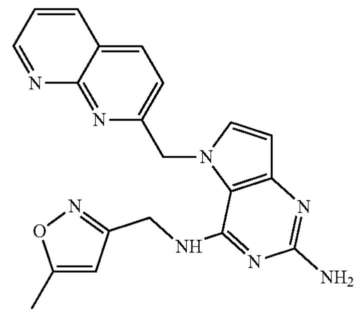 [SMILES: Cc1cc(CNc2nc(N)nc3ccn(Cc4ccc5cccnc5n4)c23)no1] | ¹H NMR (400 MHz, DMSO-d₆) δ ppm 2.07 (s, 1 H) 2.14 (s, 3 H) 4.57 (d, J = 5.72 Hz, 2 H) 5.35 (s, 1 H) 5.77-5.82 (m, 3 H) 6.06 (d, J = 2.86 Hz, 1 H) 7.18 (d, J = 8.36 Hz, 1 H) 7.51 (d, J = 2.86 Hz, 1 H) 7.56 (t, J = 5.72 Hz, 1 H) 7.64 (dd, J = 8.14, 4.18 Hz, 1 H) 8.45 (d, J = 8.36 Hz, 2 H) 9.09 (dd, J = 4.07, 1.65 Hz, 1 H) | E, 1.03 | 387 |
| 184 | 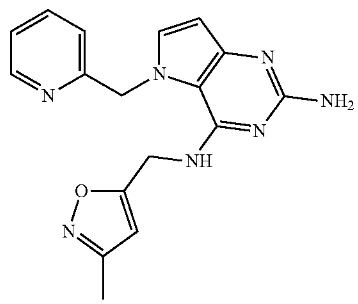 [SMILES: Cc1cc(CNc2nc(N)nc3ccn(Cc4ccccn4)c23)on1] | ¹H NMR (400 MHz, DMSO-d₆) δ ppm 2.16 (s, 3 H) 4.71 (d, J = 5.50 Hz, 2 H) 5.37 (s, 2 H) 5.50 (s, 2 H) 5.95 (s, 1 H) 5.99 (d, J = 2.86 Hz, 1 H) 7.18 (d, J = 7.70 Hz, 1 H) 7.35 (dd, J = 6.82, 5.06 Hz, 1 H) 7.42 (d, J = 3.08 Hz, 1 H) 7.81 (td, J = 7.65, 1.65 Hz, 1 H) 7.88 (t, J = 5.50 Hz, 1 H) 8.47 (d, J = 4.40 Hz, 1 H) | E, 1.11 | 336 |
| 185 | 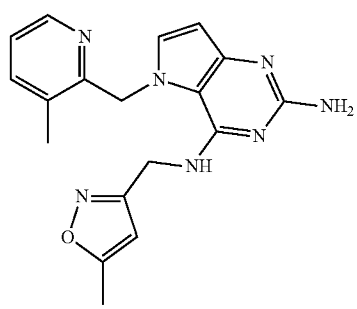 [SMILES: Cc1cc(CNc2nc(N)nc3ccn(Cc4ncccc4C)c23)no1] | ¹H NMR (400 MHz, DMSO-d₆) δ ppm 2.34 (s, 3 H) 2.42 (s, 3 H) 4.63 (d, J = 5.72 Hz, 2 H) 5.34 (s, 2 H) 5.49 (s, 2 H) 5.95 (d, J = 2.86 Hz, 1 H) 6.07 (s, 1 H) 7.27 (dd, J = 7.70, 4.84 Hz, 1 H) 7.32 (d, J = 3.08 Hz, 1 H) 7.66 (d, J = 7.48 Hz, 1 H) 8.17 (dd, J = 4.73, 0.99 Hz, 1 H) 8.35 (t, J = 5.61 Hz, 1 H) | E, 1.35 | 350 |
| 186 | 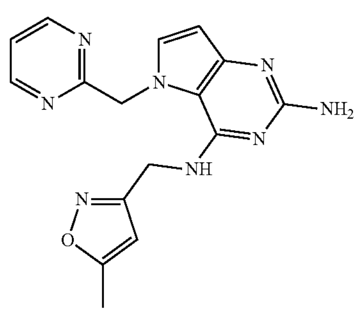 [SMILES: Cc1cc(CNc2nc(N)nc3ccn(Cc4ncccn4)c23)no1] | ¹H NMR (400 MHz, DMSO-d₆) δ ppm 2.31-2.36 (m, 3 H) 4.58 (d, J = 5.72 Hz, 2 H) 5.34 (s, 2 H) 5.62 (s, 2 H) 5.93 (d, J = 0.66 Hz, 1 H) 5.97 (d, J = 3.08 Hz, 1 H) 7.13 (t, J = 5.61 Hz, 1 H) 7.30 (d, J = 3.08 Hz, 1 H) 7.43 (t, J = 4.95 Hz, 1 H) 8.72 (d, J = 5.06 Hz, 2 H) | E, 0.98 | 337 |

TABLE 1-continued

Compounds of formula (I) and corresponding analytical data.

| # | STRUCTURE | ¹H NMR | LC Method, Rt (min) | LC-MS Mass Found |
|---|---|---|---|---|
| 187 | 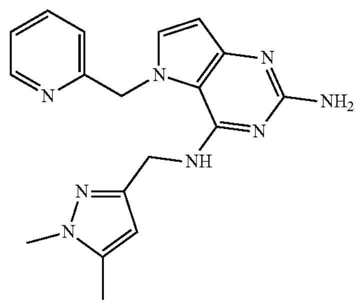 [SMILES: Cc1cc(CNc2nc(N)nc3ccn(Cc4ccccn4)c23)nn1C] | ¹H NMR (400 MHz, DMSO-d$_6$) δ ppm 2.17 (s, 3 H) 3.65 (s, 3 H) 4.46 (d, J = 5.28 Hz, 2 H) 5.29 (s, 2 H) 5.44 (s, 2 H) 5.76 (s, 1 H) 5.96 (d, J = 3.08 Hz, 1 H) 7.20 (d, J = 7.92 Hz, 1 H) 7.30-7.34 (m, 1 H) 7.38 (d, J = 3.08 Hz, 1 H) 7.51 (t, J = 5.28 Hz, 1 H) 7.78 (td, J = 7.70, 1.76 Hz, 1 H) 8.39 (d, J = 4.18 Hz, 1 H) | E, 1.16 | 349 |
| 188 | 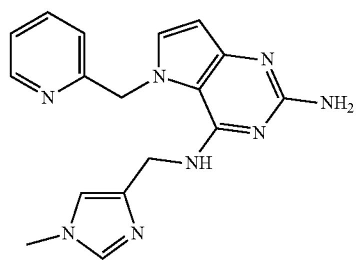 [SMILES: Cn1cnc(CNc2nc(N)nc3ccn(Cc4ccccn4)c23)c1] | ¹H NMR (400 MHz, DMSO-d$_6$) δ ppm 3.57 (s, 3 H) 4.45 (d, J = 5.06 Hz, 2 H) 5.34 (br. s., 2 H) 5.44 (s, 2 H) 5.97 (d, J = 2.86 Hz, 1 H) 6.76 (s, 1 H) 7.24 (d, J = 7.70 Hz, 1 H) 7.33 (dd, J = 7.04, 5.28 Hz, 1 H) 7.39 (d, J = 2.86 Hz, 1 H) 7.47 (s, 1 H) 7.64 (t, J = 4.84 Hz, 1 H) 7.77-7.83 (m, 1 H) 8.43 (d, J = 4.40 Hz, 1 H) | E, 0.92 | 335 |
| 189 | 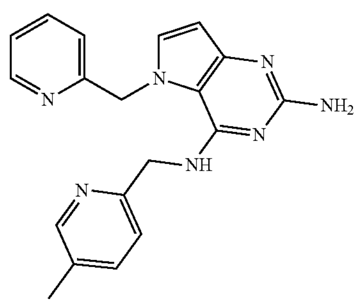 [SMILES: Cc1ccc(CNc2nc(N)nc3ccn(Cc4ccccn4)c23)nc1] | ¹H NMR (400 MHz, DMSO-d$_6$) δ ppm 2.25 (s, 3 H) 4.67 (d, J = 5.50 Hz, 2 H) 5.26 (s, 2 H) 5.54 (s, 2 H) 5.99 (d, J = 2.86 Hz, 1 H) 6.97 (d, J = 7.92 Hz, 1 H) 7.13 (d, J = 7.92 Hz, 1 H) 7.32 (ddd, J = 6.93, 5.61, 0.88 Hz, 1 H) 7.41 (d, J = 3.08 Hz, 1 H) 7.43 (dd, J = 8.14, 1.98 Hz, 1 H) 7.62 (t, J = 5.61 Hz, 1 H) 7.79 (td, J = 7.70, 1.76 Hz, 1 H) 8.30-8.32 (m, 1 H) 8.43 (dd, J = 4.95, 0.77 Hz, 1 H) | E, 1.27 | 346 |
| 190 | 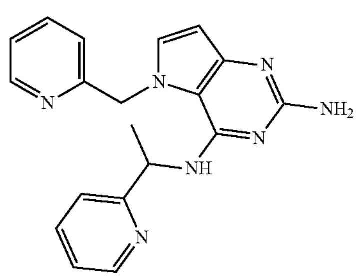 [SMILES: CC(Nc1nc(N)nc2ccn(Cc3ccccn3)c12)c1ccccn1] | ¹H NMR (400 MHz, DMSO-d$_6$) δ ppm 1.52 (d, J = 6.82 Hz, 3 H) 5.21 (s, 2 H) 5.43 (quin, J = 6.82 Hz, 1 H) 5.48-5.60 (m, 2 H) 5.97 (d, J = 2.86 Hz, 1 H) 7.18-7.25 (m, 1 H) 7.27-7.39 (m, 3 H) 7.44 (d, J = 2.86 Hz, 1 H) 7.63-7.69 (m, 1 H) 7.76 (d, J = 7.26 Hz, 1 H) 7.80-7.88 (m, 1 H) 8.46-8.52 (m, 2 H) | E, 1.31 | 346 |
| 191 | 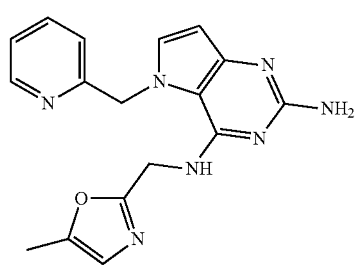 [SMILES: Cc1cnc(CNc2nc(N)nc3ccn(Cc4ccccn4)c23)o1] | ¹H NMR (400 MHz, DMSO-d$_6$) δ ppm 2.23 (d, J = 1.10 Hz, 3 H) 4.72 (d, J = 5.50 Hz, 2 H) 5.31 (s, 2 H) 5.47 (s, 2 H) 5.98 (d, J = 2.86 Hz, 1 H) 6.73 (d, J = 1.10 Hz, 1 H) 7.28-7.36 (m, 2 H) 7.42 (d, J = 3.08 Hz, 1 H) 7.81 (td, J = 7.70, 1.76 Hz, 1 H) 7.99 (t, J = 5.50 Hz, 1 H) 8.40-8.44 (m, 1 H) | E, 1.11 | 336 |

TABLE 1-continued

Compounds of formula (I) and corresponding analytical data.

| # | STRUCTURE | ¹H NMR | LC Method, Rt (min) | LC-MS Mass Found |
|---|---|---|---|---|
| 192 | 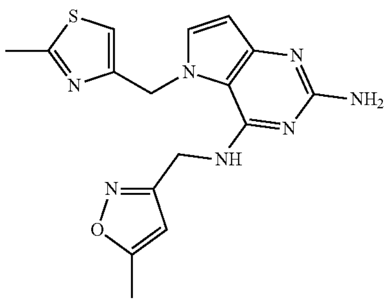 [SMILES: Cc1cc(CNc2nc(N)nc3ccn(Cc4csc(C)n4)c23)no1] | ¹H NMR (400 MHz, DMSO-d$_6$) δ ppm 2.34 (d, J = 0.7 Hz, 3 H), 2.53 (s, 3 H), 4.64 (d, J = 5.7 Hz, 2 H), 5.35 (s, 2 H), 5.41 (s, 2 H), 5.95 (d, J = 3.1 Hz, 1 H), 6 6.08 (d, J = 0.7 Hz, 1 H), 7.27 (s, 1 H), 7.31 (d, J = 3.1 Hz, 1 H), 7.57 (t, J = 5.7 Hz, 1 H) | D, 0.7 | 356 |
| 193 | 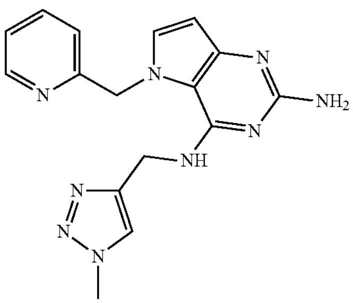 [SMILES: Cn1cc(CNc2nc(N)nc3ccn(Cc4ccccn4)c23)nn1] | ¹H NMR (400 MHz, DMSO-d$_6$) δ ppm 3.98 (s, 3 H) 4.62 (d, J = 5.28 Hz, 2 H) 5.36 (s, 2 H) 5.44 (s, 2 H) 5.96 (d, J = 2.86 Hz, 1 H) 7.25 (d, J = 7.70 Hz, 1 H) 7.31-7.35 (m, 1 H) 7.38 (d, J = 3.08 Hz, 1 H) 7.77-7.83 (m, 2 H) 7.89 (t, J = 5.39 Hz, 1 H) 8.41 (dd, J = 4.84, 0.66 Hz, 1 H) | E, 0.93 | 336 |
| 194 | 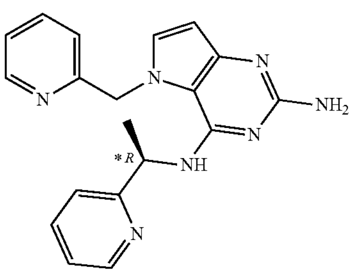 | ¹H NMR (400 MHz, DMSO-d$_6$) δ ppm 1.52 (d, J = 7.04 Hz, 3 H) 5.21 (s, 2 H) 5.43 (quin, J = 7.04 Hz, 1 H) 5.47-5.58 (m, 2 H) 5.97 (d, J = 2.86 Hz, 1 H) 7.19-7.23 (m, 1 H) 7.28-7.38 (m, 3 H) 7.44 (d, J = 3.08 Hz, 1 H) 7.66 (td, J = 7.70, 1.76 Hz, 1 H) 7.76 (d, J = 7.26 Hz, 1 H) 7.84 (td, J = 7.70, 1.76 Hz, 1 H) 8.47-8.51 (m, 2 H). | E, 1.27 | 346 |
| 195 | 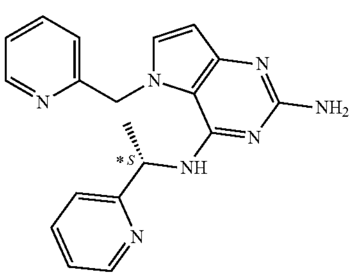 | ¹H NMR (400 MHz, DMSO-d$_6$) δ ppm 1.52 (d, J = 6.82 Hz, 3 H) 5.21 (s, 2 H) 5.42 (quin, J = 6.99 Hz, 1 H) 5.47-5.58 (m, 2 H) 5.97 (d, J = 2.86 Hz, 1 H) 7.19-7.23 (m, 1 H) 7.28-7.38 (m, 3 H) 7.44 (d, J = 3.08 Hz, 1 H) 7.66 (td, J = 7.65, 1.65 Hz, 1 H) 7.77 (d, J = 7.26 Hz, 1 H) 7.84 (td, J = 7.59, 1.32 Hz, 1 H) 8.47-8.51 (m, 2 H) | E, 1.27 | 346 |
| 196 | 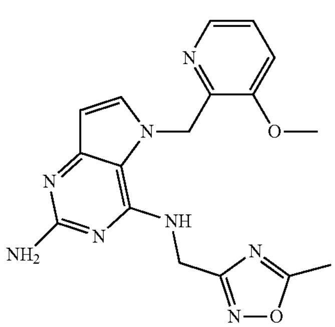 [SMILES: COc1cccnc1Cn1ccc2nc(N)nc(NCc3noc(C)n3)c21] | ¹H NMR (400 MHz, DMSO-d$_6$) δ ppm 2.56 (s, 3 H) 3.90 (s, 3 H) 4.81 (d, J = 5.72 Hz, 2 H) 5.27 (s, 2 H) 5.40 (s, 2 H) 5.93 (d, J = 3.08 Hz, 1 H) 7.25 (d, J = 3.08 Hz, 1 H) 7.40 (dd, J = 8.36, 4.84 Hz, 1 H) 7.52-7.56 (m, 1 H) 7.98 (dd, J = 4.84, 1.10 Hz, 1 H) 8.41 (t, J = 5.50 Hz, 1 H) | E, 1.24 | 367 |

TABLE 1-continued

Compounds of formula (I) and corresponding analytical data.

| # | STRUCTURE | ¹H NMR | LC Method, Rt (min) | LC-MS Mass Found |
|---|---|---|---|---|
| 197 | 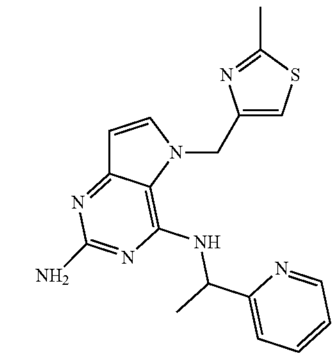 [SMILES: Cc1nc(Cn2ccc3nc(N)nc(NC(C)c4ccccn4)c32)cs1] | ¹H NMR (400 MHz, DMSO-d$_6$) δ ppm 1.55 (d, J = 7.0 Hz, 3 H), 2.58 (s, 3 H), 5.22 (s, 2 H), 5.41-5.49 (m, 1 H), 5.46 (d, J = 6.8 Hz, 2 H), 5.94 (d, J = 3.1 Hz, 1 6 H), 7.23 (ddd, J = 7.5, 4.8, 0.9 Hz, 1 H), 7.34 (d, J = 3.1 Hz, 1 H), 7.38 (d, J = 8.1 Hz, 1 H), 7.40 (s, 1 H), 7.47 (d, J = 7.5 Hz, 1 H), 7.69 (td, J = 7.7, 1.8 Hz, 1 H), 8.47-8.54 (m, 1 H) | E, 1.37 | 366 |
| 198 | 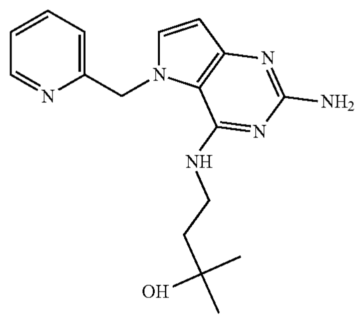 [SMILES: CC(C)(O)CCNc1nc(N)nc2ccn(Cc3ccccn3)c12] | ¹H NMR (400 MHz, DMSO-d$_6$) δ ppm 1.15 (s, 6 H) 1.69-1.74 (m, 2 H) 3.57-3.64 (m, 2 H) 5.62 (s, 2 H) 6.22 (d, J = 2.86 Hz, 1 H) 7.34-7.48 (m, 4 H) 7.67 (d, J = 3.08 Hz, 1 H) 7.91 (td, J = 7.70, 1.76 Hz, 1 H) 8.56-8.59 (m, 1 H) 8.79 (t, J = 4.80 Hz, 1 H) 12.51 (br. s., 1 H) | E, 1.09 | 327 |
| 199 | 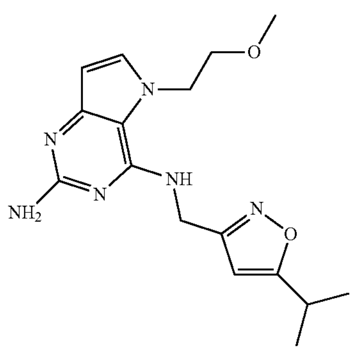 [SMILES: COCCn1ccc2nc(N)nc(NCc3cc(C(C)C)on3)c21] | ¹H NMR (400 MHz, DMSO-d$_6$) δ ppm 1.21 (d, J = 7.04 Hz, 6 H) 2.97-3.10 (m, 1 H) 3.14-3.18 (m, 3 H) 3.56 (t, J = 4.95 Hz, 2 H) 4.37 (t, J = 5.06 Hz, 2 H) 4.65 (d, J = 5.72 Hz, 2 H) 5.37 (s, 2 H) 5.93 (d, J = 3.08 Hz, 1 H) 6.18 (s, 1 H) 6.86 (t, J = 5.61 Hz, 1 H) 7.17 (d, J = 3.08 Hz, 1 H) | D, 0.74 | 331 |
| 200 | 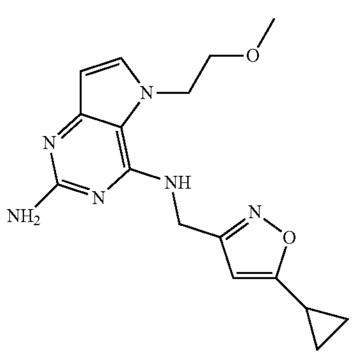 [SMILES: COCCn1ccc2nc(N)nc(NCc3cc(C4CC4)on3)c21] | ¹H NMR (400 MHz, DMSO-d$_6$) δ ppm 0.78-0.90 (m, 2 H) 0.94-1.06 (m, 2 H) 2.03-2.17 (m, 1 H) 3.11-3.18 (m, 3 H) 3.55 (t, J = 5.06 Hz, 2 H) 4.36 (t, J = 5.06 Hz, 2 H) 4.61 (d, J = 5.72 Hz, 2 H) 5.36 (s, 2 H) 5.92 (d, J = 3.08 Hz, 1 H) 6.15 (s, 1 H) 6.84 (t, J = 5.72 Hz, 1 H) 7.17 (d, J = 3.08 Hz, 1 H) | D, 0.69 | 329 |

TABLE 1-continued

Compounds of formula (I) and corresponding analytical data.

| # | STRUCTURE | ¹H NMR | LC Method, Rt (min) | LC-MS Mass Found |
|---|-----------|--------|---------------------|------------------|
| 201 | 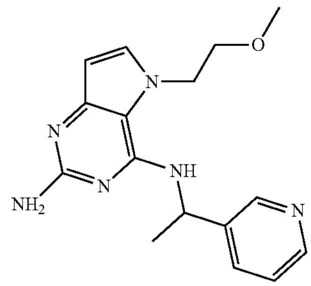 [SMILES: COCCn1ccc2nc(N)nc(NC(C)c3cccnc3)c21] | ¹H NMR (400 MHz, DMSO-d$_6$) δ ppm 1.54 (d, J = 7.04 Hz, 3 H) 3.20 (s, 3 H) 3.63 (dt, J = 5.94, 3.19 Hz, 2 H) 4.32-4.50 (m, 2 H) 5.23 (s, 2 H) 5.42 (t, J = 7.04 Hz, 1 H) 5.92 (d, J = 2.86 Hz, 1 H) 6.68 (d, J = 7.04 Hz, 1 H) 7.18 (d, J = 3.08 Hz, 1 H) 7.34 (ddd, J = 7.87, 4.68, 0.66 Hz, 1 H) 7.84 (dt, J = 7.92, 1.76 Hz, 1 H) 8.42 (dd, J = 4.62, 1.54 Hz, 1 H) 8.68 (d, J = 2.20 Hz, 1 H) | D, 0.6 | 313 |
| 202 | 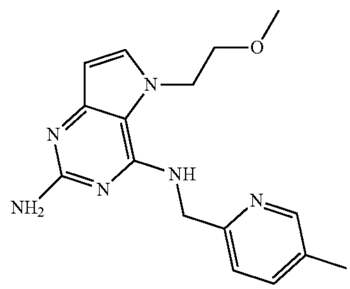 [SMILES: COCCn1ccc2nc(N)nc(NCc3ccc(C)cn3)c21] | ¹H NMR (400 MHz, DMSO-d$_6$) δ ppm 2.27 (s, 3 H) 3.17-3.19 (m, 3 H) 3.61 (t, J = 5.06 Hz, 2 H) 4.40 (t, J = 5.06 Hz, 2 H) 4.70 (d, J = 5.50 Hz, 2 H) 5.23 (s, 2 H) 5.92 (d, J = 3.08 Hz, 1 H) 6.96 (t, J = 5.61 Hz, 1 H) 7.17 (d, J = 2.86 Hz, 1 H) 7.27 (d, J = 7.92 Hz, 1 H) 7.55 (dd, J = 8.03, 1.65 Hz, 1 H) 8.26-8.42 (m, 1 H) | D, 0.64 | 313 |
| 203 | 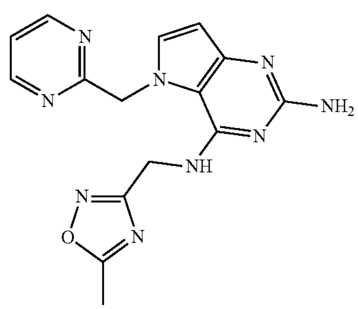 [SMILES: Cc1nc(CNc2nc(N)nc3ccn(Cc4ncccn4)c23)no1] | ¹H NMR (400 MHz, DMSO-d$_6$) δ ppm 2.54 (s, 3 H) 4.72 (d, J = 5.72 Hz, 2 H) 5.30 (s, 2 H) 5.59 (s, 2 H) 5.98 (d, J = 3.08 Hz, 1 H) 7.30-7.35 (m, 2 H) 7.45 (t, J = 4.95 Hz, 1 H) 8.75 (d, J = 4.84 Hz, 2 H) | D, 0.48 | 338 |
| 204 | 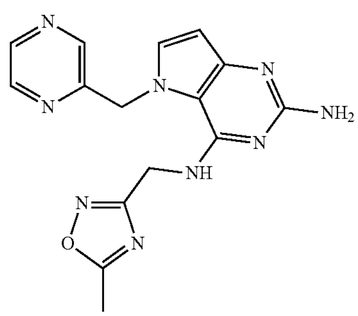 [SMILES: Cc1nc(CNc2nc(N)nc3ccn(Cc4cnccn4)c23)no1] | ¹H NMR (400 MHz, DMSO-d$_6$) δ ppm 2.54 (s, 3 H) 4.71 (d, J = 5.72 Hz, 2 H) 5.33 (s, 2 H) 5.63 (s, 2 H) 6.02 (d, J = 3.08 Hz, 1 H) 7.22-7.30 (m, 1 H) 7.41 (d, J = 3.08 Hz, 1 H) 8.43 (s, 1 H) 8.52 (dd, J = 2.42, 1.54 Hz, 1 H) 8.56 (d, J = 2.42 Hz, 1 H) | E, 0.92 | 338 |
| 205 | 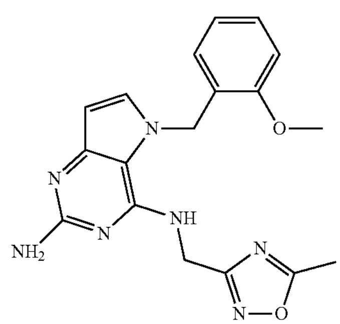 [SMILES: COc1ccccc1Cn1ccc2nc(N)nc(NCc3noc(C)n3)c21] | ¹H NMR (400 MHz, DMSO-d$_6$) δ ppm 2.57 (s, 3 H) 3.80 (s, 3 H) 4.85 (d, J = 5.72 Hz, 2 H) 5.56 (s, 2 H) 6.24 (d, J = 2.86 Hz, 1 H) 6.84-6.90 (m, 2 H) 7.03 (d, J = 8.14 Hz, 1 H) 7.28-7.34 (m, 1 H) 7.40 (d, J = 2.86 Hz, 1 H) 7.49 (br. s., 2 H) 8.22-8.28 (m, 1 H) 12.89 (br. s., 1 H) | E, 1.31 | 366 |

TABLE 1-continued

Compounds of formula (I) and corresponding analytical data.

| # | STRUCTURE | $^1$H NMR | LC Method, Rt (min) | LC-MS Mass Found |
|---|---|---|---|---|
| 206 | 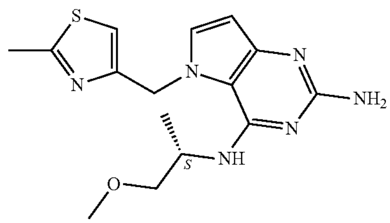 | $^1$H NMR (400 MHz, DMSO-d$_6$) δ ppm 1.21 (d, J = 6.6 Hz, 3 H), 2.65 (s, 3 H), 3.27 (s, 3 H), 3.32-3.35 (m, 1 H), 3.47 (dd, J = 9.2, 5.1 Hz, 1 H), 4.35-4.55 (m, 6 1 H), 5.25 (s, 2 H), 5.36 (d, J = 4.8 Hz, 2 H), 5.92 (d, J = 3.1 Hz, 1 H), 6.76 (d, J = 7.5 Hz, 1 H), 7.30 (d, J = 3.1 Hz, 1 H), 7.40 (s, 1 H). | E, 1.33 | 333 |
| 207 | 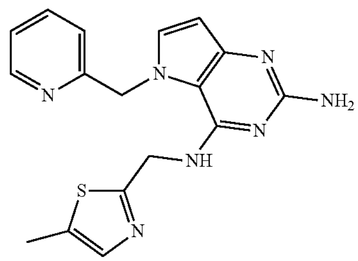 | $^1$H NMR (400 MHz, DMSO-d$_6$) δ ppm 2.37 (s, 3 H) 4.97 (d, J = 5.06 Hz, 2 H) 5.81 (s, 2 H) 6.31 (d, J = 2.86 Hz, 1 H) 7.37 (d, J = 7.70 Hz, 1 H) 7.43 (s, 1 H) 7.47-7.52 (m, 1 H) 7.57 (br. s., 1 H) 7.75 (d, J = 3.08 Hz, 1 H) 7.97 (t, J = 7.70 Hz, 1 H) 8.53 (d, J = 4.62 Hz, 1 H) 9.50 (br. s., 1 H) 12.88 (br. s., 1 H) | E, 1.21 | 352 |
| 208 | 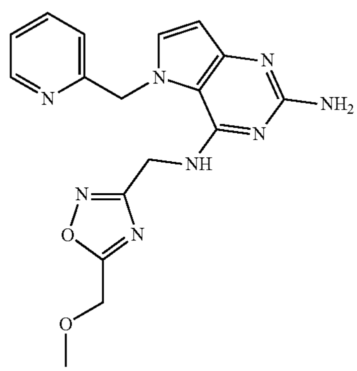 [SMILES: COCc1nc(CNc2nc(N)nc3ccn(Cc4ccccn4)c23)no1] | $^1$H NMR (400 MHz, DMSO-d$_6$) δ ppm 3.37 (s, 3 H) 4.72 (s, 2 H) 4.82 (d, J = 5.72 Hz, 2 H) 5.29 (s, 2 H) 5.46 (s, 2 H) 5.96-6.00 (m, 1 H) 7.29-7.37 (m, 2 H) 7.42 (d, J = 3.08 Hz, 1 H) 7.81 (td, J = 8.00, 1.50 Hz, 1 H) 8.12 (t, J = 6.16 Hz, 1 H) 8.45-8.50 (m, 1 H) | E, 1.15 | 367 |
| 209 | 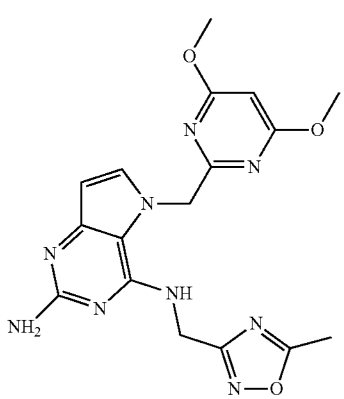 [SMILES: COc1cc(OC)nc(Cn2ccc3nc(N)nc(NCc4noc(C)n4)c32)n1] | $^1$H NMR (400 MHz, DMSO-d$_6$) δ ppm 2.49 (s, 3 H) 3.71 (s, 6 H) 4.70 (d, J = 5.72 Hz, 2 H) 5.27 (s, 2 H) 5.41 (s, 2 H) 5.98 (d, J = 2.86 Hz, 1 H) 6.11 (s, 1 H) 6.79 (t, J = 5.61 Hz, 1 H) 7.28 (d, J = 2.86 Hz, 1 H) | E, 1.23 | 398 |

TABLE 1-continued

Compounds of formula (I) and corresponding analytical data.

| # | STRUCTURE | ¹H NMR | LC Method, Rt (min) | LC-MS Mass Found |
|---|---|---|---|---|
| 210 | 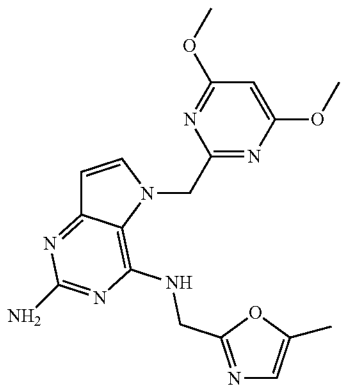 [SMILES: COc1cc(OC)nc(Cn2ccc3nc(N)nc(NCc4ncc(C)o4)c32)n1] | ¹H NMR (400 MHz, DMSO-d₆) δ ppm 2.19 (d, J = 1.10 Hz, 3 H) 3.68 (s, 6 H) 4.77 (d, J = 5.72 Hz, 2 H) 5.68 (s, 2 H) 6.12 (s, 1 H) 6.28 (d, J = 3.08 Hz, 1 H) 6.70 (d, J = 1.32 Hz, 1 H) 7.45 (br. s., 1 H) 7.59 (d, J = 3.08 Hz, 1 H) 8.12 (t, J = 5.50 Hz, 1 H) 12.59-12.72 (m, 1 H) | E, 1.27 | 397 |
| 211 | 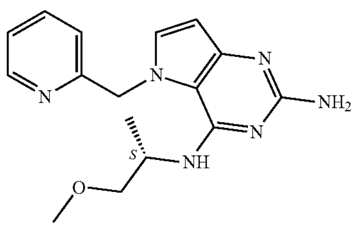 | ¹H NMR (400 MHz, DMSO-d₆) δ ppm 1.17 (d, J = 6.60 Hz, 3 H) 3.23-3.30 (m, 4 H) 3.43 (dd, J = 9.02, 5.06 Hz, 1 H) 4.36-4.44 (m, 1 H) 5.27 (br. s., 2 H) 5.36-5.47 (m, 2 H) 5.95 (d, J = 2.64 Hz, 1 H) 7.19 (d, J = 7.04 Hz, 1 H) 7.33-7.43 (m, 3 H) 7.85 (t, J = 7.37 Hz, 1 H) 8.55 (d, J = 3.96 Hz, 1 H) | E, 1.21 | 313 |
| 212 | 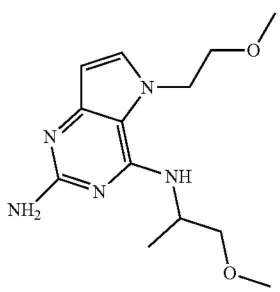 [SMILES: COCCn1ccc2nc(N)nc(NC(C)COC)c21] | ¹H NMR (400 MHz, DMSO-d₆) δ ppm 1.18 (d, J = 6.60 Hz, 3 H) 3.25 (s, 3 H) 3.29 (s, 3 H) 3.32-3.35 (m, 1 H) 3.45 (dd, J = 9.35, 5.17 Hz, 1 H) 3.61 (t, J = 4.73 Hz, 2 H) 4.28-4.39 (m, 2 H) 4.44 (dt, J = 12.71, 6.30 Hz, 1 H) 5.32 (br. s., 2 H) 5.93 (br. s., 1 H) 6.24 (d, J = 7.70 Hz, 1 H) 7.16 (s, 1 H) | E, 1.21 | 280 |
| 213 | 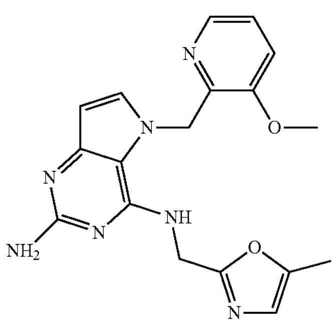 [SMILES: COc1cccnc1Cn1ccc2nc(N)nc(NCc3ncc(C)o3)c21] | ¹H NMR (400 MHz, DMSO-d₆) δ ppm 2.25 (d, J = 1.10 Hz, 3 H) 3.89 (s, 3 H) 4.76 (d, J = 5.50 Hz, 2 H) 5.29 (s, 2 H) 5.40 (s, 2 H) 5.93 (d, J = 3.08 Hz, 1 H) 6.76 (d, J = 1.10 Hz, 1 H) 7.25 (d, J = 3.08 Hz, 1 H) 7.39 (dd, J = 8.36, 4.62 Hz, 1 H) 7.53 (dd, J = 8.36, 1.10 Hz, 1 H) 7.94 (dd, J = 4.73, 1.21 Hz, 1 H) 8.36 (t, J = 5.61 Hz, 1 H) | E, 1.29 | 366 |
| 214 | 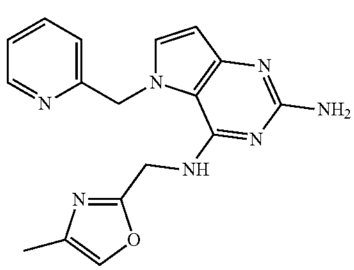 [SMILES: Cc1coc(CNc2nc(N)nc3ccn(Cc4ccccn4)c23)n1] | ¹H NMR (400 MHz, DMSO-d₆) δ ppm 2.05 (d, J = 1.32 Hz, 3 H) 4.73 (d, J = 5.72 Hz, 2 H) 5.31 (s, 2 H) 5.47 (s, 2 H) 5.98 (d, J = 3.08 Hz, 1 H) 7.29-7.35 (m, 2 H) 7.42 (d, J = 3.08 Hz, 1 H) 7.67 (d, J = 1.10 Hz, 1 H) 7.81 (td, J = 7.70, 1.76 Hz, 1 H) 7.99 (t, J = 5.61 Hz, 1 H) 8.41-8.45 (m, 1 H) | E, 1.17 | 336 |

TABLE 1-continued

Compounds of formula (I) and corresponding analytical data.

| # | STRUCTURE | ¹H NMR | LC Method, Rt (min) | LC-MS Mass Found |
|---|---|---|---|---|
| 215 | 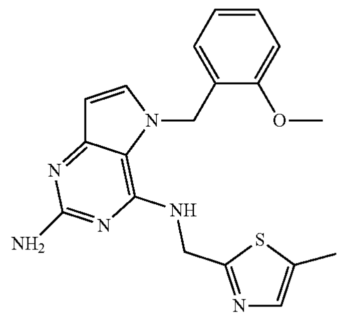 [SMILES: COc1ccccc1Cn1ccc2nc(N)nc(NCc3ncc(C)s3)c21] | ¹H NMR (400 MHz, DMSO-$d_6$) δ ppm 2.31 (s, 3 H) 3.80 (s, 3 H) 4.77 (d, J = 5.72 Hz, 2 H) 5.34 (s, 2 H) 5.43 (s, 2 H) 6.01 (d, J = 2.86 Hz, 1 H) 6.46-6.50 (m, 1 H) 6.80 (t, J = 7.26 Hz, 1 H) 6.90 (t, J = 5.83 Hz, 1 H) 7.00 (d, J = 8.14 Hz, 1 H) 7.20-7.27 (m, 2 H) 7.31 (d, J = 1.10 Hz, 1 H) | E, 1.42 | 381 |
| 216 | 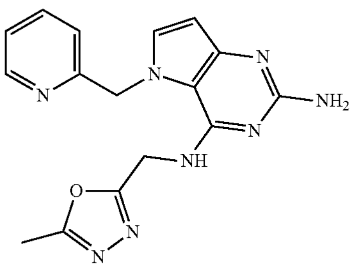 [SMILES: Cc1nnc(CNc2nc(N)nc3ccn(Cc4ccccn4)c23)o1] | ¹H NMR (400 MHz, DMSO-$d_6$) δ ppm 2.43 (s, 3 H) 4.85 (d, J = 5.72 Hz, 2 H) 5.33 (s, 2 H) 5.49 (s, 2 H) 5.99 (d, J = 3.08 Hz, 1 H) 7.24 (d, J = 7.70 Hz, 1 H) 7.34 (ddd, J = 7.54, 4.90, 0.99 Hz, 1 H) 7.43 (d, J = 3.08 Hz, 1 H) 7.80 (td, J = 7.70, 1.76 Hz, 1 H) 8.03 (t, J = 5.61 Hz, 1 H) 8.44-8.47 (m, 1 H) | E, 0.98 | 337 |

Compounds were prepared according to the methods described in the experimental section.
*$^R$ indicates a pure enantiomer of unknown configuration, drawn in R configuration.
*$^S$ indicates a pure enantiomer of unknown configuration, drawn in S configuration.

Analytical Methods.

All compounds were characterized by LC-MS according to the following LC-MS methods.

Method A.

Using a Phenomenex Kinetex column (XB-C18, 50×4.6 mm I.D. 2.6 μm) held at 35° C. MS detection: API-ES positive ionization mode, mass range 100-1200. PDA detection (λ=190-400 nm). The following gradient was used with a 2 μL injection:

| Solvent A | $H_2O$ + 0.1% Formic Acid | | |
|---|---|---|---|
| Solvent B | Acetonitrile | | |
| Time (min) | % A | % B | Flow (mL/min) |
| 0.0 | 95 | 5 | 3.0 |
| 4.2 | 5 | 95 | 3.0 |
| 4.9 | 5 | 95 | 3.0 |
| 5.0 | 95 | 5 | 3.0 |

Method B.

Reversed phase UPLC (Ultra Performance Liquid Chromatography) was carried out on a bridged ethylsiloxane/silica hybrid (BEH) C18 column (1.7 μm, 2.1×50 mm; Waters Acquity) with a flow rate of 0.8 ml/min. Two mobile phases (10 mM ammonium acetate in $H_2O$/acetonitrile 95/5; mobile phase B: acetonitrile) were used to run a gradient condition from 95% A and 5% B to 5% A and 95% B in 1.3 minutes and hold for 0.7 minutes. An injection volume of 0.75 μl was used. Cone voltage was 30 V for positive ionization mode and 30 V for negative ionization mode.

Method C.

Analyses were carried out on a Waters XTerra C18 column (100×4.6 mm I.D. 3.5 μm particles) at 40° C., with a flow rate of 1.6 mL/min. A gradient elution was performed as follows: from 100% of a solution of ammonium acetate (25 mM) in Water/Acetonitrile 90:10 to a mixture of Acetonitrile/Methanol 50:50 in 7.5 min; from the resulting composition to 100% Acetonitrile in 1.0 min; 100% Acetonitrile for 1.5 min; from 100% Acetonitrile to 100% to 100% of a solution of ammonium acetate (25 mM) in Water/Acetonitrile 90:10 (25 mM) in 3.0 minutes. The standard injection volume was 3 μL. Acquisition ranges were set to 200-400 nm for the UV.

Method D.

The LC measurement was performed using an Acquity UPLC (Waters) system comprising a binary pump, a sample organizer, a column heater (set at 55° C.), a diode-array detector (DAD) and a column as specified in the respective methods below. Flow from the column was split to a MS spectrometer. The MS detector was configured with an electrospray ionization source. Mass spectra were acquired by scanning from 100 to 1000 in 0.18 seconds using a dwell time of 0.02 seconds. The capillary needle voltage was 3.5 kV and the source temperature was maintained at 140° C. Nitrogen was used as the nebulizer gas. Reversed phase UPLC (Ultra Performance Liquid Chromatography) was carried out on a bridged ethylsiloxane/silica hybrid (BEH) C18 column (1.7 μm, 2.1×50 mm; Waters Acquity) with a flow rate of 0.8 mL/min. Two mobile phases (10 mM ammonium acetate in $H_2O$/acetonitrile 95/5; mobile phase B: acetonitrile) were used to run a gradient condition from 95% A and 5% B to 5% A and 95% B in 1.3 minutes and hold for 0.3 minutes. An injection volume of 0.5 μl was used. Cone voltage was 10 V for positive ionization mode and 20 V for negative ionization mode.

Method E

| Instrument | Column | Mobile phase | Gradient | Flow Col Temp | Run time |
|---|---|---|---|---|---|
| Waters: Acquity ® UPLC ® - DAD and SQD | Waters: HSS T3 (1.8 μm, 2.1*100 mm) | A: 10 mM $CH_3COONH_4$ in 95% $H_2O$ + 5% $CH_3CN$ B: $CH_3CN$ | From 100% A to 5% A in 2.10 min, to 0% A in 0.90 min, to 5% A in 0.5 min | 0.8 55 | 3.5 |

Method F

| Instrument | Column | Mobile phase | Gradient | Flow Col Temp | Run time |
|---|---|---|---|---|---|
| Waters: Alliance ®- DAD - ZQ and ELSD 2000 Alltech | Waters: Xterra MS C18 (3.5 µm, 4.6*100 mm) | A: 25 mM CH₃COONH₄ in 95% H2O + 5% CH₃CN, B: CH₃CN, C: CH3OH, D: (40% CH3CN and 40% CH3OH and 20% H2O with 0.25% CH3COOH | From 100% A to 1% A, 49% B and 50% C in 6.5 min, to 1% A and 99% B in 0.5 min, to 100% D in 1 min held for 1.0 min to 100% A in 0.5 min and held for 1.5 min. | 1.6 40 | 11 |

Biological Activity of Compounds of Formula (I)
Description of Biological Assays
Assessment of TLR7 and TLR8 Activity The ability of compounds to activate human TLR7 and/or TLR8 was assessed in a cellular reporter assay using HEK293 cells transiently transfected with a TLR7 or TLR8 expression vector and NFκB-luc reporter construct.

Briefly, HEK293 cells were grown in culture medium (DMEM supplemented with 10% FCS and 2 mM Glutamine). For transfection of cells in 10 cm dishes, cells were detached with Trypsin-EDTA, transfected with a mix of CMV-TLR7 or TLR8 plasmid (750 ng), NFκB-luc plasmid (375 ng) and a transfection reagent and incubated overnight at 37° C. in a humidified 5% $CO_2$ atmosphere. Transfected cells were then detached with Trypsin-EDTA, washed in PBS and resuspended in medium to a density of $1.67 \times 10^5$ cells/mL. Thirty microliters of cells were then dispensed into each well in 384-well plates, where 10 µL of compound in 4% DMSO was already present. Following 6 hours incubation at 37° C., 5% $CO_2$, the luciferase activity was determined by adding 15 µL of Steady Lite Plus substrate (Perkin Elmer) to each well and readout performed on a ViewLux ultraHTS microplate imager (Perkin Elmer). Dose response curves were generated from measurements performed in quadruplicates. Lowest effective concentrations (LEC) values, defined as the concentration that induces an effect which is at least two fold above the standard deviation of the assay, were determined for each compound.

Compound toxicity was determined in parallel using a similar dilution series of compound with 30 µL per well of cells transfected with the CMV-TLR7 construct alone ($1.67 \times 10^5$ cells/mL), in 384-well plates. Cell viability was measured after 6 hours incubation at 37° C., 5% $CO_2$ by adding 15 µL of ATP lite (Perkin Elmer) per well and reading on a ViewLux ultraHTS microplate imager (Perkin Elmer). Data was reported as $CC_{50}$.

In parallel, a similar dilution series of compound was used (10 µL of compound in 4% DMSO) with 30 µL per well of cells transfected with NFκB-luc reporter construct alone ($1.67 \times 10^5$ cells/mL). Six hours after incubation at 37° C., 5% $CO_2$, the luciferase activity was determined by adding 15 µl of Steady Lite Plus substrate (Perkin Elmer) to each well and readout performed on a ViewLux ultraHTS microplate imager (Perkin Elmer). Counterscreen data is reported as LEC.

Activation of ISRE Promoter Elements

The potential of compounds to induce IFN-I was also evaluated by measuring the activation of interferon-stimulated responsive elements (ISRE) by conditioned media from PBMC. The ISRE element of sequence GAAACT-GAAACT is highly responsive to the STAT1-STAT2-IRF9 transcription factor, activated upon binding of IFN-I to their receptor IFNAR (Clontech, PT3372-5W). The plasmid pISRE-Luc from Clontech (ref. 631913) contains 5 copies of this ISRE element, followed by the firefly luciferase ORF. A HEK293 cell line stably transfected with pISRE-Luc (HEK-ISREluc) was established to profile of the conditioned PBMC cell culture media.

Briefly, PBMCs were prepared from buffy coats of at least two donors using a standard Ficoll centrifugation protocol. Isolated PBMCs were resuspended in RPMI medium supplemented with 10% human AB serum and $2 \times 10^5$ cells/well were dispensed into 384-well plates containing compounds (70 µL total volume). After overnight incubation, 10 µL of supernatant was transferred to 384-well plates containing $5 \times 10^3$ HEK-ISREluc cells/well in 30 µL (plated the day before). Following 24 hours of incubation, activation of the ISRE elements was measured by assaying luciferase activity using 40 µL/well Steady Lite Plus substrate (Perkin Elmer) and measured with ViewLux ultraHTS microplate imager (Perkin Elmer). The stimulating activity of each compound on the HEK-ISREluc cells was reported as LEC value, defined as the compound concentration applied to the PBMCs resulting in a luciferase activity at least two fold above the standard deviation of the assay. The LEC in turn indicates the degree of ISRE activation on transfer of a defined amount of PBMC culture medium. Recombinant interferon α-2a (Roferon-A) was used as a standard control compound.

TABLE 2

Activity of compounds of formula (I). All compounds showed no activity (LEC >25 µM) in the HEK 293 NF-kB counterscreen assay described above.

| # | STRUCTURE | TLR7 LEC (µM) | TLR8 LEC (µM) | PBMC LEC (µM) |
|---|---|---|---|---|
| 1 | (benzyl-substituted pyrrolopyrimidine with propylamino group) | 0.20 | >25 | 0.20 |

TABLE 2-continued

*Activity of compounds of formula (I). All compounds showed no activity (LEC >25 μM) in the HEK 293 NF-kB counterscreen assay described above.*

| # | STRUCTURE | TLR7 LEC (μM) | TLR8 LEC (μM) | PBMC LEC (μM) |
|---|---|---|---|---|
| 2 | 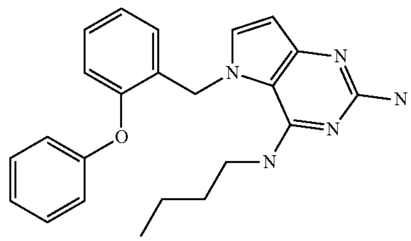 [SMILES: CCCCNc1nc(N)nc2ccn(Cc3ccccc3Oc3ccccc3)c12] | 0.50 | >25 | 0.60 |
| 3 | 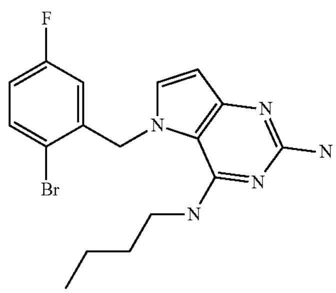 [SMILES: CCCCNc1nc(N)nc2ccn(Cc3cc(F)ccc3Br)c12] | 2.6 | >25 | 1.2 |
| 4 | 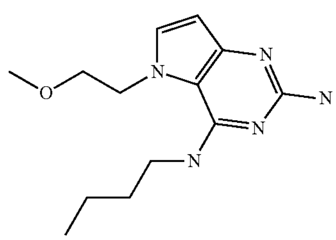 [SMILES: CCCCNc1nc(N)nc2ccn(CCOC)c12] | 0.60 | 13.5 | 0.4 |
| 5 | 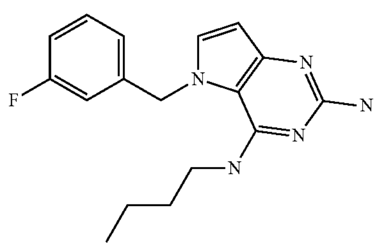 [SMILES: CCCCNc1nc(N)nc2ccn(Cc3cccc(F)c3)c12] | 0.30 | >25 | 0.2 |
| 6 | 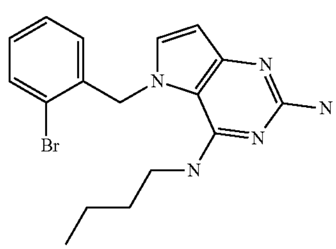 [SMILES: CCCCNc1nc(N)nc2ccn(Cc3ccccc3Br)c12] | 1.3 | >25 | 0.7 |

TABLE 2-continued

*Activity of compounds of formula (I). All compounds showed no activity (LEC >25 μM) in the HEK 293 NF-kB counterscreen assay described above.*

| # | STRUCTURE | TLR7 LEC (μM) | TLR8 LEC (μM) | PBMC LEC (μM) |
|---|---|---|---|---|
| 7 | 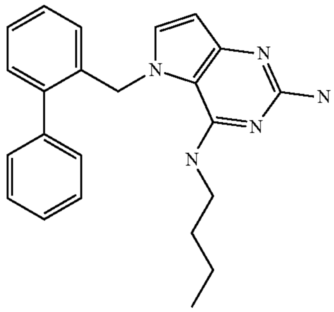 [SMILES: CCCCNc1nc(N)nc2ccn(Cc3ccccc3-c3ccccc3)c12] | 0.61 | >25 | 0.8 |
| 8 | 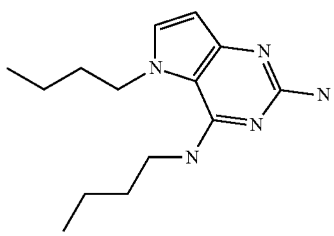 [SMILES: CCCCNc1nc(N)nc2ccn(CCCC)c12] | 0.49 | 1.7 | 0.15 |
| 9 | 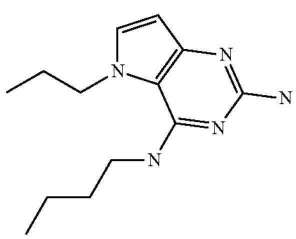 [SMILES: CCCCNc1nc(N)nc2ccn(CCC)c12] | 0.53 | 2.1 | 0.22 |
| 10 | 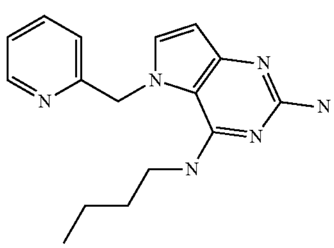 | 0.15 | >25 | 0.06 |
| 11 | 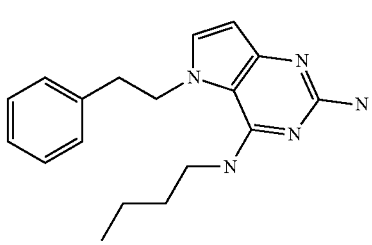 [SMILES: CCCCNc1nc(N)nc2ccn(CCc3ccccc3)c12] | 1.5 | 3.5 | 0.56 |

TABLE 2-continued
*Activity of compounds of formula (I). All compounds showed no activity (LEC >25 μM) in the HEK 293 NF-kB counterscreen assay described above.*
| # | STRUCTURE | TLR7 LEC (μM) | TLR8 LEC (μM) | PBMC LEC (μM) |
|---|---|---|---|---|
| 12 | 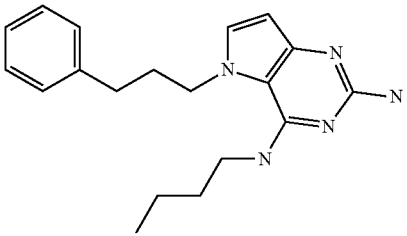 | 0.14 | 0.7 | 0.05 |
| 13 | 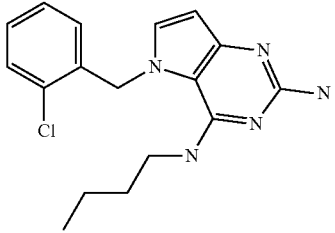 [SMILES: CCCCNc1nc(N)nc2ccn(Cc3ccccc3Cl)c12] | 0.80 | >25 | 0.89 |
| 14 | 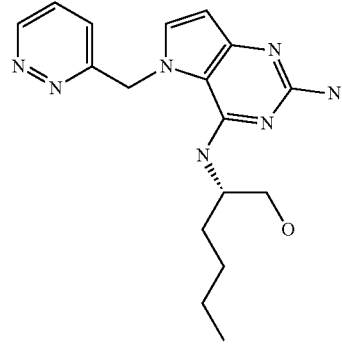 [SMILES: CCCC[C@@H](CO)Nc1nc(N)nc2ccn(Cc3cccnn3)c12] | 0.52 | 6.57 | 0.01 |
| 15 | 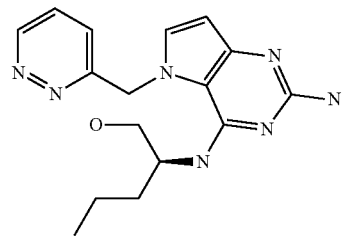 [SMILES: CCC[C@@H](CO)Nc1nc(N)nc2ccn(Cc3cccnn3)c12] | 5.84 | >25 | 0.1 |
| 16 | 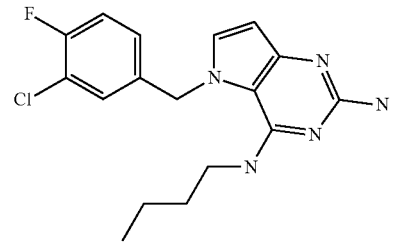 [SMILES: CCCCNc1nc(N)nc2ccn(Cc3ccc(F)c(Cl)c3)c12] | 0.89 | >25 | 0.6 |

TABLE 2-continued
Activity of compounds of formula (I). All compounds showed no activity
(LEC >25 μM) in the HEK 293 NF-kB counterscreen assay described above.
| # | STRUCTURE | TLR7 LEC (μM) | TLR8 LEC (μM) | PBMC LEC (μM) |
|---|---|---|---|---|
| 17 | 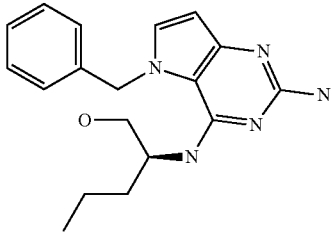 [SMILES: CCC[C@@H](CO)Nc1nc(N)nc2ccn(Cc3ccccc3)c12] | 0.07 | 12.5 | 0.01 |
| 18 | 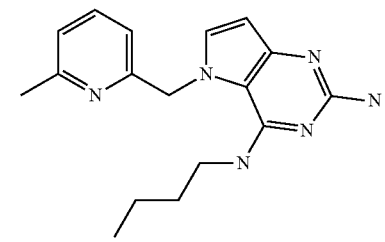 [SMILES: CCCCNc1nc(N)nc2ccn(Cc3cccc(C)n3)c12] | 0.07 | >25 | 0.01 |
| 19 | 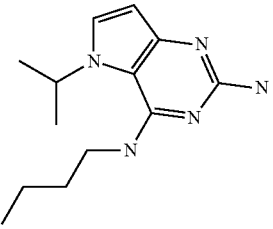 [SMILES: CCCCNc1nc(N)nc2ccn(C(C)C)c12] | 2.5 | 7.06 | 0.62 |
| 20 | 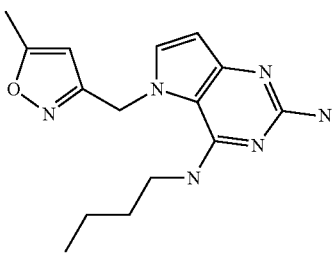 [SMILES: CCCCNc1nc(N)nc2ccn(Cc3cc(C)on3)c12] | 0.14 | 1.3 | 0.02 |
| 21 | 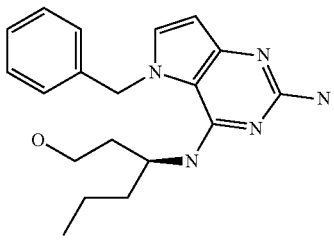 [SMILES: CCC[C@@H](CCO)Nc1nc(N)nc2ccn(Cc3ccccc3)c12] | 0.009 | 7.4 | 0.0007 |
| 22 | 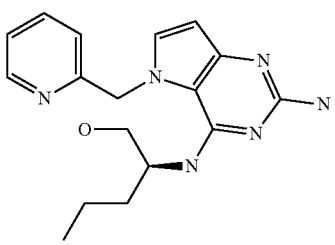 [SMILES: CCC[C@@H](CO)Nc1nc(N)nc2ccn(Cc3ccccn3)c12] | 0.48 | 9.2 | 0.02 |

TABLE 2-continued

Activity of compounds of formula (I). All compounds showed no activity
(LEC >25 μM) in the HEK 293 NF-kB counterscreen assay described above.

| # | STRUCTURE | TLR7 LEC (μM) | TLR8 LEC (μM) | PBMC LEC (μM) |
|---|---|---|---|---|
| 23 | 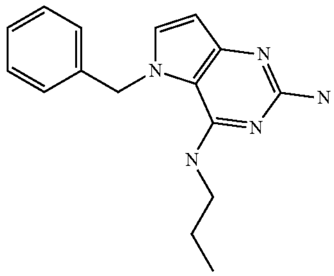 [SMILES: CCCNc1nc(N)nc2ccn(Cc3ccccc3)c12] | 0.83 | >25 | 0.27 |
| 24 | 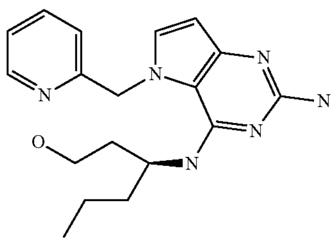 [SMILES: CCC[C@@H](CCO)Nc1nc(N)nc2ccn(Cc3ccccn3)c12] | 0.02 | 6.47 | 0.0007 |
| 25 | 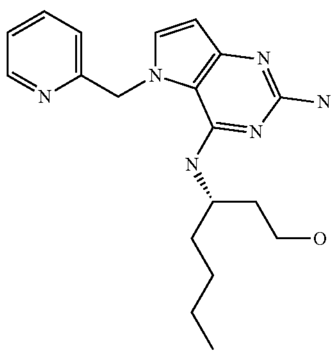 [SMILES: CCCC[C@@H](CCO)Nc1nc(N)nc2ccn(Cc3ccccn3)c12] | 0.01 | 2.84 | 0.001 |
| 26 | 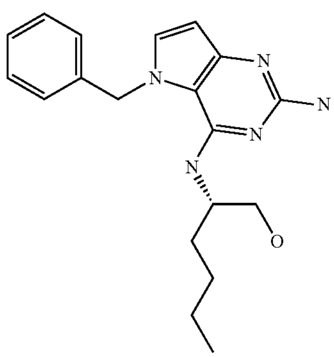 [SMILES: CCCC[C@@H](CO)Nc1nc(N)nc2ccn(Cc3ccccc3)c12] | 0.03 | 1.95 | 0.002 |
| 27 | 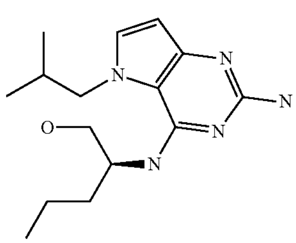 [SMILES: CCC[C@@H](CO)Nc1nc(N)nc2ccn(CC(C)C)c12] | 0.15 | 0.85 | 0.17 |

TABLE 2-continued

Activity of compounds of formula (I). All compounds showed no activity
(LEC >25 μM) in the HEK 293 NF-kB counterscreen assay described above.

| # | STRUCTURE | TLR7 LEC (μM) | TLR8 LEC (μM) | PBMC LEC (μM) |
| --- | --- | --- | --- | --- |
| 28 | 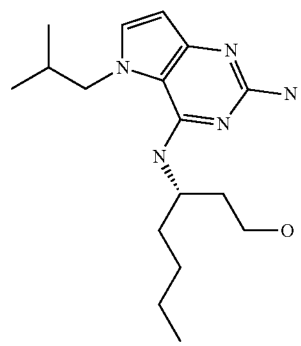 [SMILES: CCCC[C@@H](CCO)Nc1nc(N)nc2ccn(CC(C)C)c12] | 0.11 | 1.1 | 0.03 |
| 29 | 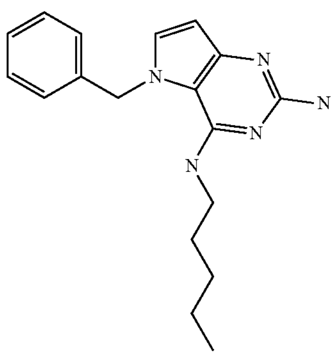 [SMILES: CCCCCNc1nc(N)nc2ccn(Cc3ccccc3)c12] | 0.15 | >25 | 0.04 |
| 30 | 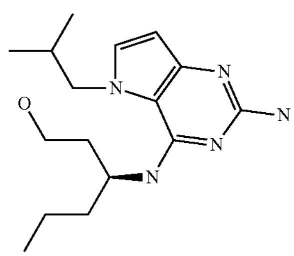 [SMILES: CCC[C@@H](CCO)Nc1nc(N)nc2ccn(CC(C)C)c12] | 0.16 | 0.67 | 0.05 |
| 31 | 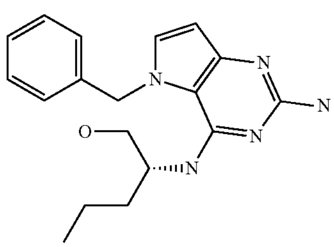 [SMILES: CCC[C@H](CO)Nc1nc(N)nc2ccn(Cc3ccccc3)c12] | 0.22 | >25 | 0.16 |
| 32 | 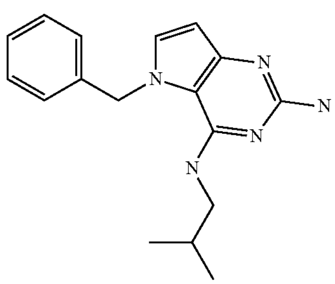 [SMILES: CC(C)CNc1nc(N)nc2ccn(Cc3ccccc3)c12] | 0.91 | >25 | 0.52 |

TABLE 2-continued

Activity of compounds of formula (I). All compounds showed no activity (LEC >25 μM) in the HEK 293 NF-kB counterscreen assay described above.

| # | STRUCTURE | TLR7 LEC (μM) | TLR8 LEC (μM) | PBMC LEC (μM) |
|---|---|---|---|---|
| 33 | 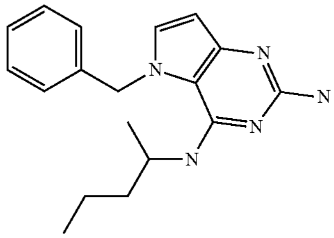 [SMILES: CCCC(C)Nc1nc(N)nc2ccn(Cc3ccccc3)c12] | 0.03 | >25 | 0.04 |
| 34 | 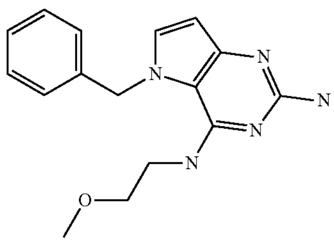 [SMILES: COCCNc1nc(N)nc2ccn(Cc3ccccc3)c12] | 0.91 | >25 | 0.54 |
| 35 | 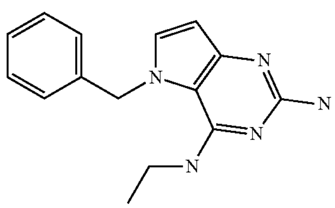 [SMILES: CCNc1nc(N)nc2ccn(Cc3ccccc3)c12] | 1.49 | >25 | 0.70 |
| 36 | 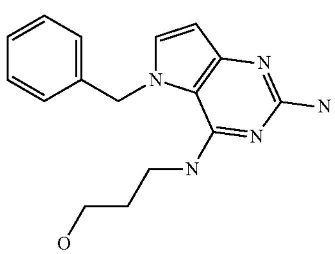 [SMILES: Nc1nc(NCCCO)c2c(ccn2Cc2ccccc2)n1] | 1.06 | >25 | 0.59 |
| 37 | 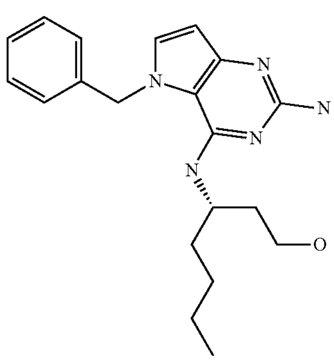 [SMILES: CCCC[C@@H](CCO)Nc1nc(N)nc2ccn(Cc3ccccc3)c12] | 0.005 | >25 | 0.007 |

TABLE 2-continued

*Activity of compounds of formula (I). All compounds showed no activity (LEC >25 µM) in the HEK 293 NF-kB counterscreen assay described above.*

| # | STRUCTURE | TLR7 LEC (µM) | TLR8 LEC (µM) | PBMC LEC (µM) |
|---|---|---|---|---|
| 38 | 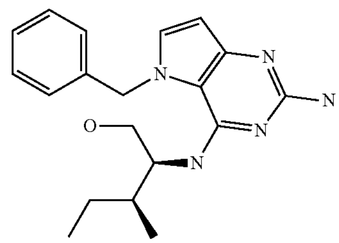 [SMILES: CC[C@H](C)[C@@H](CO)Nc1nc(N)nc2ccn(Cc3ccccc3)c12] | 0.54 | >25 | 0.63 |
| 39 | 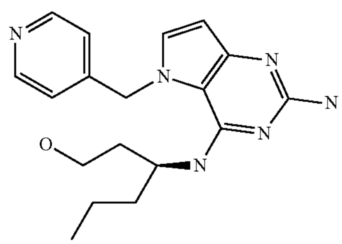 [SMILES: CCC[C@@H](CCO)Nc1nc(N)nc2ccn(Cc3ccncc3)c12] | 0.17 | >25 | 0.009 |
| 40 | 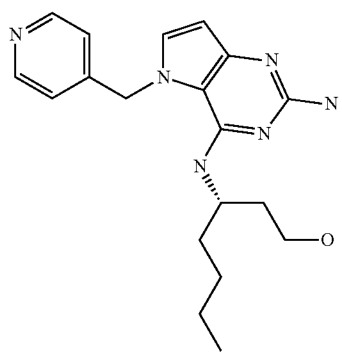 [SMILES: CCCC[C@@H](CCO)Nc1nc(N)nc2ccn(Cc3ccncc3)c12] | 0.12 | 24.61 | 0.004 |
| 41 | 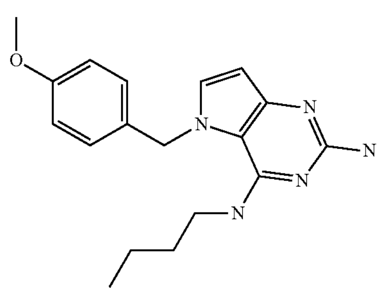 [SMILES: CCCCNc1nc(N)nc2ccn(Cc3ccc(OC)cc3)c12] | 0.09 | >25 | 0.11 |
| 42 | 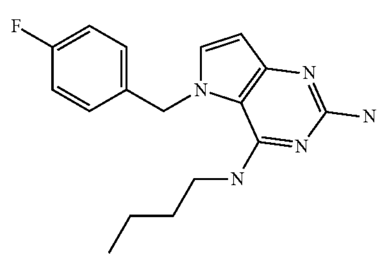 [SMILES: CCCCNc1nc(N)nc2ccn(Cc3ccc(F)cc3)c12] | 0.28 | >25 | 0.16 |

TABLE 2-continued

*Activity of compounds of formula (I). All compounds showed no activity (LEC >25 μM) in the HEK 293 NF-kB counterscreen assay described above.*

| # | STRUCTURE | TLR7 LEC (μM) | TLR8 LEC (μM) | PBMC LEC (μM) |
|---|---|---|---|---|
| 43 | 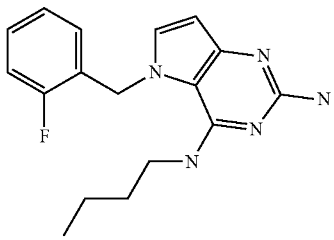 [SMILES: CCCCNc1nc(N)nc2ccn(Cc3ccccc3F)c12] | 0.11 | >25 | 0.17 |
| 44 | 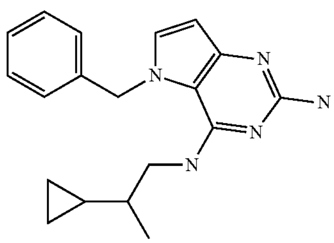 [SMILES: CC(CNc1nc(N)nc2ccn(Cc3ccccc3)c12)C1CC1] | 1.51 | >25 | 2.45 |
| 45 | 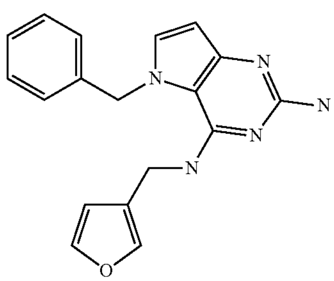 [SMILES: Nc1nc(NCc2ccoc2)c2c(ccn2Cc2ccccc2)n1] | 19.9 | >25 | 0.74 |
| 46 | 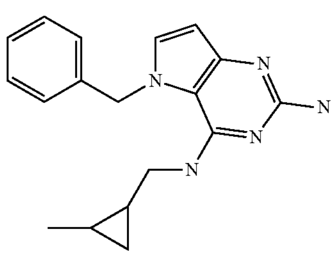 [SMILES: CC1CC1CNc1nc(N)nc2ccn(Cc3ccccc3)c12] | 0.83 | >25 | 0.17 |
| 47 | 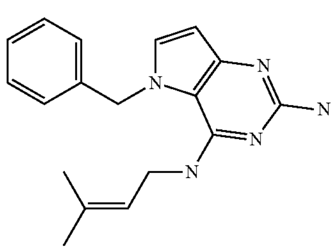 [SMILES: CC(C)=CCNc1nc(N)nc2ccn(Cc3ccccc3)c12] | 17.5 | >25 | 1.79 |

TABLE 2-continued

*Activity of compounds of formula (I). All compounds showed no activity (LEC >25 μM) in the HEK 293 NF-kB counterscreen assay described above.*

| # | STRUCTURE | TLR7 LEC (μM) | TLR8 LEC (μM) | PBMC LEC (μM) |
|---|---|---|---|---|
| 48 | 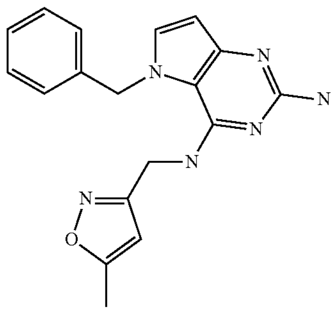 [SMILES: Cc1cc(CNc2nc(N)nc3ccn(Cc4ccccc4)c23)no1] | 0.05 | >25 | 0.03 |
| 49 | 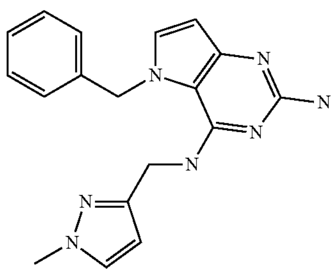 [SMILES: Cn1ccc(CNc2nc(N)nc3ccn(Cc4ccccc4)c23)n1] | 22.43 | >25 | 2.34 |
| 50 | 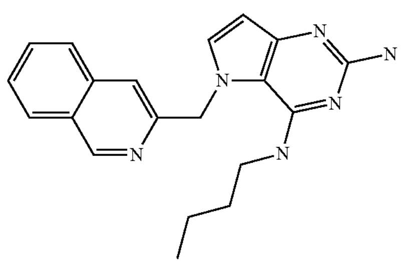 [SMILES: CCCCNc1nc(N)nc2ccn(Cc3cc4ccccc4cn3)c12] | 1.01 | >25 | 0.13 |
| 51 | 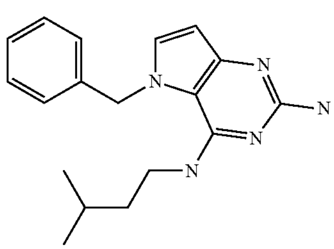 [SMILES: CC(C)CCNc1nc(N)nc2ccn(Cc3ccccc3)c12] | 5.14 | >25 | 0.59 |
| 52 | 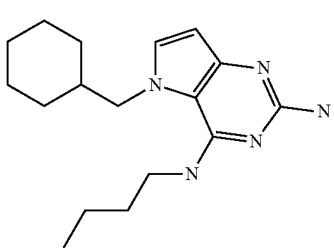 [SMILES: CCCCNc1nc(N)nc2ccn(CC3CCCCC3)c12] | 0.12 | >25 | 0.09 |

TABLE 2-continued

Activity of compounds of formula (I). All compounds showed no activity
(LEC >25 μM) in the HEK 293 NF-kB counterscreen assay described above.

| # | STRUCTURE | TLR7 LEC (μM) | TLR8 LEC (μM) | PBMC LEC (μM) |
|---|---|---|---|---|
| 53 | 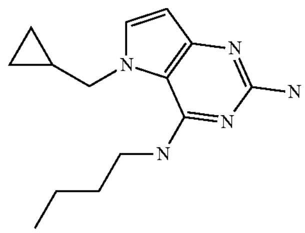 [SMILES: CCCCNc1nc(N)nc2ccn(CC3CC3)c12] | 0.38 | 2.78 | 0.07 |
| 54 | 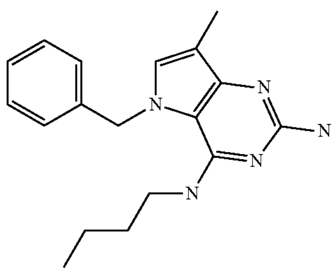 [SMILES: CCCCNc1nc(N)nc2c(C)cn(Cc3ccccc3)c12] | 1.68 | >25 | 0.90 |
| 55 | 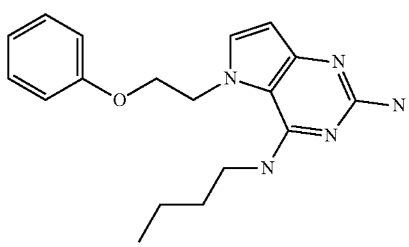 [SMILES: CCCCNc1nc(N)nc2ccn(CCOc3ccccc3)c12] | 0.08 | 0.81 | 0.06 |
| 56 | 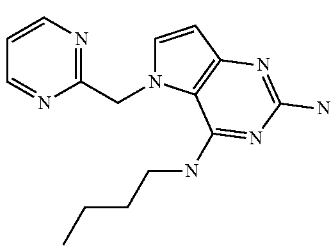 [SMILES: CCCCNc1nc(N)nc2ccn(Cc3ncccn3)c12] | 0.99 | 17.5 | 0.07 |
| 57 | 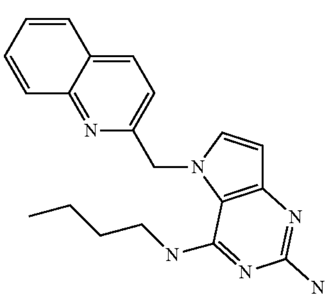 [SMILES: CCCCNc1nc(N)nc2ccn(Cc3ccc4ccccc4n3)c12] | 0.33 | >25 | 0.28 |

TABLE 2-continued

Activity of compounds of formula (I). All compounds showed no activity
(LEC >25 μM) in the HEK 293 NF-kB counterscreen assay described above.

| # | STRUCTURE | TLR7 LEC (μM) | TLR8 LEC (μM) | PBMC LEC (μM) |
|---|---|---|---|---|
| 58 | 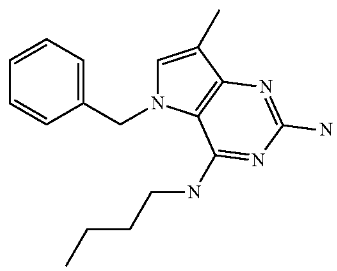 [SMILES: CCCCNc1nc(N)nc2c(C)cn(Cc3ccccc3)c12] | 0.24 | >25 | 0.90 |
| 59 | 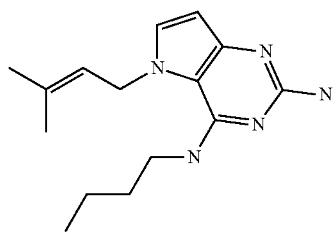 [SMILES: CCCCNc1nc(N)nc2ccn(CC=C(C)C)c12] | 0.37 | >25 | 0.22 |
| 60 | 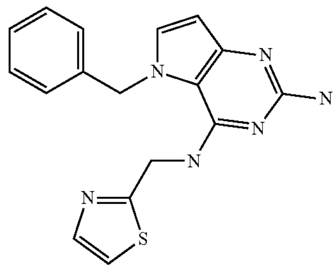 [SMILES: Nc1nc(NCc2nccs2)c2c(ccn2Cc2ccccc2)n1] | 0.39 | >25 | 0.33 |
| 61 | 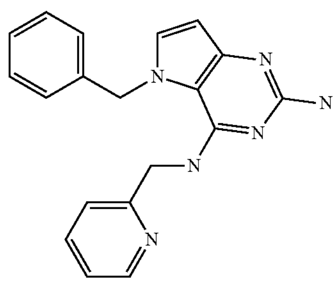 [SMILES: Nc1nc(NCc2ccccn2)c2c(ccn2Cc2ccccc2)n1] | 1.01 | >25 | 1.95 |
| 62 | 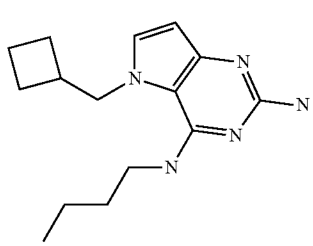 [SMILES: CCCCNc1nc(N)nc2ccn(CC3CCC3)c12] | 0.06 | 0.9934 | 0.06 |

TABLE 2-continued

Activity of compounds of formula (I). All compounds showed no activity (LEC >25 μM) in the HEK 293 NF-kB counterscreen assay described above.

| # | STRUCTURE | TLR7 LEC (μM) | TLR8 LEC (μM) | PBMC LEC (μM) |
|---|-----------|---------------|---------------|---------------|
| 63 | 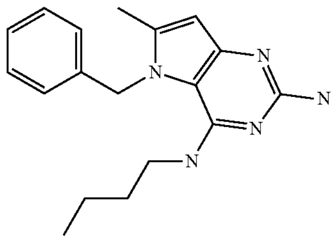 [SMILES: CCCCNc1nc(N)nc2cc(C)n(Cc3ccccc3)c12] | 0.67 | >25 | 0.18 |
| 64 | 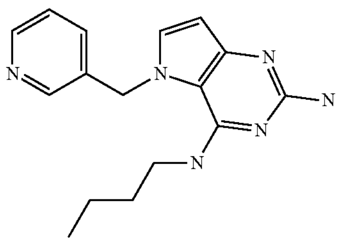 [SMILES: CCCCNc1nc(N)nc2ccn(Cc3cccnc3)c12] | 1.36 | >25 | 0.26 |
| 65 | 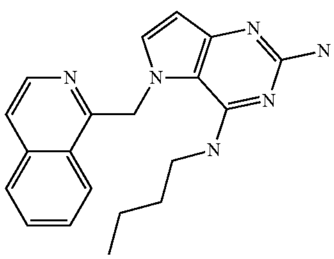 [SMILES: CCCCNc1nc(N)nc2ccn(Cc3nccc4ccccc34)c12] | 0.1687 | >25 | 0.08 |
| 66 | 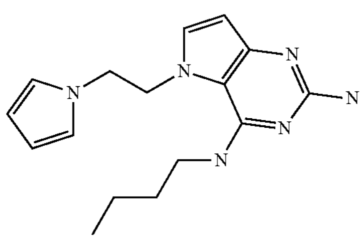 [SMILES: CCCCNc1nc(N)nc2ccn(CCn3cccc3)c12] | 2.57 | 3.96 | 0.91 |
| 67 | 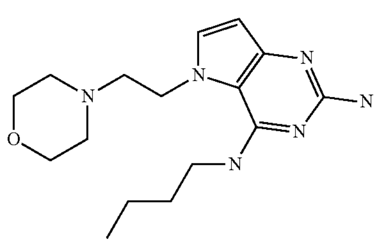 [SMILES: CCCCNc1nc(N)nc2ccn(CCN3CCOCC3)c12] | 0.056 | 6.71 | 0.04 |
| 68 | 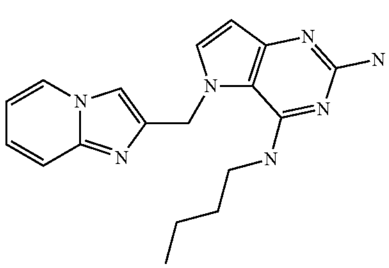 [SMILES: CCCCNc1nc(N)nc2ccn(Cc3cn4ccccc4n3)c12] | 0.19 | >25 | 0.04 |

TABLE 2-continued

Activity of compounds of formula (I). All compounds showed no activity (LEC >25 μM) in the HEK 293 NF-kB counterscreen assay described above.

| # | STRUCTURE | TLR7 LEC (μM) | TLR8 LEC (μM) | PBMC LEC (μM) |
|---|---|---|---|---|
| 69 | 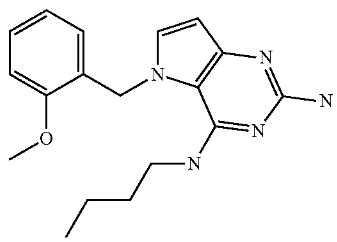 [SMILES: CCCCNc1nc(N)nc2ccn(Cc3ccccc3OC)c12] | 0.004 | 0.71 | 0.002 |
| 70 | 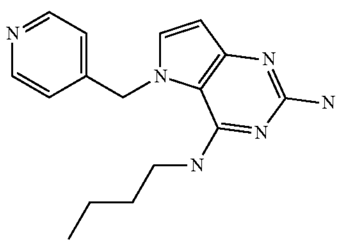 [SMILES: CCCCNc1nc(N)nc2ccn(Cc3ccncc3)c12] | 1.53 | >25 | 0.75 |
| 71 | 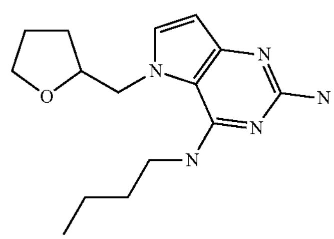 [SMILES: CCCCNc1nc(N)nc2ccn(CC3CCCO3)c12] | 0.32 | 4.68 | 0.24 |
| 72 | 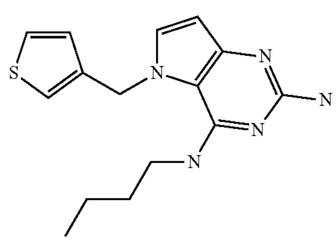 [SMILES: CCCCNc1nc(N)nc2ccn(Cc3ccsc3)c12] | 0.13 | >25 | 0.04 |
| 73 | 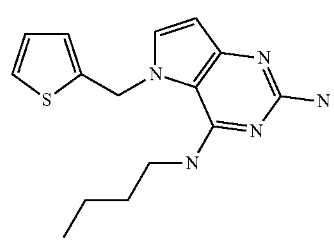 [SMILES: CCCCNc1nc(N)nc2ccn(Cc3cccs3)c12] | 0.28 | >25 | 0.13 |
| 74 | 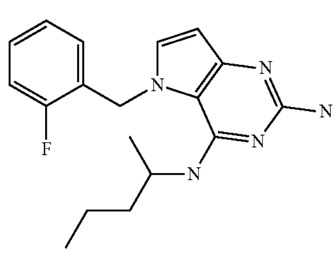 [SMILES: CCCC(C)Nc1nc(N)nc2ccn(Cc3ccccc3F)c12] | 0.10 | >25 | 0.04 |

TABLE 2-continued

Activity of compounds of formula (I). All compounds showed no activity
(LEC >25 μM) in the HEK 293 NF-kB counterscreen assay described above.

| # | STRUCTURE | TLR7 LEC (μM) | TLR8 LEC (μM) | PBMC LEC (μM) |
|---|---|---|---|---|
| 75 | 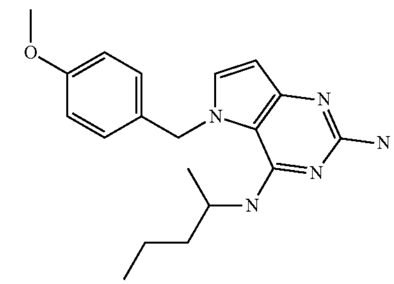 [SMILES: CCCC(C)Nc1nc(N)nc2ccn(Cc3ccc(OC)cc3)c12] | 0.04 | >25 | 0.04 |
| 76 | 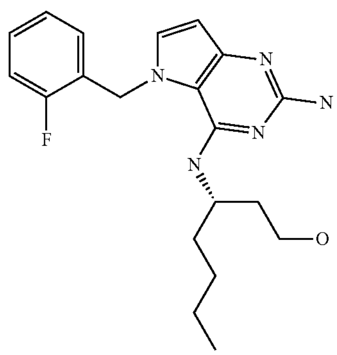 [SMILES: CCCC[C@@H](CCO)Nc1nc(N)nc2ccn(Cc3ccccc3F)c12] | 0.01 | 4.09 | 0.007 |
| 77 | 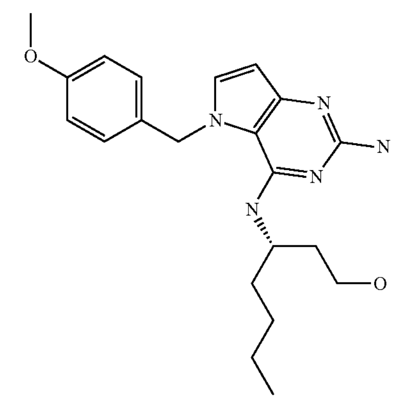 [SMILES: CCCC[C@@H](CCO)Nc1nc(N)nc2ccn(Cc3ccc(OC)cc3)c12] | 0.008 | 2.62 | 0.002 |
| 78 | 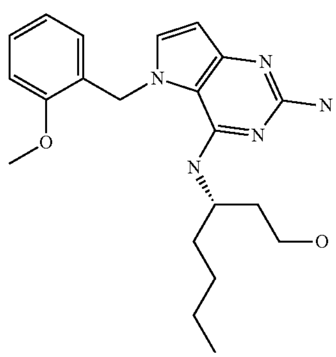 [SMILES: CCCC[C@@H](CCO)Nc1nc(N)nc2ccn(Cc3ccccc3OC)c12] | 0.0004 | 0.5577 | <0.0004 |

TABLE 2-continued

*Activity of compounds of formula (I). All compounds showed no activity (LEC >25 μM) in the HEK 293 NF-kB counterscreen assay described above.*

| # | STRUCTURE | TLR7 LEC (μM) | TLR8 LEC (μM) | PBMC LEC (μM) |
|---|---|---|---|---|
| 79 | 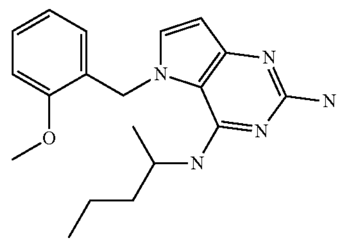 [SMILES: CCCC(C)Nc1nc(N)nc2ccn(Cc3ccccc3OC)c12] | 0.004 | 0.94 | 0.001 |
| 80 | 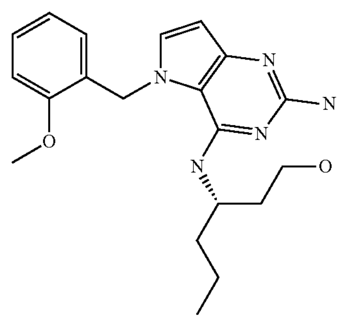 [SMILES: CCC[C@@H](CCO)Nc1nc(N)nc2ccn(Cc3ccccc3OC)c12] | <0.0006 | 0.689 | <0.0004 |
| 81 | 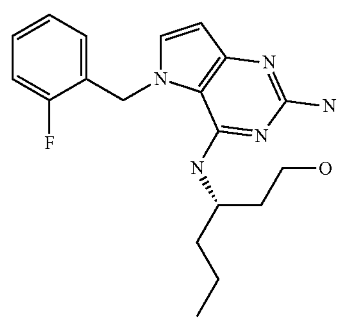 [SMILES: CCC[C@@H](CCO)Nc1nc(N)nc2ccn(Cc3ccccc3F)c12] | 0.01 | 22.02 | 0.002 |
| 82 | 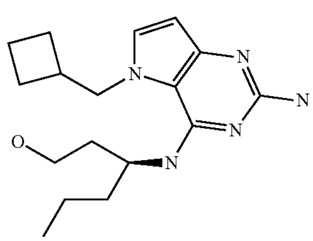 [SMILES: CCC[C@@H](CCO)Nc1nc(N)nc2ccn(CC3CCC3)c12] | 0.07 | 0.57 | 0.01 |
| 83 | 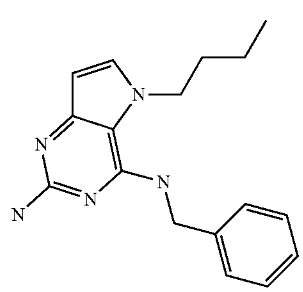 [SMILES: CCCCn1ccc2nc(N)nc(NCc3ccccc3)c21] | 1.57 | >25 | 2.3 |

TABLE 2-continued

Activity of compounds of formula (I). All compounds showed no activity (LEC >25 μM) in the HEK 293 NF-kB counterscreen assay described above.

| # | STRUCTURE | TLR7 LEC (μM) | TLR8 LEC (μM) | PBMC LEC (μM) |
|---|---|---|---|---|
| 84 | 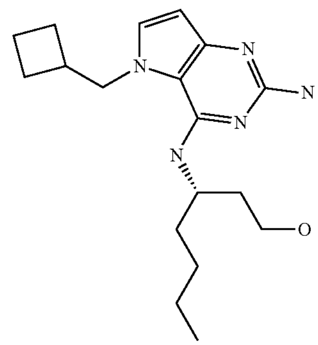 [SMILES: CCCC[C@@H](CCO)Nc1nc(N)nc2ccn(CC3CCC3)c12] | 0.04 | 1.14 | 0.01 |
| 85 | 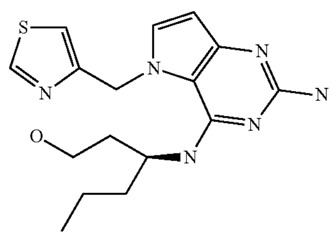 [SMILES: CCC[C@@H](CCO)Nc1nc(N)nc2ccn(Cc3cscn3)c12] | 0.03 | 10.14 | 0.002 |
| 86 | 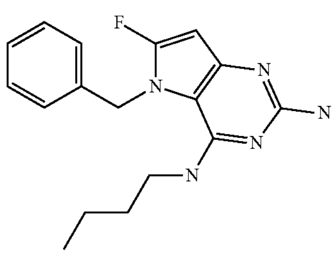 [SMILES: CCCCNc1nc(N)nc2cc(F)n(Cc3ccccc3)c12] | 1.63 | >25 | 0.47 |
| 87 | 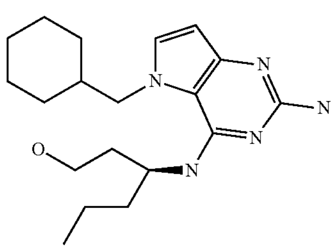 [SMILES: CCC[C@@H](CCO)Nc1nc(N)nc2ccn(CC3CCCCC3)c12] | 0.01 | >25 | 0.008 |
| 88 | 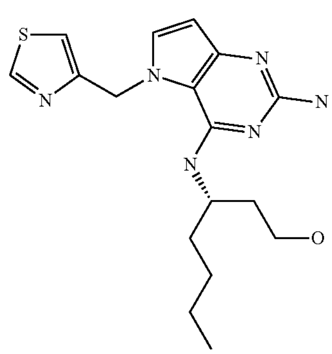 [SMILES: CCCC[C@@H](CCO)Nc1nc(N)nc2ccn(Cc3cscn3)c12] | 0.01 | 2.46 | 0.0006 |

TABLE 2-continued

Activity of compounds of formula (I). All compounds showed no activity (LEC >25 μM) in the HEK 293 NF-kB counterscreen assay described above.

| # | STRUCTURE | TLR7 LEC (μM) | TLR8 LEC (μM) | PBMC LEC (μM) |
|---|---|---|---|---|
| 89 | 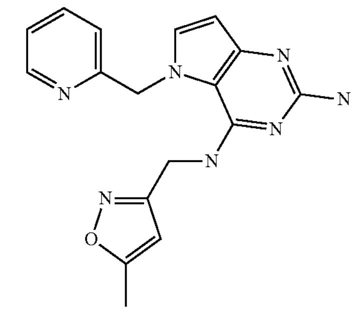 | 0.04 | >25 | 0.006 |
| 90 | 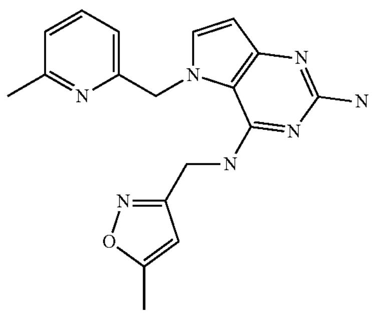 [SMILES: Cc1cccc(Cn2ccc3nc(N)nc(NCc4cc(C)on4)c32)n1] | 0.03 | >25 | 0.01 |
| 91 | 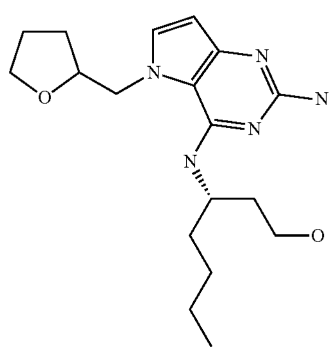 [SMILES: CCCC[C@@H](CCO)Nc1nc(N)nc2ccn(CC3CCCO3)c12] | 0.05 | 2.17 | 0.02 |
| 92 | 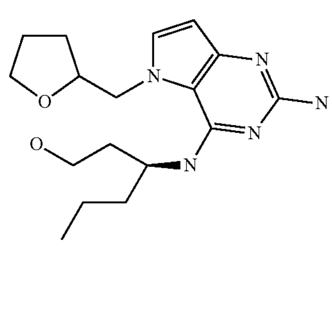 [SMILES: CCC[C@@H](CCO)Nc1nc(N)nc2ccn(CC3CCCO3)c12] | 0.10 | 4.46 | 0.02 |

TABLE 2-continued

*Activity of compounds of formula (I). All compounds showed no activity (LEC >25 μM) in the HEK 293 NF-kB counterscreen assay described above.*

| # | STRUCTURE | TLR7 LEC (μM) | TLR8 LEC (μM) | PBMC LEC (μM) |
|---|---|---|---|---|
| 93 | 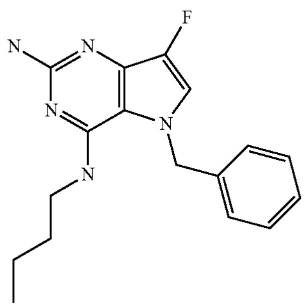 [SMILES: CCCCNc1nc(N)nc2c(F)cn(Cc3ccccc3)c12] | 0.26 | >25 | 0.12 |
| 94 | 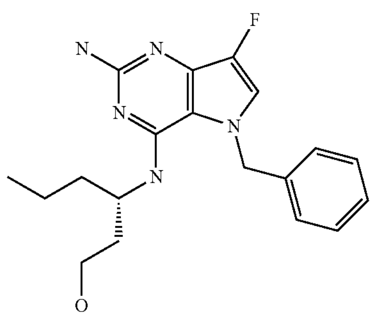 [SMILES: CCC[C@@H](CCO)Nc1nc(N)nc2c(F)cn(Cc3ccccc3)c12] | 0.01 | >25 | 0.01 |
| 95 | 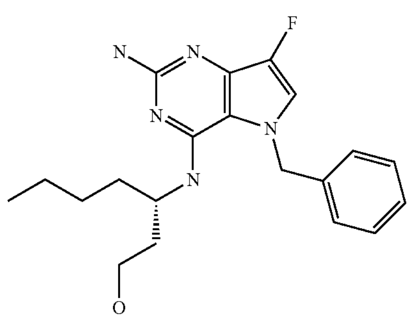 [SMILES: CCCC[C@@H](CCO)Nc1nc(N)nc2c(F)cn(Cc3ccccc3)c12] | 0.01 | 3.26 | 0.007 |
| 96 | 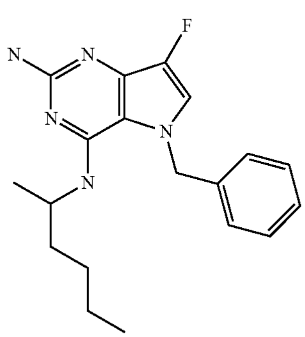 [SMILES: CCCCC(C)Nc1nc(N)nc2c(F)cn(Cc3ccccc3)c12] | 0.05 | >25 | 0.04 |

TABLE 2-continued

Activity of compounds of formula (I). All compounds showed no activity
(LEC >25 μM) in the HEK 293 NF-kB counterscreen assay described above.

| # | STRUCTURE | TLR7 LEC (μM) | TLR8 LEC (μM) | PBMC LEC (μM) |
|---|---|---|---|---|
| 97 | 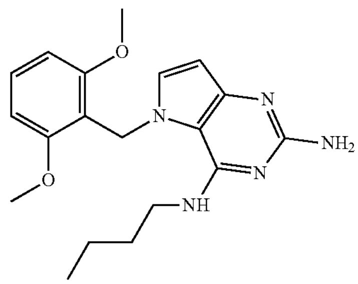 [SMILES: CCCCNc1nc(N)nc2ccn(Cc3c(OC)cccc3OC)c12] | <0.01 | 0.23 | 0.001 |
| 98 | 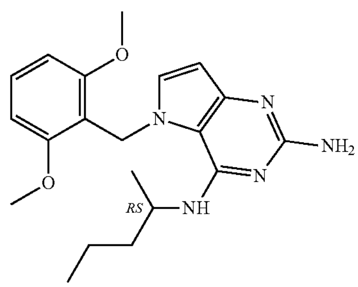 [SMILES: CCCC(C)Nc1nc(N)nc2ccn(Cc3c(OC)cccc3OC)c12] | <0.01 | 0.22 | 0.001 |
| 99 | 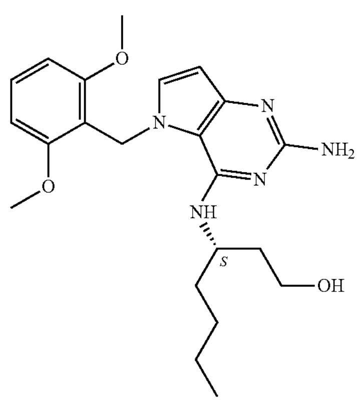 | <0.01 | 0.1 | <0.001 |
| 100 | 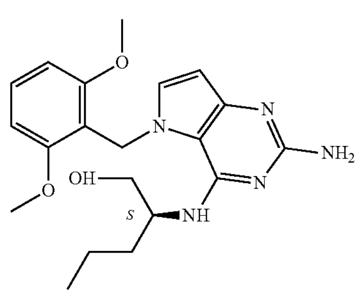 | <0.01 | 0.04 | <0.001 |

TABLE 2-continued

Activity of compounds of formula (I). All compounds showed no activity (LEC >25 μM) in the HEK 293 NF-kB counterscreen assay described above.

| # | STRUCTURE | TLR7 LEC (μM) | TLR8 LEC (μM) | PBMC LEC (μM) |
|---|---|---|---|---|
| 101 | 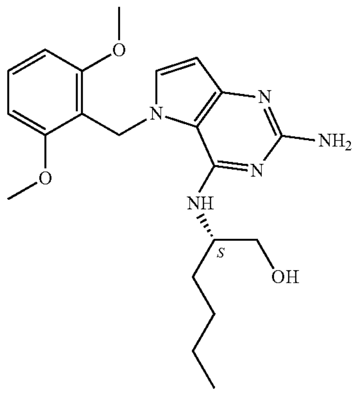 | <0.01 | 0.08 | <0.001 |
| 102 | 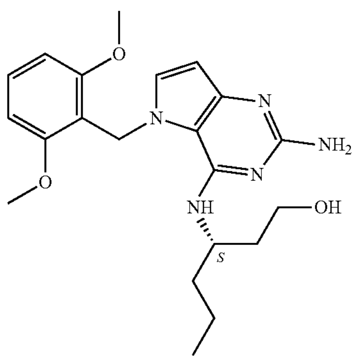 | <0.01 | 0.14 | <0.001 |
| 103 | 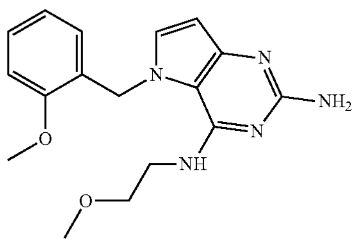 [SMILES: COCCNc1nc(N)nc2ccn(Cc3ccccc3OC)c12] | 0.032 | >25 | 0.018 |
| 104 | 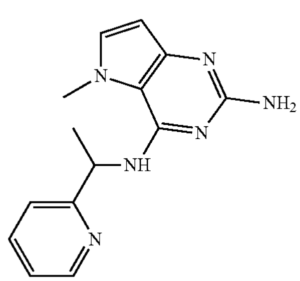 [SMILES: CC(Nc1nc(N)nc2ccn(C)c12)c1ccccn1] | 11.960 | >25 | 1.980 |

TABLE 2-continued

*Activity of compounds of formula (I). All compounds showed no activity (LEC >25 µM) in the HEK 293 NF-kB counterscreen assay described above.*

| # | STRUCTURE | TLR7 LEC (µM) | TLR8 LEC (µM) | PBMC LEC (µM) |
|---|---|---|---|---|
| 105 | 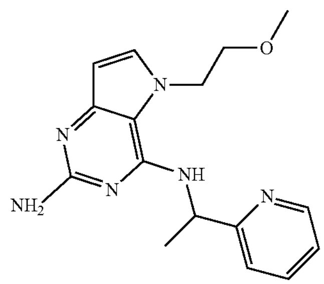 [SMILES: COCCn1ccc2nc(N)nc(NC(C)c3ccccn3)c21] | 0.827 | >25 | 0.194 |
| 106 | 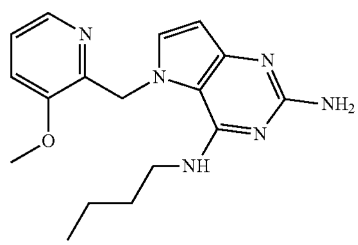 [SMILES: CCCCNc1nc(N)nc2ccn(Cc3ncccc3OC)c12] | 0.008 | 0.59 | 0.005 |
| 107 | 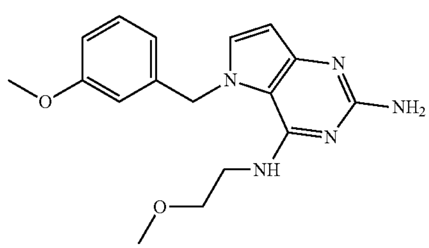 [SMILES: COCCNc1nc(N)nc2ccn(Cc3cccc(OC)c3)c12] | 2.030 | >25 | 2.130 |
| 108 | 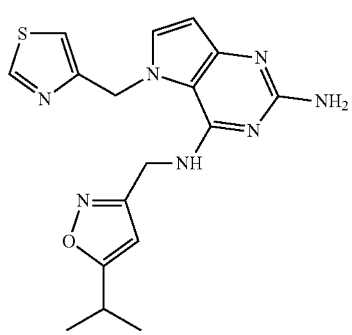 [SMILES: CC(C)c1cc(CNc2nc(N)nc3ccn(Cc4cscn4)c23)no1] | 0.126 | >25 | 0.070 |
| 109 | 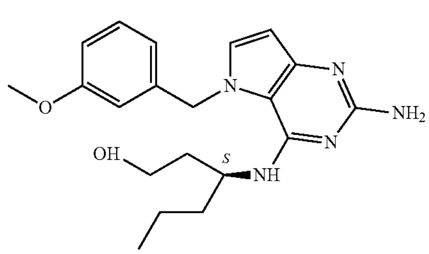 | 0.005 | 7.17 | 0.003 |

TABLE 2-continued

*Activity of compounds of formula (I). All compounds showed no activity (LEC >25 μM) in the HEK 293 NF-kB counterscreen assay described above.*

| # | STRUCTURE | TLR7 LEC (μM) | TLR8 LEC (μM) | PBMC LEC (μM) |
|---|---|---|---|---|
| 110 | 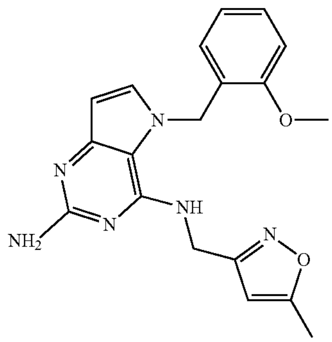 [SMILES: COc1ccccc1Cn1ccc2nc(N)nc(NCc3cc(C)on3)c21] | 0.002 | >25 | 0.001 |
| 111 | 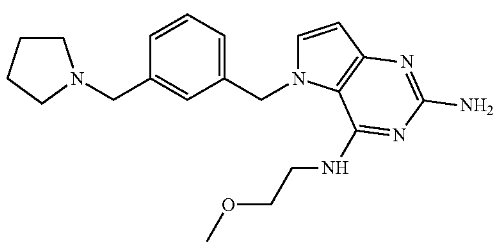 [SMILES: COCCNc1nc(N)nc2ccn(Cc3cccc(CN4CCCC4)c3)c12] | 0.637 | >25 | 0.293 |
| 112 | 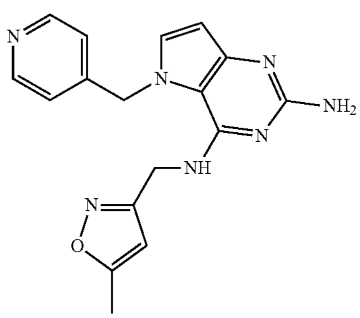 [SMILES: Cc1cc(CNc2nc(N)nc3ccn(Cc4ccncc4)c23)no1] | 0.741 | >25 | 0.209 |
| 113 | 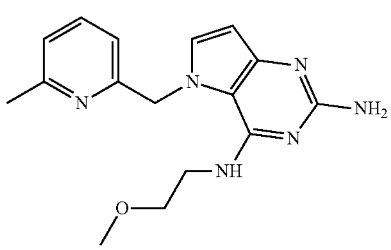 [SMILES: COCCNc1nc(N)nc2ccn(Cc3cccc(C)n3)c12] | 1.320 | >25 | 0.807 |
| 114 | 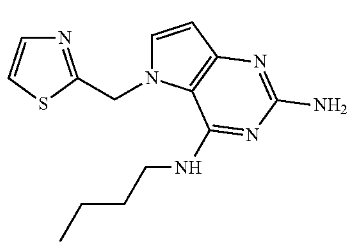 [SMILES: CCCCNc1nc(N)nc2ccn(Cc3nccs3)c12] | 0.186 | 2.27 | 0.133 |

TABLE 2-continued

*Activity of compounds of formula (I). All compounds showed no activity (LEC >25 μM) in the HEK 293 NF-kB counterscreen assay described above.*

| # | STRUCTURE | TLR7 LEC (μM) | TLR8 LEC (μM) | PBMC LEC (μM) |
|---|---|---|---|---|
| 115 | 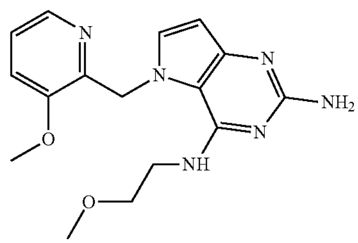 [SMILES: COCCNc1nc(N)nc2ccn(Cc3ncccc3OC)c12] | 0.241 | 7.93 | 0.079 |
| 116 | 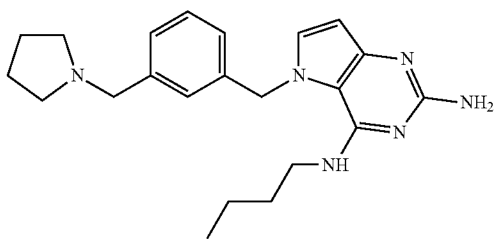 [SMILES: CCCCNc1nc(N)nc2ccn(Cc3cccc(CN4CCCC4)c3)c12] | 0.049 | >25 | 0.022 |
| 117 | 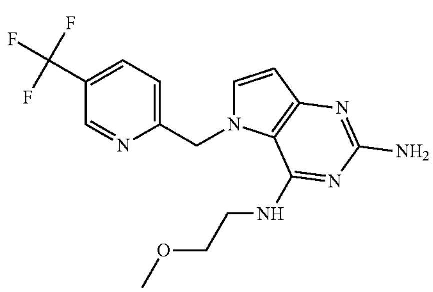 [SMILES: COCCNc1nc(N)nc2ccn(Cc3ccc(C(F)(F)F)cn3)c12] | 2.950 | >22.7 | 1.430 |
| 118 | 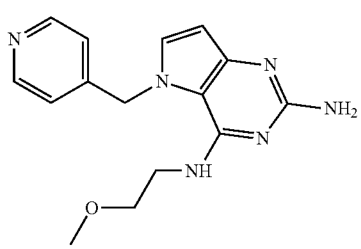 [SMILES: COCCNc1nc(N)nc2ccn(Cc3ccncc3)c12] | 1.650 | >25 | 3.010 |
| 119 | 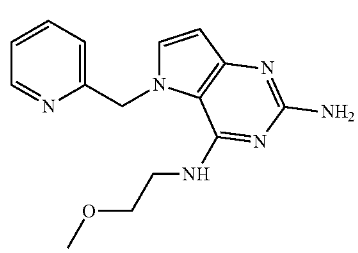 [SMILES: COCCNc1nc(N)nc2ccn(Cc3ccccn3)c12] | 1.810 | >25 | 2.180 |

TABLE 2-continued

Activity of compounds of formula (I). All compounds showed no activity
(LEC >25 μM) in the HEK 293 NF-kB counterscreen assay described above.

| # | STRUCTURE | TLR7 LEC (μM) | TLR8 LEC (μM) | PBMC LEC (μM) |
|---|---|---|---|---|
| 120 | 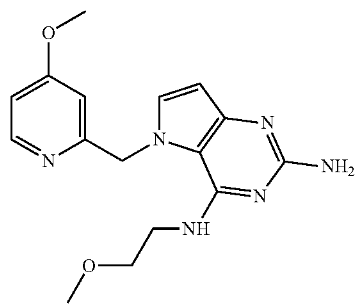 [SMILES: COCCNc1nc(N)nc2ccn(Cc3cc(OC)ccn3)c12] | 3.220 | >25 | 2.160 |
| 121 | 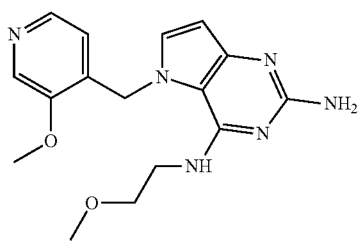 [SMILES: COCCNc1nc(N)nc2ccn(Cc3ccncc3OC)c12] | 0.172 | >25 | 0.046 |
| 122 | 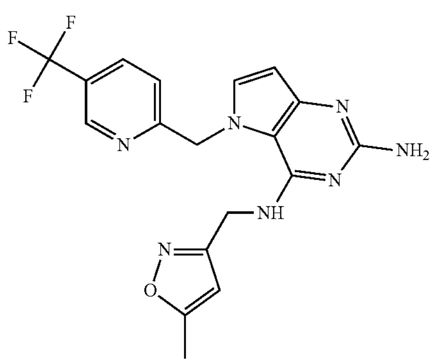 [SMILES: Cc1cc(CNc2nc(N)nc3ccn(Cc4ccc(C(F)(F)F)cn4)c23)no1] | 0.050 | >25 | 0.030 |
| 123 | 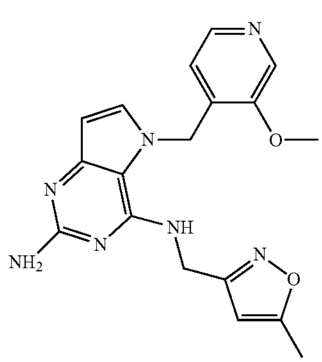 [SMILES: COc1cnccc1Cn1ccc2nc(N)nc(NCc3cc(C)on3)c21] | 0.026 | >25 | 0.002 |

TABLE 2-continued

Activity of compounds of formula (I). All compounds showed no activity (LEC >25 μM) in the HEK 293 NF-kB counterscreen assay described above.

| # | STRUCTURE | TLR7 LEC (μM) | TLR8 LEC (μM) | PBMC LEC (μM) |
|---|---|---|---|---|
| 124 | 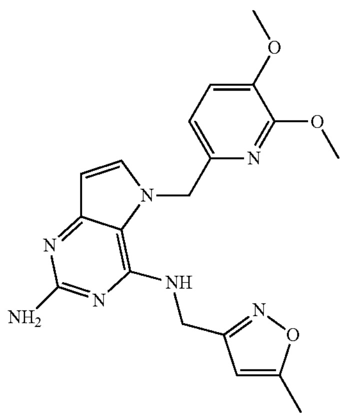 [SMILES: COc1ccc(Cn2ccc3nc(N)nc(NCc4cc(C)on4)c32)nc1OC] | 0.003 | >22 | 0.001 |
| 125 | 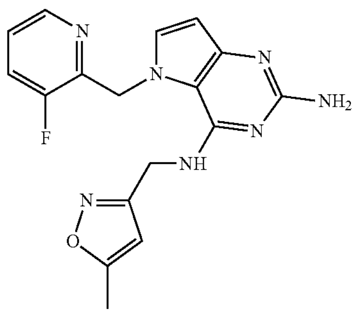 [SMILES: Cc1cc(CNc2nc(N)nc3ccn(Cc4ncccc4F)c23)no1] | 0.086 | >25 | 0.009 |
| 126 | 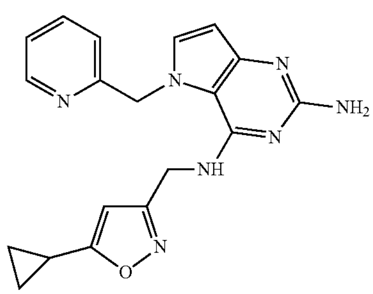 [SMILES: Nc1nc(NCc2cc(C3CC3)on2)c2c(ccn2Cc2ccccn2)n1] | 0.054 | >25 | 0.008 |
| 127 | 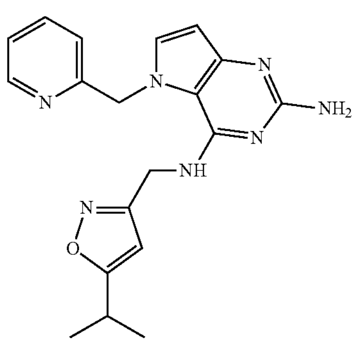 [SMILES: CC(C)c1cc(CNc2nc(N)nc3ccn(Cc4ccccn4)c23)no1] | 0.337 | >25 | 0.019 |

TABLE 2-continued

Activity of compounds of formula (I). All compounds showed no activity (LEC >25 μM) in the HEK 293 NF-kB counterscreen assay described above.

| # | STRUCTURE | TLR7 LEC (μM) | TLR8 LEC (μM) | PBMC LEC (μM) |
|---|---|---|---|---|
| 128 | 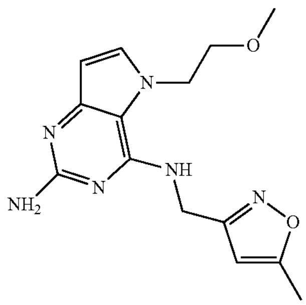 [SMILES: COCCn1ccc2nc(N)nc(NCc3cc(C)on3)c21] | 0.342 | >25 | 0.062 |
| 129 | 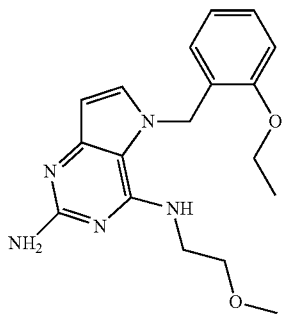 [SMILES: CCOc1ccccc1Cn1ccc2nc(N)nc(NCCOC)c21] | 0.670 | >25 | 0.122 |
| 130 | 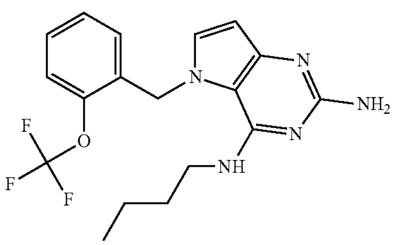 [SMILES: CCCCNc1nc(N)nc2ccn(Cc3ccccc3OC(F)(F)F)c12] | 1.940 | >25 | 0.804 |
| 131 | 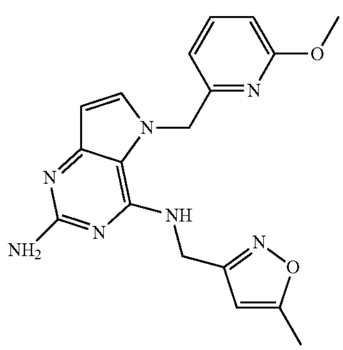 [SMILES: COc1cccc(Cn2ccc3nc(N)nc(NCc4cc(C)on4)c32)n1] | 0.004 | 24.6 | 0.001 |
| 132 | 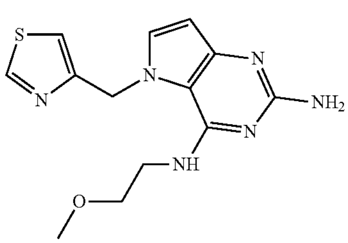 [SMILES: COCCNc1nc(N)nc2ccn(Cc3cscn3)c12] | 5.99 | >25 | 0.879 |

TABLE 2-continued
Activity of compounds of formula (I). All compounds showed no activity (LEC >25 μM) in the HEK 293 NF-kB counterscreen assay described above.
| # | STRUCTURE | TLR7 LEC (μM) | TLR8 LEC (μM) | PBMC LEC (μM) |
|---|---|---|---|---|
| 133 | 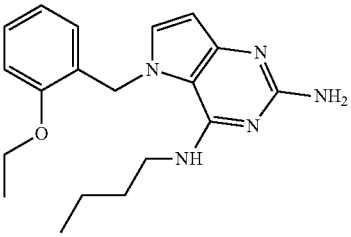 [SMILES: CCCCNc1nc(N)nc2ccn(Cc3ccccc3OCC)c12] | 0.07 | >25 | 0.023 |
| 134 | 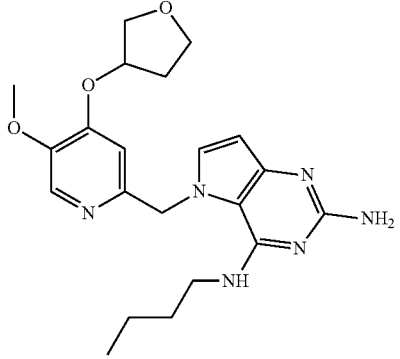 [SMILES: CCCCNc1nc(N)nc2ccn(Cc3cc(OC4CCOC4)c(OC)cn3)c12] | 1.20 | >25 | 0.104 |
| 135 | 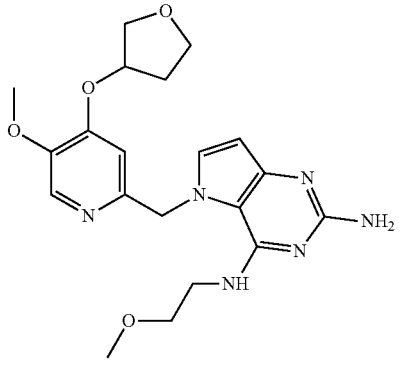 [SMILES: COCCNc1nc(N)nc2ccn(Cc3cc(OC4CCOC4)c(OC)cn3)c12] | 12.5 | >25 | 4.050 |
| 136 | 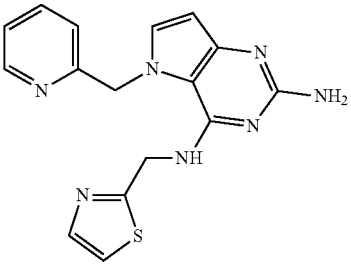 [SMILES: Nc1nc(NCc2nccs2)c2c(ccn2Cc2ccccn2)n1] | 3.04 | >25 | 0.559 |

TABLE 2-continued

Activity of compounds of formula (I). All compounds showed no activity (LEC >25 μM) in the HEK 293 NF-kB counterscreen assay described above.

| # | STRUCTURE | TLR7 LEC (μM) | TLR8 LEC (μM) | PBMC LEC (μM) |
|---|---|---|---|---|
| 137 | 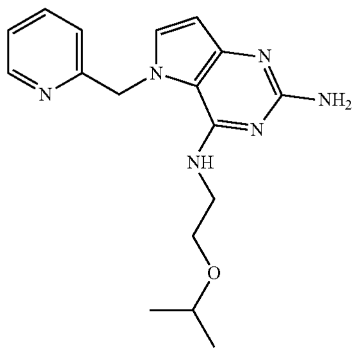 [SMILES: CC(C)OCCNc1nc(N)nc2ccn(Cc3ccccn3)c12] | 13.8 | >25 | 2.030 |
| 138 | 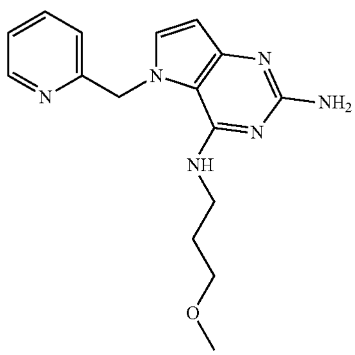 [SMILES: COCCCNc1nc(N)nc2ccn(Cc3ccccn3)c12] | 4.45 | >25 | 0.502 |
| 139 | 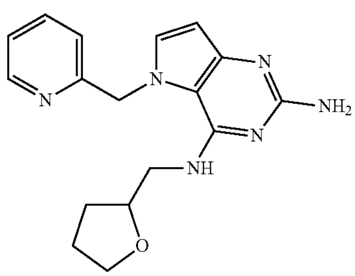 [SMILES: Nc1nc(NCC2CCCO2)c2c(ccn2Cc2ccccn2)n1] | 1.41 | >25 | 0.588 |
| 140 | 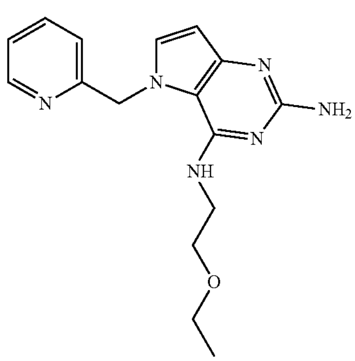 [SMILES: CCOCCNc1nc(N)nc2ccn(Cc3ccccn3)c12] | 1.24 | >25 | 0.513 |

TABLE 2-continued

Activity of compounds of formula (I). All compounds showed no activity (LEC >25 μM) in the HEK 293 NF-kB counterscreen assay described above.

| # | STRUCTURE | TLR7 LEC (μM) | TLR8 LEC (μM) | PBMC LEC (μM) |
|---|---|---|---|---|
| 141 | 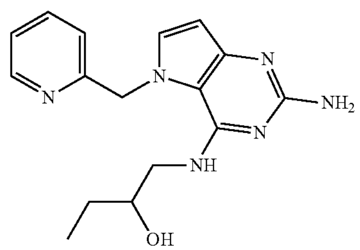 [SMILES: CCC(O)CNc1nc(N)nc2ccn(Cc3ccccn3)c12] | 0.43 | >25 | 0.048 |
| 142 | 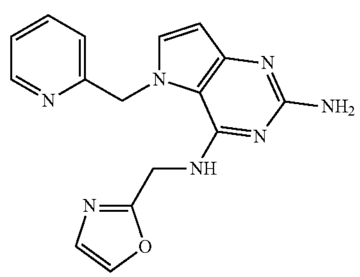 | 0.52 | >25 | 0.134 |
| 143 | 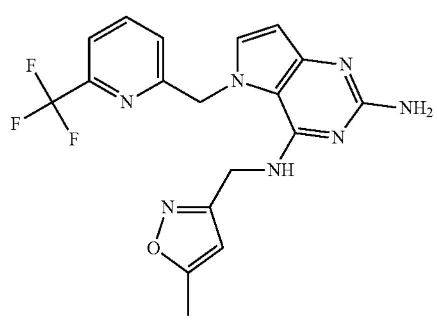 [SMILES: Cc1cc(CNc2nc(N)nc3ccn(Cc4cccc(C(F)(F)F)n4)c23)no1] | 0.10 | >25 | 0.016 |
| 144 | 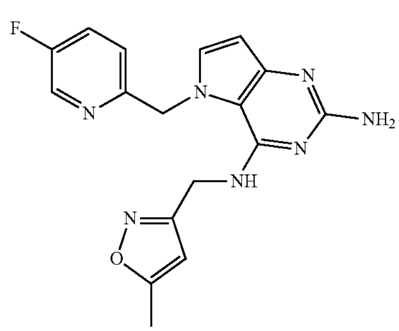 [SMILES: Cc1cc(CNc2nc(N)nc3ccn(Cc4ccc(F)cn4)c23)no1] | 0.07 | >25 | 0.009 |

TABLE 2-continued

Activity of compounds of formula (I). All compounds showed no activity (LEC >25 μM) in the HEK 293 NF-kB counterscreen assay described above.

| # | STRUCTURE | TLR7 LEC (μM) | TLR8 LEC (μM) | PBMC LEC (μM) |
|---|---|---|---|---|
| 145 | 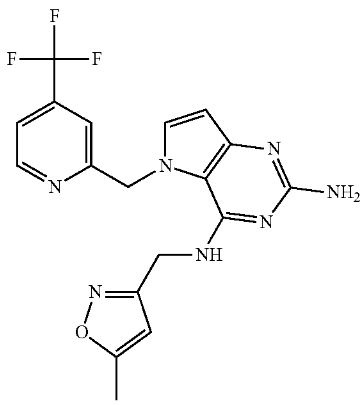 [SMILES: Cc1cc(CNc2nc(N)nc3ccn(Cc4cc(C(F)(F)F)ccn4)c23)no1] | 0.05 | >25 | 0.021 |
| 146 | 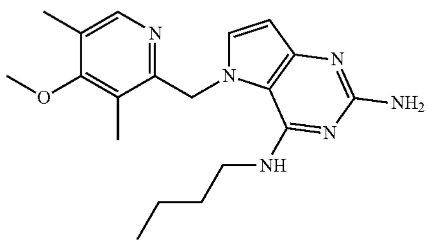 [SMILES: CCCCNc1nc(N)nc2ccn(Cc3ncc(C)c(OC)c3C)c12] | 0.20 | >25 | 0.139 |
| 147 | 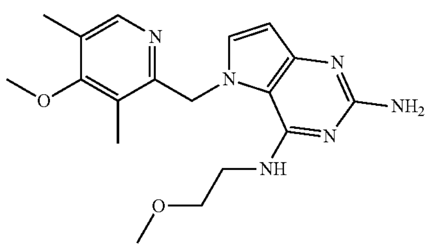 [SMILES: COCCNc1nc(N)nc2ccn(Cc3ncc(C)c(OC)c3C)c12] | 4.49 | >25 | 2.020 |
| 148 | 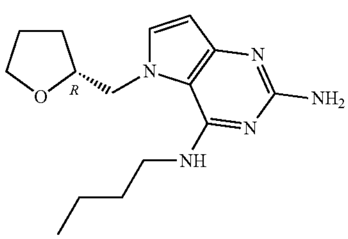 | 0.16 | 3.93 | 0.056 |
| 149 | 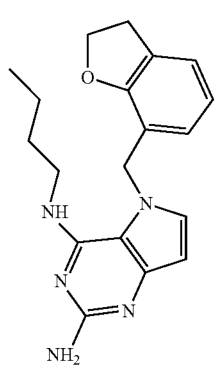 [SMILES: CCCCNc1nc(N)nc2ccn(Cc3cccc4c3OCC4)c12] | 0.02 | >25 | 0.006 |

TABLE 2-continued
Activity of compounds of formula (I). All compounds showed no activity
(LEC >25 µM) in the HEK 293 NF-kB counterscreen assay described above.
| # | STRUCTURE | TLR7 LEC (µM) | TLR8 LEC (µM) | PBMC LEC (µM) |
|---|---|---|---|---|
| 150 | 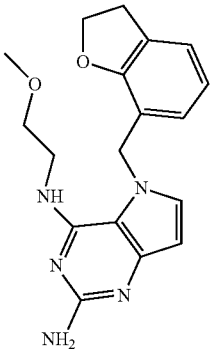 [SMILES: COCCNc1nc(N)nc2ccn(Cc3cccc4c3OCC4)c12] | 0.25 | >25 | 0.054 |
| 151 | 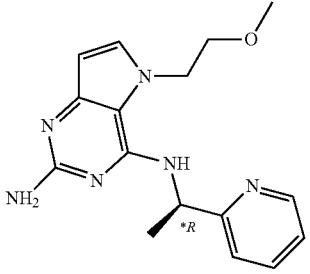 [SMILES: COCCn1ccc2nc(N)nc(N[C@H](C)c3ccccn3)c21] | 12.8 | >25 | 2.580 |
| 152 | 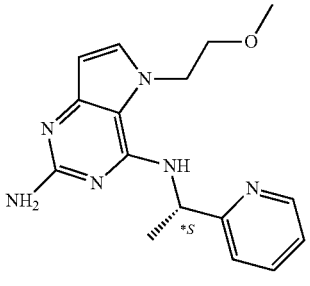 [SMILES: COCCn1ccc2nc(N)nc(N[C@@H](C)c3ccccn3)c21] | 0.73 | >25 | 0.142 |
| 153 | 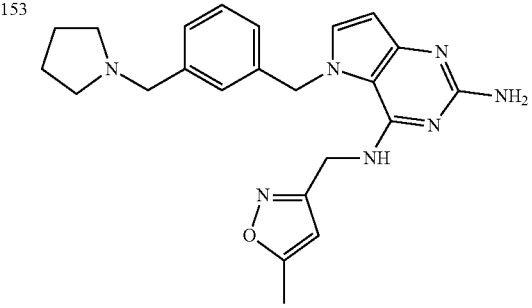 | 0.05 | >25 | 0.002 |

TABLE 2-continued

Activity of compounds of formula (I). All compounds showed no activity
(LEC >25 μM) in the HEK 293 NF-kB counterscreen assay described above.

| # | STRUCTURE | TLR7 LEC (μM) | TLR8 LEC (μM) | PBMC LEC (μM) |
|---|---|---|---|---|
| 154 | 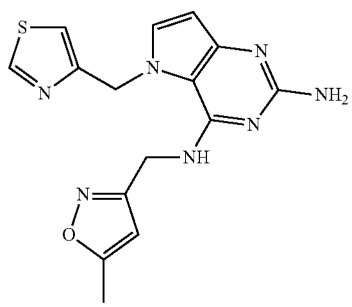 [SMILES: Cc1cc(CNc2nc(N)nc3ccn(Cc4cscn4)c23)no1] | 0.08 | >25 | 0.017 |
| 155 | 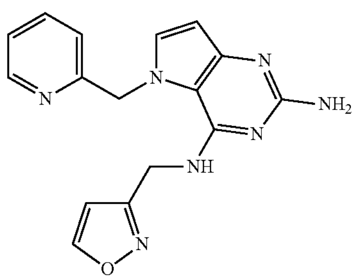 [SMILES: Nc1nc(NCc2ccon2)c2c(ccn2Cc2ccccn2)n1] | 0.90 | >25 | 0.415 |
| 156 | 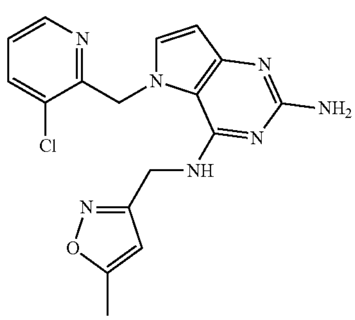 [SMILES: Cc1cc(CNc2nc(N)nc3ccn(Cc4ncccc4Cl)c23)no1] | 0.05 | >25 | 0.040 |
| 157 | 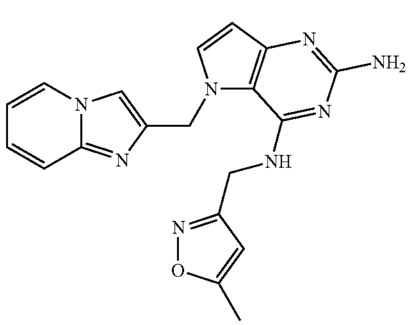 [SMILES: Cc1cc(CNc2nc(N)nc3ccn(Cc4cn5ccccc5n4)c23)no1] | 0.03 | >25 | 0.003 |

TABLE 2-continued
Activity of compounds of formula (I). All compounds showed no activity (LEC >25 μM) in the HEK 293 NF-kB counterscreen assay described above.
| # | STRUCTURE | TLR7 LEC (μM) | TLR8 LEC (μM) | PBMC LEC (μM) |
|---|---|---|---|---|
| 158 | 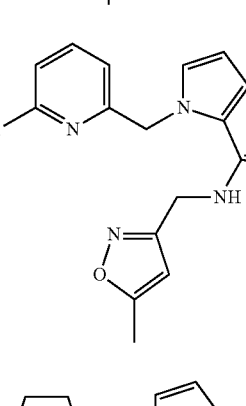 | 0.05 | >25 | 0.020 |
| 159 | 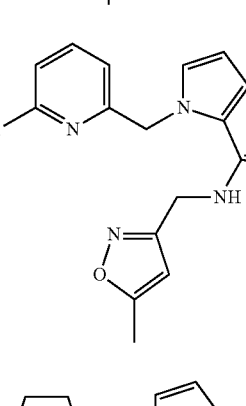 | 0.05 | >25 | 0.019 |
| 160 | 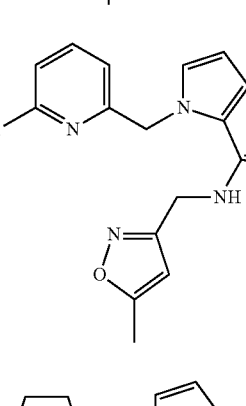 | 8.07 | >25 | 1.810 |
| 161 | 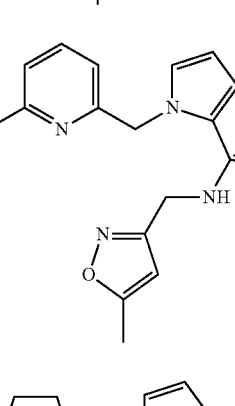 | 0.02 | >25 | 0.009 |
| 162 | 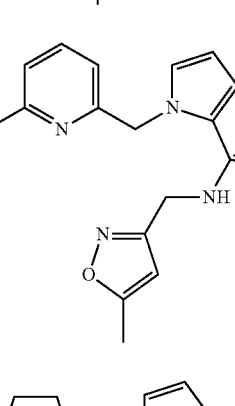 | 0.32 | >25 | 0.128 |

TABLE 2-continued

*Activity of compounds of formula (I). All compounds showed no activity (LEC >25 μM) in the HEK 293 NF-kB counterscreen assay described above.*

| # | STRUCTURE | TLR7 LEC (μM) | TLR8 LEC (μM) | PBMC LEC (μM) |
|---|-----------|---------------|---------------|---------------|
| 163 | 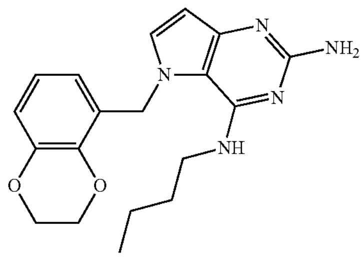 [SMILES: CCCCNc1nc(N)nc2ccn(Cc3cccc4c3OCCO4)c12] | <0.01 | 0.75 | 0.001 |
| 164 | 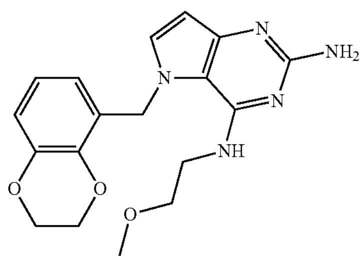 [SMILES: COCCNc1nc(N)nc2ccn(Cc3cccc4c3OCCO4)c12] | 0.04 | 15.93 | 0.025 |
| 165 | 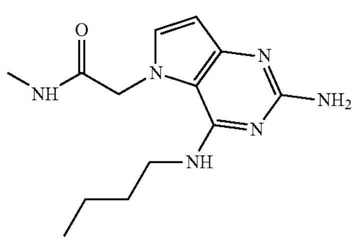 [SMILES: CCCCNc1nc(N)nc2ccn(CC(=O)NC)c12] | 4.94 | >25 | 0.957 |
| 166 | 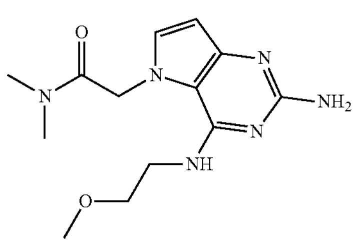 [SMILES: COCCNc1nc(N)nc2ccn(CC(=O)N(C)C)c12] | 4.88 | NA | NA |
| 167 | 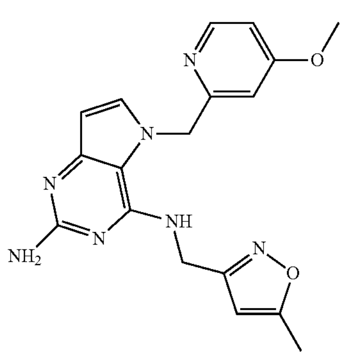 [SMILES: COc1ccnc(Cn2ccc3nc(N)nc(NCc4cc(C)on4)c32)c1] | 0.09 | >25 | 0.008 |

TABLE 2-continued
Activity of compounds of formula (I). All compounds showed no activity
(LEC >25 μM) in the HEK 293 NF-kB counterscreen assay described above.
| # | STRUCTURE | TLR7 LEC (μM) | TLR8 LEC (μM) | PBMC LEC (μM) |
|---|---|---|---|---|
| 168 | 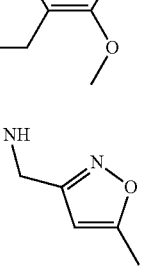 | 0.09 | >25 | 0.011 |
| 169 | 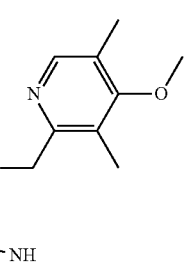 | 0.04 | >25 | 0.011 |
| 170 | 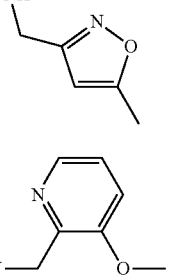 | 0.01 | >25 | 0.002 |
| 171 | 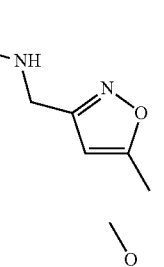 | 0.02 | >25 | NA |

TABLE 2-continued

*Activity of compounds of formula (I). All compounds showed no activity (LEC >25 μM) in the HEK 293 NF-kB counterscreen assay described above.*

| # | STRUCTURE | TLR7 LEC (μM) | TLR8 LEC (μM) | PBMC LEC (μM) |
|---|---|---|---|---|
| 172 | 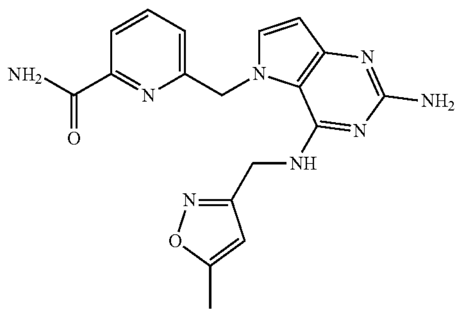 [SMILES: Cc1cc(CNc2nc(N)nc3ccn(Cc4cccc(C(N)=O)n4)c23)no1] | 1.40 | >25 | 0.017 |
| 173 | 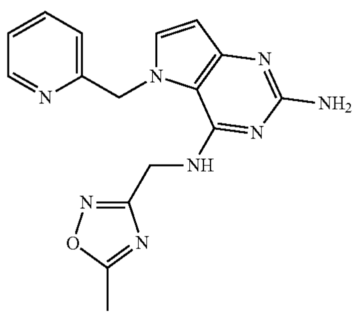 | 0.53 | >25 | 0.066 |
| 174 | 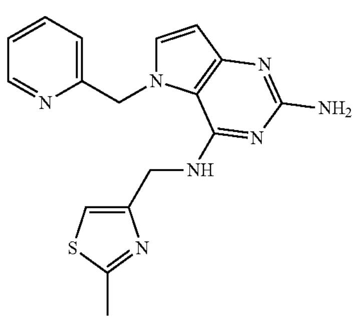 | 6.13 | >25 | 2.200 |
| 175 | 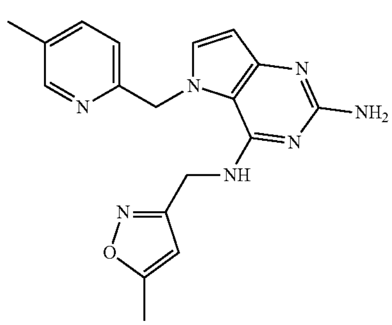 [SMILES: Cc1ccc(Cn2ccc3nc(N)nc(NCc4cc(C)on4)c32)nc1] | 0.02 | >25 | 0.009 |

TABLE 2-continued
Activity of compounds of formula (I). All compounds showed no activity (LEC >25 μM) in the HEK 293 NF-kB counterscreen assay described above.
| # | STRUCTURE | TLR7 LEC (μM) | TLR8 LEC (μM) | PBMC LEC (μM) |
|---|---|---|---|---|
| 176 | 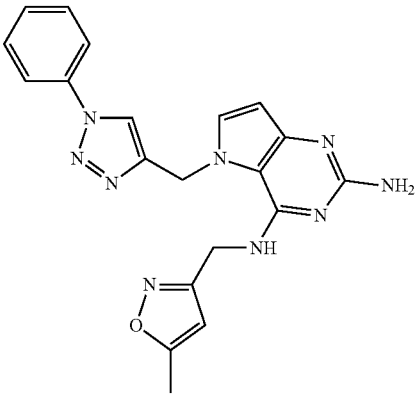 [SMILES: Cc1cc(CNc2nc(N)nc3ccn(Cc4cn(-c5ccccc5)nn4)c23)no1] | 0.04 | >25 | 0.009 |
| 177 | 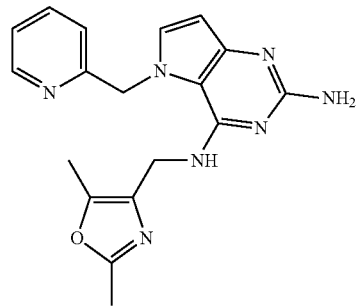 [SMILES: Cc1nc(CNc2nc(N)nc3ccn(Cc4ccccn4)c23)c(C)o1] | 8.67 | >25 | 3.930 |
| 178 | 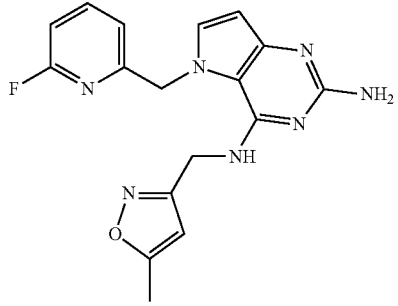 [SMILES: Cc1cc(CNc2nc(N)nc3ccn(Cc4cccc(F)n4)c23)no1] | 0.15 | >25 | 0.014 |
| 179 | 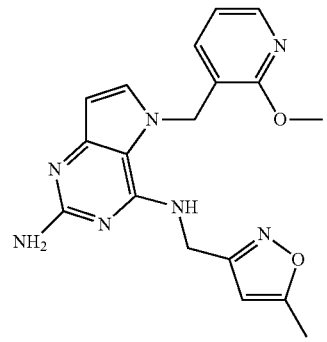 [SMILES: COc1ncccc1Cn1ccc2nc(N)nc(NCc3cc(C)on3)c21] | 0.02 | >25 | 0.003 |

TABLE 2-continued

*Activity of compounds of formula (I). All compounds showed no activity (LEC >25 μM) in the HEK 293 NF-kB counterscreen assay described above.*

| # | STRUCTURE | TLR7 LEC (μM) | TLR8 LEC (μM) | PBMC LEC (μM) |
|---|-----------|---------------|---------------|----------------|
| 180 | 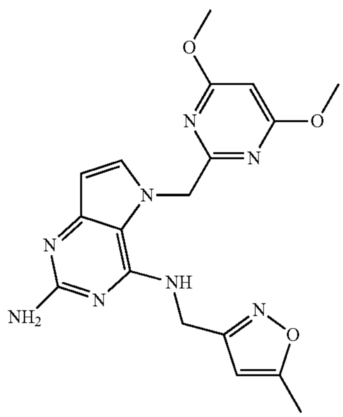 [SMILES: COc1cc(OC)nc(Cn2ccc3nc(N)nc(NCc4cc(C)on4)c32)n1] | 0.01 | >25 | 0.004 |
| 181 | 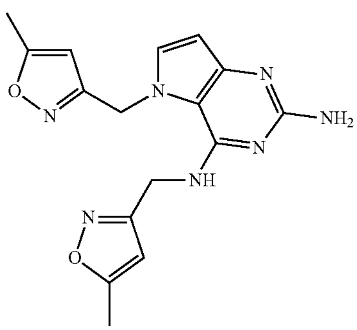 [SMILES: Cc1cc(CNc2nc(N)nc3ccn(Cc4cc(C)on4)c23)no1] | 0.06 | 20.2 | 0.015 |
| 182 | 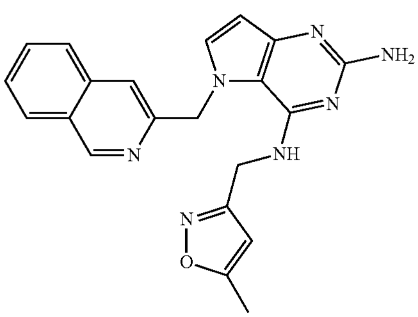 [SMILES: Cc1cc(CNc2nc(N)nc3ccn(Cc4cc5ccccc5cn4)c23)no1] | 0.05 | >25 | 0.018 |
| 183 | 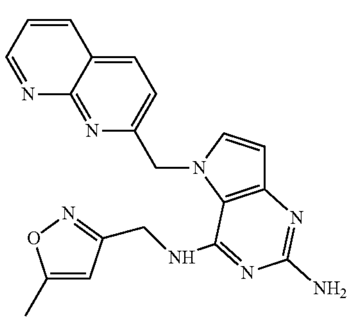 [SMILES: Cc1cc(CNc2nc(N)nc3ccn(Cc4ccc5cccnc5n4)c23)no1] | 0.59 | >25 | 0.009 |

TABLE 2-continued

*Activity of compounds of formula (I). All compounds showed no activity (LEC >25 μM) in the HEK 293 NF-kB counterscreen assay described above.*

| # | STRUCTURE | TLR7 LEC (μM) | TLR8 LEC (μM) | PBMC LEC (μM) |
|---|---|---|---|---|
| 184 | 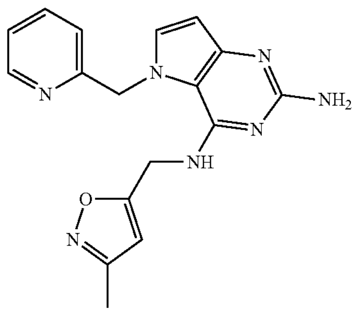 [SMILES: Cc1cc(CNc2nc(N)nc3ccn(Cc4ccccn4)c23)on1] | 0.49 | >25 | 0.131 |
| 185 | 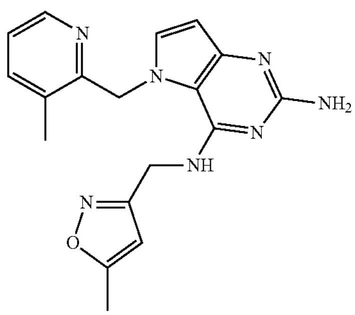 [SMILES: Cc1cc(CNc2nc(N)nc3ccn(Cc4ncccc4C)c23)no1] | 0.07 | >25 | 0.018 |
| 186 | 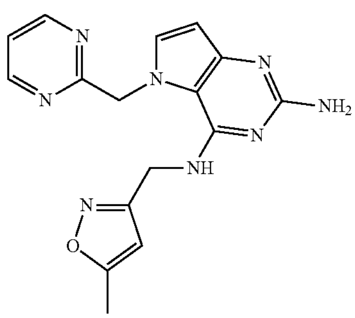 [SMILES: Cc1cc(CNc2nc(N)nc3ccn(Cc4ncccn4)c23)no1] | 0.14 | >25 | 0.035 |
| 187 | 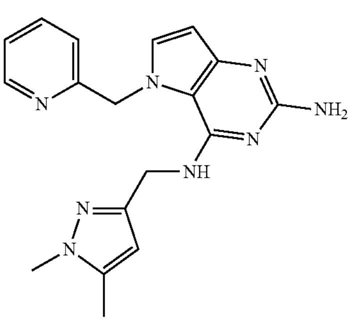 [SMILES: Cc1cc(CNc2nc(N)nc3ccn(Cc4ccccn4)c23)nn1C] | 4.78 | >25 | 0.520 |

TABLE 2-continued

Activity of compounds of formula (I). All compounds showed no activity
(LEC >25 μM) in the HEK 293 NF-kB counterscreen assay described above.

| # | STRUCTURE | TLR7 LEC (μM) | TLR8 LEC (μM) | PBMC LEC (μM) |
|---|---|---|---|---|
| 188 | 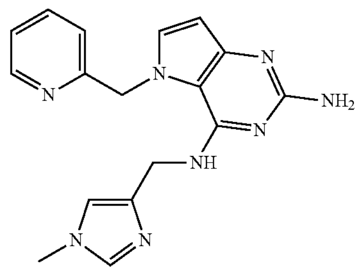 [SMILES: Cn1cnc(CNc2nc(N)nc3ccn(Cc4ccccn4)c23)c1] | 7.62 | >25 | 0.047 |
| 189 | 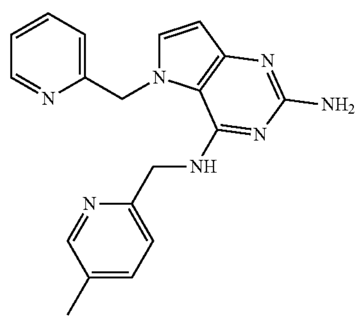 [SMILES: Cc1ccc(CNc2nc(N)nc3ccn(Cc4ccccn4)c23)nc1] | 0.40 | >25 | 0.074 |
| 190 | 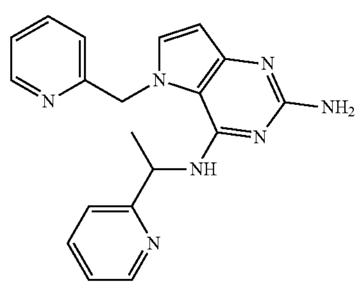 [SMILES: CC(Nc1nc(N)nc2ccn(Cc3ccccn3)c12)c1ccccn1] | 0.26 | >25 | 0.038 |
| 191 | 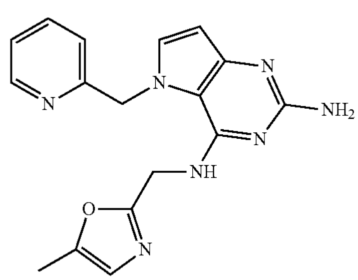 [SMILES: Cc1cnc(CNc2nc(N)nc3ccn(Cc4ccccn4)c23)o1] | 0.06 | >24 | 0.006 |
| 192 | 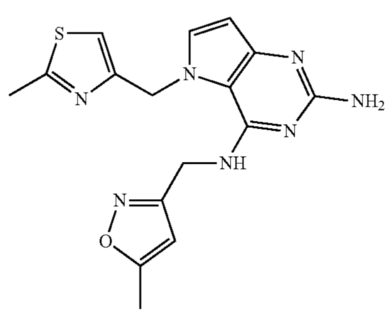 [SMILES: Cc1cc(CNc2nc(N)nc3ccn(Cc4csc(C)n4)c23)no1] | 0.07 | >25 | 0.030 |

TABLE 2-continued

Activity of compounds of formula (I). All compounds showed no activity
(LEC >25 μM) in the HEK 293 NF-kB counterscreen assay described above.

| # | STRUCTURE | TLR7 LEC (μM) | TLR8 LEC (μM) | PBMC LEC (μM) |
|---|---|---|---|---|
| 193 | 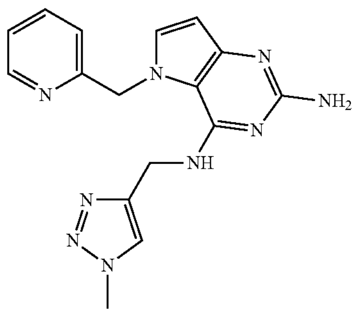 [SMILES: Cn1cc(CNc2nc(N)nc3ccn(Cc4ccccn4)c23)nn1] | 11.3 | >25 | 0.447 |
| 194 | 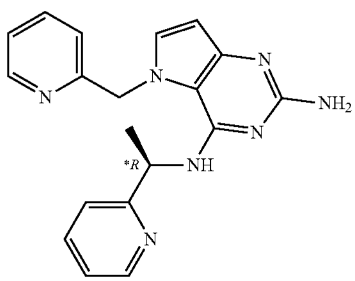 [SMILES: C[C@@H](Nc1nc(N)nc2ccn(Cc3ccccn3)c12)c1ccccn1] | 2.38 | >25 | 0.507 |
| 195 | 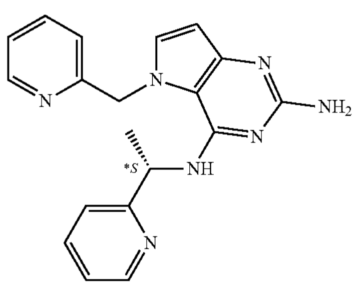 [SMILES: C[C@H](Nc1nc(N)nc2ccn(Cc3ccccn3)c12)c1ccccn1] | 0.16 | >25 | 0.024 |
| 196 | 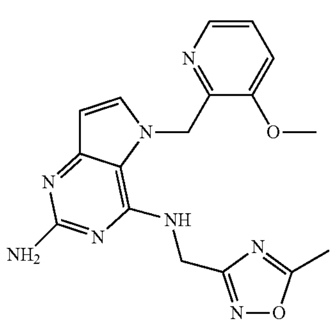 [SMILES: COc1cccnc1Cn1ccc2nc(N)nc(NCc3noc(C)n3)c21] | 0.01 | 12.6 | 0.002 |

TABLE 2-continued

Activity of compounds of formula (I). All compounds showed no activity (LEC >25 μM) in the HEK 293 NF-kB counterscreen assay described above.

| # | STRUCTURE | TLR7 LEC (μM) | TLR8 LEC (μM) | PBMC LEC (μM) |
|---|---|---|---|---|
| 197 | 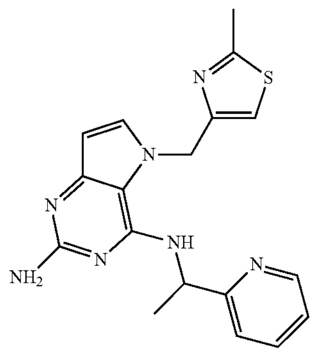 [SMILES: Cc1nc(Cn2ccc3nc(N)nc(NC(C)c4ccccn4)c32)cs1] | 0.39 | >25 | 0.040 |
| 198 | 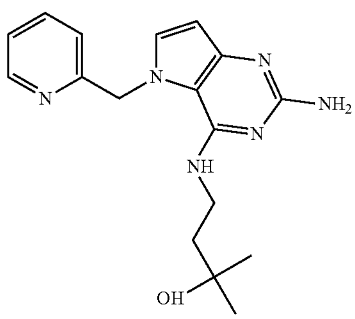 [SMILES: CC(C)(O)CCNc1nc(N)nc2ccn(Cc3ccccn3)c12] | 8.76 | >25 | 0.617 |
| 199 | 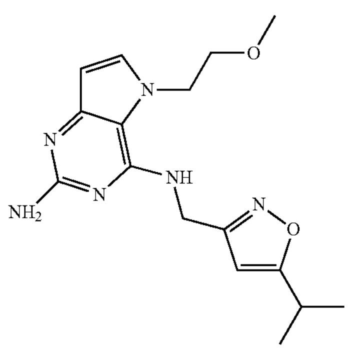 [SMILES: COCCn1ccc2nc(N)nc(NCc3cc(C(C)C)on3)c21] | 0.60 | 23.5 | 0.032 |
| 200 | 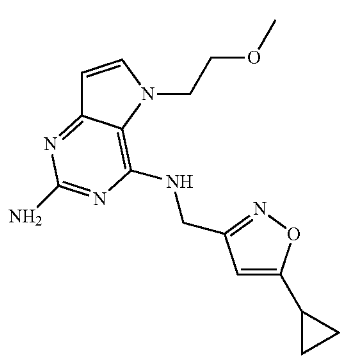 [SMILES: COCCn1ccc2nc(N)nc(NCc3cc(C4CC4)on3)c21] | 0.17 | 11.4 | 0.035 |

TABLE 2-continued

Activity of compounds of formula (I). All compounds showed no activity (LEC >25 μM) in the HEK 293 NF-kB counterscreen assay described above.

| # | STRUCTURE | TLR7 LEC (μM) | TLR8 LEC (μM) | PBMC LEC (μM) |
|---|---|---|---|---|
| 201 | 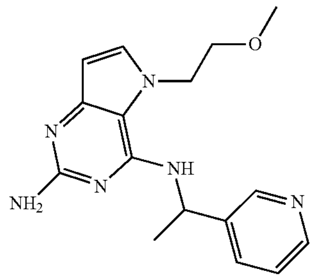 [SMILES: COCCn1ccc2nc(N)nc(NC(C)c3cccnc3)c21] | 7.30 | >25 | 0.978 |
| 202 | 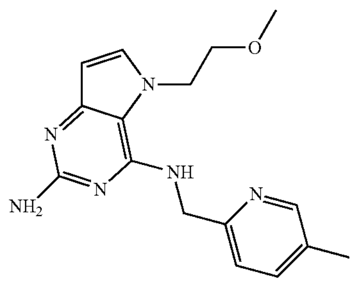 [SMILES: COCCn1ccc2nc(N)nc(NCc3ccc(C)cn3)c21] | 1.61 | >25 | 0.580 |
| 203 | 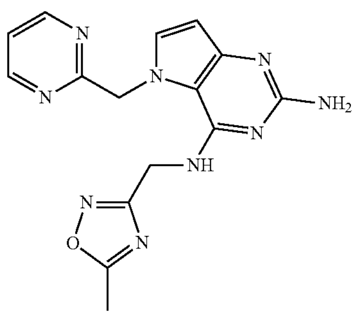 [SMILES: Cc1nc(CNc2nc(N)nc3ccn(Cc4ncccn4)c23)no1] | 1.04 | >25 | 0.138 |
| 204 | 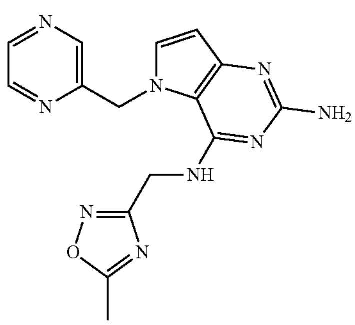 [SMILES: Cc1nc(CNc2nc(N)nc3ccn(Cc4cnccn4)c23)no1] | 1.78 | >25 | 0.188 |
| 205 | 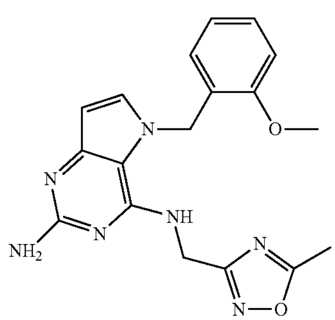 [SMILES: COc1ccccc1Cn1ccc2nc(N)nc(NCc3noc(C)n3)c21] | <0.01 | 7.7 | 0.001 |

TABLE 2-continued

*Activity of compounds of formula (I). All compounds showed no activity (LEC >25 µM) in the HEK 293 NF-kB counterscreen assay described above.*

| # | STRUCTURE | TLR7 LEC (µM) | TLR8 LEC (µM) | PBMC LEC (µM) |
|---|---|---|---|---|
| 206 | 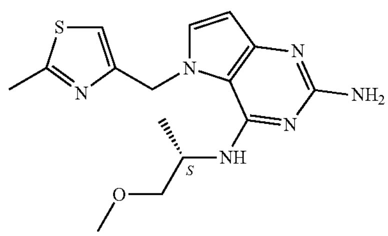 | 0.74 | 15 | 0.129 |
| 207 | 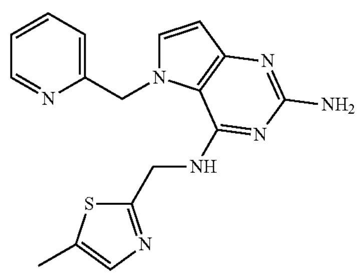 [SMILES: Cc1cnc(CNc2nc(N)nc3ccn(Cc4ccccn4)c23)s1] | 0.06 | 23 | 0.009 |
| 208 | 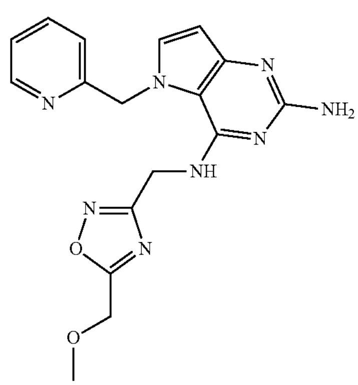 [SMILES: COCc1nc(CNc2nc(N)nc3ccn(Cc4ccccn4)c23)no1] | 5.14 | >25 | 0.402 |
| 209 | 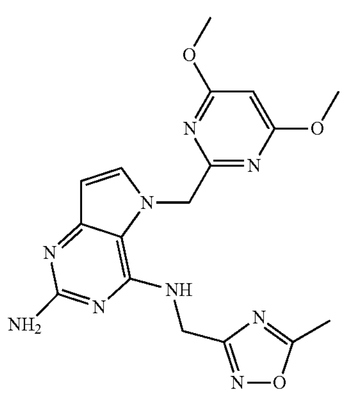 [SMILES: COc1cc(OC)nc(Cn2ccc3nc(N)nc(NCc4noc(C)n4)c32)n1] | 0.04 | >25 | 0.008 |

TABLE 2-continued

Activity of compounds of formula (I). All compounds showed no activity
(LEC >25 μM) in the HEK 293 NF-kB counterscreen assay described above.

| # | STRUCTURE | TLR7 LEC (μM) | TLR8 LEC (μM) | PBMC LEC (μM) |
|---|---|---|---|---|
| 210 | 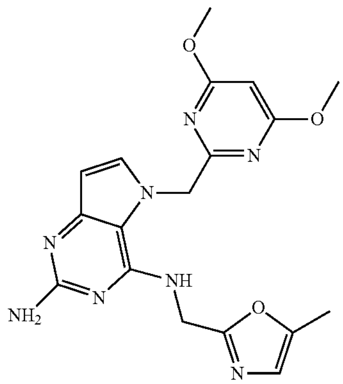 [SMILES: COc1cc(OC)nc(Cn2ccc3nc(N)nc(NCc4ncc(C)o4)c32)n1] | 0.02 | >25 | 0.003 |
| 211 | 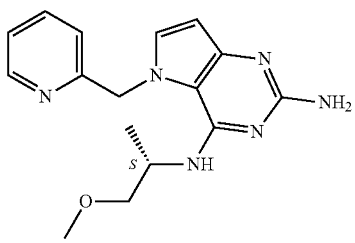 | 6.94 | 22 | 0.470 |
| 212 | 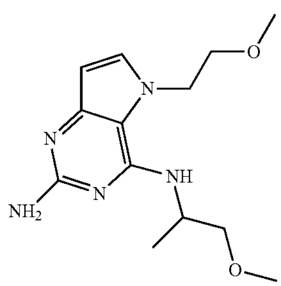 [SMILES: COCCn1ccc2nc(N)nc(NC(C)COC)c21] | 7.60 | >25 | 2.090 |
| 213 | 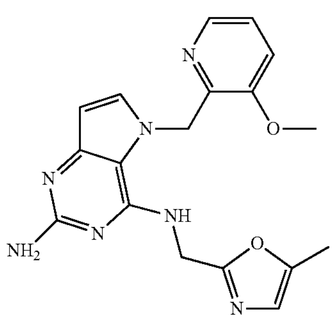 [SMILES: COc1cccnc1Cn1ccc2nc(N)nc(NCc3ncc(C)o3)c21] | <0.01 | >25 | 0.001 |
| 214 | 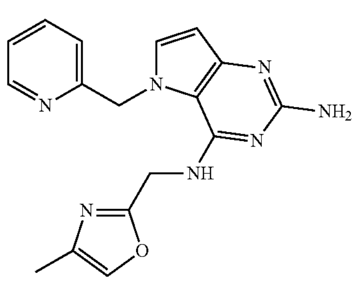 [SMILES: Cc1coc(CNc2nc(N)nc3ccn(Cc4ccccn4)c23)n1] | 1.16 | >25 | 0.151 |

TABLE 2-continued

Activity of compounds of formula (I). All compounds showed no activity (LEC >25 µM) in the HEK 293 NF-kB counterscreen assay described above.

| # | STRUCTURE | TLR7 LEC (µM) | TLR8 LEC (µM) | PBMC LEC (µM) |
|---|---|---|---|---|
| 215 | 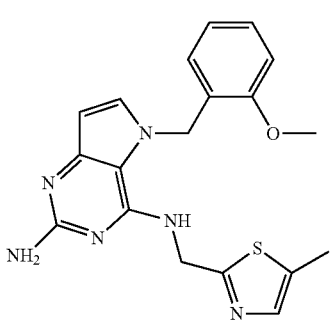 [SMILES: COc1ccccc1Cn1ccc2nc(N)nc(NCc3ncc(C)s3)c21] | <0.01 | >25 | 0.001 |
| 216 | 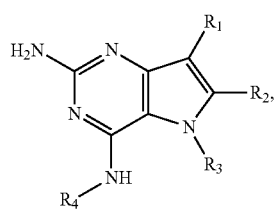 | 1.24 | >25 | 0.091 |

The invention claimed is:

1. A compound of formula (I)

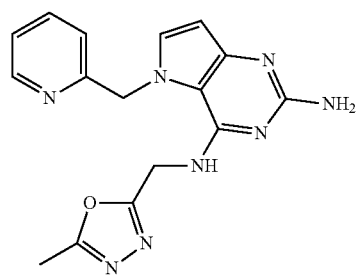 [SMILES: Cc1nnc(CNc2nc(N)nc3ccn(Cc4ccccn4)c23)o1]

a pharmaceutically acceptable salt or solvate thereof wherein;

$R_1$ is H, fluorine or methyl;

$R_2$ is H, halogen or $C_{1-3}$ alkyl;

$R_3$ is $C_{1-6}$ alkyl optionally substituted by aryl wherein said aryl is optionally-substituted by one or more substituents independently selected from the group consisting of aryloxy, halogen, aryl, alkylamino, dialkylamino, $C_{1-6}$ alkyl, —$CO_2H$, —$C(O)OC_{1-6}$ alkyl, —$CONH_2$, —CN, and $C_{1-6}$ alkoxy; or $R_3$ is $C_{1-6}$ alkyl optionally substituted by $C_{1-6}$ alkene, $C_{3-7}$ cycloalkyl or $C_{3-7}$ heterocycloalkyl; or $R_3$ is $C_{1-6}$ alkyl optionally substituted by $C_{1-6}$ alkoxy wherein said $C_{1-6}$ alkoxy is optionally substituted by aryl; and $R_4$ is $C_{1-8}$ alkyl optionally substituted by one or more substituents independently selected from the group consisting of hydroxyl, $C_{1-6}$ alkoxy, $C_{1-6}$ alkyl, $C_{3-7}$ cycloalkyl, $C_{2-6}$ alkenyl, aryl, heteroaryl, and $C_{3-7}$ cycloalkyl wherein said heteroaryl and said $C_{3-7}$ cycloalkyl are optionally substituted by $C_{1-6}$ alkyl;

with the proviso that 2-amino, 4-(N-butylamino)-5-(alphamethylbenzyl)pyrrolo[3,2-d] pyrimidine is excluded.

2. A compound as claimed in claim 1, wherein $R_3$ is methyl optionally substituted by aryl.

3. A compound as claimed in claim 1, wherein each of $R_3$ and $R_4$ is independently $C_{1-3}$ alkyl substituted by aryl.

4. A compound as claimed in claim 1, wherein $R_1$ is fluorine and $R_2$ is hydrogen.

5. A pharmaceutical composition comprising a compound as claimed in claim 1 together with one or more pharmaceutically acceptable excipients, diluents or carriers.

6. A compound as claimed in claim 1, wherein $R_3$ is aryl-substituted $C_{1-3}$ alkyl and the aryl in said aryl-substituted $C_{1-3}$ alkyl is optionally substituted by one or more substituents independently selected from the group consisting of aryloxy, halogen, aryl, alkylamino, dialkylamino, $C_{1-6}$ alkyl, —$CO_2H$, $C(O)OC_{1-6}$ alkyl, —$CONH_2$, —CN, and $C_{1-6}$ alkoxy; and $R_4$ is aryl-substituted $C_{1-3}$ alkyl.

* * * * *